(12) United States Patent
Vendely et al.

(10) Patent No.: US 10,524,788 B2
(45) Date of Patent: Jan. 7, 2020

(54) COMPRESSIBLE ADJUNCT WITH ATTACHMENT REGIONS

(71) Applicant: Ethicon Endo-Surgery, LLC, Guaynabo, PR (US)

(72) Inventors: Michael J. Vendely, Lebanon, OH (US); Emily A. Schellin, Cincinnati, OH (US); Taylor W. Aronhalt, Loveland, OH (US); Trevor J. Barton, Cincinnati, OH (US); Lauren S. Weaner, Cincinnati, OH (US); Jason L. Harris, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 819 days.

(21) Appl. No.: 14/871,153

(22) Filed: Sep. 30, 2015

(65) Prior Publication Data

US 2017/0086843 A1 Mar. 30, 2017

(51) Int. Cl.
*A61B 17/072* (2006.01)
*A61B 17/064* (2006.01)
(Continued)

(52) U.S. Cl.
CPC ...... *A61B 17/07207* (2013.01); *A61B 17/068* (2013.01); *A61B 17/0644* (2013.01);
(Continued)

(58) Field of Classification Search
CPC ..... A61B 17/08; A61B 17/105; A61B 17/068; A61B 17/072; A61B 17/07292;
(Continued)

(56) References Cited

U.S. PATENT DOCUMENTS 66,052 A 6/1867 Smith
662,587 A 11/1900 Blake
(Continued)

FOREIGN PATENT DOCUMENTS

AU 2008207624 A1 3/2009
AU 2010214687 A1 9/2010
(Continued)

OTHER PUBLICATIONS

Disclosed Anonymously, "Motor-Driven Surgical Stapler Improvements," Research Disclosure Database No. 526041, Published: Feb. 2008.
(Continued)

*Primary Examiner* — Robert F Long

(57) ABSTRACT

A compressible adjunct is used with a surgical instrument including a staple cartridge deck. The compressible adjunct includes a first biocompatible material, a second biocompatible material with a lower melting temperature than the first biocompatible material, and a body including a face positionable against a length of the staple cartridge deck. The face includes a plurality of attachment regions spaced apart from one another, wherein the plurality of attachment regions include the second biocompatible material, wherein the face is selectively attachable to the staple cartridge deck at said plurality of attachment regions, and a plurality of non-attachment regions extending between the plurality of attachment regions, wherein the second biocompatible material is selectively disposed outside said non-attachment regions.

19 Claims, 98 Drawing Sheets

(51) Int. Cl.
  *A61B 17/068* (2006.01)
  *A61B 17/10* (2006.01)
  *A61B 17/00* (2006.01)

(52) U.S. Cl.
  CPC ...... *A61B 17/07292* (2013.01); *A61B 17/105* (2013.01); *A61B 2017/00477* (2013.01); *A61B 2017/00526* (2013.01); *A61B 2017/00831* (2013.01); *A61B 2017/00955* (2013.01); *A61B 2017/00964* (2013.01); *A61B 2017/0725* (2013.01); *A61B 2017/07221* (2013.01); *A61B 2017/07235* (2013.01); *A61B 2017/07242* (2013.01); *A61B 2017/07257* (2013.01); *A61B 2017/07271* (2013.01); *A61B 2017/07278* (2013.01); *A61B 2017/07285* (2013.01)

(58) Field of Classification Search
  CPC ........... A61B 2017/07235; A61B 2017/07271; A61B 17/064; A61B 17/07207; A61B 17/0644; A61B 2017/07242; A61B 2017/07257; A61B 2017/07278; A61B 2017/00477; A61B 2017/00955; A61B 2017/00526; A61B 2017/00831; A61B 2017/00964; A61B 2017/07285; A61B 2017/0725; A61B 2017/07221
  USPC ............ 227/175.1–182.1; 606/216, 219–221
  See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Lee |
| 2,441,096 A | 5/1948 | Happe |
| 2,448,741 A | 9/1948 | Scott et al. |
| 2,450,527 A | 10/1948 | Smith |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,981,051 A | 9/1976 | Brumlik |
| 4,025,216 A | 5/1977 | Hives |
| 4,027,746 A | 6/1977 | Kine |
| 4,034,143 A | 7/1977 | Sweet |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |

(56) References Cited

U.S. PATENT DOCUMENTS

| | | |
|---|---|---|
| 4,106,446 A | 8/1978 | Yamada et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A * | 10/1981 | Campbell ............ A47L 23/266  428/314.8 |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,461,305 A | 7/1984 | Cibley |
| 4,467,805 A | 8/1984 | Fukuda |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,914 A | 10/1986 | Ueda |
| 4,619,262 A | 10/1986 | Taylor |
| 4,619,391 A | 10/1986 | Sharkany et al. |
| D287,278 S | 12/1986 | Spreckelmeier |

(56) References Cited

U.S. PATENT DOCUMENTS

| | | | |
|---|---|---|---|
| 4,628,459 | A | 12/1986 | Shinohara et al. |
| 4,629,107 | A | 12/1986 | Fedotov et al. |
| 4,632,290 | A | 12/1986 | Green et al. |
| 4,633,861 | A | 1/1987 | Chow et al. |
| 4,633,874 | A | 1/1987 | Chow et al. |
| 4,634,419 | A | 1/1987 | Kreizman et al. |
| 4,635,638 | A | 1/1987 | Weintraub et al. |
| 4,641,076 | A | 2/1987 | Linden |
| 4,642,618 | A | 2/1987 | Johnson et al. |
| 4,643,173 | A | 2/1987 | Bell et al. |
| 4,643,731 | A | 2/1987 | Eckenhoff |
| 4,646,722 | A | 3/1987 | Silverstein et al. |
| 4,646,745 | A | 3/1987 | Noiles |
| 4,652,820 | A | 3/1987 | Maresca |
| 4,654,028 | A | 3/1987 | Suma |
| 4,655,222 | A | 4/1987 | Florez et al. |
| 4,662,555 | A | 5/1987 | Thornton |
| 4,663,874 | A | 5/1987 | Sano et al. |
| 4,664,305 | A | 5/1987 | Blake, III et al. |
| 4,665,916 | A | 5/1987 | Green |
| 4,667,674 | A | 5/1987 | Korthoff et al. |
| 4,669,647 | A | 6/1987 | Storace |
| 4,671,278 | A | 6/1987 | Chin |
| 4,671,280 | A | 6/1987 | Dorband et al. |
| 4,671,445 | A | 6/1987 | Barker et al. |
| 4,672,964 | A | 6/1987 | Dee et al. |
| 4,675,944 | A | 6/1987 | Wells |
| 4,676,245 | A | 6/1987 | Fukuda |
| 4,679,460 | A | 7/1987 | Yoshigai |
| 4,679,719 | A | 7/1987 | Kramer |
| 4,684,051 | A | 8/1987 | Akopov et al. |
| 4,688,555 | A | 8/1987 | Wardle |
| 4,691,703 | A | 9/1987 | Auth et al. |
| 4,693,248 | A | 9/1987 | Failla |
| 4,698,579 | A | 10/1987 | Richter et al. |
| 4,700,703 | A | 10/1987 | Resnick et al. |
| 4,705,038 | A | 11/1987 | Sjostrom et al. |
| 4,708,141 | A | 11/1987 | Inoue et al. |
| 4,709,120 | A | 11/1987 | Pearson |
| 4,715,520 | A | 12/1987 | Roehr, Jr. et al. |
| 4,719,917 | A | 1/1988 | Barrows et al. |
| 4,721,099 | A | 1/1988 | Chikama |
| 4,724,840 | A | 2/1988 | McVay et al. |
| 4,727,308 | A | 2/1988 | Huljak et al. |
| 4,728,020 | A | 3/1988 | Green et al. |
| 4,728,876 | A | 3/1988 | Mongeon et al. |
| 4,729,260 | A | 3/1988 | Dudden |
| 4,730,726 | A | 3/1988 | Holzwarth |
| 4,741,336 | A | 5/1988 | Failla et al. |
| 4,743,214 | A | 5/1988 | Tai-Cheng |
| 4,744,363 | A | 5/1988 | Hasson |
| 4,747,820 | A | 5/1988 | Hornlein et al. |
| 4,750,902 | A | 6/1988 | Wuchinich et al. |
| 4,752,024 | A | 6/1988 | Green et al. |
| 4,754,909 | A | 7/1988 | Barker et al. |
| 4,761,326 | A | 8/1988 | Barnes et al. |
| 4,763,669 | A | 8/1988 | Jaeger |
| 4,767,044 | A | 8/1988 | Green |
| D297,764 | S | 9/1988 | Hunt et al. |
| 4,773,420 | A | 9/1988 | Green |
| 4,777,780 | A | 10/1988 | Holzwarth |
| 4,781,186 | A | 11/1988 | Simpson et al. |
| 4,784,137 | A | 11/1988 | Kulik et al. |
| 4,787,387 | A | 11/1988 | Burbank, III et al. |
| D298,967 | S | 12/1988 | Hunt |
| 4,790,225 | A | 12/1988 | Moody et al. |
| 4,790,314 | A | 12/1988 | Weaver |
| 4,805,617 | A | 2/1989 | Bedi et al. |
| 4,805,823 | A | 2/1989 | Rothfuss |
| 4,807,628 | A | 2/1989 | Peters et al. |
| 4,809,695 | A | 3/1989 | Gwathmey et al. |
| 4,815,460 | A | 3/1989 | Porat et al. |
| 4,817,643 | A | 4/1989 | Olson |
| 4,817,847 | A | 4/1989 | Redtenbacher et al. |
| 4,819,853 | A | 4/1989 | Green |
| 4,821,939 | A | 4/1989 | Green |
| 4,827,911 | A | 5/1989 | Broadwin et al. |
| 4,828,542 | A | 5/1989 | Hermann |
| 4,828,944 | A | 5/1989 | Yabe et al. |
| 4,830,855 | A | 5/1989 | Stewart |
| 4,832,158 | A | 5/1989 | Farrar et al. |
| 4,833,937 | A | 5/1989 | Nagano |
| 4,834,720 | A | 5/1989 | Blinkhorn |
| 4,838,859 | A | 6/1989 | Strassmann |
| 4,844,068 | A | 7/1989 | Arata et al. |
| 4,848,637 | A | 7/1989 | Pruitt |
| 4,856,078 | A | 8/1989 | Konopka |
| 4,860,644 | A | 8/1989 | Kohl et al. |
| 4,862,891 | A | 9/1989 | Smith |
| 4,863,423 | A | 9/1989 | Wallace |
| 4,865,030 | A | 9/1989 | Polyak |
| 4,868,530 | A | 9/1989 | Ahs |
| 4,869,414 | A | 9/1989 | Green et al. |
| 4,869,415 | A | 9/1989 | Fox |
| 4,873,977 | A | 10/1989 | Avant et al. |
| 4,875,486 | A | 10/1989 | Rapoport et al. |
| 4,880,015 | A | 11/1989 | Nierman |
| 4,890,613 | A | 1/1990 | Golden et al. |
| 4,892,244 | A | 1/1990 | Fox et al. |
| 4,893,622 | A | 1/1990 | Green et al. |
| 4,894,051 | A | 1/1990 | Shiber |
| 4,896,584 | A | 1/1990 | Stoll et al. |
| 4,896,678 | A | 1/1990 | Ogawa |
| 4,900,303 | A | 2/1990 | Lemelson |
| 4,903,697 | A | 2/1990 | Resnick et al. |
| 4,909,789 | A | 3/1990 | Taguchi et al. |
| 4,915,100 | A | 4/1990 | Green |
| 4,919,679 | A | 4/1990 | Averill et al. |
| 4,921,479 | A | 5/1990 | Grayzel |
| 4,925,082 | A | 5/1990 | Kim |
| 4,928,699 | A | 5/1990 | Sasai |
| 4,930,503 | A | 6/1990 | Pruitt |
| 4,930,674 | A * | 6/1990 | Barak ............... A61B 17/072 227/179.1 |
| 4,931,047 | A | 6/1990 | Broadwin et al. |
| 4,931,737 | A | 6/1990 | Hishiki |
| 4,932,960 | A | 6/1990 | Green et al. |
| 4,933,800 | A | 6/1990 | Yang |
| 4,933,843 | A | 6/1990 | Scheller et al. |
| D309,350 | S | 7/1990 | Sutherland et al. |
| 4,938,408 | A | 7/1990 | Bedi et al. |
| 4,941,623 | A | 7/1990 | Pruitt |
| 4,943,182 | A | 7/1990 | Hoblingre |
| 4,944,443 | A | 7/1990 | Oddsen et al. |
| 4,946,067 | A | 8/1990 | Kelsall |
| 4,948,327 | A | 8/1990 | Crupi, Jr. |
| 4,949,707 | A | 8/1990 | LeVahn et al. |
| 4,951,860 | A | 8/1990 | Peters et al. |
| 4,951,861 | A | 8/1990 | Schulze et al. |
| 4,955,959 | A | 9/1990 | Tompkins et al. |
| 4,957,212 | A | 9/1990 | Duck et al. |
| 4,962,877 | A | 10/1990 | Hervas |
| 4,964,559 | A | 10/1990 | Deniega et al. |
| 4,964,863 | A | 10/1990 | Kanshin et al. |
| 4,965,709 | A | 10/1990 | Ngo |
| 4,973,274 | A | 11/1990 | Hirukawa |
| 4,973,302 | A | 11/1990 | Armour et al. |
| 4,978,049 | A | 12/1990 | Green |
| 4,978,333 | A | 12/1990 | Broadwin et al. |
| 4,979,952 | A | 12/1990 | Kubota et al. |
| 4,984,564 | A | 1/1991 | Yuen |
| 4,986,808 | A | 1/1991 | Broadwin et al. |
| 4,987,049 | A | 1/1991 | Komamura et al. |
| 4,988,334 | A | 1/1991 | Hornlein et al. |
| 4,995,877 | A | 2/1991 | Ams et al. |
| 4,995,959 | A | 2/1991 | Metzner |
| 4,996,975 | A | 3/1991 | Nakamura |
| 5,002,543 | A | 3/1991 | Bradshaw et al. |
| 5,002,553 | A | 3/1991 | Shiber |
| 5,005,754 | A | 4/1991 | Van Overloop |
| 5,009,661 | A | 4/1991 | Michelson |
| 5,012,411 | A | 4/1991 | Policastro et al. |
| 5,014,898 | A | 5/1991 | Heidrich |
| 5,014,899 | A | 5/1991 | Presty et al. |

(56) References Cited

U.S. PATENT DOCUMENTS

| | | |
|---|---|---|
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,877 A | 11/1993 | Fine et al. |
| 5,261,922 A | 11/1993 | Hood |
| 5,263,629 A * | 11/1993 | Trumbull ......... A61B 17/07207 128/898 |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |
| 5,293,024 A | 3/1994 | Sugahara et al. |
| 5,297,714 A | 3/1994 | Kramer |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |

(56) References Cited

U.S. PATENT DOCUMENTS

| | | |
|---|---|---|
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |

(56) References Cited

U.S. PATENT DOCUMENTS

| | | |
|---|---|---|
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A * | 4/1996 | Cooper ............ A61B 17/07207 606/148 |
| 5,505,363 A | 4/1996 | Green et al. |
| 5,507,425 A | 4/1996 | Ziglioli |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |

(56) References Cited

U.S. PATENT DOCUMENTS

| | | |
|---|---|---|
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A * | 8/1997 | Strecker .............. A61F 2/04 623/1.11 |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A * | 12/1997 | Rayburn .......... A61B 17/07207 227/176.1 |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |

(56) References Cited

U.S. PATENT DOCUMENTS

| | | |
|---|---|---|
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A * | 6/1998 | Igaki ............... A61B 17/07207 606/139 |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |

(56) References Cited

U.S. PATENT DOCUMENTS

| | | |
|---|---|---|
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |

(56) References Cited

U.S. PATENT DOCUMENTS

| | | | |
|---|---|---|---|
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,142,149 A | 11/2000 | Steen |
| 6,142,933 A | 11/2000 | Longo et al. |
| 6,147,135 A * | 11/2000 | Yuan ................ A61F 2/30965 523/105 |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,904 B1 | 3/2001 | Ouchi |
| 6,209,414 B1 | 4/2001 | Uneme |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 * | 12/2001 | Hamilton .......... A61B 17/07207 227/175.1 |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |

(56) References Cited

U.S. PATENT DOCUMENTS

| | | |
|---|---|---|
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,885 B1 | 12/2002 | Dhindsa |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,527,782 B2 | 3/2003 | Hogg et al. |
| 6,527,785 B2 | 3/2003 | Sancoff et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| 6,539,816 B2 | 4/2003 | Kogiso et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |

(56) References Cited

U.S. PATENT DOCUMENTS

| | | |
|---|---|---|
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |

(56) References Cited

U.S. PATENT DOCUMENTS

| | | |
|---|---|---|
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,687 B1 | 5/2006 | Reuss et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |

(56) References Cited

U.S. PATENT DOCUMENTS

| | | |
|---|---|---|
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,412 B2 | 8/2006 | Wang et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |

(56) References Cited

U.S. PATENT DOCUMENTS

| | | |
|---|---|---|
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,377,918 B2 | 5/2008 | Amoah |
| 7,377,928 B2 | 5/2008 | Zubik et al. |
| RE40,388 E | 6/2008 | Gines |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |

(56) References Cited

U.S. PATENT DOCUMENTS

| | | |
|---|---|---|
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |

(56) References Cited

U.S. PATENT DOCUMENTS

| | | |
|---|---|---|
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,712,182 B2 | 5/2010 | Zeiler et al. |
| 7,713,190 B2 | 5/2010 | Brock et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,612 B2 | 7/2010 | Shipp |
| 7,762,462 B2 | 7/2010 | Gelbman |
| 7,762,998 B2 | 7/2010 | Birk et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |

(56) References Cited

U.S. PATENT DOCUMENTS

| | | |
|---|---|---|
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |

(56) References Cited

U.S. PATENT DOCUMENTS

| | | |
|---|---|---|
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |

(56) References Cited

U.S. PATENT DOCUMENTS

| | | | |
|---|---|---|---|
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 * | 7/2012 | Tarinelli ............ A61B 17/07207 227/175.1 |
| 8,235,272 B2 | 8/2012 | Nicholas et al. |
| 8,236,010 B2 | 8/2012 | Ortiz et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,262,560 B2 | 9/2012 | Whitman |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,287,487 B2 | 10/2012 | Estes |
| 8,287,522 B2 | 10/2012 | Moses et al. |
| 8,287,561 B2 | 10/2012 | Nunez et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,801 B2 | 10/2012 | Dejima et al. |
| 8,292,888 B2 | 10/2012 | Whitman |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |

(56) References Cited

U.S. PATENT DOCUMENTS

| | | |
|---|---|---|
| 8,308,725 B2 | 11/2012 | Bell et al. |
| 8,310,188 B2 | 11/2012 | Nakai |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,343,150 B2 | 1/2013 | Artale |
| 8,347,978 B2 | 1/2013 | Forster et al. |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,161 B2 | 1/2013 | Mueller |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,787 B2 | 2/2013 | Brown et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,382,773 B2 | 2/2013 | Whitfield et al. |
| 8,382,790 B2 | 2/2013 | Uenohara et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,851 B2 | 3/2013 | Byun |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 * | 6/2013 | Hull ............. A61B 17/00491 227/179.1 |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,946 B2 | 6/2013 | Sugita |

(56) References Cited

U.S. PATENT DOCUMENTS

| | | |
|---|---|---|
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 * | 7/2013 | Hodgkinson .... A61B 17/07292 227/175.1 |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,490,851 B2 | 7/2013 | Blier et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,518,024 B2 | 8/2013 | Williams et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |

(56) References Cited

U.S. PATENT DOCUMENTS

| | | |
|---|---|---|
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,795,324 B2 | 8/2014 | Kawai et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,219 B2 | 9/2014 | Pierce |
| 8,833,630 B2 | 9/2014 | Milliman |
| 8,833,632 B2 | 9/2014 | Swensgard |
| 8,834,498 B2 | 9/2014 | Byrum et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,851,215 B2 | 10/2014 | Goto |
| 8,851,354 B2 | 10/2014 | Swensgard et al. |
| 8,852,174 B2 | 10/2014 | Burbank |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |

(56) References Cited

U.S. PATENT DOCUMENTS

| | | |
|---|---|---|
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,986,302 B2 | 3/2015 | Aldridge et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |

(56) References Cited

U.S. PATENT DOCUMENTS

| | | |
|---|---|---|
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| D750,122 S | 2/2016 | Shardlow et al. |
| 9,254,131 B2 | 2/2016 | Soltz et al. |
| 9,259,274 B2 | 2/2016 | Prisco |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |

(56) References Cited

U.S. PATENT DOCUMENTS

| | | |
|---|---|---|
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,784 B2 | 3/2016 | Eggert et al. |
| 9,301,691 B2 | 4/2016 | Hufnagel et al. |
| 9,301,752 B2 * | 4/2016 | Mandakolathur Vasudevan ......... A61B 17/00491 |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,339,226 B2 | 5/2016 | van der Walt et al. |
| 9,345,477 B2 | 5/2016 | Anim et al. |
| 9,345,480 B2 | 5/2016 | Hessler et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| D758,433 S | 6/2016 | Lee et al. |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,255 B2 | 6/2016 | Houser et al. |
| 9,381,058 B2 | 7/2016 | Houser et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,398,911 B2 | 7/2016 | Auld |
| 9,402,604 B2 | 8/2016 | Williams et al. |
| 9,402,626 B2 | 8/2016 | Ortiz et al. |
| 9,402,627 B2 | 8/2016 | Stevenson et al. |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,427,223 B2 | 8/2016 | Park et al. |
| 9,427,231 B2 | 8/2016 | Racenet et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,451,958 B2 | 9/2016 | Shelton, IV et al. |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,504,521 B2 | 11/2016 | Deutmeyer et al. |
| D775,336 S | 12/2016 | Shelton, IV et al. |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,564 B2 | 12/2016 | Rusin |
| D777,773 S | 1/2017 | Shi |
| 9,532,783 B2 | 1/2017 | Swayze et al. |
| 9,539,726 B2 | 1/2017 | Simaan et al. |
| 9,545,258 B2 | 1/2017 | Smith et al. |
| 9,549,732 B2 | 1/2017 | Yates et al. |

(56) References Cited

U.S. PATENT DOCUMENTS

| | | | |
|---|---|---|---|
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,062 B2 | 2/2017 | Boudreaux |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| D781,879 S | 3/2017 | Butcher et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| D788,140 S | 5/2017 | Hemsley et al. |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 * | 7/2017 | Schellin ............ B29C 55/00 |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,026 B2 | 7/2017 | Malackowski et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D800,904 S | 10/2017 | Leimbach et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,635 B2 | 10/2017 | Takei |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,214 B2 | 10/2017 | Houser et al. |

(56) References Cited

U.S. PATENT DOCUMENTS

| | | |
|---|---|---|
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,795,379 B2 | 10/2017 | Leimbach et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,561 B2 | 11/2017 | Forsell |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 * | 12/2017 | Harris ............. A61B 17/0686 |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,877,723 B2 | 1/2018 | Hall et al. |
| 9,883,843 B2 | 2/2018 | Garlow |
| 9,883,860 B2 | 2/2018 | Leimbach et al. |
| 9,883,861 B2 | 2/2018 | Shelton, IV et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,907,456 B2 | 3/2018 | Miyoshi |
| 9,907,553 B2 | 3/2018 | Cole et al. |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,918,704 B2 | 3/2018 | Shelton, IV et al. |
| 9,918,715 B2 | 3/2018 | Menn |
| 9,918,716 B2 | 3/2018 | Baxter, III et al. |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,955,965 B2 | 5/2018 | Chen et al. |
| 9,955,966 B2 | 5/2018 | Zergiebel |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,095 B2 | 6/2018 | Chowaniec et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,426 B2 | 6/2018 | Moore et al. |
| 9,999,431 B2 | 6/2018 | Shelton, IV et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,022,125 B2 | 7/2018 | (Prommersberger) Stopek et al. |
| 10,024,407 B2 | 7/2018 | Aranyi et al. |

(56) References Cited

U.S. PATENT DOCUMENTS

| | | |
|---|---|---|
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,125 B2 | 7/2018 | Shapiro et al. |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| D831,209 S | 10/2018 | Huitema et al. |
| 10,085,624 B2 | 10/2018 | Isoda et al. |
| 10,085,728 B2 | 10/2018 | Jogasaki et al. |
| 10,085,748 B2 | 10/2018 | Morgan et al. |
| 10,085,751 B2 | 10/2018 | Overmyer et al. |
| 10,085,806 B2 | 10/2018 | Hagn et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,642 B2 | 10/2018 | Baxter, III et al. |
| 10,099,303 B2 | 10/2018 | Yoshida et al. |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,111,679 B2 | 10/2018 | Baber et al. |
| 10,111,702 B2 | 10/2018 | Kostrzewski |
| 10,117,649 B2 | 11/2018 | Baxter, III et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,154,841 B2 | 12/2018 | Weaner et al. |
| 10,159,482 B2 | 12/2018 | Swayze et al. |
| 10,159,483 B2 | 12/2018 | Beckman et al. |
| 10,163,589 B2 | 12/2018 | Zergiebel et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,616 B2 | 1/2019 | Murray et al. |
| 10,172,617 B2 | 1/2019 | Shelton, IV et al. |
| 10,172,620 B2 * | 1/2019 | Harris .................. A61B 17/068 |
| 10,172,636 B2 | 1/2019 | Stulen et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,188,385 B2 | 1/2019 | Kerr et al. |
| 10,188,393 B2 | 1/2019 | Smith et al. |
| 10,188,394 B2 | 1/2019 | Shelton, IV et al. |
| 10,194,904 B2 | 2/2019 | Viola et al. |
| 10,194,910 B2 | 2/2019 | Shelton, IV et al. |
| 10,194,913 B2 | 2/2019 | Nalagatla et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,211,586 B2 | 2/2019 | Adams et al. |
| 10,213,201 B2 | 2/2019 | Shelton, IV et al. |
| 10,213,203 B2 | 2/2019 | Swayze et al. |
| 10,213,262 B2 | 2/2019 | Shelton, IV et al. |
| 10,219,832 B2 | 3/2019 | Bagwell et al. |
| 10,226,249 B2 | 3/2019 | Jaworek et al. |
| 10,226,250 B2 | 3/2019 | Beckman et al. |
| 10,231,634 B2 | 3/2019 | Zand et al. |
| 10,231,653 B2 | 3/2019 | Bohm et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,285,699 B2 * | 5/2019 | Vendely .............. A61B 17/068 |
| 10,307,160 B2 * | 6/2019 | Vendely .............. A61B 17/072 |
| 10,238,391 B2 | 7/2019 | Leimbach et al. |
| 2001/0000531 A1 | 4/2001 | Casscells et al. |
| 2001/0025183 A1 | 9/2001 | Shahidi |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0158593 A1 | 10/2002 | Henderson et al. |
| 2002/0165562 A1 * | 11/2002 | Grant .................... A61B 17/072 606/151 |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0023316 A1 * | 1/2003 | Brown .................. A61F 2/0063 623/23.72 |

(56) References Cited

U.S. PATENT DOCUMENTS

| | | |
|---|---|---|
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0085180 A1 | 5/2004 | Juang |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122423 A1 | 6/2004 | Dycus et al. |
| 2004/0133095 A1 | 7/2004 | Dunki-Jacobs et al. |
| 2004/0138762 A1* | 7/2004 | Therin ............... A61F 2/0063 623/23.75 |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079879 A1 | 4/2006 | Faller et al. |
| 2006/0086032 A1 | 4/2006 | Valencic et al. |

(56) References Cited

U.S. PATENT DOCUMENTS

| | | |
|---|---|---|
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0100649 A1 | 5/2006 | Hart |
| 2006/0111210 A1 | 5/2006 | Hinman |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0176031 A1 | 8/2006 | Forman et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0235368 A1 | 10/2006 | Oz |
| 2006/0244460 A1 | 11/2006 | Weaver |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0027553 A1 * | 2/2007 | Biran .................. A61L 31/146 623/23.74 |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0262592 A1 | 11/2007 | Hwang et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0042861 A1 | 2/2008 | Dacquay et al. |
| 2008/0051833 A1 | 2/2008 | Gramuglia et al. |
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0183193 A1 | 7/2008 | Omori et al. |
| 2008/0190989 A1 | 8/2008 | Crews et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0234709 A1 | 9/2008 | Houser |
| 2008/0242939 A1 | 10/2008 | Johnston |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0287944 A1 | 11/2008 | Pearson et al. |
| 2008/0293910 A1 | 11/2008 | Kapiamba et al. |

(56) References Cited

U.S. PATENT DOCUMENTS

| | | |
|---|---|---|
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0092651 A1 | 4/2009 | Shah et al. |
| 2009/0099579 A1 | 4/2009 | Nentwick et al. |
| 2009/0099876 A1 | 4/2009 | Whitman |
| 2009/0119011 A1 | 5/2009 | Kondo et al. |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0221993 A1 | 9/2009 | Sohi et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0248041 A1 | 10/2009 | Williams et al. |
| 2009/0253959 A1 | 10/2009 | Yoshie et al. |
| 2009/0255974 A1 | 10/2009 | Viola |
| 2009/0262078 A1 | 10/2009 | Pizzi |
| 2009/0270895 A1 | 10/2009 | Churchill et al. |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2010/0012703 A1 | 1/2010 | Calabrese et al. |
| 2010/0016888 A1 | 1/2010 | Calabrese et al. |
| 2010/0023024 A1 | 1/2010 | Zeiner et al. |
| 2010/0030233 A1 | 2/2010 | Whitman et al. |
| 2010/0036370 A1 | 2/2010 | Mirel et al. |
| 2010/0065604 A1 | 3/2010 | Weng |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0204717 A1 | 8/2010 | Knodel |
| 2010/0222901 A1 | 9/2010 | Swayze et al. |
| 2010/0241137 A1 | 9/2010 | Doyle et al. |
| 2010/0249497 A1 | 9/2010 | Peine et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0034910 A1 | 2/2011 | Ross et al. |
| 2011/0036891 A1 | 2/2011 | Zemlok et al. |
| 2011/0046667 A1 | 2/2011 | Culligan et al. |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0095064 A1 | 4/2011 | Taylor et al. |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0121049 A1 | 5/2011 | Malinouskas et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0230713 A1 | 9/2011 | Kleemann et al. |
| 2011/0238044 A1 | 9/2011 | Main et al. |
| 2011/0241597 A1 | 10/2011 | Zhu et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078139 A1 | 3/2012 | Aldridge et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |

(56) References Cited

U.S. PATENT DOCUMENTS

| | | |
|---|---|---|
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0118595 A1 | 5/2012 | Pellenc |
| 2012/0123203 A1 | 5/2012 | Riva |
| 2012/0125792 A1 | 5/2012 | Cassivi |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0197272 A1 | 8/2012 | Oray et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0241493 A1* | 9/2012 | Baxter, III ........ A61B 17/07292 227/175.1 |
| 2012/0241499 A1* | 9/2012 | Baxter, III ........ A61B 17/07207 227/176.1 |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0303002 A1 | 11/2012 | Chowaniec et al. |
| 2013/0006227 A1 | 1/2013 | Takashino |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0105548 A1* | 5/2013 | Hodgkinson ........ A61B 17/072 227/176.1 |
| 2013/0105552 A1 | 5/2013 | Weir et al. |
| 2013/0112731 A1* | 5/2013 | Hodgkinson ...... A61B 17/0682 227/176.1 |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0146643 A1* | 6/2013 | Schmid .............. A61B 17/0682 227/180.1 |
| 2013/0153636 A1 | 6/2013 | Shelton, IV et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0172878 A1 | 7/2013 | Smith |
| 2013/0175317 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0209659 A1* | 8/2013 | Racenet ............... A61L 31/145 427/2.1 |
| 2013/0214025 A1 | 8/2013 | Zemlok et al. |
| 2013/0214030 A1* | 8/2013 | Aronhalt ........... A61B 17/0682 227/176.1 |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0270322 A1 | 10/2013 | Scheib et al. |
| 2013/0277410 A1 | 10/2013 | Fernandez et al. |
| 2013/0317753 A1 | 11/2013 | Kamen et al. |
| 2013/0324982 A1 | 12/2013 | Smith et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012289 A1 | 1/2014 | Snow et al. |
| 2014/0012299 A1 | 1/2014 | Stoddard et al. |
| 2014/0014705 A1 | 1/2014 | Baxter, III |
| 2014/0018832 A1 | 1/2014 | Shelton, IV |
| 2014/0039549 A1 | 2/2014 | Belsky et al. |
| 2014/0048580 A1* | 2/2014 | Merchant ............ A61B 17/064 227/176.1 |
| 2014/0081176 A1 | 3/2014 | Hassan |
| 2014/0100558 A1 | 4/2014 | Schmitz et al. |
| 2014/0107640 A1 | 4/2014 | Yates et al. |
| 2014/0110456 A1 | 4/2014 | Taylor |
| 2014/0115229 A1 | 4/2014 | Kothamasu et al. |
| 2014/0131418 A1 | 5/2014 | Kostrzewski |
| 2014/0151433 A1 | 6/2014 | Shelton, IV et al. |
| 2014/0158747 A1 | 6/2014 | Measamer et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0188159 A1 | 7/2014 | Steege |
| 2014/0200561 A1 | 7/2014 | Ingmanson et al. |
| 2014/0203061 A1* | 7/2014 | Hodgkinson ..... A61B 17/07207 227/175.1 |
| 2014/0207124 A1 | 7/2014 | Aldridge et al. |
| 2014/0207125 A1 | 7/2014 | Applegate et al. |
| 2014/0224857 A1 | 8/2014 | Schmid |
| 2014/0228867 A1 | 8/2014 | Thomas et al. |
| 2014/0230595 A1 | 8/2014 | Butt et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0309666 A1 | 10/2014 | Shelton, IV et al. |
| 2014/0316443 A1 | 10/2014 | Fanton et al. |
| 2014/0330161 A1 | 11/2014 | Swayze et al. |
| 2014/0367445 A1 | 12/2014 | Ingmanson et al. |
| 2014/0374130 A1 | 12/2014 | Nakamura et al. |

(56) References Cited

U.S. PATENT DOCUMENTS

| | | |
|---|---|---|
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0108199 A1 | 4/2015 | Shelton, IV et al. |
| 2015/0122870 A1 | 5/2015 | Zemlok et al. |
| 2015/0133995 A1* | 5/2015 | Shelton, IV ......... A61B 17/064 606/219 |
| 2015/0134077 A1 | 5/2015 | Shelton, IV et al. |
| 2015/0148830 A1 | 5/2015 | Stulen et al. |
| 2015/0150554 A1 | 6/2015 | Soltz |
| 2015/0150620 A1 | 6/2015 | Miyamoto et al. |
| 2015/0173744 A1 | 6/2015 | Shelton, IV et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0182220 A1 | 7/2015 | Yates et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196348 A1 | 7/2015 | Yates et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0222212 A1 | 8/2015 | Iwata |
| 2015/0231409 A1 | 8/2015 | Racenet et al. |
| 2015/0238118 A1 | 8/2015 | Legassey et al. |
| 2015/0238185 A1* | 8/2015 | Schellin ............ A61B 17/07207 227/175.1 |
| 2015/0238186 A1* | 8/2015 | Aronhalt ................. B29C 55/00 227/175.2 |
| 2015/0238188 A1* | 8/2015 | Vendely ............ A61B 17/07207 227/175.1 |
| 2015/0239180 A1* | 8/2015 | Schellin .................. B29C 43/00 264/28 |
| 2015/0245835 A1 | 9/2015 | Racenet et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272604 A1 | 10/2015 | Chowaniec et al. |
| 2015/0282810 A1 | 10/2015 | Shelton, IV et al. |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1* | 10/2015 | Harris ................ A61B 17/0644 227/176.1 |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0327864 A1 | 11/2015 | Hodgkinson et al. |
| 2015/0336249 A1 | 11/2015 | Iwata et al. |
| 2015/0342607 A1 | 12/2015 | Shelton, IV et al. |
| 2015/0351762 A1 | 12/2015 | Vendely et al. |
| 2015/0351765 A1 | 12/2015 | Valentine et al. |
| 2015/0352699 A1 | 12/2015 | Sakai et al. |
| 2015/0366220 A1 | 12/2015 | Zhang et al. |
| 2015/0372265 A1 | 12/2015 | Morisaku et al. |
| 2015/0374360 A1 | 12/2015 | Scheib et al. |
| 2015/0374361 A1 | 12/2015 | Gettinger et al. |
| 2015/0374363 A1 | 12/2015 | Laurent, IV et al. |
| 2015/0374368 A1 | 12/2015 | Swayze et al. |
| 2015/0374369 A1 | 12/2015 | Yates et al. |
| 2015/0374371 A1 | 12/2015 | Richard et al. |
| 2015/0374372 A1 | 12/2015 | Zergiebel et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0015391 A1 | 1/2016 | Shelton, IV et al. |
| 2016/0023342 A1 | 1/2016 | Koenig et al. |
| 2016/0030042 A1 | 2/2016 | Heinrich et al. |
| 2016/0051257 A1 | 2/2016 | Shelton, IV et al. |
| 2016/0058443 A1 | 3/2016 | Yates et al. |
| 2016/0066913 A1 | 3/2016 | Swayze et al. |
| 2016/0069449 A1 | 3/2016 | Kanai et al. |
| 2016/0074040 A1 | 3/2016 | Widenhouse et al. |
| 2016/0074103 A1 | 3/2016 | Sartor |
| 2016/0082161 A1 | 3/2016 | Zilberman et al. |
| 2016/0089137 A1 | 3/2016 | Hess et al. |
| 2016/0089142 A1 | 3/2016 | Harris et al. |
| 2016/0089146 A1 | 3/2016 | Harris et al. |
| 2016/0089149 A1 | 3/2016 | Harris et al. |
| 2016/0089198 A1 | 3/2016 | Arya et al. |
| 2016/0095585 A1 | 4/2016 | Zergiebel et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0166248 A1 | 6/2016 | Deville et al. |
| 2016/0166256 A1 | 6/2016 | Baxter, III et al. |
| 2016/0166308 A1 | 6/2016 | Manwaring et al. |
| 2016/0174972 A1 | 6/2016 | Shelton, IV et al. |
| 2016/0174974 A1 | 6/2016 | Schmid et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192933 A1 | 7/2016 | Shelton, IV |
| 2016/0192977 A1 | 7/2016 | Manwaring et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206310 A1 | 7/2016 | Shelton, IV |

(56) References Cited

U.S. PATENT DOCUMENTS

| | | |
|---|---|---|
| 2016/0206314 A1 | 7/2016 | Scheib et al. |
| 2016/0220248 A1 | 8/2016 | Timm et al. |
| 2016/0220249 A1 | 8/2016 | Shelton, IV et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249916 A1 | 9/2016 | Shelton, IV et al. |
| 2016/0249922 A1 | 9/2016 | Morgan et al. |
| 2016/0256071 A1 | 9/2016 | Shelton, IV et al. |
| 2016/0256154 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256161 A1 | 9/2016 | Overmyer et al. |
| 2016/0256185 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0270780 A1 | 9/2016 | Hall et al. |
| 2016/0278765 A1* | 9/2016 | Shelton, IV ......... A61B 17/068 |
| 2016/0287249 A1 | 10/2016 | Alexander, III et al. |
| 2016/0287250 A1 | 10/2016 | Shelton, IV et al. |
| 2016/0287253 A1 | 10/2016 | Shelton, IV et al. |
| 2016/0287279 A1 | 10/2016 | Bovay et al. |
| 2016/0310143 A1* | 10/2016 | Bettuchi ............... A61B 17/115 |
| 2016/0331375 A1 | 11/2016 | Shelton, IV et al. |
| 2016/0345976 A1 | 12/2016 | Gonzalez et al. |
| 2016/0346034 A1 | 12/2016 | Arya et al. |
| 2016/0354085 A1 | 12/2016 | Shelton, IV et al. |
| 2016/0367122 A1 | 12/2016 | Ichimura et al. |
| 2016/0367246 A1 | 12/2016 | Baxter, III et al. |
| 2016/0367254 A1 | 12/2016 | Baxter, III et al. |
| 2016/0367255 A1 | 12/2016 | Wise et al. |
| 2016/0374672 A1 | 12/2016 | Bear et al. |
| 2016/0374675 A1 | 12/2016 | Shelton, IV et al. |
| 2017/0000485 A1 | 1/2017 | Shelton, IV et al. |
| 2017/0007236 A1 | 1/2017 | Shelton, IV et al. |
| 2017/0007237 A1 | 1/2017 | Yates et al. |
| 2017/0007238 A1 | 1/2017 | Yates et al. |
| 2017/0007239 A1 | 1/2017 | Shelton, IV |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007246 A1 | 1/2017 | Shelton, IV et al. |
| 2017/0007247 A1 | 1/2017 | Shelton, IV et al. |
| 2017/0007248 A1 | 1/2017 | Shelton, IV et al. |
| 2017/0007249 A1 | 1/2017 | Shelton, IV et al. |
| 2017/0007250 A1 | 1/2017 | Shelton, IV et al. |
| 2017/0007251 A1 | 1/2017 | Yates et al. |
| 2017/0007255 A1 | 1/2017 | Jaworek et al. |
| 2017/0007347 A1 | 1/2017 | Jaworek et al. |
| 2017/0014125 A1 | 1/2017 | Shelton, IV et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0049444 A1 | 2/2017 | Schellin et al. |
| 2017/0049447 A1 | 2/2017 | Barton et al. |
| 2017/0049448 A1 | 2/2017 | Widenhouse et al. |
| 2017/0055986 A1 | 3/2017 | Harris et al. |
| 2017/0055989 A1* | 3/2017 | Shelton, IV ......... A61B 17/072 |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056002 A1 | 3/2017 | Nalagatla et al. |
| 2017/0056005 A1 | 3/2017 | Shelton, IV et al. |
| 2017/0056006 A1 | 3/2017 | Shelton, IV et al. |
| 2017/0056007 A1 | 3/2017 | Eckert et al. |
| 2017/0079640 A1 | 3/2017 | Overmyer et al. |
| 2017/0079642 A1 | 3/2017 | Overmyer et al. |
| 2017/0079643 A1 | 3/2017 | Yates et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086832 A1 | 3/2017 | Harris et al. |
| 2017/0086835 A1 | 3/2017 | Harris et al. |
| 2017/0086836 A1 | 3/2017 | Harris et al. |
| 2017/0086837 A1 | 3/2017 | Vendely et al. |
| 2017/0086838 A1 | 3/2017 | Harris et al. |
| 2017/0086839 A1 | 3/2017 | Vendely et al. |
| 2017/0086841 A1 | 3/2017 | Vendely et al. |
| 2017/0086842 A1 | 3/2017 | Shelton, IV et al. |
| 2017/0086844 A1 | 3/2017 | Vendely et al. |
| 2017/0086845 A1 | 3/2017 | Vendely et al. |
| 2017/0086936 A1 | 3/2017 | Shelton, IV et al. |
| 2017/0095250 A1 | 4/2017 | Kostrzewski et al. |
| 2017/0119386 A1 | 5/2017 | Scheib et al. |
| 2017/0119387 A1 | 5/2017 | Dalessandro et al. |
| 2017/0119389 A1 | 5/2017 | Turner et al. |
| 2017/0119390 A1 | 5/2017 | Schellin et al. |
| 2017/0119392 A1 | 5/2017 | Shelton, IV et al. |
| 2017/0119397 A1 | 5/2017 | Harris et al. |
| 2017/0128149 A1 | 5/2017 | Heinrich et al. |
| 2017/0135695 A1 | 5/2017 | Shelton, IV et al. |
| 2017/0135697 A1 | 5/2017 | Mozdzierz et al. |
| 2017/0150983 A1 | 6/2017 | Ingmanson et al. |
| 2017/0172672 A1 | 6/2017 | Bailey et al. |
| 2017/0182211 A1 | 6/2017 | Raxworthy et al. |
| 2017/0189018 A1 | 7/2017 | Harris et al. |
| 2017/0189019 A1 | 7/2017 | Harris et al. |
| 2017/0189020 A1 | 7/2017 | Harris et al. |
| 2017/0196558 A1 | 7/2017 | Morgan et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196649 A1 | 7/2017 | Yates et al. |
| 2017/0202596 A1 | 7/2017 | Shelton, IV et al. |
| 2017/0209145 A1 | 7/2017 | Swayze et al. |
| 2017/0209146 A1 | 7/2017 | Yates et al. |
| 2017/0209226 A1 | 7/2017 | Overmyer et al. |
| 2017/0215881 A1 | 8/2017 | Shelton, IV et al. |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224333 A1 | 8/2017 | Hunter et al. |
| 2017/0224334 A1 | 8/2017 | Worthington et al. |
| 2017/0224335 A1 | 8/2017 | Weaner et al. |
| 2017/0224336 A1 | 8/2017 | Hunter et al. |
| 2017/0224339 A1 | 8/2017 | Huang et al. |
| 2017/0224342 A1 | 8/2017 | Worthington et al. |
| 2017/0224343 A1 | 8/2017 | Baxter, III et al. |
| 2017/0231623 A1 | 8/2017 | Shelton, IV et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |
| 2017/0249431 A1 | 8/2017 | Shelton, IV et al. |
| 2017/0258469 A1 | 9/2017 | Shelton, IV et al. |
| 2017/0265856 A1 | 9/2017 | Shelton, IV et al. |
| 2017/0281155 A1 | 10/2017 | Shelton, IV et al. |
| 2017/0281161 A1 | 10/2017 | Shelton, IV et al. |
| 2017/0281162 A1 | 10/2017 | Shelton, IV et al. |
| 2017/0281163 A1 | 10/2017 | Shelton, IV et al. |
| 2017/0281164 A1 | 10/2017 | Harris et al. |
| 2017/0281165 A1 | 10/2017 | Harris et al. |
| 2017/0281166 A1 | 10/2017 | Morgan et al. |

(56) References Cited

U.S. PATENT DOCUMENTS

| | | |
|---|---|---|
| 2017/0281167 A1 | 10/2017 | Shelton, IV et al. |
| 2017/0281168 A1 | 10/2017 | Shelton, IV et al. |
| 2017/0281169 A1 | 10/2017 | Harris et al. |
| 2017/0281170 A1 | 10/2017 | Shelton, IV et al. |
| 2017/0281171 A1 | 10/2017 | Shelton, IV et al. |
| 2017/0281172 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281177 A1 | 10/2017 | Harris et al. |
| 2017/0281178 A1 | 10/2017 | Shelton, IV et al. |
| 2017/0281179 A1 | 10/2017 | Shelton, IV et al. |
| 2017/0281180 A1 | 10/2017 | Morgan et al. |
| 2017/0281183 A1 | 10/2017 | Miller et al. |
| 2017/0281184 A1 | 10/2017 | Shelton, IV et al. |
| 2017/0281185 A1 | 10/2017 | Miller et al. |
| 2017/0281186 A1 | 10/2017 | Shelton, IV et al. |
| 2017/0281187 A1 | 10/2017 | Shelton, IV et al. |
| 2017/0281188 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296170 A1 | 10/2017 | Shelton, IV et al. |
| 2017/0296171 A1 | 10/2017 | Shelton, IV et al. |
| 2017/0296172 A1 | 10/2017 | Harris et al. |
| 2017/0296173 A1 | 10/2017 | Shelton, IV et al. |
| 2017/0296177 A1 | 10/2017 | Harris et al. |
| 2017/0296178 A1 | 10/2017 | Miller et al. |
| 2017/0296179 A1 | 10/2017 | Shelton, IV et al. |
| 2017/0296180 A1 | 10/2017 | Harris et al. |
| 2017/0296183 A1 | 10/2017 | Shelton, IV et al. |
| 2017/0296184 A1 | 10/2017 | Harris et al. |
| 2017/0296185 A1 | 10/2017 | Swensgard et al. |
| 2017/0296189 A1 | 10/2017 | Vendely et al. |
| 2017/0296190 A1 | 10/2017 | Aronhalt et al. |
| 2017/0296191 A1 | 10/2017 | Shelton, IV et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0311950 A1 | 11/2017 | Shelton, IV et al. |
| 2017/0312040 A1 | 11/2017 | Giordano et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0319777 A1 | 11/2017 | Shelton, IV et al. |
| 2017/0325813 A1 | 11/2017 | Aranyi et al. |
| 2017/0333033 A1 | 11/2017 | Valentine et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348043 A1 | 12/2017 | Wang et al. |
| 2017/0354415 A1 | 12/2017 | Casasanta, Jr. et al. |
| 2017/0360441 A1 | 12/2017 | Sgroi |
| 2017/0360442 A1 | 12/2017 | Shelton, IV et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367699 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008269 A1 | 1/2018 | Moore et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055510 A1 | 3/2018 | Schmid et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070939 A1 | 3/2018 | Giordano et al. |
| 2018/0070942 A1 | 3/2018 | Shelton, IV et al. |
| 2018/0070946 A1 | 3/2018 | Shelton, IV et al. |
| 2018/0078248 A1 | 3/2018 | Swayze et al. |
| 2018/0085116 A1 | 3/2018 | Yates et al. |
| 2018/0085117 A1 | 3/2018 | Shelton, IV et al. |
| 2018/0085123 A1 | 3/2018 | Shelton, IV et al. |
| 2018/0103952 A1 | 4/2018 | Aronhalt et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110518 A1 | 4/2018 | Overmyer et al. |
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0126504 A1 | 5/2018 | Shelton, IV et al. |
| 2018/0132845 A1 | 5/2018 | Schmid et al. |
| 2018/0132850 A1 | 5/2018 | Leimbach et al. |
| 2018/0132851 A1 | 5/2018 | Hall et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168583 A1 | 6/2018 | Hunter et al. |
| 2018/0168584 A1 | 6/2018 | Harris et al. |
| 2018/0168585 A1 | 6/2018 | Shelton, IV et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |

(56) References Cited

U.S. PATENT DOCUMENTS

| | | |
|---|---|---|
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168643 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0250001 A1 | 9/2018 | Aronhalt et al. |
| 2018/0256184 A1 | 9/2018 | Shelton, IV et al. |
| 2018/0271520 A1 | 9/2018 | Shelton, IV et al. |
| 2018/0273597 A1 | 9/2018 | Stimson |
| 2018/0280020 A1 | 10/2018 | Hess et al. |
| 2018/0280021 A1 | 10/2018 | Timm et al. |
| 2018/0280022 A1 | 10/2018 | Timm et al. |
| 2018/0280023 A1 | 10/2018 | Timm et al. |
| 2018/0286274 A1 | 10/2018 | Kamiguchi et al. |
| 2018/0289369 A1 | 10/2018 | Shelton, IV et al. |
| 2018/0296211 A1 | 10/2018 | Timm et al. |
| 2018/0296215 A1 | 10/2018 | Baxter, III et al. |
| 2018/0296216 A1 | 10/2018 | Shelton, IV et al. |
| 2018/0296217 A1 | 10/2018 | Moore et al. |
| 2018/0303481 A1 | 10/2018 | Shelton, IV et al. |
| 2018/0303482 A1 | 10/2018 | Shelton, IV et al. |
| 2018/0310931 A1 | 11/2018 | Hall et al. |
| 2018/0311002 A1 | 11/2018 | Giordano et al. |
| 2018/0317917 A1 | 11/2018 | Huang et al. |
| 2018/0317918 A1 | 11/2018 | Shelton, IV |
| 2018/0317919 A1 | 11/2018 | Shelton, IV et al. |
| 2018/0333155 A1 | 11/2018 | Hall et al. |
| 2018/0333169 A1 | 11/2018 | Leimbach et al. |
| 2018/0344319 A1 | 12/2018 | Shelton, IV et al. |
| 2018/0353170 A1 | 12/2018 | Overmyer et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360443 A1 | 12/2018 | Shelton, IV et al. |
| 2018/0360444 A1 | 12/2018 | Harris et al. |
| 2018/0360445 A1 | 12/2018 | Shelton, IV et al. |
| 2018/0360446 A1 | 12/2018 | Shelton, IV et al. |
| 2018/0360447 A1 | 12/2018 | Shelton, IV et al. |
| 2018/0360448 A1 | 12/2018 | Harris et al. |
| 2018/0360449 A1 | 12/2018 | Shelton, IV et al. |
| 2018/0360450 A1 | 12/2018 | Shelton, IV et al. |
| 2018/0360451 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360455 A1 | 12/2018 | Shelton, IV et al. |
| 2018/0360456 A1 | 12/2018 | Shelton, IV et al. |
| 2018/0360469 A1 | 12/2018 | Shelton, IV et al. |
| 2018/0360470 A1 | 12/2018 | Parfett et al. |
| 2018/0360471 A1 | 12/2018 | Parfett et al. |
| 2018/0360472 A1 | 12/2018 | Harris et al. |
| 2018/0360473 A1 | 12/2018 | Shelton, IV et al. |
| 2018/0368822 A1 | 12/2018 | Shelton, IV et al. |
| 2018/0368833 A1 | 12/2018 | Shelton, IV et al. |
| 2018/0368837 A1 | 12/2018 | Morgan et al. |
| 2018/0368838 A1 | 12/2018 | Shelton, IV et al. |
| 2018/0368839 A1 | 12/2018 | Shelton, IV et al. |
| 2018/0368840 A1 | 12/2018 | Shelton, IV et al. |
| 2018/0368841 A1 | 12/2018 | Shelton, IV et al. |
| 2018/0368842 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2018/0368847 A1 | 12/2018 | Shelton, IV et al. |
| 2019/0000446 A1 | 1/2019 | Shelton, IV et al. |
| 2019/0000447 A1 | 1/2019 | Shelton, IV et al. |
| 2019/0000448 A1 | 1/2019 | Shelton, IV et al. |
| 2019/0000450 A1 | 1/2019 | Shelton, IV et al. |
| 2019/0000454 A1 | 1/2019 | Swayze et al. |
| 2019/0000456 A1 | 1/2019 | Shelton, IV et al. |
| 2019/0000457 A1 | 1/2019 | Shelton, IV et al. |
| 2019/0000458 A1 | 1/2019 | Shelton, IV et al. |
| 2019/0000459 A1 | 1/2019 | Shelton, IV et al. |
| 2019/0000460 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000463 A1 | 1/2019 | Shelton, IV et al. |
| 2019/0000464 A1 | 1/2019 | Shelton, IV et al. |
| 2019/0000465 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000469 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000473 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000479 A1 | 1/2019 | Harris et al. |
| 2019/0000525 A1 | 1/2019 | Messerly et al. |
| 2019/0000528 A1 | 1/2019 | Yates et al. |
| 2019/0000530 A1 | 1/2019 | Yates et al. |
| 2019/0000534 A1 | 1/2019 | Messerly et al. |
| 2019/0000565 A1 | 1/2019 | Shelton, IV et al. |
| 2019/0000577 A1 | 1/2019 | Shelton, IV et al. |
| 2019/0008509 A1 | 1/2019 | Shelton, IV et al. |
| 2019/0008511 A1 | 1/2019 | Kerr et al. |
| 2019/0015096 A1 | 1/2019 | Shelton, IV et al. |
| 2019/0015102 A1 | 1/2019 | Baber et al. |
| 2019/0015165 A1 | 1/2019 | Giordano et al. |
| 2019/0029675 A1 | 1/2019 | Yates et al. |
| 2019/0029676 A1 | 1/2019 | Yates et al. |
| 2019/0029677 A1 | 1/2019 | Yates et al. |
| 2019/0029678 A1 | 1/2019 | Shelton, IV et al. |
| 2019/0029681 A1 | 1/2019 | Swayze et al. |
| 2019/0029682 A1 | 1/2019 | Huitema et al. |

(56) References Cited

U.S. PATENT DOCUMENTS

| | | | |
|---|---|---|---|
| 2019/0029701 | A1 | 1/2019 | Shelton, IV et al. |
| 2019/0033955 | A1 | 1/2019 | Leimbach et al. |
| 2019/0038279 | A1 | 2/2019 | Shelton, IV et al. |
| 2019/0038281 | A1 | 2/2019 | Shelton, IV et al. |
| 2019/0038282 | A1 | 2/2019 | Shelton, IV et al. |
| 2019/0038283 | A1 | 2/2019 | Shelton, IV et al. |
| 2019/0046187 | A1 | 2/2019 | Yates et al. |
| 2019/0059886 | A1 | 2/2019 | Shelton, IV et al. |

FOREIGN PATENT DOCUMENTS

| | | | |
|---|---|---|---|
| AU | 2011218702 | B2 | 6/2013 |
| AU | 2012200178 | B2 | 7/2013 |
| CA | 1015829 | A | 8/1977 |
| CA | 1125615 | A | 6/1982 |
| CA | 2458946 | A1 | 3/2003 |
| CA | 2477181 | A1 | 4/2004 |
| CA | 2512960 | A1 | 1/2006 |
| CA | 2514274 | A1 | 1/2006 |
| CA | 2639177 | A1 | 2/2009 |
| CA | 2664874 | A1 | 11/2009 |
| CA | 2576347 | C | 8/2015 |
| CA | 2940510 | A1 | 8/2015 |
| CN | 86100996 | A | 9/1986 |
| CN | 1163558 | A | 10/1997 |
| CN | 2488482 | Y | 5/2002 |
| CN | 1424891 | A | 6/2003 |
| CN | 1523725 | A | 8/2004 |
| CN | 1545154 | A | 11/2004 |
| CN | 1634601 | A | 7/2005 |
| CN | 1636525 | A | 7/2005 |
| CN | 1636526 | A | 7/2005 |
| CN | 2716900 | Y | 8/2005 |
| CN | 2738962 | Y | 11/2005 |
| CN | 1726874 | A | 2/2006 |
| CN | 1726878 | A | 2/2006 |
| CN | 1868411 | A | 11/2006 |
| CN | 1915180 | A | 2/2007 |
| CN | 2868212 | Y | 2/2007 |
| CN | 1960679 | A | 5/2007 |
| CN | 101011286 | A | 8/2007 |
| CN | 200942099 | Y | 9/2007 |
| CN | 200991269 | Y | 12/2007 |
| CN | 101095621 | A | 1/2008 |
| CN | 101111196 | A | 1/2008 |
| CN | 201001747 | Y | 1/2008 |
| CN | 101137402 | A | 3/2008 |
| CN | 101143105 | A | 3/2008 |
| CN | 201029899 | Y | 3/2008 |
| CN | 101224122 | A | 7/2008 |
| CN | 101224124 | A | 7/2008 |
| CN | 101254126 | A | 9/2008 |
| CN | 101507620 | A | 8/2009 |
| CN | 101507622 | A | 8/2009 |
| CN | 101507623 | A | 8/2009 |
| CN | 101507625 | A | 8/2009 |
| CN | 101507628 | A | 8/2009 |
| CN | 101522120 | A | 9/2009 |
| CN | 101534724 | A | 9/2009 |
| CN | 101626731 | A | 1/2010 |
| CN | 101669833 | A | 3/2010 |
| CN | 101675898 | A | 3/2010 |
| CN | 101683280 | A | 3/2010 |
| CN | 101721236 | A | 6/2010 |
| CN | 101801284 | A | 8/2010 |
| CN | 101828940 | A | 9/2010 |
| CN | 101868203 | A | 10/2010 |
| CN | 101873834 | A | 10/2010 |
| CN | 101073509 | B | 12/2010 |
| CN | 101912285 | A | 12/2010 |
| CN | 101028205 | B | 1/2011 |
| CN | 101933824 | A | 1/2011 |
| CN | 101934098 | A | 1/2011 |
| CN | 201719298 | U | 1/2011 |
| CN | 102038531 | A | 5/2011 |
| CN | 102038532 | A | 5/2011 |
| CN | 101534722 | B | 6/2011 |
| CN | 201879759 | U | 6/2011 |
| CN | 101361666 | B | 8/2011 |
| CN | 201949071 | U | 8/2011 |
| CN | 101224119 | B | 9/2011 |
| CN | 101336835 | B | 9/2011 |
| CN | 102188270 | A | 9/2011 |
| CN | 101779977 | B | 12/2011 |
| CN | 101534723 | B | 1/2012 |
| CN | 101310680 | B | 4/2012 |
| CN | 101912284 | B | 7/2012 |
| CN | 202397539 | U | 8/2012 |
| CN | 202426586 | U | 9/2012 |
| CN | 101317782 | B | 10/2012 |
| CN | 202489990 | U | 10/2012 |
| CN | 101507639 | B | 11/2012 |
| CN | 101541251 | A | 11/2012 |
| CN | 102835977 | A | 12/2012 |
| CN | 101507633 | B | 2/2013 |
| CN | 101023879 | B | 3/2013 |
| CN | 101507624 | B | 3/2013 |
| CN | 101327137 | B | 6/2013 |
| CN | 101401736 | B | 6/2013 |
| CN | 101332110 | B | 7/2013 |
| CN | 101683281 | B | 1/2014 |
| CN | 103648408 | A | 3/2014 |
| CN | 203564285 | U | 4/2014 |
| CN | 203564287 | U | 4/2014 |
| CN | 203597997 | U | 5/2014 |
| CN | 103829983 | A | 6/2014 |
| CN | 103908313 | A | 7/2014 |
| CN | 203736251 | U | 7/2014 |
| CN | 103981635 | A | 8/2014 |
| CN | 102783741 | B | 10/2014 |
| CN | 102973300 | B | 10/2014 |
| CN | 102793571 | B | 12/2014 |
| CN | 104337556 | A | 2/2015 |
| CN | 102166129 | B | 3/2015 |
| CN | 102469995 | B | 3/2015 |
| CN | 102113902 | B | 4/2015 |
| CN | 102247177 | B | 2/2016 |
| CN | 103750872 | B | 5/2016 |
| DE | 273689 | C | 5/1914 |
| DE | 1775926 | A | 1/1972 |
| DE | 3036217 | A1 | 4/1982 |
| DE | 3212828 | A1 | 11/1982 |
| DE | 3210466 | A1 | 9/1983 |
| DE | 3709067 | A1 | 9/1988 |
| DE | 4228909 | A1 | 3/1994 |
| DE | 9412228 | U1 | 9/1994 |
| DE | 19509116 | A1 | 9/1996 |
| DE | 19534043 | A1 | 3/1997 |
| DE | 19707373 | C1 | 2/1998 |
| DE | 19851291 | A1 | 1/2000 |
| DE | 19924311 | A1 | 11/2000 |
| DE | 69328576 | T2 | 1/2001 |
| DE | 20016423 | U1 | 2/2001 |
| DE | 19941859 | A1 | 3/2001 |
| DE | 10052679 | A1 | 5/2001 |
| DE | 20112837 | U1 | 10/2001 |
| DE | 20121753 | U1 | 4/2003 |
| DE | 10314827 | B3 | 4/2004 |
| DE | 202004012389 | U1 | 9/2004 |
| DE | 10314072 | A1 | 10/2004 |
| DE | 202007003114 | U1 | 6/2007 |
| DE | 102010013150 | A1 | 9/2011 |
| EP | 0000756 | A1 | 2/1979 |
| EP | 0033633 | A2 | 8/1981 |
| EP | 0122046 | A1 | 10/1984 |
| EP | 0070230 | B1 | 4/1985 |
| EP | 0156774 | A2 | 10/1985 |
| EP | 0072754 | B1 | 4/1986 |
| EP | 0033548 | B1 | 5/1986 |
| EP | 0077262 | B1 | 8/1986 |
| EP | 0189807 | A2 | 8/1986 |
| EP | 0212278 | A2 | 3/1987 |
| EP | 0129442 | B1 | 11/1987 |
| EP | 0255631 | A1 | 2/1988 |

(56) References Cited

FOREIGN PATENT DOCUMENTS

| | | |
|---|---|---|
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0541950 A1 | 5/1993 |
| EP | 0545029 A1 | 6/1993 |
| EP | 0548998 A1 | 6/1993 |
| EP | 0379721 B1 | 9/1993 |
| EP | 0277959 B1 | 10/1993 |
| EP | 0233940 B1 | 11/1993 |
| EP | 0261230 B1 | 11/1993 |
| EP | 0324636 B1 | 3/1994 |
| EP | 0591946 A1 | 4/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0623311 A2 | 11/1994 |
| EP | 0630612 A1 | 12/1994 |
| EP | 0630614 A1 | 12/1994 |
| EP | 0634144 A1 | 1/1995 |
| EP | 0639349 A2 | 2/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0676173 B1 | 10/1995 |
| EP | 0679367 A2 | 11/1995 |
| EP | 0392547 B1 | 12/1995 |
| EP | 0685204 A1 | 12/1995 |
| EP | 0686374 A2 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0541987 B1 | 7/1996 |
| EP | 0667119 B1 | 7/1996 |
| EP | 0737446 A1 | 10/1996 |
| EP | 0741996 B1 | 11/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0623312 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0484677 B2 | 7/2000 |
| EP | 0830094 B1 | 9/2000 |
| EP | 1034747 A1 | 9/2000 |
| EP | 1034748 A1 | 9/2000 |
| EP | 0726632 B1 | 10/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 1234587 A1 | 8/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0717967 B1 | 5/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1453432 A2 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |

(56) References Cited

FOREIGN PATENT DOCUMENTS

| | | | |
|---|---|---|---|
| EP | 1256318 | B1 | 2/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621143 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1230899 | B1 | 5/2006 |
| EP | 1652481 | A2 | 5/2006 |
| EP | 1382303 | B1 | 6/2006 |
| EP | 1253866 | B1 | 7/2006 |
| EP | 1676539 | A1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1723914 | A1 | 11/2006 |
| EP | 1256317 | B1 | 12/2006 |
| EP | 1285633 | B1 | 12/2006 |
| EP | 1728473 | A1 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1563792 | B1 | 4/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1791473 | A2 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1974678 | A2 | 10/2008 |
| EP | 1980213 | A2 | 10/2008 |
| EP | 1980214 | A2 | 10/2008 |
| EP | 1759645 | B1 | 11/2008 |
| EP | 1987780 | A2 | 11/2008 |
| EP | 1990014 | A2 | 11/2008 |
| EP | 1992296 | A1 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000101 | A2 | 12/2008 |
| EP | 2000102 | A2 | 12/2008 |
| EP | 2005894 | A2 | 12/2008 |
| EP | 2005897 | A2 | 12/2008 |
| EP | 2005901 | A1 | 12/2008 |
| EP | 2008595 | A2 | 12/2008 |
| EP | 2025293 | A1 | 2/2009 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2100562 | A2 | 9/2009 |
| EP | 2110082 | A1 | 10/2009 |
| EP | 2110083 | A2 | 10/2009 |
| EP | 2110084 | A2 | 10/2009 |
| EP | 2111803 | A2 | 10/2009 |
| EP | 1813208 | B1 | 11/2009 |
| EP | 1908426 | B1 | 11/2009 |

(56) References Cited

FOREIGN PATENT DOCUMENTS

| | | |
|---|---|---|
| EP | 2116195 A1 | 11/2009 |
| EP | 2116196 A2 | 11/2009 |
| EP | 2116197 A2 | 11/2009 |
| EP | 1607050 B1 | 12/2009 |
| EP | 1762190 B8 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165654 A1 | 3/2010 |
| EP | 2165656 A2 | 3/2010 |
| EP | 2165660 A2 | 3/2010 |
| EP | 2165663 A2 | 3/2010 |
| EP | 2165664 A2 | 3/2010 |
| EP | 1566150 B1 | 4/2010 |
| EP | 1813206 B1 | 4/2010 |
| EP | 2184014 A2 | 5/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 2214610 A1 | 8/2010 |
| EP | 2218409 A1 | 8/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2245994 A1 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2258282 A2 | 12/2010 |
| EP | 2263568 A2 | 12/2010 |
| EP | 1994890 B1 | 1/2011 |
| EP | 2005900 B1 | 1/2011 |
| EP | 2277667 A1 | 1/2011 |
| EP | 2283780 A2 | 2/2011 |
| EP | 2286738 A2 | 2/2011 |
| EP | 1494595 B1 | 3/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A1 | 4/2011 |
| EP | 2316345 A1 | 5/2011 |
| EP | 2316366 A2 | 5/2011 |
| EP | 2319443 A1 | 5/2011 |
| EP | 2324776 A2 | 5/2011 |
| EP | 1813205 B1 | 6/2011 |
| EP | 2042107 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 1728475 B1 | 8/2011 |
| EP | 2353545 A1 | 8/2011 |
| EP | 2361562 A1 | 8/2011 |
| EP | 2377472 A1 | 10/2011 |
| EP | 1836986 B1 | 11/2011 |
| EP | 1908414 B1 | 11/2011 |
| EP | 2153781 B1 | 11/2011 |
| EP | 2387943 A2 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 1316290 B1 | 2/2012 |
| EP | 1962711 B1 | 2/2012 |
| EP | 2415416 A1 | 2/2012 |
| EP | 2090253 B1 | 3/2012 |
| EP | 2430986 A2 | 3/2012 |
| EP | 1347638 B1 | 5/2012 |
| EP | 1943956 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2478845 A2 | 7/2012 |
| EP | 2005895 B1 | 8/2012 |
| EP | 2090248 B1 | 8/2012 |
| EP | 2481359 A1 | 8/2012 |
| EP | 2484304 A2 | 8/2012 |
| EP | 2486860 A2 | 8/2012 |
| EP | 2486862 A2 | 8/2012 |
| EP | 2486868 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2286735 B1 | 3/2013 |
| EP | 2090238 B1 | 4/2013 |
| EP | 1806103 B1 | 5/2013 |
| EP | 2586380 A1 | 5/2013 |
| EP | 2586383 A2 | 5/2013 |
| EP | 2606812 A1 | 6/2013 |
| EP | 2606834 A2 | 6/2013 |
| EP | 1982657 B1 | 7/2013 |
| EP | 2614782 A2 | 7/2013 |
| EP | 2617369 A1 | 7/2013 |
| EP | 2620117 A1 | 7/2013 |
| EP | 2090234 B1 | 9/2013 |
| EP | 2633830 A1 | 9/2013 |
| EP | 2090244 B1 | 10/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 1997438 B1 | 11/2013 |
| EP | 2684529 A2 | 1/2014 |
| EP | 2687164 A2 | 1/2014 |
| EP | 2700367 A1 | 2/2014 |
| EP | 2713902 A1 | 4/2014 |
| EP | 1772105 B1 | 5/2014 |
| EP | 2743042 A2 | 6/2014 |
| EP | 2759267 A1 | 7/2014 |
| EP | 2764826 A1 | 8/2014 |
| EP | 2764827 A2 | 8/2014 |
| EP | 2767243 A2 | 8/2014 |
| EP | 2772206 A2 | 9/2014 |
| EP | 2772209 A2 | 9/2014 |
| EP | 2777520 A1 | 9/2014 |
| EP | 2777524 A2 | 9/2014 |
| EP | 2777528 A2 | 9/2014 |
| EP | 2777537 A1 | 9/2014 |
| EP | 2777538 A2 | 9/2014 |
| EP | 2786714 A2 | 10/2014 |
| EP | 2792313 A2 | 10/2014 |

(56) References Cited

FOREIGN PATENT DOCUMENTS

| | | |
|---|---|---|
| EP | 2803324 A2 | 11/2014 |
| EP | 2815704 A1 | 12/2014 |
| EP | 2446835 B1 | 1/2015 |
| EP | 2842500 A1 | 3/2015 |
| EP | 2845545 A1 | 3/2015 |
| EP | 1943960 B1 | 4/2015 |
| EP | 2090255 B1 | 4/2015 |
| EP | 2853220 A1 | 4/2015 |
| EP | 2923647 A2 | 9/2015 |
| EP | 2923653 A2 | 9/2015 |
| EP | 2923660 A2 | 9/2015 |
| EP | 2932913 A1 | 10/2015 |
| EP | 2944270 A1 | 11/2015 |
| EP | 1774914 B1 | 12/2015 |
| EP | 2090235 B1 | 4/2016 |
| EP | 2823773 B1 | 4/2016 |
| EP | 2131750 B1 | 5/2016 |
| EP | 2298220 B1 | 6/2016 |
| EP | 2510891 B1 | 6/2016 |
| EP | 1915957 B1 | 8/2016 |
| EP | 2296559 B1 | 8/2016 |
| EP | 2586379 B1 | 8/2016 |
| EP | 2777533 B1 | 10/2016 |
| EP | 2364651 B1 | 11/2016 |
| EP | 2747235 B1 | 11/2016 |
| EP | 2116192 B1 | 3/2017 |
| EP | 2789299 B1 | 5/2017 |
| EP | 2311386 B1 | 6/2017 |
| EP | 2839787 B1 | 6/2017 |
| EP | 2745782 B1 | 10/2017 |
| EP | 3363378 A1 | 8/2018 |
| ES | 2396594 T3 | 2/2013 |
| FR | 459743 A | 11/1913 |
| FR | 999646 A | 2/1952 |
| FR | 1112936 A | 3/1956 |
| FR | 2452275 B1 | 4/1983 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2426391 A | 11/2006 |
| GB | 2423199 B | 5/2009 |
| GB | 2509523 A | 7/2014 |
| GR | 930100110 A | 11/1993 |
| JP | S4711908 Y1 | 5/1972 |
| JP | S5033988 U | 4/1975 |
| JP | S56112235 A | 9/1981 |
| JP | S58500053 A | 1/1983 |
| JP | S58501360 A | 8/1983 |
| JP | S59174920 A | 10/1984 |
| JP | S60100955 A | 6/1985 |
| JP | S63147449 A | 10/1985 |
| JP | S6198249 A | 5/1986 |
| JP | S60212152 A | 9/1986 |
| JP | S62170011 U | 10/1987 |
| JP | S6359764 A | 3/1988 |
| JP | S63147449 A | 6/1988 |
| JP | S63203149 A | 8/1988 |
| JP | S63270040 A | 11/1988 |
| JP | H0129503 B2 | 6/1989 |
| JP | H02279149 A | 11/1990 |
| JP | H0312126 A | 1/1991 |
| JP | H0318354 A | 1/1991 |
| JP | H0378514 U | 8/1991 |
| JP | H0385009 U | 8/1991 |
| JP | H04131860 U | 2/1992 |
| JP | H04215747 A | 8/1992 |
| JP | H0584252 A | 4/1993 |
| JP | H05123325 A | 5/1993 |
| JP | H05212039 A | 8/1993 |
| JP | H 05226945 A | 9/1993 |
| JP | H067357 A | 1/1994 |
| JP | H0630945 A | 2/1994 |
| JP | H0654857 A | 3/1994 |
| JP | H0663054 A | 3/1994 |
| JP | H0626812 U | 4/1994 |
| JP | H06121798 A | 5/1994 |
| JP | H06125913 A | 5/1994 |
| JP | H06197901 A | 7/1994 |
| JP | H06237937 A | 8/1994 |
| JP | H06327684 A | 11/1994 |
| JP | H079622 U | 2/1995 |
| JP | H0731623 A | 2/1995 |
| JP | H0747070 A | 2/1995 |
| JP | H0751273 A | 2/1995 |
| JP | H07124166 A | 5/1995 |
| JP | H07163573 A | 6/1995 |
| JP | H07163574 A | 6/1995 |
| JP | H07171163 A | 7/1995 |
| JP | H07255735 A | 10/1995 |
| JP | H07285089 A | 10/1995 |
| JP | H07299074 A | 11/1995 |
| JP | H0833641 A | 2/1996 |
| JP | H0833642 A | 2/1996 |
| JP | H08164141 A | 6/1996 |
| JP | H08173437 A | 7/1996 |
| JP | H08182684 A | 7/1996 |
| JP | H08215201 A | 8/1996 |
| JP | H08507708 A | 8/1996 |
| JP | H08229050 A | 9/1996 |
| JP | H08289895 A | 11/1996 |
| JP | H08336540 A | 12/1996 |
| JP | H08336544 A | 12/1996 |
| JP | H09501081 A | 2/1997 |
| JP | H09501577 A | 2/1997 |
| JP | H09164144 A | 6/1997 |
| JP | H09-323068 A | 12/1997 |
| JP | H10113352 A | 5/1998 |
| JP | H10118090 A | 5/1998 |
| JP | H10-200699 A | 7/1998 |
| JP | H 10296660 A | 11/1998 |
| JP | H10512465 A | 12/1998 |
| JP | H10512469 A | 12/1998 |
| JP | 2000014632 A | 1/2000 |
| JP | 2000033071 A | 2/2000 |
| JP | 2000112002 A | 4/2000 |
| JP | 3056672 B2 | 6/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001037763 A | 2/2001 |
| JP | 2001046384 A | 2/2001 |
| JP | 2001087272 A | 4/2001 |
| JP | 2001514541 A | 9/2001 |
| JP | 2001276091 A | 10/2001 |
| JP | 2001286477 A | 10/2001 |
| JP | 2001517473 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002204801 A | 7/2002 |
| JP | 2002528161 A | 9/2002 |
| JP | 2002314298 A | 10/2002 |
| JP | 2002369820 A | 12/2002 |
| JP | 2002542186 A | 12/2002 |
| JP | 2003000603 A | 1/2003 |
| JP | 2003500153 A | 1/2003 |
| JP | 2003504104 A | 2/2003 |
| JP | 2003135473 A | 5/2003 |
| JP | 2003148903 A | 5/2003 |

(56) References Cited

FOREIGN PATENT DOCUMENTS

| | | |
|---|---|---|
| JP | 2003164066 A | 6/2003 |
| JP | 2003521301 A | 7/2003 |
| JP | 2003521304 A | 7/2003 |
| JP | 2003523251 A | 8/2003 |
| JP | 2003523254 A | 8/2003 |
| JP | 2003524431 A | 8/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2004524076 A | 8/2004 |
| JP | 2004531280 A | 10/2004 |
| JP | 2004532084 A | 10/2004 |
| JP | 2004532676 A | 10/2004 |
| JP | 2004-535217 A | 11/2004 |
| JP | 2004329624 A | 11/2004 |
| JP | 2004337617 A | 12/2004 |
| JP | 2004344662 A | 12/2004 |
| JP | 2004344663 A | 12/2004 |
| JP | 2005013573 A | 1/2005 |
| JP | 2005028147 A | 2/2005 |
| JP | 2005028148 A | 2/2005 |
| JP | 2005028149 A | 2/2005 |
| JP | 2005505309 A | 2/2005 |
| JP | 2005505322 A | 2/2005 |
| JP | 2005505334 A | 2/2005 |
| JP | 2005080702 A | 3/2005 |
| JP | 2005103280 A | 4/2005 |
| JP | 2005103281 A | 4/2005 |
| JP | 2005103293 A | 4/2005 |
| JP | 2005511131 A | 4/2005 |
| JP | 2005511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005137919 A | 6/2005 |
| JP | 2005144183 A | 6/2005 |
| JP | 2005152416 A | 6/2005 |
| JP | 2005516714 A | 6/2005 |
| JP | 2005187954 A | 7/2005 |
| JP | 2005521109 A | 7/2005 |
| JP | 2005523105 A | 8/2005 |
| JP | 2005524474 A | 8/2005 |
| JP | 2005296412 A | 10/2005 |
| JP | 2005529675 A | 10/2005 |
| JP | 2005529677 A | 10/2005 |
| JP | 2005328882 A | 12/2005 |
| JP | 2005335432 A | 12/2005 |
| JP | 2005342267 A | 12/2005 |
| JP | 2006034975 A | 2/2006 |
| JP | 2006034977 A | 2/2006 |
| JP | 2006034978 A | 2/2006 |
| JP | 2006034980 A | 2/2006 |
| JP | 2006043451 A | 2/2006 |
| JP | 2006506106 A | 2/2006 |
| JP | 2006510879 A | 3/2006 |
| JP | 3791856 B2 | 6/2006 |
| JP | 2006187649 A | 7/2006 |
| JP | 2006218228 A | 8/2006 |
| JP | 2006218297 A | 8/2006 |
| JP | 2006223872 A | 8/2006 |
| JP | 2006281405 A | 10/2006 |
| JP | 2006289064 A | 10/2006 |
| JP | 2006334412 A | 12/2006 |
| JP | 2006334417 A | 12/2006 |
| JP | 2006346445 A | 12/2006 |
| JP | 2007000634 A | 1/2007 |
| JP | 2007050253 A | 3/2007 |
| JP | 2007061628 A | 3/2007 |
| JP | 3906843 B2 | 4/2007 |
| JP | 2007083051 A | 4/2007 |
| JP | 2007098130 A | 4/2007 |
| JP | 2007105481 A | 4/2007 |
| JP | 2007117725 A | 5/2007 |
| JP | 2007130471 A | 5/2007 |
| JP | 2007130479 A | 5/2007 |
| JP | 3934161 B2 | 6/2007 |
| JP | 2007203047 A | 8/2007 |
| JP | 2007203049 A | 8/2007 |
| JP | 2007203051 A | 8/2007 |
| JP | 2007203055 A | 8/2007 |
| JP | 2007203057 A | 8/2007 |
| JP | 2007524435 A | 8/2007 |
| JP | 2007222615 A | 9/2007 |
| JP | 2007229448 A | 9/2007 |
| JP | 2007526026 A | 9/2007 |
| JP | 4001860 B2 | 10/2007 |
| JP | 2007252916 A | 10/2007 |
| JP | 2007307373 A | 11/2007 |
| JP | 2007325922 A | 12/2007 |
| JP | 2008068073 A | 3/2008 |
| JP | 2008510515 A | 4/2008 |
| JP | 2008516669 A | 5/2008 |
| JP | 2008528203 A | 7/2008 |
| JP | 2008-220032 A | 9/2008 |
| JP | 2008206967 A | 9/2008 |
| JP | 2008212637 A | 9/2008 |
| JP | 2008212638 A | 9/2008 |
| JP | 2008212640 A | 9/2008 |
| JP | 2008220956 A | 9/2008 |
| JP | 2008237881 A | 10/2008 |
| JP | 2008259860 A | 10/2008 |
| JP | 2008264535 A | 11/2008 |
| JP | 2008283459 A | 11/2008 |
| JP | 2008307393 A | 12/2008 |
| JP | 2009000531 A | 1/2009 |
| JP | 2009006137 A | 1/2009 |
| JP | 2009502351 A | 1/2009 |
| JP | 2009502352 A | 1/2009 |
| JP | 2009022742 A | 2/2009 |
| JP | 2009506799 A | 2/2009 |
| JP | 2009507526 A | 2/2009 |
| JP | 2009072595 A | 4/2009 |
| JP | 2009072599 A | 4/2009 |
| JP | 2009090113 A | 4/2009 |
| JP | 2009106752 A | 5/2009 |
| JP | 2009189821 A | 8/2009 |
| JP | 2009189823 A | 8/2009 |
| JP | 2009189836 A | 8/2009 |
| JP | 2009189837 A | 8/2009 |
| JP | 2009189838 A | 8/2009 |
| JP | 2009189846 A | 8/2009 |
| JP | 2009189847 A | 8/2009 |
| JP | 2009201998 A | 9/2009 |
| JP | 2009207260 A | 9/2009 |
| JP | 2009226028 A | 10/2009 |
| JP | 2009536082 A | 10/2009 |
| JP | 2009261944 A | 11/2009 |
| JP | 2009268908 A | 11/2009 |
| JP | 2009538684 A | 11/2009 |
| JP | 2009539420 A | 11/2009 |
| JP | 2009291604 A | 12/2009 |
| JP | 2010504808 A | 2/2010 |
| JP | 2010504809 A | 2/2010 |
| JP | 2010504813 A | 2/2010 |
| JP | 2010504846 A | 2/2010 |
| JP | 2010505524 A | 2/2010 |
| JP | 2010069307 A | 4/2010 |
| JP | 2010069310 A | 4/2010 |
| JP | 2010075694 A | 4/2010 |
| JP | 2010075695 A | 4/2010 |
| JP | 2010088876 A | 4/2010 |
| JP | 2010094514 A | 4/2010 |
| JP | 2010098844 A | 4/2010 |
| JP | 4461008 B2 | 5/2010 |
| JP | 2010-520025 A | 6/2010 |
| JP | 2010-148879 A | 7/2010 |
| JP | 2010142636 A | 7/2010 |
| JP | 4549018 B2 | 9/2010 |
| JP | 2010214166 A | 9/2010 |

(56) References Cited

FOREIGN PATENT DOCUMENTS

| | | |
|---|---|---|
| JP | 2010-240429 A | 10/2010 |
| JP | 2010240411 A | 10/2010 |
| JP | 2010246948 A | 11/2010 |
| JP | 2010-540041 A | 12/2010 |
| JP | 2010279690 A | 12/2010 |
| JP | 2010540192 A | 12/2010 |
| JP | 2011005260 A | 1/2011 |
| JP | 2011504391 A | 2/2011 |
| JP | 2011509786 A | 3/2011 |
| JP | 2011072574 A | 4/2011 |
| JP | 2011072797 A | 4/2011 |
| JP | 2011078763 A | 4/2011 |
| JP | 2011-115594 A | 6/2011 |
| JP | 2011-520564 A | 7/2011 |
| JP | 4722849 B2 | 7/2011 |
| JP | 4783373 B2 | 9/2011 |
| JP | 2011524199 A | 9/2011 |
| JP | 2011251156 A | 12/2011 |
| JP | 2012040398 A | 3/2012 |
| JP | 2012507356 A | 3/2012 |
| JP | 2012517289 A | 8/2012 |
| JP | 5140421 B2 | 2/2013 |
| JP | 5154710 B1 | 2/2013 |
| JP | 5162595 B2 | 3/2013 |
| JP | 2013517891 A | 5/2013 |
| JP | 2013526342 A | 6/2013 |
| JP | 2013128791 A | 7/2013 |
| JP | 5333899 B2 | 11/2013 |
| JP | 2014121599 A | 7/2014 |
| JP | 2016-512057 A | 4/2016 |
| KR | 20100110134 A | 10/2010 |
| KR | 20110003229 A | 1/2011 |
| RU | 1814161 A1 | 5/1993 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2007103563 A | 8/2008 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 886900 A1 | 12/1981 |
| SU | 1009439 A | 4/1983 |
| SU | 1022703 A1 | 6/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO-8202824 A1 | 9/1982 |
| WO | WO-8602254 A1 | 4/1986 |
| WO | WO-9115157 A1 | 10/1991 |
| WO | WO-9220295 A1 | 11/1992 |
| WO | WO-9221300 A1 | 12/1992 |
| WO | WO-9308755 A1 | 5/1993 |
| WO | WO-9313718 A1 | 7/1993 |
| WO | WO-9314690 A1 | 8/1993 |
| WO | WO-9315648 A1 | 8/1993 |
| WO | WO-9315850 A1 | 8/1993 |
| WO | WO-9319681 A1 | 10/1993 |
| WO | WO-9400060 A1 | 1/1994 |
| WO | WO-9411057 A1 | 5/1994 |
| WO | WO-94/14129 A1 | 6/1994 |
| WO | WO-9412108 A1 | 6/1994 |
| WO | WO-9417737 A1 | 8/1994 |
| WO | WO-9418893 A1 | 9/1994 |
| WO | WO-9420030 A1 | 9/1994 |
| WO | WO-9422378 A1 | 10/1994 |
| WO | WO-9423659 A1 | 10/1994 |
| WO | WO-9424943 A1 | 11/1994 |
| WO | WO-9424947 A1 | 11/1994 |
| WO | WO-9502369 A1 | 1/1995 |
| WO | WO-9503743 A1 | 2/1995 |
| WO | WO-9506817 A1 | 3/1995 |
| WO | WO-9509576 A1 | 4/1995 |
| WO | WO-9509577 A1 | 4/1995 |
| WO | WO-9514436 A1 | 6/1995 |
| WO | WO-9517855 A1 | 7/1995 |
| WO | WO-9518383 A1 | 7/1995 |
| WO | WO-9518572 A1 | 7/1995 |
| WO | WO-9519739 A1 | 7/1995 |
| WO | WO-9520360 A1 | 8/1995 |
| WO | WO-9523557 A1 | 9/1995 |
| WO | WO-9524865 A1 | 9/1995 |
| WO | WO-9525471 A3 | 9/1995 |
| WO | WO-9526562 A1 | 10/1995 |
| WO | WO-9529639 A1 | 11/1995 |
| WO | WO-9604858 A1 | 2/1996 |
| WO | WO-9618344 A2 | 6/1996 |
| WO | WO-9619151 A1 | 6/1996 |
| WO | WO-9619152 A1 | 6/1996 |
| WO | WO-9620652 A1 | 7/1996 |
| WO | WO-9621119 A1 | 7/1996 |
| WO | WO-9622055 A1 | 7/1996 |
| WO | WO-9623448 A1 | 8/1996 |
| WO | WO-9624301 A1 | 8/1996 |
| WO | WO-9627337 A1 | 9/1996 |
| WO | WO-9631155 A1 | 10/1996 |
| WO | WO-9635464 A1 | 11/1996 |
| WO | WO-9639085 A1 | 12/1996 |
| WO | WO-9639086 A1 | 12/1996 |
| WO | WO-9639087 A1 | 12/1996 |
| WO | WO-9639088 A1 | 12/1996 |
| WO | WO-9639089 A1 | 12/1996 |
| WO | WO-9700646 A1 | 1/1997 |
| WO | WO-9700647 A1 | 1/1997 |
| WO | WO-9701989 A1 | 1/1997 |
| WO | WO-9706582 A1 | 2/1997 |
| WO | WO-9710763 A1 | 3/1997 |
| WO | WO-9710764 A1 | 3/1997 |
| WO | WO-9711648 A2 | 4/1997 |
| WO | WO-9711649 A1 | 4/1997 |
| WO | WO-9715237 A1 | 5/1997 |
| WO | WO-9724073 A1 | 7/1997 |
| WO | WO-9724993 A1 | 7/1997 |
| WO | WO-9730644 A1 | 8/1997 |
| WO | WO-9730659 A1 | 8/1997 |
| WO | WO-9734533 A1 | 9/1997 |
| WO | WO-9737598 A1 | 10/1997 |
| WO | WO-9739688 A2 | 10/1997 |
| WO | WO-9741767 A2 | 11/1997 |
| WO | WO-9801080 A1 | 1/1998 |
| WO | WO-9817180 A1 | 4/1998 |
| WO | WO-9822154 A2 | 5/1998 |
| WO | WO-9827880 A1 | 7/1998 |
| WO | WO-9830153 A1 | 7/1998 |
| WO | WO-9847436 A1 | 10/1998 |
| WO | WO-9858589 A1 | 12/1998 |
| WO | WO-9902090 A1 | 1/1999 |
| WO | WO-9903407 A1 | 1/1999 |
| WO | WO-9903408 A1 | 1/1999 |
| WO | WO-9903409 A1 | 1/1999 |
| WO | WO-9912483 A1 | 3/1999 |
| WO | WO-9912487 A1 | 3/1999 |

(56) References Cited

FOREIGN PATENT DOCUMENTS

| | | |
|---|---|---|
| WO | WO-9912488 A1 | 3/1999 |
| WO | WO-9915086 A1 | 4/1999 |
| WO | WO-9915091 A1 | 4/1999 |
| WO | WO-9923933 A2 | 5/1999 |
| WO | WO-9923959 A1 | 5/1999 |
| WO | WO-9925261 A1 | 5/1999 |
| WO | WO-9929244 A1 | 6/1999 |
| WO | WO-9934744 A1 | 7/1999 |
| WO | WO-9945849 A1 | 9/1999 |
| WO | WO-9948430 A1 | 9/1999 |
| WO | WO-9951158 A1 | 10/1999 |
| WO | WO-0024330 A1 | 5/2000 |
| WO | WO-2000024322 A1 | 5/2000 |
| WO | WO-0033755 A1 | 6/2000 |
| WO | WO-0041638 A1 | 7/2000 |
| WO | WO-0048506 A1 | 8/2000 |
| WO | WO-0053112 A2 | 9/2000 |
| WO | WO-0054653 A1 | 9/2000 |
| WO | WO-0057796 A1 | 10/2000 |
| WO | WO-0064365 A1 | 11/2000 |
| WO | WO-0072762 A1 | 12/2000 |
| WO | WO-0072765 A1 | 12/2000 |
| WO | WO-0078222 A1 | 12/2000 |
| WO | WO-0103587 A1 | 1/2001 |
| WO | WO-0105702 A1 | 1/2001 |
| WO | WO-0110482 A1 | 2/2001 |
| WO | WO-0135845 A1 | 5/2001 |
| WO | WO-0154594 A1 | 8/2001 |
| WO | WO-0158371 A1 | 8/2001 |
| WO | WO-0162158 A2 | 8/2001 |
| WO | WO-0162161 A1 | 8/2001 |
| WO | WO-0162162 A1 | 8/2001 |
| WO | WO-0162163 A1 | 8/2001 |
| WO | WO-0162164 A2 | 8/2001 |
| WO | WO-0162169 A2 | 8/2001 |
| WO | WO-0178605 A2 | 10/2001 |
| WO | WO-0180757 A2 | 11/2001 |
| WO | WO-0191646 A1 | 12/2001 |
| WO | WO-0200121 A1 | 1/2002 |
| WO | WO-0207608 A2 | 1/2002 |
| WO | WO-0207618 A1 | 1/2002 |
| WO | WO-0217799 A1 | 3/2002 |
| WO | WO-0219920 A1 | 3/2002 |
| WO | WO-0219932 A1 | 3/2002 |
| WO | WO-0226143 A1 | 4/2002 |
| WO | WO-0230297 A2 | 4/2002 |
| WO | WO-0232322 A2 | 4/2002 |
| WO | WO-0236028 A1 | 5/2002 |
| WO | WO-0243571 A2 | 6/2002 |
| WO | WO-02058568 A1 | 8/2002 |
| WO | WO-02060328 A1 | 8/2002 |
| WO | WO-02065933 A2 | 8/2002 |
| WO | WO-02067785 A2 | 9/2002 |
| WO | WO-02080781 A2 | 10/2002 |
| WO | WO-02085218 A2 | 10/2002 |
| WO | WO-02087586 A1 | 11/2002 |
| WO | WO-02098302 A1 | 12/2002 |
| WO | WO-03000138 A2 | 1/2003 |
| WO | WO-03001329 A2 | 1/2003 |
| WO | WO-03001986 A2 | 1/2003 |
| WO | WO-03013363 A1 | 2/2003 |
| WO | WO-03013372 A2 | 2/2003 |
| WO | WO-03015604 A2 | 2/2003 |
| WO | WO-03020106 A2 | 3/2003 |
| WO | WO-03020139 A2 | 3/2003 |
| WO | WO-03024339 A1 | 3/2003 |
| WO | WO-03030743 A2 | 4/2003 |
| WO | WO-03037193 A1 | 5/2003 |
| WO | WO-03055402 A1 | 7/2003 |
| WO | WO-03057048 A1 | 7/2003 |
| WO | WO-03057058 A1 | 7/2003 |
| WO | WO-03063694 A1 | 8/2003 |
| WO | WO-03077769 A1 | 9/2003 |
| WO | WO-03079911 A1 | 10/2003 |
| WO | WO-03082126 A1 | 10/2003 |
| WO | WO-03086206 A1 | 10/2003 |
| WO | WO-03088845 A2 | 10/2003 |
| WO | WO-03047436 A3 | 11/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105698 A2 | 12/2003 |
| WO | WO-03105702 A2 | 12/2003 |
| WO | WO-2004004578 A1 | 1/2004 |
| WO | WO-2004006980 A2 | 1/2004 |
| WO | WO-2004011037 A2 | 2/2004 |
| WO | WO-2004014238 A2 | 2/2004 |
| WO | WO-03079909 A3 | 3/2004 |
| WO | WO-2004019769 A1 | 3/2004 |
| WO | WO-2004019803 A1 | 3/2004 |
| WO | WO-2004021868 A2 | 3/2004 |
| WO | WO-2004028585 A2 | 4/2004 |
| WO | WO-2004030554 A1 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004032783 A1 | 4/2004 |
| WO | WO-2004034875 A2 | 4/2004 |
| WO | WO-2004047626 A1 | 6/2004 |
| WO | WO-2004047653 A2 | 6/2004 |
| WO | WO-2004049956 A2 | 6/2004 |
| WO | WO-2004050971 A2 | 6/2004 |
| WO | WO-2004052426 A2 | 6/2004 |
| WO | WO-2004056276 A1 | 7/2004 |
| WO | WO-2004056277 A1 | 7/2004 |
| WO | WO-2004062516 A1 | 7/2004 |
| WO | WO-2004064600 A2 | 8/2004 |
| WO | WO-2004078050 A2 | 9/2004 |
| WO | WO-2004078051 A2 | 9/2004 |
| WO | WO-2004078236 A2 | 9/2004 |
| WO | WO-2004086987 A1 | 10/2004 |
| WO | WO-2004096015 A2 | 11/2004 |
| WO | WO-2004096057 A2 | 11/2004 |
| WO | WO-2004103157 A2 | 12/2004 |
| WO | WO-2004105593 A2 | 12/2004 |
| WO | WO-2004105621 A1 | 12/2004 |
| WO | WO-2004112618 A2 | 12/2004 |
| WO | WO-2004112652 A2 | 12/2004 |
| WO | WO-2005027983 A2 | 3/2005 |
| WO | WO-2005037329 A2 | 4/2005 |
| WO | WO-2005042041 A1 | 5/2005 |
| WO | WO-2005044078 A2 | 5/2005 |
| WO | WO-2005048809 A1 | 6/2005 |
| WO | WO-2005055846 A2 | 6/2005 |
| WO | WO-2005072634 A2 | 8/2005 |
| WO | WO-2005078892 A1 | 8/2005 |
| WO | WO-2005079675 A2 | 9/2005 |
| WO | WO-2005087128 A1 | 9/2005 |
| WO | WO-2005096954 A2 | 10/2005 |
| WO | WO-2005110243 A2 | 11/2005 |
| WO | WO-2005112806 A2 | 12/2005 |
| WO | WO-2005112808 A1 | 12/2005 |
| WO | WO-2005115251 A1 | 12/2005 |
| WO | WO-2005115253 A2 | 12/2005 |
| WO | WO-2005117735 A1 | 12/2005 |
| WO | WO-2005122936 A1 | 12/2005 |
| WO | WO-2006/026520 A2 | 3/2006 |
| WO | WO-2006023486 A2 | 3/2006 |
| WO | WO-2006023578 A2 | 3/2006 |
| WO | WO-2006027014 A1 | 3/2006 |
| WO | WO-2006028314 A1 | 3/2006 |
| WO | WO-2006044490 A2 | 4/2006 |
| WO | WO-2006044581 A2 | 4/2006 |
| WO | WO-2006044810 A2 | 4/2006 |
| WO | WO-2006049852 A2 | 5/2006 |
| WO | WO-2006050360 A1 | 5/2006 |
| WO | WO-2006051252 A1 | 5/2006 |
| WO | WO-2006/057702 A2 | 6/2006 |
| WO | WO-2006059067 A1 | 6/2006 |
| WO | WO-2006/073581 A2 | 7/2006 |

(56) References Cited

FOREIGN PATENT DOCUMENTS

| | | |
|---|---|---|
| WO | WO-2006083748 A1 | 8/2006 |
| WO | WO-2006085389 A1 | 8/2006 |
| WO | WO-2006092563 A1 | 9/2006 |
| WO | WO-2006092565 A1 | 9/2006 |
| WO | WO-2006115958 A1 | 11/2006 |
| WO | WO-2006125940 A1 | 11/2006 |
| WO | WO-2006132992 A2 | 12/2006 |
| WO | WO-2007002180 A2 | 1/2007 |
| WO | WO-2007014355 A2 | 2/2007 |
| WO | WO-2007015971 A2 | 2/2007 |
| WO | WO-2007016290 A2 | 2/2007 |
| WO | WO-2007018898 A2 | 2/2007 |
| WO | WO-2007034161 A2 | 3/2007 |
| WO | WO-2007051000 A2 | 5/2007 |
| WO | WO-2007059233 A2 | 5/2007 |
| WO | WO-2007074430 A1 | 7/2007 |
| WO | WO-2007089603 A2 | 8/2007 |
| WO | WO-2007098220 A2 | 8/2007 |
| WO | WO-2007121579 A1 | 11/2007 |
| WO | WO-2007129121 A1 | 11/2007 |
| WO | WO-2007131110 A2 | 11/2007 |
| WO | WO-2007137304 A2 | 11/2007 |
| WO | WO-2007139734 A2 | 12/2007 |
| WO | WO-2007142625 A2 | 12/2007 |
| WO | WO-2007145825 A2 | 12/2007 |
| WO | WO-2007146987 A2 | 12/2007 |
| WO | WO-2007147439 A1 | 12/2007 |
| WO | WO-2008020964 A2 | 2/2008 |
| WO | WO-2008021687 A1 | 2/2008 |
| WO | WO-2008021969 A2 | 2/2008 |
| WO | WO-2008027972 A1 | 3/2008 |
| WO | WO-2008039237 A1 | 4/2008 |
| WO | WO-2008039249 A1 | 4/2008 |
| WO | WO-2008039270 A1 | 4/2008 |
| WO | WO-2008045383 A2 | 4/2008 |
| WO | WO-2008/061566 A1 | 5/2008 |
| WO | WO-2008057281 A2 | 5/2008 |
| WO | WO-2008070763 A1 | 6/2008 |
| WO | WO-2008080148 A2 | 7/2008 |
| WO | WO-2008089404 A2 | 7/2008 |
| WO | WO-2008101080 A1 | 8/2008 |
| WO | WO-2008101228 A2 | 8/2008 |
| WO | WO-2008103797 A2 | 8/2008 |
| WO | WO-2008109123 A2 | 9/2008 |
| WO | WO-2008109125 A1 | 9/2008 |
| WO | WO-2008112912 A2 | 9/2008 |
| WO | WO-2008118728 A1 | 10/2008 |
| WO | WO-2008118928 A2 | 10/2008 |
| WO | WO-2008124748 A1 | 10/2008 |
| WO | WO-2008131357 A1 | 10/2008 |
| WO | WO-2009005969 A2 | 1/2009 |
| WO | WO-2009022614 A1 | 2/2009 |
| WO | WO-2009023851 A1 | 2/2009 |
| WO | WO-2009033057 A2 | 3/2009 |
| WO | WO-2009039506 A1 | 3/2009 |
| WO | WO-2009046394 A1 | 4/2009 |
| WO | WO-2009066105 A1 | 5/2009 |
| WO | WO-2009067649 A2 | 5/2009 |
| WO | WO-2009091497 A2 | 7/2009 |
| WO | WO-2009120944 A2 | 10/2009 |
| WO | WO-2009137761 A2 | 11/2009 |
| WO | WO-2009143092 A1 | 11/2009 |
| WO | WO-2009143331 A1 | 11/2009 |
| WO | WO-2009150650 A2 | 12/2009 |
| WO | WO-2009152307 A1 | 12/2009 |
| WO | WO-2010028332 A2 | 3/2010 |
| WO | WO-2010030434 A1 | 3/2010 |
| WO | WO-2010045425 A1 | 4/2010 |
| WO | WO-2010050771 A2 | 5/2010 |
| WO | WO-2010054404 A1 | 5/2010 |
| WO | WO-2010056714 A1 | 5/2010 |
| WO | WO-2010063795 A1 | 6/2010 |
| WO | WO-2010090940 A1 | 8/2010 |
| WO | WO-2010093333 A1 | 8/2010 |
| WO | WO-2010098871 A2 | 9/2010 |
| WO | WO-2010134913 A1 | 11/2010 |
| WO | WO-2011008672 A2 | 1/2011 |
| WO | WO-2011013103 A1 | 2/2011 |
| WO | WO-2011044343 A2 | 4/2011 |
| WO | WO-2011056458 A1 | 5/2011 |
| WO | WO-2011060311 A2 | 5/2011 |
| WO | WO-2011084969 A1 | 7/2011 |
| WO | WO-2011127137 A1 | 10/2011 |
| WO | WO-2012006306 A2 | 1/2012 |
| WO | WO-2012009431 A2 | 1/2012 |
| WO | WO-2012/013577 A1 | 2/2012 |
| WO | WO-2012021671 A1 | 2/2012 |
| WO | WO-2012040438 A1 | 3/2012 |
| WO | WO-2012044551 A1 | 4/2012 |
| WO | WO-2012044554 A1 | 4/2012 |
| WO | WO-2012044597 A1 | 4/2012 |
| WO | WO-2012044606 A2 | 4/2012 |
| WO | WO-2012044820 A1 | 4/2012 |
| WO | WO-2012044844 A2 | 4/2012 |
| WO | WO-2012044853 A1 | 4/2012 |
| WO | WO-2012044854 A1 | 4/2012 |
| WO | WO-2012058213 A2 | 5/2012 |
| WO | WO-2012068156 A2 | 5/2012 |
| WO | WO-2012109760 A1 | 8/2012 |
| WO | WO-2012127462 A2 | 9/2012 |
| WO | WO-2012135705 A1 | 10/2012 |
| WO | WO-2012143913 A2 | 10/2012 |
| WO | WO-2012148667 A2 | 11/2012 |
| WO | WO-2012148668 A2 | 11/2012 |
| WO | WO-2012148703 A2 | 11/2012 |
| WO | WO-2012160163 A1 | 11/2012 |
| WO | WO-2012166503 A1 | 12/2012 |
| WO | WO-2013009252 A2 | 1/2013 |
| WO | WO-2013009699 A2 | 1/2013 |
| WO | WO-2013023114 A1 | 2/2013 |
| WO | WO-2013036409 A1 | 3/2013 |
| WO | WO-2013043707 A2 | 3/2013 |
| WO | WO-2013043717 A1 | 3/2013 |
| WO | WO-2013043721 A2 | 3/2013 |
| WO | WO-2013062978 A2 | 5/2013 |
| WO | WO-2013116869 A1 | 8/2013 |
| WO | WO-2013148762 A2 | 10/2013 |
| WO | WO-2013151888 A1 | 10/2013 |
| WO | WO-2013167427 A1 | 11/2013 |
| WO | WO-2013188130 A1 | 12/2013 |
| WO | WO-2014/008289 A2 | 1/2014 |
| WO | WO-2014004199 A1 | 1/2014 |
| WO | WO-2014004209 A2 | 1/2014 |
| WO | WO-2014004294 A2 | 1/2014 |
| WO | WO-2014/113438 A1 | 7/2014 |
| WO | WO-2014/134034 A2 | 9/2014 |
| WO | WO-2014/172213 A2 | 10/2014 |
| WO | WO-2014158882 A2 | 10/2014 |
| WO | WO-2015/032797 A1 | 3/2015 |
| WO | WO-2015138760 A1 | 9/2015 |
| WO | WO-2015/148136 A1 | 10/2015 |
| WO | WO-2015148141 A1 | 10/2015 |
| WO | WO-2015153642 A1 | 10/2015 |
| WO | WO-2015187107 A1 | 12/2015 |

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

(56) References Cited

OTHER PUBLICATIONS

Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
Pitt et al., "Attachment of Hyaluronan to Metallic Surfaces," J. Biomed. Mater. Res. 68A: pp. 95-106, 2004.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
"Indian Standard: Automotive Vehicles—Brakes and Braking Systems (IS 11852-1:2001)", Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Covidien Brochure "iDrive™ Ultra Powered Stapling System," (6 pages).
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.

Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
"Biomedical Coatings," Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al, Comparison of the effects of Mg—6Zn and Ti—3Al—2.5V alloys on TGF-β/TNF-α/VEGF/b-FGF in the healing of the intestinal track in vivo, Biomed. Mater. 9 (2014), 11 pages.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue

(56) References Cited

OTHER PUBLICATIONS

Engineering Part B—Reviews, vol. 19, No. 6, Dec. 1, 2013, pp. 485-502.

\* cited by examiner

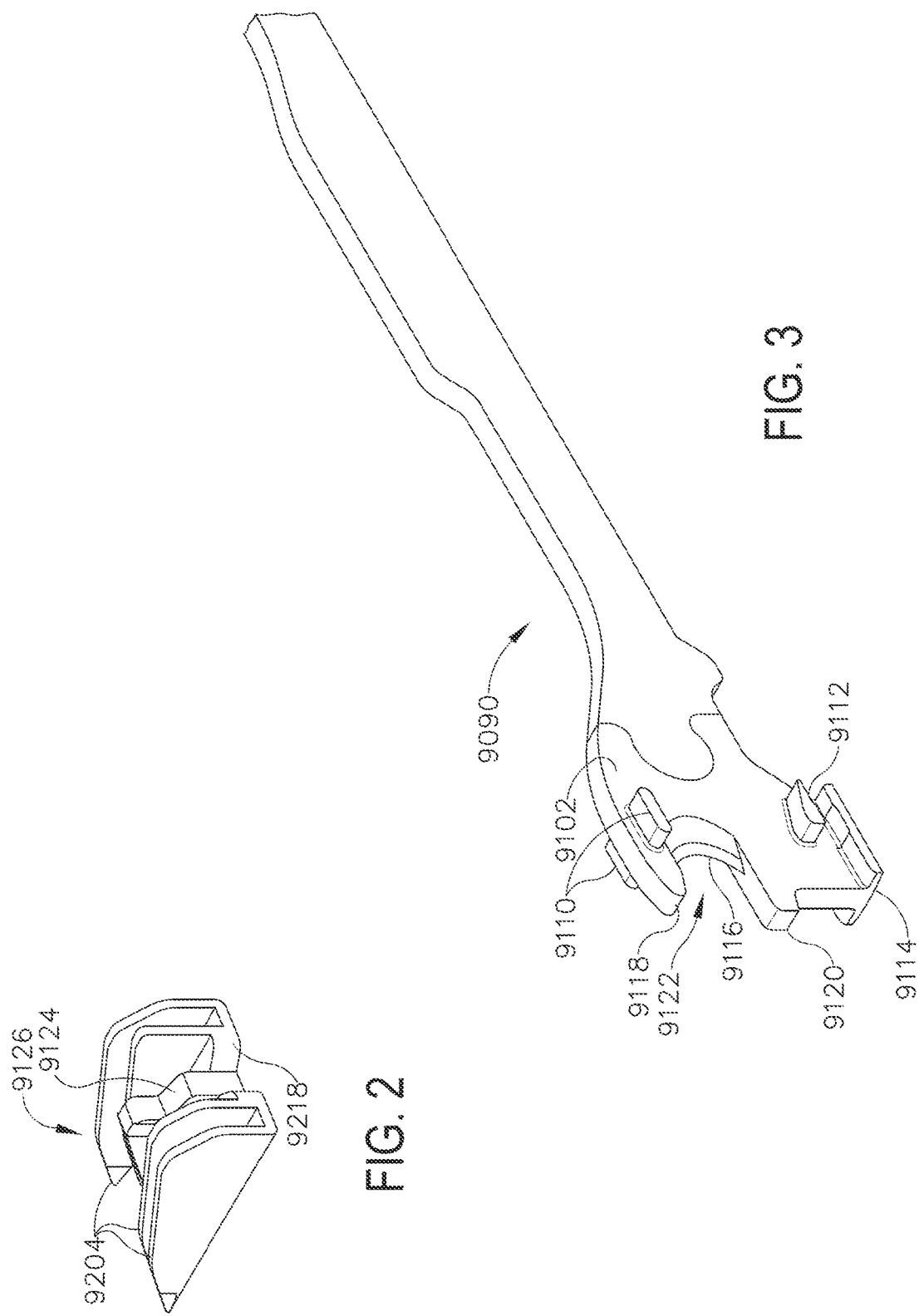

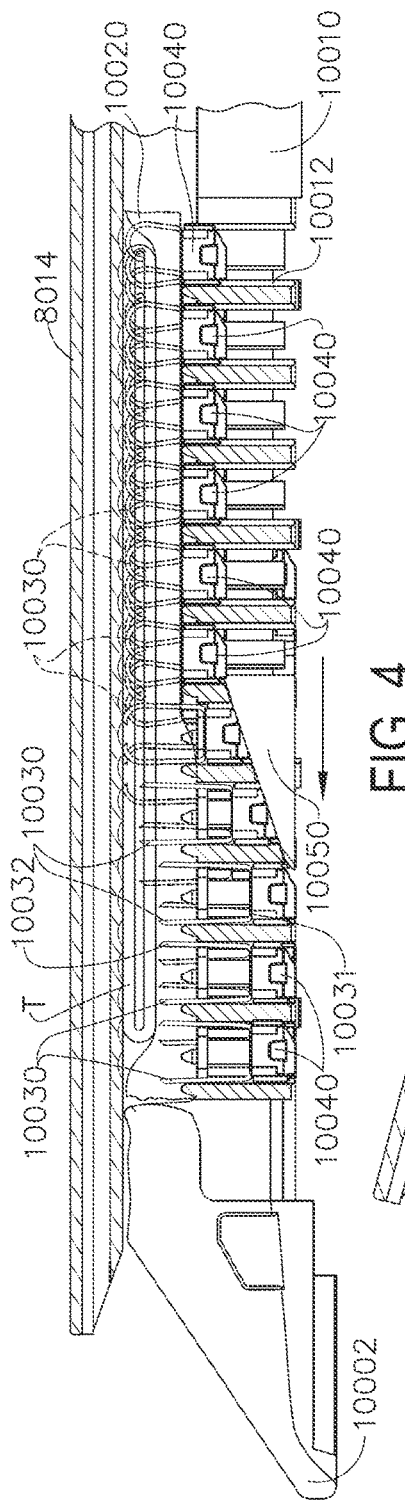
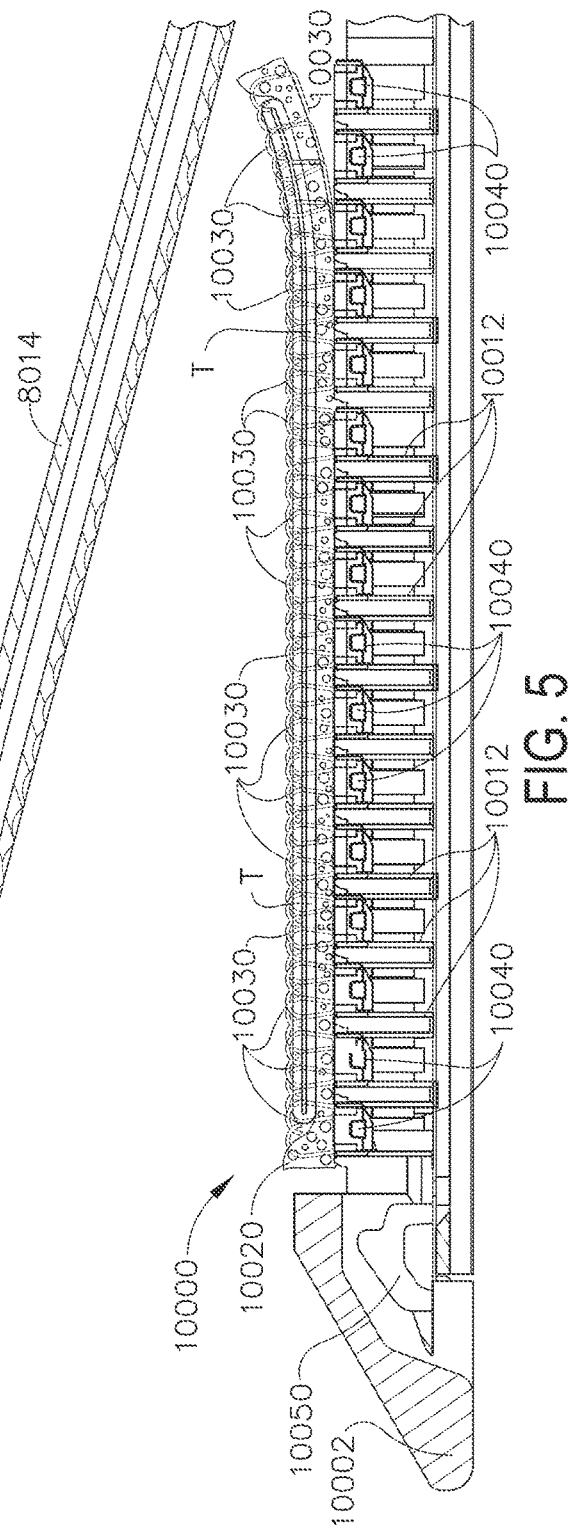
FIG. 4
FIG. 5

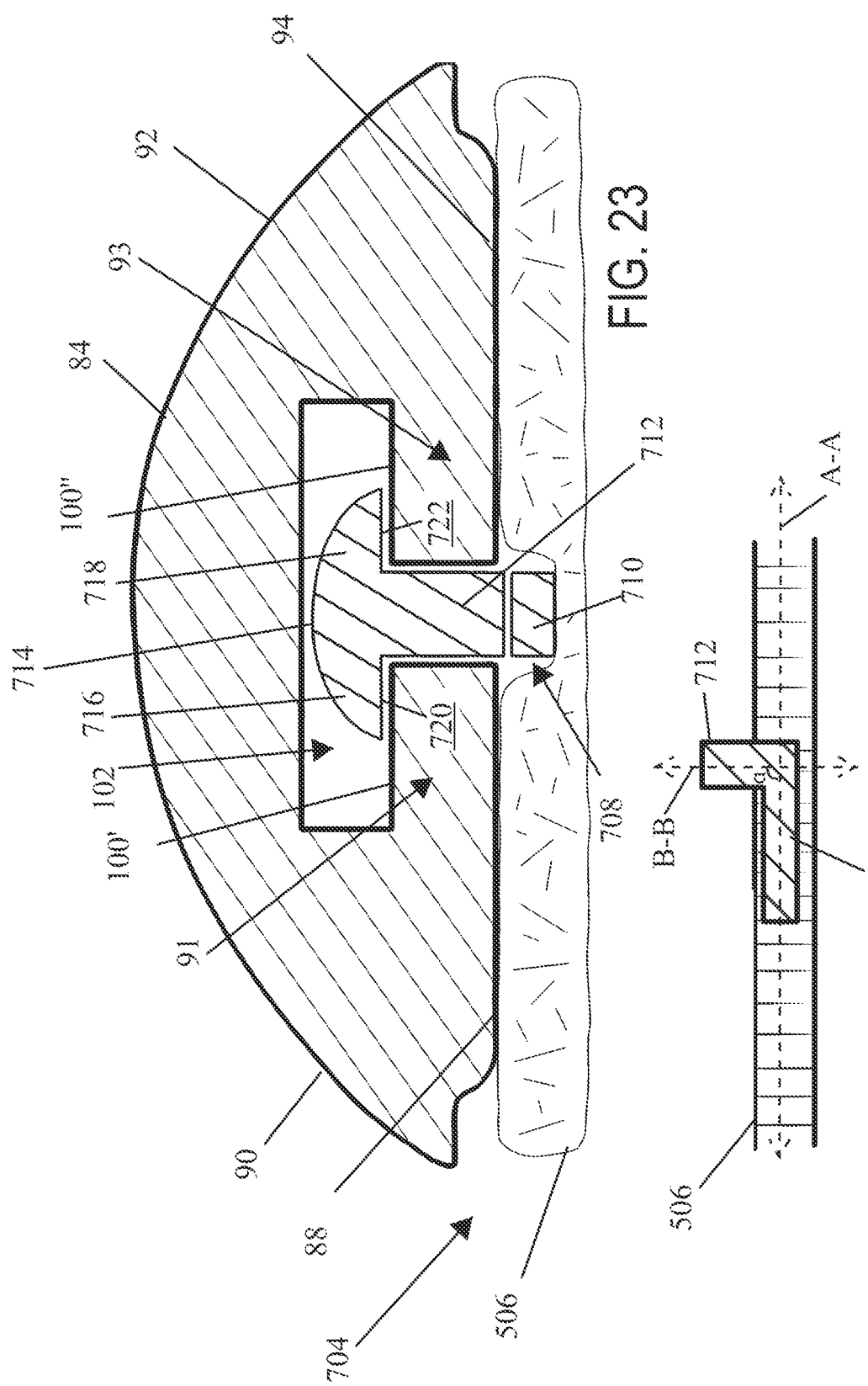

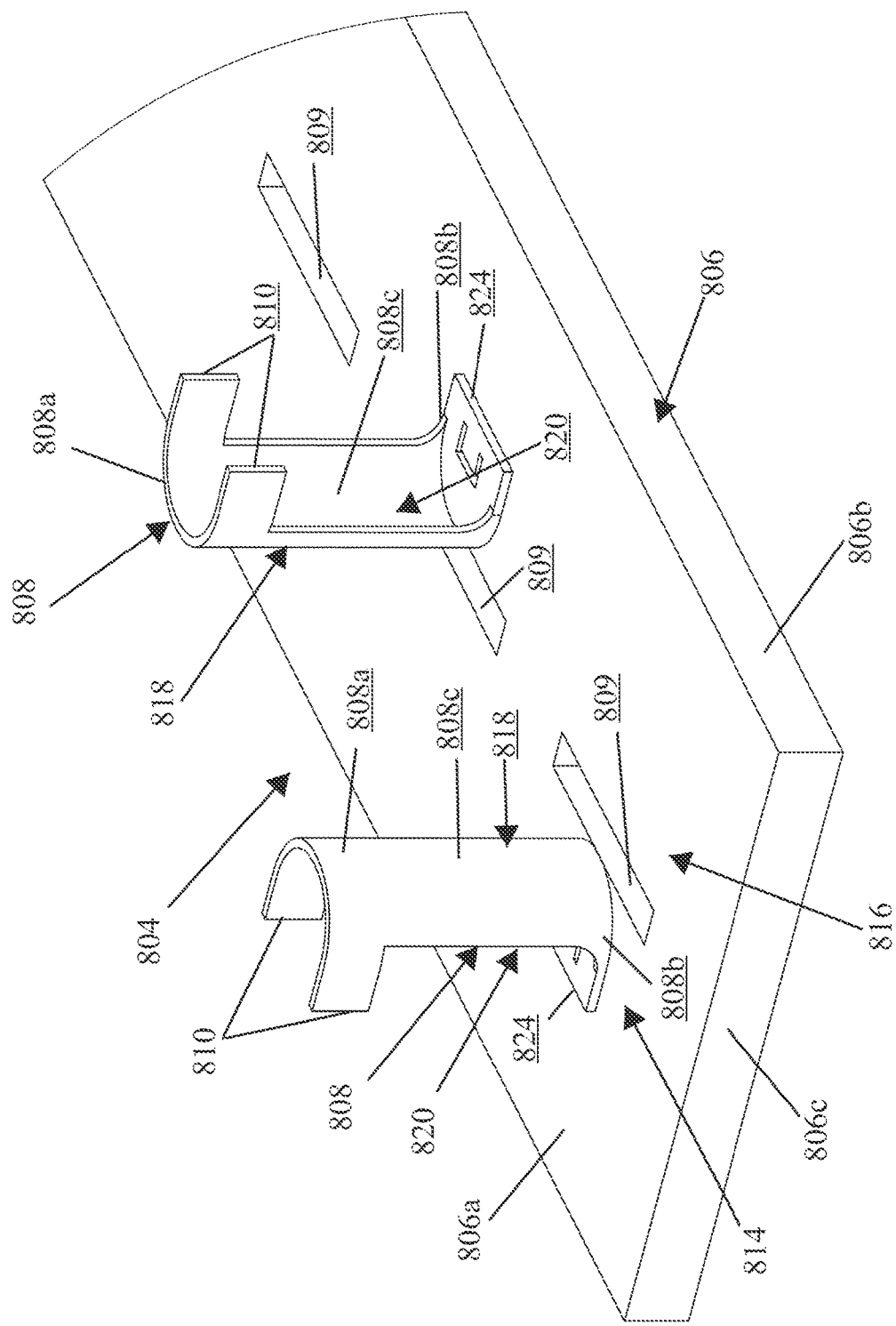

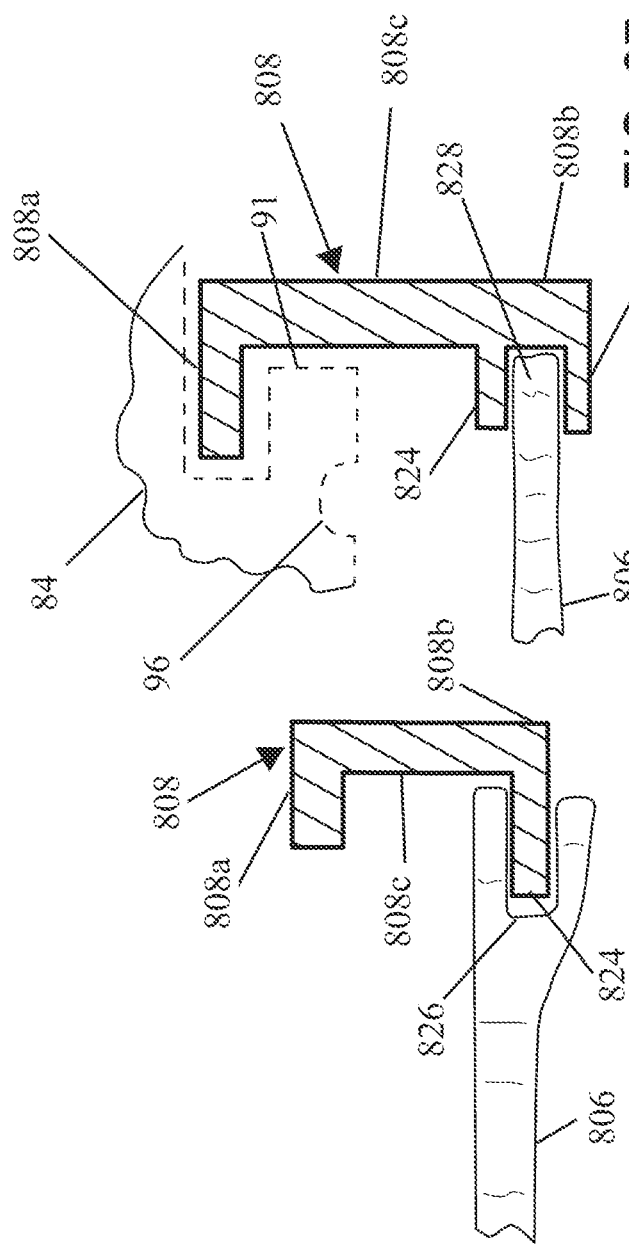

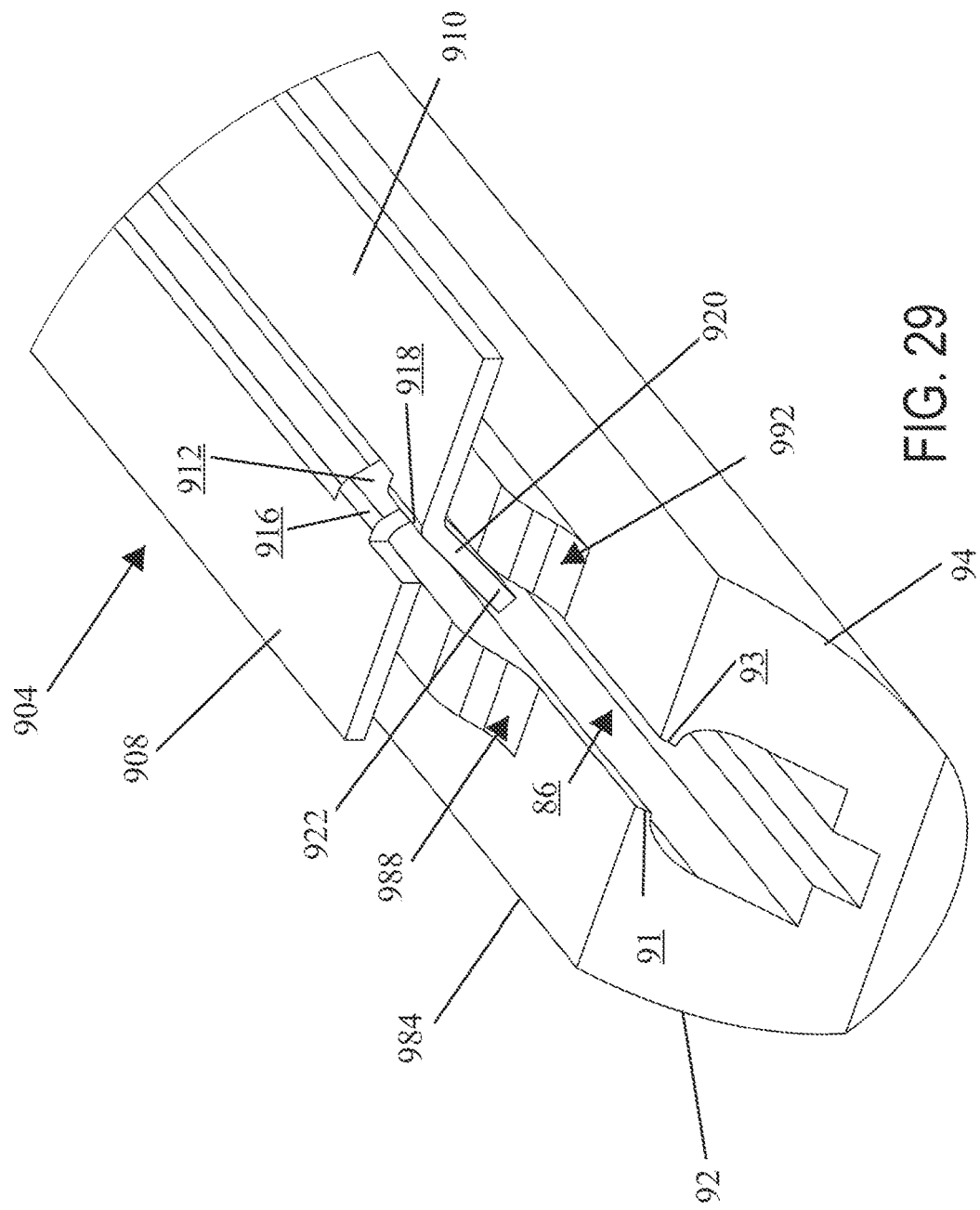

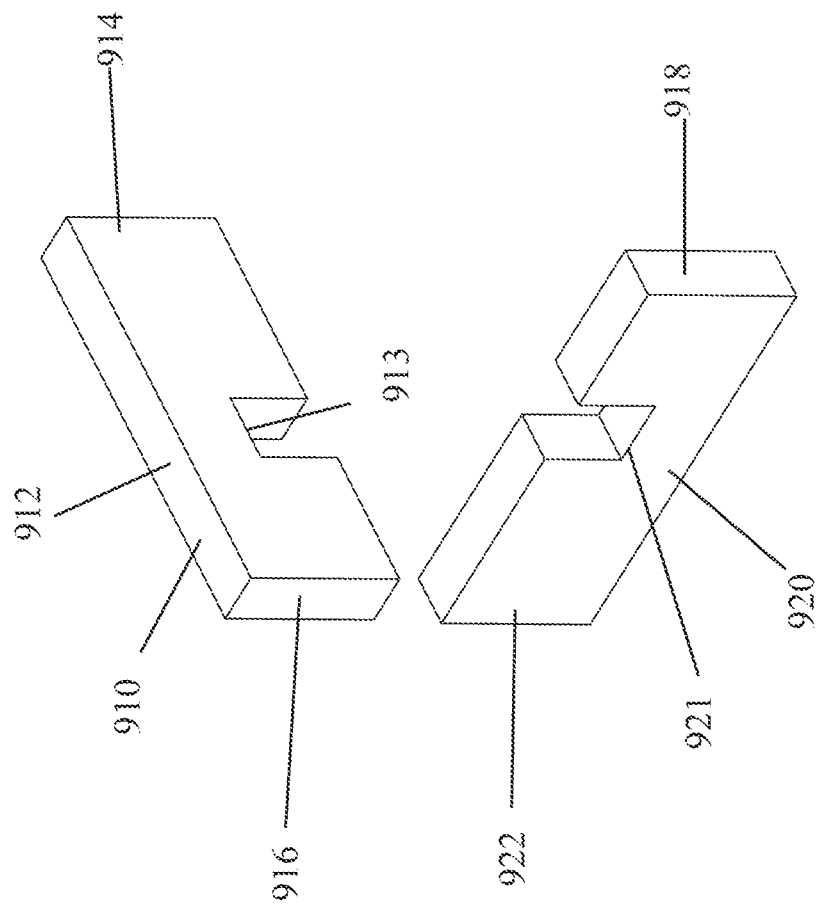

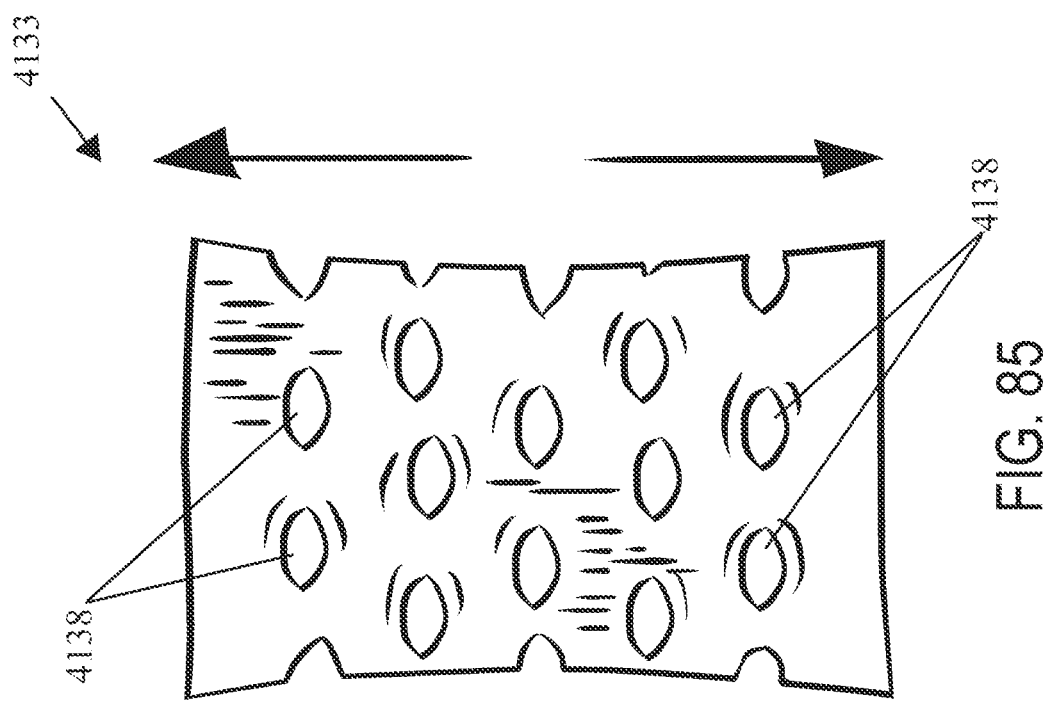

COMPRESSIBLE ADJUNCT WITH ATTACHMENT REGIONS

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIG. 2 is a perspective view of a wedge sled of a staple cartridge of the surgical stapling and severing instrument of FIG. 1;

FIG. 3 is a perspective view of a two-piece knife and firing bar ("E-beam") of the surgical stapling and severing instrument of FIG. 1;

FIG. 4 is a longitudinal cross-sectional view of an anvil in a closed position, a staple cartridge comprising a rigid support portion, and a compressible adjunct illustrated with staples being moved from an unfired position to a fired position during a firing sequence;

FIG. 5 is another cross-sectional view of the anvil and the staple cartridge of FIG. 4 illustrating the anvil in an open position after the firing sequence has been completed;

FIG. 23 is a transverse cross-sectional view of an anvil assembled with the compressible adjunct assembly of FIG. 22;

FIG. 24 is a partial longitudinal cross-sectional view of the compressible adjunct assembly of FIG. 22;

FIG. 25 is a partial perspective view of a compressible adjunct assembly including a compressible layer and a plurality of attachment members in accordance with at least one embodiment described herein;

FIG. 26 is a partial longitudinal cross-sectional view of an attachment member attached to a compressible layer in accordance with at least one embodiment described herein;

FIG. 27 is a partial longitudinal cross-sectional view of an attachment member attached to a compressible layer in accordance with at least one embodiment described herein;

FIG. 28 is a partial longitudinal cross-sectional view of an attachment member attached to a compressible layer in accordance with at least one embodiment described herein;

FIG. 29 is a partial perspective view of an anvil assembled with two attachment layers in accordance with at least one embodiment described herein;

FIG. 30 is a perspective view of attachment members of the attachment layers of FIG. 29;

FIG. 85 illustrates the implantable layer portion of FIG. 84 in a stretched condition;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
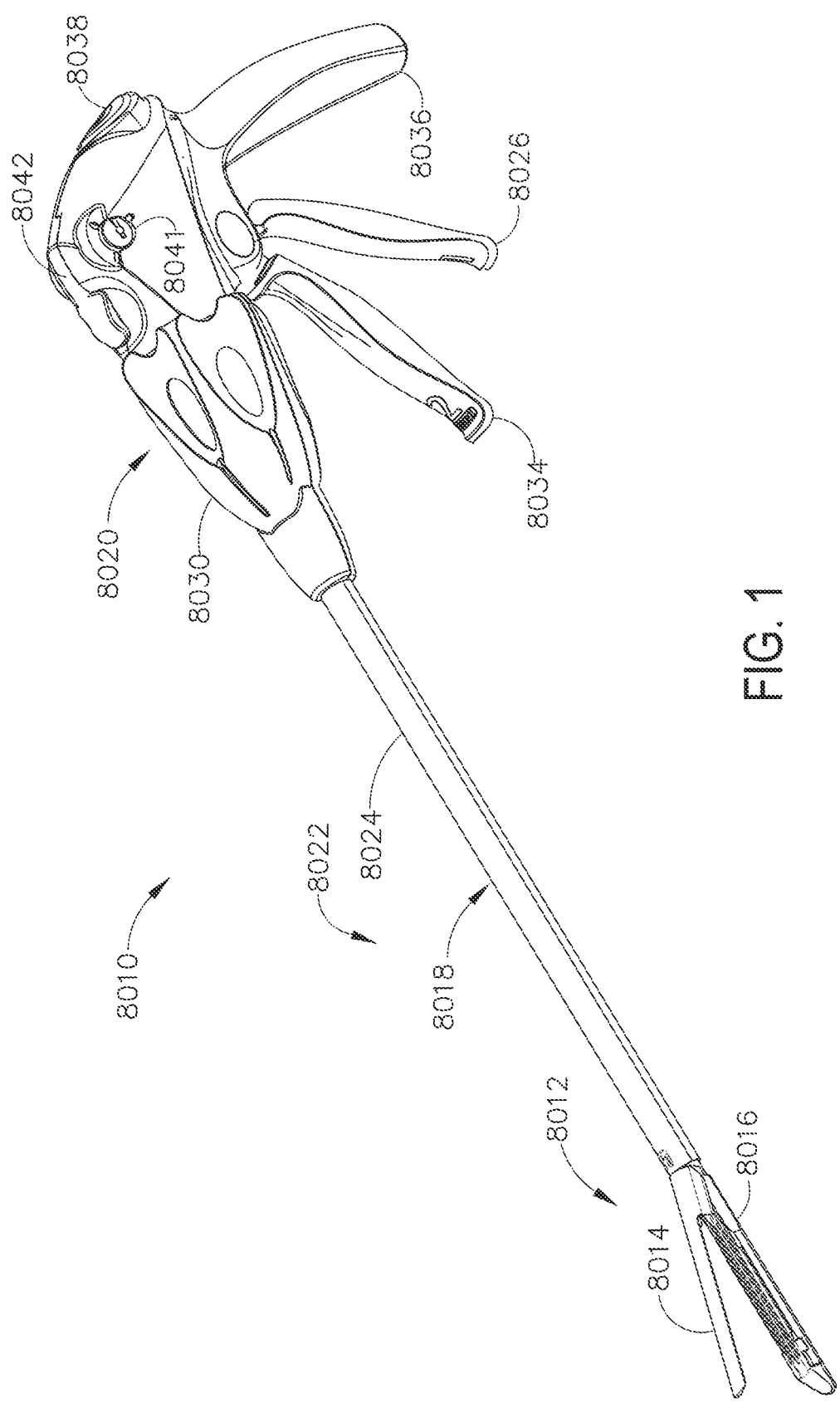
FIG. 1 is a perspective view of a surgical stapling and severing instrument comprising a handle, a shaft extending from the handle, and an end effector extending including an anvil and a staple cartridge.

The Applicant of the present application owns the following U.S. Patent Applications that were filed on Sep. 30, 2015 and which are each herein incorporated by reference in their respective entireties:

U.S. patent application Ser. No. 14/871,036, entitled IMPLANTABLE LAYER COMPRISING PLASTICALLY DEFORMED FIBERS, now U.S. Pat. No. 10,327,777;

U.S. patent application Ser. No. 14/871,056, entitled IMPLANTABLE LAYER COMPRISING A CONSTRICTED CONFIGURATION, now U.S. Patent Application Publication No. 2017/0086836;

U.S. patent application Ser. No. 14/871,078, entitled TUBULAR ABSORBABLE CONSTRUCTS, now U.S. Patent Application Publication No. 2017/0086832;

U.S. patent application Ser. No. 14/871,087, entitled IMPLANTABLE ADJUNCT COMPRISING BONDED LAYERS, now U.S. Patent Application Publication No. 2017/0086838;

U.S. patent application Ser. No. 14/871,107, entitled COMPRESSIBLE ADJUNCTS WITH BONDING NODES, now U.S. Pat. No. 10,172,620;

U.S. patent application Ser. No. 14/871,057, entitled COMPRESSIBLE ADJUNCT WITH INTERMEDIATE SUPPORTING STRUCTURES, now U.S. Patent Application Publication No. 2017/0086829;

U.S. patent application Ser. No. 14/871,071, entitled COMPRESSIBLE ADJUNCT WITH CROSSING SPACER FIBERS, now U.S. Patent Application Publication No. 2017/0086837;

U.S. patent application Ser. No. 14/871,083, entitled COMPRESSIBLE ADJUNCT WITH LOOPING MEMBERS, now U.S. Patent Application Publication No. 2017/0086827;

U.S. patent application Ser. No. 14/871,089, entitled WOVEN CONSTRUCTS WITH INTERLOCKED STANDING FIBERS, now U.S. Pat. No. 10,271,849;

U.S. patent application Ser. No. 14/871,119, entitled COMPRESSIBLE ADJUNCT AND METHODS FOR MAKING THE SAME, now U.S. Pat. No. 10,285,699;

U.S. patent application Ser. No. 14/871,131, entitled METHOD FOR APPLYING AN IMPLANTABLE LAYER TO A FASTENER CARTRIDGE, now U.S. Patent Application Publication No. 2017/0086842;

U.S. patent application Ser. No. 14/871,176, entitled PROGRESSIVELY RELEASABLE IMPLANTABLE ADJUNCT FOR USE WITH A SURGICAL STAPLING INSTRUMENT, now U.S. Patent Application Publication No. 2017/0086844; and U.S. patent application Ser. No. 14/871,195, entitled COMPRESSIBLE ADJUNCT ASSEMBLIES WITH ATTACHMENT LAYERS, now U.S. Pat. No. 10,307,160.

The Applicant of the present application also owns the U.S. patent applications identified below which are each herein incorporated by reference in their respective entireties:

U.S. patent application Ser. No. 12/894,311, entitled SURGICAL INSTRUMENTS WITH RECONFIGURABLE SHAFT SEGMENTS; now U.S. Pat. No. 8,763,877;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS; now U.S. Pat. No. 8,899,463;

U.S. patent application Ser. No. 12/894,327, entitled JAW CLOSURE ARRANGEMENTS FOR SURGICAL INSTRUMENTS; now U.S. Pat. No. 8,978,956;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS; now U.S. Pat. No. 9,113,864;

U.S. patent application Ser. No. 12/894,338, entitled IMPLANTABLE FASTENER CARTRIDGE HAVING A NON-UNIFORM ARRANGEMENT; now U.S. Pat. No. 8,864,007;

U.S. patent application Ser. No. 12/894,369, entitled IMPLANTABLE FASTENER CARTRIDGE COMPRISING A SUPPORT RETAINER; now U.S. Patent Application Publication No. 2012/0080344;

U.S. patent application Ser. No. 12/894,312, entitled IMPLANTABLE FASTENER CARTRIDGE COMPRISING MULTIPLE LAYERS; now U.S. Pat. No. 8,925,782;

U.S. patent application Ser. No. 12/894,377, entitled SELECTIVELY ORIENTABLE IMPLANTABLE FASTENER CARTRIDGE; now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT; now U.S. Pat. No. 8,840,003;

U.S. patent application Ser. No. 12/894,360, entitled SURGICAL STAPLING INSTRUMENT WITH A VARIABLE STAPLE FORMING SYSTEM; now U.S. Pat. No. 9,113,862;

U.S. patent application Ser. No. 12/894,322, entitled SURGICAL STAPLING INSTRUMENT WITH INTERCHANGEABLE STAPLE CARTRIDGE ARRANGEMENTS; now U.S. Pat. No. 8,740,034;

U.S. patent application Ser. No. 12/894,350, entitled SURGICAL STAPLE CARTRIDGES WITH DETACHABLE SUPPORT STRUCTURES; now U.S. Patent Application Publication No. 2012/0080478;

U.S. patent application Ser. No. 12/894,383, entitled IMPLANTABLE FASTENER CARTRIDGE COMPRISING BIOABSORBABLE LAYERS; now U.S. Pat. No. 8,752,699;

U.S. patent application Ser. No. 12/894,389, entitled COMPRESSIBLE FASTENER CARTRIDGE; now U.S. Pat. No. 8,740,037;

U.S. patent application Ser. No. 12/894,345, entitled FASTENERS SUPPORTED BY A FASTENER CARTRIDGE SUPPORT; now U.S. Pat. No. 8,783,542;

U.S. patent application Ser. No. 12/894,306, entitled COLLAPSIBLE FASTENER CARTRIDGE; now U.S. Pat. No. 9,044,227;

U.S. patent application Ser. No. 12/894,318, entitled FASTENER SYSTEM COMPRISING A PLURALITY OF CONNECTED RETENTION MATRIX ELEMENTS; now U.S. Pat. No. 8,814,024;

U.S. patent application Ser. No. 12/894,330, entitled FASTENER SYSTEM COMPRISING A RETENTION MATRIX AND AN ALIGNMENT MATRIX; now U.S. Pat. No. 8,757,465;

U.S. patent application Ser. No. 12/894,361, entitled FASTENER SYSTEM COMPRISING A RETENTION MATRIX; now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX; now U.S. Pat. No. 9,033,203;

U.S. patent application Ser. No. 12/894,388, entitled FASTENER SYSTEM COMPRISING A RETENTION MATRIX AND A COVER; now U.S. Pat. No. 8,474,677;

U.S. patent application Ser. No. 12/894,376, entitled FASTENER SYSTEM COMPRISING A PLURALITY OF FASTENER CARTRIDGES; now U.S. Pat. No. 9,044,228;

U.S. patent application Ser. No. 13/097,865, entitled SURGICAL STAPLER ANVIL COMPRISING A PLURALITY OF FORMING POCKETS; now U.S. Patent Application Publication No. 2012/0080488;

U.S. patent application Ser. No. 13/097,936, entitled TISSUE THICKNESS COMPENSATOR FOR A SURGICAL STAPLER; now U.S. Pat. No. 8,657,176;

U.S. patent application Ser. No. 13/097,954, entitled STAPLE CARTRIDGE COMPRISING A VARIABLE THICKNESS COMPRESSIBLE PORTION; now U.S. Patent Application Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF; now U.S. Patent Application Publication No. 2012/0080336;

U.S. patent application Ser. No. 13/097,928, entitled TISSUE THICKNESS COMPENSATOR COMPRISING DETACHABLE PORTIONS; now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL; now U.S. Pat. No. 8,864,009;

U.S. patent application Ser. No. 13/097,948, entitled STAPLE CARTRIDGE COMPRISING AN ADJUSTABLE DISTAL PORTION; now U.S. Pat. No. 8,978,954;

U.S. patent application Ser. No. 13/097,907, entitled COMPRESSIBLE STAPLE CARTRIDGE ASSEMBLY; now U.S. Patent Application Publication No. 2012/0080338;

U.S. patent application Ser. No. 13/097,861, entitled TISSUE THICKNESS COMPENSATOR COMPRISING PORTIONS HAVING DIFFERENT PROPERTIES; now U.S. Pat. No. 9,113,865;

U.S. patent application Ser. No. 13/097,869, entitled STAPLE CARTRIDGE LOADING ASSEMBLY; now U.S. Pat. No. 8,857,694;

U.S. patent application Ser. No. 13/097,917, entitled COMPRESSIBLE STAPLE CARTRIDGE COMPRISING ALIGNMENT MEMBERS; now U.S. Pat. No. 8,777,004;

U.S. patent application Ser. No. 13/097,873, entitled STAPLE CARTRIDGE COMPRISING A RELEASABLE PORTION; now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS; now U.S. Pat. No. 9,016,542;

U.S. patent application Ser. No. 13/097,924, entitled STAPLE CARTRIDGE COMPRISING A TISSUE THICKNESS COMPENSATOR; now U.S. Patent Application Publication No. 2012/0083835;

U.S. patent application Ser. No. 13/242,029, entitled SURGICAL STAPLER WITH FLOATING ANVIL; now U.S. Pat. No. 8,893,949;

U.S. patent application Ser. No. 13/242,066, entitled CURVED END EFFECTOR FOR A STAPLING INSTRUMENT; now U.S. Patent Application Publication No. 2012/0080498;

U.S. patent application Ser. No. 13/242,086, entitled STAPLE CARTRIDGE INCLUDING COLLAPSIBLE DECK; now U.S. Pat. No. 9,055,941;

U.S. patent application Ser. No. 13/241,912, entitled STAPLE CARTRIDGE INCLUDING COLLAPSIBLE DECK ARRANGEMENT; now U.S. Pat. No. 9,050,084;

U.S. patent application Ser. No. 13/241,922, entitled SURGICAL STAPLER WITH STATIONARY STAPLE DRIVERS; now U.S. Patent Application Publication No. 2013/0075449;

U.S. patent application Ser. No. 13/241,637, entitled SURGICAL INSTRUMENT WITH TRIGGER ASSEMBLY FOR GENERATING MULTIPLE ACTUATION MOTIONS; now U.S. Pat. No. 8,789,741;

U.S. patent application Ser. No. 13/241,629, entitled SURGICAL INSTRUMENT WITH SELECTIVELY ARTICULATABLE END EFFECTOR; now U.S. Patent Application Publication No. 2012/0074200;

U.S. patent application Ser. No. 13/433,096, entitled TISSUE THICKNESS COMPENSATOR COMPRISING A PLURALITY OF CAPSULES; now U.S. Patent Application Publication No. 2012/0241496;

U.S. patent application Ser. No. 13/433,103, entitled TISSUE THICKNESS COMPENSATOR COMPRISING A PLURALITY OF LAYERS; now U.S. Patent Application Publication No. 2012/0241498;

U.S. patent application Ser. No. 13/433,098, entitled EXPANDABLE TISSUE THICKNESS COMPENSATOR; now U.S. Patent Application Publication No. 2012/0241491;

U.S. patent application Ser. No. 13/433,102, entitled TISSUE THICKNESS COMPENSATOR COMPRISING A RESERVOIR; now U.S. Patent Application Publication No. 2012/0241497;

U.S. patent application Ser. No. 13/433,114, entitled RETAINER ASSEMBLY INCLUDING A TISSUE THICKNESS COMPENSATOR; now U.S. Patent Application Publication No. 2012/0241499;

U.S. patent application Ser. No. 13/433,136, entitled TISSUE THICKNESS COMPENSATOR COMPRISING AT LEAST ONE MEDICAMENT; now U.S. Patent Application Publication No. 2012/0241492;

U.S. patent application Ser. No. 13/433,141, entitled TISSUE THICKNESS COMPENSATOR COMPRISING CONTROLLED RELEASE AND EXPANSION; now U.S. Patent Application Publication No. 2012/0241493;

U.S. patent application Ser. No. 13/433,144, entitled TISSUE THICKNESS COMPENSATOR COMPRISING FIBERS TO PRODUCE A RESILIENT LOAD; now U.S. Patent Application Publication No. 2012/0241500;

U.S. patent application Ser. No. 13/433,148, entitled TISSUE THICKNESS COMPENSATOR COMPRISING STRUCTURE TO PRODUCE A RESILIENT LOAD; now U.S. Patent Application Publication No. 2012/0241501;

U.S. patent application Ser. No. 13/433,155, entitled TISSUE THICKNESS COMPENSATOR COMPRISING RESILIENT MEMBERS; now U.S. Patent Application Publication No. 2012/0241502;

U.S. patent application Ser. No. 13/433,163, entitled METHODS FOR FORMING TISSUE THICKNESS COMPENSATOR ARRANGEMENTS FOR SURGICAL STAPLERS; now U.S. Patent Application Publication No. 2012/0248169;

U.S. patent application Ser. No. 13/433,167, entitled TISSUE THICKNESS COMPENSATORS; now U.S. Patent Application Publication No. 2012/0241503;

U.S. patent application Ser. No. 13/433,175, entitled LAYERED TISSUE THICKNESS COMPENSATOR; now U.S. Patent Application Publication No. 2012/0253298;

U.S. patent application Ser. No. 13/433,179, entitled TISSUE THICKNESS COMPENSATORS FOR CIRCULAR SURGICAL STAPLERS; now U.S. Patent Application Publication No. 2012/0241505;

U.S. patent application Ser. No. 13/763,028, entitled ADHESIVE FILM LAMINATE; now U.S. Patent Application Publication No. 2013/0146643;

U.S. patent application Ser. No. 13/433,115, entitled TISSUE THICKNESS COMPENSATOR COMPRISING CAPSULES DEFINING A LOW PRESSURE ENVIRONMENT; now U.S. Patent Application Publication No. 2013/0256372;

U.S. patent application Ser. No. 13/433,118, entitled TISSUE THICKNESS COMPENSATOR COMPRISED OF A PLURALITY OF MATERIALS; now U.S. Patent Application Publication No. 2013/0256365;

U.S. patent application Ser. No. 13/433,135, entitled MOVABLE MEMBER FOR USE WITH A TISSUE THICKNESS COMPENSATOR; now U.S. Patent Application Publication No. 2013/0256382;

U.S. patent application Ser. No. 13/433,140, entitled TISSUE THICKNESS COMPENSATOR AND METHOD FOR MAKING THE SAME; now U.S. Patent Application Publication No. 2013/0256368;

U.S. patent application Ser. No. 13/433,129, entitled TISSUE THICKNESS COMPENSATOR COMPRISING A PLURALITY OF MEDICAMENTS; now U.S. Patent Application Publication No. 2013/0256367;

U.S. patent application Ser. No. 11/216,562, entitled STAPLE CARTRIDGES FOR FORMING STAPLES HAVING DIFFERING FORMED STAPLE HEIGHTS, now U.S. Pat. No. 7,669,746;

U.S. patent application Ser. No. 11/714,049, entitled SURGICAL STAPLING DEVICE WITH ANVIL HAVING STAPLE FORMING POCKETS OF VARYING DEPTHS, now U.S. Patent Application Publication No. 2007/0194082;

U.S. patent application Ser. No. 11/711,979, entitled SURGICAL STAPLING DEVICES THAT PRODUCE FORMED STAPLES HAVING DIFFERENT LENGTHS, now U.S. Pat. No. 8,317,070;

U.S. patent application Ser. No. 11/711,975, entitled SURGICAL STAPLING DEVICE WITH STAPLE DRIVERS OF DIFFERENT HEIGHT, now U.S. Patent Application Publication No. 2007/0194079;

U.S. patent application Ser. No. 11/711,977, entitled SURGICAL STAPLING DEVICE WITH STAPLE DRIVER THAT SUPPORTS MULTIPLE WIRE DIAMETER STAPLES, now U.S. Pat. No. 7,673,781;

U.S. patent application Ser. No. 11/712,315, entitled SURGICAL STAPLING DEVICE WITH MULTIPLE STACKED ACTUATOR WEDGE CAMS FOR DRIVING STAPLE DRIVERS, now U.S. Pat. No. 7,500,979;

U.S. patent application Ser. No. 12/038,939, entitled STAPLE CARTRIDGES FOR FORMING STAPLES HAVING DIFFERING FORMED STAPLE HEIGHTS, now U.S. Pat. No. 7,934,630;

U.S. patent application Ser. No. 13/020,263, entitled SURGICAL STAPLING SYSTEMS THAT PRODUCE FORMED STAPLES HAVING DIFFERENT LENGTHS, now U.S. Pat. No. 8,636,187;

U.S. patent application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Patent Application Publication No. 2011/0290851;

U.S. patent application Ser. No. 13/369,629, entitled ROBOTICALLY-CONTROLLED CABLE-BASED SURGICAL END EFFECTORS, now U.S. Pat. No. 8,800,838;

U.S. patent application Ser. No. 12/695,359, entitled SURGICAL STAPLING DEVICES FOR FORMING STAPLES WITH DIFFERENT FORMED HEIGHTS, now U.S. Pat. No. 8,464,923;

U.S. patent application Ser. No. 13/072,923, entitled STAPLE CARTRIDGES FOR FORMING STAPLES HAVING DIFFERING FORMED STAPLE HEIGHTS, now U.S. Pat. No. 8,567,656;

U.S. patent application Ser. No. 13/766,325, entitled LAYER OF MATERIAL FOR A SURGICAL END EFFECTOR; now U.S. Patent Application Publication No. 2013/0256380;

U.S. patent application Ser. No. 13/763,078, entitled ANVIL LAYER ATTACHED TO A PROXIMAL END OF AN END EFFECTOR; now U.S. Patent Application Publication No. 2013/0256383;

U.S. patent application Ser. No. 13/763,094, entitled LAYER COMPRISING DEPLOYABLE ATTACHMENT MEMBERS; now U.S. Patent Application Publication No. 2013/0256377;

U.S. patent application Ser. No. 13/763,106, entitled END EFFECTOR COMPRISING A DISTAL TISSUE ABUTMENT MEMBER; now U.S. Patent Application Publication No. 2013/0256378;

U.S. patent application Ser. No. 13/433,147, entitled TISSUE THICKNESS COMPENSATOR COMPRISING CHANNELS; now U.S. Patent Application Publication No. 2013/0256369;

U.S. patent application Ser. No. 13/763,112, entitled SURGICAL STAPLING CARTRIDGE WITH LAYER RETENTION FEATURES; now U.S. Patent Application Publication No. 2013/0256379;

U.S. patent application Ser. No. 13/763,035, entitled ACTUATOR FOR RELEASING A TISSUE THICKNESS COMPENSATOR FROM A FASTENER CARTRIDGE; now U.S. Patent Application Publication No. 2013/0214030;

U.S. patent application Ser. No. 13/763,042, entitled RELEASABLE TISSUE THICKNESS COMPENSATOR AND FASTENER CARTRIDGE HAVING THE SAME; now U.S. Patent Application Publication No. 2013/0221063;

U.S. patent application Ser. No. 13/763,048, entitled FASTENER CARTRIDGE COMPRISING A RELEASABLE TISSUE THICKNESS COMPENSATOR; now U.S. Patent Application Publication No. 2013/0221064;

U.S. patent application Ser. No. 13/763,054, entitled FASTENER CARTRIDGE COMPRISING A CUTTING MEMBER FOR RELEASING A TISSUE THICKNESS COMPENSATOR; now U.S. Patent Application Publication No. 2014/0097227;

U.S. patent application Ser. No. 13/763,065, entitled FASTENER CARTRIDGE COMPRISING A RELEASABLY ATTACHED TISSUE THICKNESS COMPENSATOR; now U.S. Patent Application Publication No. 2013/0221065;

U.S. patent application Ser. No. 13/763,021, entitled STAPLE CARTRIDGE COMPRISING A RELEASABLE COVER; now U.S. Patent Application Publication No. 2014/0224686;

U.S. patent application Ser. No. 13/763,078, entitled ANVIL LAYER ATTACHED TO A PROXIMAL END OF AN END EFFECTOR; now U.S. Patent Application Publication No. 2013/0256383;

U.S. patent application Ser. No. 13/763,095, entitled LAYER ARRANGEMENTS FOR SURGICAL STAPLE CARTRIDGES; now U.S. Patent Application Publication No. 2013/0161374;

U.S. patent application Ser. No. 13/763,147, entitled IMPLANTABLE ARRANGEMENTS FOR SURGICAL STAPLE CARTRIDGES; now U.S. Patent Application Publication No. 2013/0153636;

U.S. patent application Ser. No. 13/763,192, entitled MULTIPLE THICKNESS IMPLANTABLE LAYERS FOR SURGICAL STAPLING DEVICES; now U.S. Patent Application Publication No. 2013/0146642;

U.S. patent application Ser. No. 13/763,161, entitled RELEASABLE LAYER OF MATERIAL AND SURGICAL END EFFECTOR HAVING THE SAME; now U.S. Patent Application Publication No. 2013/0153641;

U.S. patent application Ser. No. 13/763,177, entitled ACTUATOR FOR RELEASING A LAYER OF MATERIAL FROM A SURGICAL END EFFECTOR; now U.S. Patent Application Publication No. 2013/0146641;

U.S. patent application Ser. No. 13/763,037, entitled STAPLE CARTRIDGE COMPRISING A COMPRESSIBLE PORTION; now U.S. Patent Application Publication No. 2014/0224857;

U.S. patent application Ser. No. 13/433,126, entitled TISSUE THICKNESS COMPENSATOR COMPRISING TISSUE INGROWTH FEATURES; now U.S. Patent Application Publication No. 2013/0256366;

U.S. patent application Ser. No. 13/433,132, entitled DEVICES AND METHODS FOR ATTACHING TISSUE THICKNESS COMPENSATING MATERIALS TO SURGICAL STAPLING INSTRUMENTS; now U.S. Patent Application Publication No. 2013/0256373;

U.S. patent application Ser. No. 13/851,703, entitled FASTENER CARTRIDGE COMPRISING A TISSUE THICKNESS COMPENSATOR INCLUDING OPENINGS THEREIN; now U.S. Patent Application Publication No. 2014/0291382;

U.S. patent application Ser. No. 13/851,676, entitled TISSUE THICKNESS COMPENSATOR COMPRISING A CUTTING MEMBER PATH; now U.S. Patent Application Publication No. 2014/0291379;

U.S. patent application Ser. No. 13/851,693, entitled FASTENER CARTRIDGE ASSEMBLIES; now U.S. Patent Application Publication No. 2014/0291381;

U.S. patent application Ser. No. 13/851,684, entitled FASTENER CARTRIDGE COMPRISING A TISSUE THICKNESS COMPENSATOR AND A GAP SETTING ELEMENT; now U.S. Patent Application Publication No. 2014/0291380;

U.S. patent application Ser. No. 14/187,387, entitled STAPLE CARTRIDGE INCLUDING A BARBED STAPLE, now U.S. Patent Application Publication No. 2014/0166724;

U.S. patent application Ser. No. 14/187,395, entitled STAPLE CARTRIDGE INCLUDING A BARBED STAPLE, now U.S. Patent Application Publication No. 2014/0166725;

U.S. patent application Ser. No. 14/187,400, entitled STAPLE CARTRIDGE INCLUDING A BARBED STAPLE, now U.S. Patent Application Publication No. 2014/0166726;

U.S. patent application Ser. No. 14/187,383, entitled IMPLANTABLE LAYERS AND METHODS FOR ALTERING IMPLANTABLE LAYERS FOR USE WITH SURGICAL FASTENING INSTRUMENTS, now U.S. Patent Application Publication No. 2015/0238185;

U.S. patent application Ser. No. 14/187,386, entitled IMPLANTABLE LAYERS AND METHODS FOR ALTERING ONE OR MORE PROPERTIES OF IMPLANTABLE LAYERS FOR USE WITH FASTENING INSTRUMENTS, now U.S. Patent Application Publication No. 2015/0239180;

U.S. patent application Ser. No. 14/187,390, entitled IMPLANTABLE LAYERS AND METHODS FOR MODIFYING THE SHAPE OF THE IMPLANTABLE LAYERS FOR USE WITH A SURGICAL FASTENING INSTRUMENT, now U.S. Patent Application Publication No. 2015/0238188;

U.S. patent application Ser. No. 14/187,389, entitled IMPLANTABLE LAYER ASSEMBLIES, now U.S. Patent Application Publication No. 2015/0238187;

U.S. patent application Ser. No. 14/187,385, entitled IMPLANTABLE LAYERS COMPRISING A PRESSED REGION, now U.S. Patent Application Publication No. 2015/0238191;

U.S. patent application Ser. No. 14/187,384, entitled FASTENING SYSTEM COMPRISING A FIRING MEMBER LOCKOUT, now U.S. Patent Application Publication No. 2015/0238186;

U.S. patent application Ser. No. 14/827,856, entitled IMPLANTABLE LAYERS FOR A SURGICAL INSTRUMENT;

U.S. patent application Ser. No. 14/827,907, entitled IMPLANTABLE LAYERS FOR A SURGICAL INSTRUMENT;

U.S. patent application Ser. No. 14/827,932, entitled IMPLANTABLE LAYERS FOR A SURGICAL INSTRUMENT;

U.S. patent application Ser. No. 14/667,874, entitled MALLEABLE BIOABSORBABLE POLYMER ADHESIVE FOR RELEASABLY ATTACHING A STAPLE BUTTRESS TO A SURGICAL STAPLER;

U.S. patent application Ser. No. 14/300,954, entitled ADJUNCT MATERIALS AND METHODS OF USING SAME IN SURGICAL METHODS FOR TISSUE SEALING;

U.S. patent application Ser. No. 14/840,613, entitled DRUG ELUTING ADJUNCTS AND METHODS OF USING DRUG ELUTING ADJUNCTS;

U.S. patent application Ser. No. 14/498,145, entitled METHOD FOR CREATING A FLEXIBLE STAPLE LINE; and U.S. patent application Ser. No. 14/865,306, entitled IMPLANTABLE ADJUNCT SYSTEMS FOR DETERMINING ADJUNCT SKEW.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which an end effector and elongated shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

The staple cartridge can also include an implantable layer. The implantable layer is configured to be captured within a staple along with tissue when the staple is deployed by the corresponding driver. The implantable layer can comprise a buttress, a tissue thickness compensator, and/or other adjunct material. A tissue thickness compensator is configured to compensate for variations in tissue properties, such as variations in the thickness of tissue, for example, along a staple line. A tissue thickness compensator can be compressible and resilient. In use, a tissue thickness compensator prevents or limits the over-compression of stapled tissue while facilitating adequate tissue compression within and between staples.

The implantable layer of a staple cartridge can be releasably secured to the body of the staple cartridge. For example, the implantable layer can be releasably secured to the deck of the staple cartridge with a releasable adhesive, at least one attachment tab, and/or other attachment features. Additionally or alternatively, an implantable layer can be releasably secured to the first jaw or the second jaw. An implantable layer can be positioned on the cartridge-side of an end effector and/or the anvil-side of the end effector, for example.

An implantable layer can be configured to promote tissue ingrowth. In various instances, it is desirable to promote the ingrowth of tissue into an implantable layer to promote the healing of the treated tissue (e.g. stapled and/or incised tissue) and/or to accelerate the patient's recovery. More specifically, the ingrowth of tissue into an implantable layer may reduce the incidence, extent, and/or duration of inflammation at the surgical site. Tissue ingrowth into and/or around the implantable layer may manage the spread of infections at the surgical site, for example. The ingrowth of blood vessels, especially white blood cells, for example, into and/or around the implantable layer may fight infections in and/or around the implantable layer and the adjacent tissue. Tissue ingrowth may also encourage the acceptance of foreign matter (e.g. the implantable layer and the staples) by the patient's body and may reduce the likelihood of the patient's body rejecting the foreign matter. Rejection of foreign matter may cause infection and/or inflammation at the surgical site.

Turning to the Drawings wherein like numerals denote like components throughout the several views, FIG. 1 illustrates an exemplary surgical stapling and severing instrument 8010 suitable for use with an implantable adjunct such as, for example, a tissue thickness compensator. The surgical stapling and severing instrument 8010 can comprise an anvil 8014 which may be repeatedly opened and closed about its pivotal attachment to an elongate staple channel 8016. A staple applying assembly 8012 may comprise the anvil 8014 and the channel 8016, wherein the assembly 8012 can be proximally attached to an elongate shaft 8018 forming an implement portion 8022. When the staple applying assembly 8012 is closed, or at least substantially closed, the implement portion 8022 can present a sufficiently small cross-section suitable for inserting the staple applying assembly 8012 through a trocar.

In various circumstances, the staple cartridge assembly 8012 is manipulated by a handle 8020 connected to the elongate shaft 8018. The handle 8020 can comprise user controls such as a rotation knob 8030 that rotates the elongate shaft 8018 and the staple applying assembly 8012 about a longitudinal axis of the shaft 8018 and a closure trigger 8026, which can pivot in front of a pistol grip 8036 to close the staple applying assembly 8012. A closure release button 8038 is outwardly presented on the handle 8020 when the closure trigger 8026 is clamped such that the release button 8038 can be depressed to unclamp the closure trigger 8026 and open the staple applying assembly 8012, for example.

A firing trigger 8034, which can pivot in front of the closure trigger 8026, causes the staple applying assembly 8012 to simultaneously sever and staple tissue clamped therein. In various circumstances, multiple firing strokes can be employed using the firing trigger 8034 to reduce the amount of force required to be applied by the surgeon's hand per stroke. In certain embodiments, the handle 8020 can comprise one or more rotatable indicator wheels such as, for example, rotatable indicator wheel 8041 which can indicate the firing progress. A manual firing release lever 8042 can allow the firing system to be retracted before full firing travel has been completed, if desired, and, in addition, the firing release lever 8042 can allow a surgeon, or other clinician, to retract the firing system in the event that the firing system binds and/or fails.

Additional details on the surgical stapling and severing instrument 8010 and other surgical stapling and severing instruments suitable for use with the present disclosure are described, for example, in U.S. patent application Ser. No. 13/851,693, entitled FASTENER CARTRIDGE ASSEMBLY, and filed on Mar. 27, 2013, now U.S. Patent Application Publication No. 2014/0291381, the entire disclosure of which is incorporated herein by reference. Furthermore, powered surgical stapling and severing instruments can also be utilized with the present disclosure. See, for example, U.S. Patent Application Publication No. 2009/0090763, entitled POWERED SURGICAL STAPLING DEVICE, and filed on Aug. 12, 2008, the entire disclosure of which is incorporated herein by reference.

With reference to FIGS. 2 and 3, a firing assembly such as, for example, firing assembly 9090 can be utilized with the surgical stapling and severing instrument 8010 to advance a wedge sled 9126 which comprises a plurality of wedges 9204 configured to deploy staples from the staple applying assembly 8012 into tissue captured between the anvil 8014 and the elongate staple channel 8016. Furthermore, an E-beam 9102 at a distal portion of the firing assembly 9090 may fire the stales from the staple applying assembly 8012 as well as position the anvil 8014 relative to the elongate staple channel 8016 during firing. The E-beam 9102 includes a pair of top pins 9110, a pair of middle pins 9112 which may follow portion 9218 of the wedge sled 9126, and a bottom pin or foot 9114, as well as a sharp cutting edge 9116 which can be configured to sever the captured tissue as the firing assembly 9090 is advanced distally. In addition, integrally formed and proximally projecting top guide 9118 and middle guide 9120 bracketing each vertical end of the cutting edge 9116 may further define a tissue staging area 9122 assisting in guiding tissue to the sharp cutting edge 9116 prior to being severed. The middle guide 9120 may also serve to engage and fire the staple applying assembly 8012 by abutting a stepped central member 9124 of the wedge sled 9126 (FIG. 2) that effects staple formation by the staple applying assembly 8012.

In various circumstances, a staple cartridge can comprise means for compensating for the thickness of tissue captured within staples deployed from a staple cartridge. Referring to FIG. 4, a staple cartridge, such as staple cartridge 10000, for example, can be utilized with the surgical stapling and severing instrument 8010 and can include a rigid first portion, such as support portion 10010, for example, and a compressible second portion, such as tissue thickness compensator 10020, for example. The support portion 10010 can comprise a cartridge body and a plurality of staple cavities 10012. A staple 10030, for example, can be removably positioned in each staple cavity 10012. Referring primarily to FIGS. 4 and 5, each staple 10030 can comprise a base 10031 and one or more legs 10032 extending from the base 10031. Prior to the staples 10030 being deployed, the bases 10031 of the staples 10030 can be supported by staple drivers positioned within the support portion 10010 and, concurrently, the legs 10032 of the staples 10030 can be at least partially contained within the staple cavities 10012.

In various circumstances, the staples 10030 can be deployed between an unfired position and a fired position such that the legs 10032 move through the tissue thickness compensator 10020, penetrate through a top surface of the tissue thickness compensator 10020, penetrate the tissue T, and contact an anvil positioned opposite the staple cartridge 10000. As the legs 10032 are deformed against the anvil, the legs 10032 of each staple 10030 can capture a portion of the tissue thickness compensator 10020 and a portion of the tissue T within each staple 10030 and apply a compressive force to the tissue. Further to the above, the legs 10032 of each staple 10030 can be deformed downwardly toward the base 10031 of the staple to form a staple entrapment area in which the tissue T and the tissue thickness compensator 10020 can be captured. In various circumstances, the staple entrapment area can be defined between the inner surfaces of the deformed legs 10032 and the inner surface of the base 10031. The size of the entrapment area for a staple can depend on several factors such as the length of the legs, the diameter of the legs, the width of the base, and/or the extent in which the legs are deformed, for example.

In use, further to the above and referring primarily to FIG. 4, an anvil, such as anvil 8014 of the surgical stapling and severing instrument 8010, can be moved into a closed position opposite the staple cartridge 10000 by depressing the closure trigger 8026 to advance the E-beam 9102. The anvil 8014 can position tissue against the tissue thickness compensator 10020 and, in various circumstances, compress the tissue thickness compensator 10020 against the support portion 10010, for example. Once the anvil 8014 has been suitably positioned, the staples 10030 can be deployed, as also illustrated in FIG. 4.

In various circumstances, as mentioned above, a staple-firing sled 10050, which is similar in many respects to the sled 9126 (See FIG. 3), can be moved from a proximal end of the staple cartridge 10000 toward a distal end 10002, as illustrated in FIG. 5. As the firing assembly 9090 is advanced, the sled 10050 can contact the staple drivers 10040 and lift the staple drivers 10040 upwardly within the staple cavities 10012. In at least one example, the sled 10050 and the staple drivers 10040 can each comprise one or more ramps, or inclined surfaces, which can co-operate to move the staple drivers 10040 upwardly from their unfired positions. As the staple drivers 10040 are lifted upwardly within their respective staple cavities 10012, the staple drivers 10040 can lift the staples 10030 upwardly such that the staples 10030 can emerge from their staple cavities 10012. In various circumstances, the sled 10050 can move several staples upwardly at the same time as part of a firing sequence.

Referring to FIG. 5, the staple legs 10032 of the staples 10030 can extend into the compensator 10020 beyond the support portion 10010 when the staples 10030 are in their unfired positions. In various circumstances, the tips of the staple legs 10032, or any other portion of the staple legs 10032, may not protrude through a top tissue-contacting surface 10021 of the tissue thickness compensator 10020 when the staples 10030 are in their unfired positions. In certain circumstances, the tips of the staple legs 10032 can comprise sharp tips which can incise and penetrate the tissue thickness compensator 10020.

Figure 6:
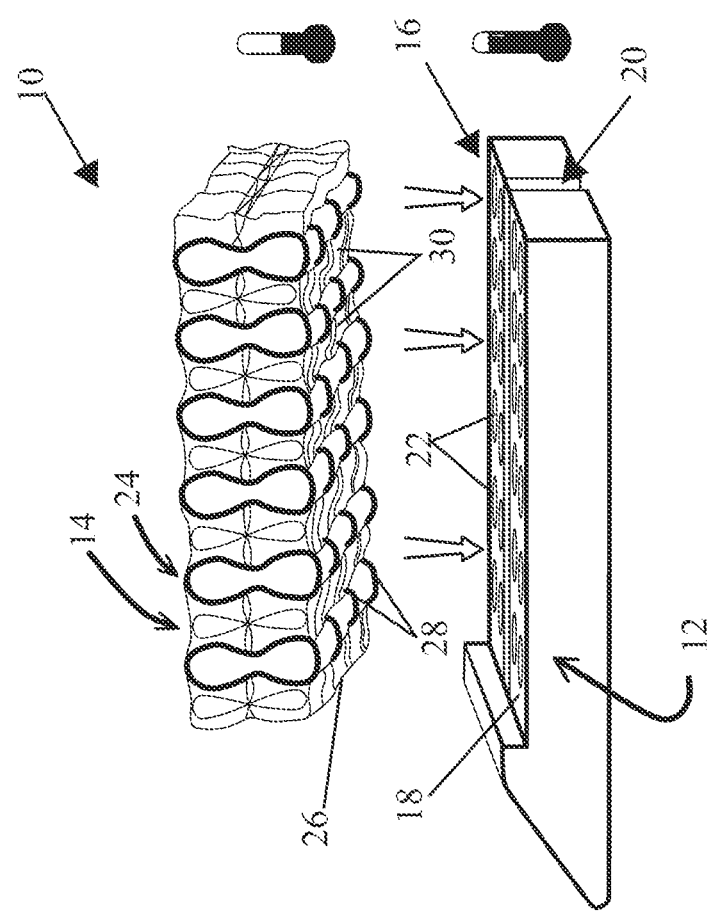
FIG. 6 is a side view of a compressible adjunct and a staple cartridge in accordance with at least one embodiment.

Referring to FIG. 6, a staple cartridge assembly 10 is illustrated. The staple cartridge assembly 10 includes a staple cartridge 12. The staple cartridge 12 is similar in many respects to the staple cartridge 10000. Like the staple cartridge 10000, the staple cartridge 12 includes a plurality of staples which are housed in a plurality of cavities or pockets 22 defined in the staple cartridge 12. Also, the plurality of staples of the staple cartridge 12 can be deployed by the surgical stapling and severing instrument 8010.

The staple cartridge 12 further includes a cartridge deck 16 with an outer surface 18. The staple cartridge 12 also includes a knife slot 20 that accommodates the cutting edge 9116 as it is advanced to cut tissue captured by the surgical stapling and severing instrument 8010. The plurality of pockets 22 may extend from the outer surface 18 into the staple cartridge 12 for housing the plurality of staples. Advancement of the sled 10050 through the staple cartridge 12 causes the staples of staple cartridge 12 to be deployed from their respective pockets 22 into tissue in the same, or substantially the same, manner that the staples 10030 are deployed from the staple cartridge 10000, as described above.

Referring again to FIG. 6, the staple cartridge assembly 10 further includes a tissue thickness compensator or compressible adjunct 14. The compressible adjunct 14 is attached to the outer surface 18 by partially melting the compressible adjunct 14 onto the outer surface 18 to allow the melted portions of the compressible adjunct 14 to flow onto the outer surface 18. The melted portions of the compressible adjunct 14 are resolidified by cooling, for example, which causes the compressible adjunct 14 to be attached to the outer surface 18.

In certain instances, the staple cartridge 12 may include one or more heating elements (not shown) configured to heat the outer surface 18. The heated outer surface 18 can melt the portions of the compressible adjunct 14 in contact therewith. Upon resolidifying, the melted portions of the compressible adjunct 14 can define attachment regions that secure the compressible adjunct 14 to the outer surface the outer surface 18.

In at least one instance, the outer surface 18 is heated uniformly. Alternatively, specific zones of the outer surface

18 are directly heated while other zones are not directly heated. The zones that are not directly heated can be referred to herein as "unheated." The portions of the compressible adjunct 14 in contact with, or in close proximity to, the directly heated zones can be melted and then resolidified to define the attachment regions between the compressible adjunct 14 and the outer surface 18. The portions of the compressible adjunct 14 in contact with, or in close proximity to, the unheated zones remain unattached to the outer surface 18.

In at least one instance, the outer surface 18 is uniformly, or at least substantially uniformly, heated but certain zones of the outer surface 18 may have greater thermal conductivity than other zones of the outer surface 18. In such instances, the portions of the compressible adjunct 14 in contact with, or in close proximity to, the higher thermal conductivity zones can be melted and resolidified to define the attachment regions between the compressible adjunct 14 and the outer surface 18, while the portions of the compressible adjunct 14 in contact with, or in close proximity to, the lower thermal conductivity zones remain unattached to the outer surface 18.

As described above, selective or localized heating of certain zones of the outer surface 18 can be used to define or create discrete attachment regions between the compressible adjunct 14 and the outer surface 18. Alternatively, the compressible adjunct 14 can be especially designed, as illustrated in FIG. 6, to yield selective attachment regions in the presence of a uniformly heated outer surface 18.

In various instances, the zones of the outer surface 18 destined to bond with the compressible adjunct 14 are treated to improve the bond. In at least one instance, one or more of such bonding zones may comprise an irregular topography. For example, such bonding zones may comprise a greater roughness than the remainder of the outer surface 18. Under one non-limiting theory, the greater roughness may improve bonding with the melted portions of the compressible adjunct 14 by increasing the surface area available for contact with the melted portions of the compressible adjunct 14.

The desired roughness of the bonding zones can be achieved by any suitable process such as, for example, mechanical abrading, chemical etching, shot peening, laser peening, and/or plasma spraying. Other processes for producing the desired roughness are contemplated by the present disclosure.

Further to the above, the compressible adjunct 14 includes a body 24. The body 24 includes a face 26 positionable against at least a portion of the outer surface 18 of the staple cartridge 12. The face 26 may include a plurality of attachment regions 28 and a plurality of non-attachment regions 30, as illustrated in FIG. 6. Selective attachment of the compressible adjunct 14 to the outer surface 18 at the attachment regions 28 can reduce the force needed to release the compressible adjunct 14 from the cartridge deck 16 as compared to where the entire face of a compressible adjunct is attached to the surface 18.

The attachment regions 28 are comprised of one or more biocompatible materials. Likewise, the non-attachment regions 30 are comprised of one or more biocompatible materials. In various instances, at least one of the biocompatible materials forming the attachment regions 28 is excluded from the biocompatible materials forming the non-attachment regions 30. In such instances, the one or more biocompatible materials forming the non-attachment regions 30 have melting temperatures that are greater than the melting temperature of the excluded biocompatible material of the attachment regions 28. In certain instances, the attachment regions 28 are comprised of a biocompatible material "A", a biocompatible material "B", and a biocompatible material "C," while the non-attachment regions 30 are comprised of the biocompatible material "A" and the biocompatible material "B" but exclude the biocompatible material "C." In such instances, the biocompatible material "C" has a lower melting temperature than the biocompatible material "A" and the biocompatible material "B." Upon heating the attachment regions 28 and the non-attachment regions 30 to the melting temperature of the biocompatible material "C," the biocompatible material "C" melts and flows from the attachment regions 28 onto the outer surface 18. Once the biocompatible material "C" is resolidified bonding is established between the attachment regions 28 and the outer surface 18.

In at least one instance, the non-attachment regions 30 may be comprised of a first biocompatible material, and the attachment regions 28 may be comprised of a second biocompatible material which is different from the first biocompatible material. The second biocompatible material may have a lower melting temperature than the first biocompatible material. In such instances, exposing the face 26 to the outer surface 18, which is uniformly heated to a temperature greater than or equal to the melting temperature of the second biocompatible material but lower than the melting temperature of the first biocompatible material, causes the attachment regions 28 to melt and flow onto the outer surface 18. The non-attachment regions 30, however, will remain in their solid state as the temperature of the outer surface 18 is below the melting temperature of the first biocompatible material. Upon resolidifying, the attachment regions 28 releasably secure the body 24 of the compressible adjunct 14 to the outer surface 18 of the cartridge deck 16.

In various instances, one or more of the non-attachment regions 30 and/or one or more of the attachment regions 28 may comprise bioabsorbable materials such as, for example, polyglycolic acid (PGA) which is marketed under the trade name VICRYL, polylactic acid (PLA or PLLA), polydioxanone (PDS), polyhydroxyalkanoate (PHA), poliglecaprone 25 (PGCL) which is marketed under the trade name Monocryl, and/or polycaprolactone (PCL). In certain instances, one or more of the attachment regions 28 and/or the non-attachment regions 30 may comprise one or more composite materials that include two or more polymers, the polymers selected from a group including PGA, PLA, PDS, PHA, PGCL and/or PCL, for example. In at least one instance, the second biocompatible material is comprised of PDS.

In at least one instance, the compressible adjunct 14 is secured to the cartridge deck 16 by causing a temporary phase transition in the second biocompatible material of the attachment regions 28 while the compressible adjunct 14 is pressed, or positioned, against the cartridge deck 16. In certain instances, the temporary phase transition in the second biocompatible material is not accompanied by a phase transition in the first biocompatible material of the non-attachment regions 30.

In certain instances, the attachment regions 28 are resolidified by removing or deactivating the heat source. In at least one instance, the heat source is an oven, which is configured to receive the staple cartridge 12 and the compressible adjunct 14 positioned against the cartridge deck 16. The oven can be heated to a suitable temperature prior to and/or after receiving the staple cartridge 12 and the compressible adjunct 14. In at least one instance, the heat source can be a thermal resistance circuit, which can be activated to heat the outer surface 18. The thermal resistance circuit can be arranged under the cartridge deck 16, for example. Other suitable heat sources are contemplated by the present disclosure. In certain instances, the attachment regions 28 are resolidified by active cooling in addition to removing or deactivating the heat source. For example, a fan or any other cooling system can be employed to cool the attachment regions 28 to a temperature below the melting temperature of the second biocompatible material.

In at least one instance, the non-attachment regions 30 may be comprised of a plurality biocompatible materials with melting temperatures that are greater than a predetermined temperature. Likewise, the attachment regions 28 may be comprised of a plurality of biocompatible materials; however, the biocompatible materials of the attachment regions 28 include at least one biocompatible material having a melting temperature that is equal to or less than the predetermined melting temperature. Said another way, the biocompatible materials of the attachment regions 28 include at least one biocompatible material having a melting temperature that is less than the melting temperatures of the biocompatible materials of the non-attachment regions 30. Upon heating the face 26 of the compressible adjunct 14 to the predetermined temperature, the attachment regions 28 are melted, or at least partially melted, for bonding with the outer surface 18, while the non-attachment regions 30 remain in their solid phase and do not bond to the outer surface 18.

In various instances, further to the above, the non-attachment regions 30 need only exclude biocompatible materials with melting temperatures that are equal to or less than the melting temperature of the biocompatible material with the lowest melting temperature in the attachment regions 28. That said the attachment regions 28 need not be limited in composition to one biocompatible material. On the contrary, the attachment regions 28 can be comprised of a plurality of biocompatible materials as long as the plurality of biocompatible materials of the attachment regions 28 includes at least one biocompatible material with a melting temperature that is less than the melting temperature(s) of the biocompatible material(s) of the non-attachment regions 30.

Referring again to FIG. 6, the body 24 of the compressible adjunct 14 may include a fibrous construct comprising a plurality of fibers. Suitable compressible adjuncts may include meshes, other filamentous structures, non-woven structures, sponges, woven or non-woven materials, knit or non-knit materials, felts, salt eluted porous materials, molded porous materials, and/or 3D-printing generated adjuncts, for example. Other techniques for preparing the compressible adjunct 14 are contemplated by the present disclosure.

In at least one instance, the non-attachment regions 30 may include a first plurality of fibers, and the attachment regions 28 may include a second plurality of fibers different from the first plurality of fibers. For example, the second plurality of fibers may have a lower melting temperature than the first plurality of fibers. In such instances, exposing the face 26 of the compressible adjunct 14 to the outer surface 18, which is uniformly heated to a temperature which is greater than or equal to the melting temperature of the second plurality of fibers but lower than the melting temperature of the first plurality of fibers, causes the second plurality of fibers of the attachment regions 28 to melt and flow onto the outer surface 18. The first plurality of fibers of the non-attachment regions 30, however, will remain in their solid state as the temperature of the outer surface 18 is below the melting temperature of the first plurality of fibers.

The fibrous construct of the body 24 of the compressible adjunct 14 can be pressed onto or positioned against the outer surface 18 which is uniformly heated to a temperature sufficient to melt the fibers of the attachment regions 28 but not the fibers of the non-attachment regions 30. Upon resolidifying, the melted fibers of the attachment regions 28 secure the body 24 of the compressible adjunct 14 to the outer surface 18 of the cartridge deck 16.

In various instances, the outer surface 18 may comprise bonding zones for bonding with the attachment regions 28. In certain instances, the bonding zones are treated to improve the bond between the attachment regions 28 and the outer surface 18. In at least one instance, one or more of the bonding zones may comprise an irregular topography that increases the roughness of the bonding zones compared to the remainder of the outer surface 18. As described above, the increased roughness may correspond to an increase in the surface area of the bonding zones available for bonding with the attachment regions 28.

Figure 7:
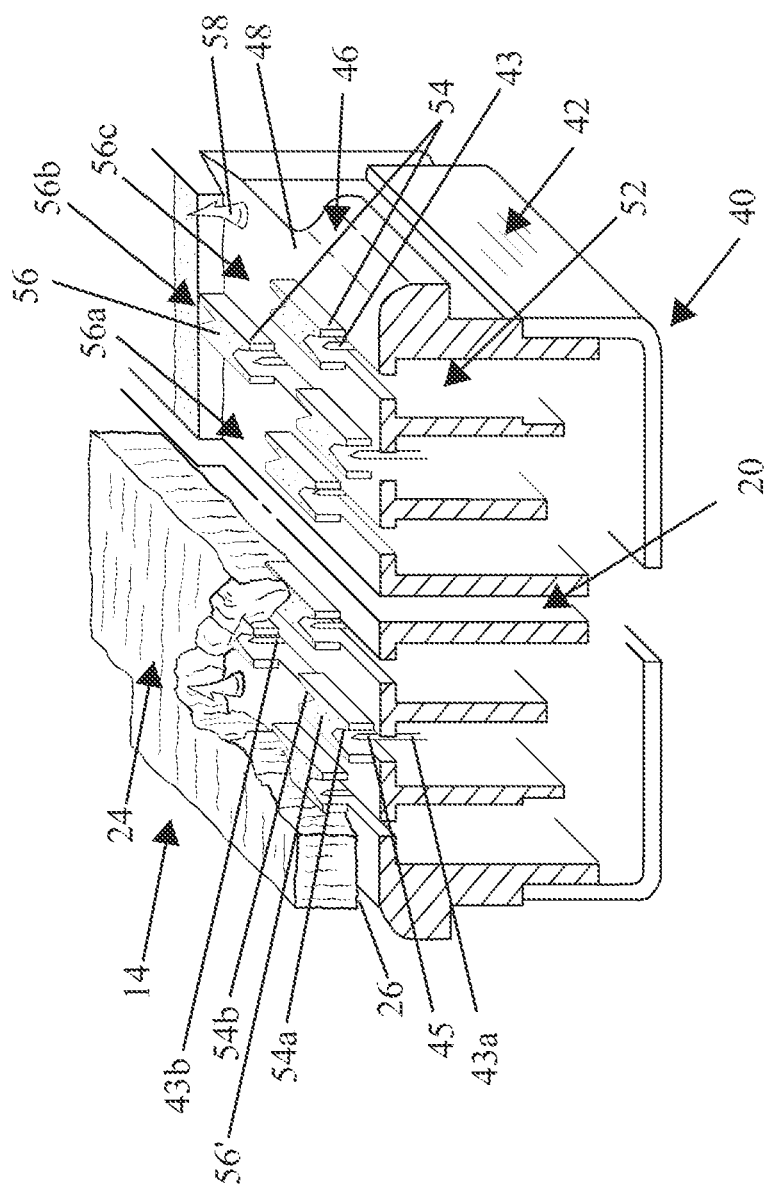
FIG. 7 is a transverse cross-sectional view of a staple cartridge assembly including a staple cartridge and a compressible layer, wherein a portion of the compressible adjunct has been removed for the purpose of illustration.

Referring to FIG. 7, a staple cartridge assembly 40 includes a staple cartridge 42 which is similar in many respects to the staple cartridges 12 and 10000. Like the staple cartridge 10000, the staple cartridge 42 includes a plurality of staples such as, for example, a plurality of staples 43 which are housed in the staple cartridge 42 in a plurality of cavities or pockets 52. Furthermore, like the staples of the staple cartridge 10000, the staples 43 can be deployed from the staple cartridge 42 into captured tissue by the surgical stapling and severing instrument 8010.

The staple cartridge 42 includes a cartridge deck 46. Like the cartridge deck 16, the cartridge deck 46 includes an outer surface such as, for example, an outer surface 48. The plurality of pockets 52 extend from the cartridge deck 46 into the staple cartridge 42 and are configured to house the plurality of staples 43, as illustrated in FIG. 7. When the staple cartridge 42 is used with the surgical stapling and severing instrument 8010, the advancement of the sled 10050 through the staple cartridge 42 causes the staples 43 to be deployed from their respective pockets 52 into tissue in the same, or substantially the same, manner that the staples 10030 are deployed from the staple cartridge 10000.

The staple cartridge assembly 40 includes a layer such as, for example, a tissue thickness compensator or compressible adjunct. In the illustrated in embodiment, the staple cartridge assembly 40 includes a compressible adjunct 14. The compressible adjunct 14 is assembled with, or positioned against, the cartridge deck 46 of the staple cartridge 42. The compressible adjunct 14 is secured to a plurality of bonding zones 56 on the cartridge deck 46, as described in greater detail below.

In certain instances, the bonding zones 56 can be arranged in rows. Each row may include a plurality of the bonding zones 56. In the embodiment illustrated in FIG. 7, the bonding zones 56 are arranged in three parallel rows 56a-56c extending along a length of the cartridge deck 46 on each side of the knife slot 20. Alternatively, the bonding zones 56 may be arranged in two parallel rows along a length of the cartridge deck 46 on each side of the knife slot 20. Alternatively, the bonding zones 56 may be arranged in a single row along a length of the cartridge deck 46 on each side of the knife slot 20. Alternatively, the bonding zones 56 may be arranged in non-parallel rows. In certain instances, the bonding zones 56 may be arranged along a perimeter, or a periphery, of the cartridge deck 46.

The middle row 56b is offset from the outer rows 56a, 56c. Said another way, a pair of the bonding zones of the outer rows 56a, 56c is laterally aligned with a gap between two consecutive bonding zones of the middle row 56b. The gap may include a pocket 52. In certain instances, a plurality of bonding zones 56 and a plurality of pockets 52 may be arranged in a row such that each bonding zone 56 is disposed between two consecutive pockets 52, as illustrated in FIG. 7. Other arrangements of the bonding zones 56 with respect to the cartridge deck 46 are contemplated by the present disclosure.

As illustrated in FIG. 7, the cartridge deck 42 may include a plurality of pocket extenders 54 which extend from the outer surface 48. The pocket extenders 54 can serve a number of functions. For example, the pockets extenders 54 may protect the legs of the staples 43 that extend outside the pockets 52 in their unfired positions. Also, the pocket extenders 54 may guide the staples 43 as they are being fired. A bonding zone 56 may extend between two adjacent pocket extenders 54 of two different pockets 52. Said another way, the bonding zone 56 may extend between two adjacent atraumatic pocket extenders 54 each protecting a staple leg of a different staple.

In certain instances, a plurality of pocket extenders 54 may be arranged with a plurality of bonding zones 56 in a row such as, for example, the rows 56a-56c. In at least one instance, each of the plurality of bonding zones 56 in such a row can be positioned between two consecutive atraumatic pocket extenders 54. For example, as illustrated in FIG. 7, a bonding zone 56' is positioned between a distal staple 43a and proximal staple 43b such that the bonding zone 56' extends between a first pocket extender 54a protecting a proximal leg 45 of the distal staple 43a and a second pocket extender 54b protecting a distal leg (not shown) of the proximal staple 43b.

As indicated above, the bonding zones 56 of the cartridge deck 46 may extend from the outer surface 48. In other words, the bonding zones 56 may be elevated, or stepped up, relative to the outer surface 48, as illustrated in FIG. 7. In various instances, the attachment regions 28 can be positioned on the bonding zones 56. The elevation of the bonding zones 56 relative to the outer surface 48 can prevent, or at least limit, overflow of the melted material of the attachment regions 28 outside the bonding zones 56, which can help maintain the attachment between the compressible adjunct 14 and the cartridge deck 46 to discrete regions defined by the bonding zones 56.

In various instances, the bonding zones 56 of the cartridge deck 46 are treated to improve their attachment to corresponding attachment regions 28 of the compressible adjunct 14. In at least one instance, one or more of the bonding zones 56 may comprise an irregular topography, as illustrated in FIG. 7. In other words, the bonding zones 56 may comprise a greater roughness than the remainder of the outer surface 48. The greater roughness improves bonding with the melted attachment regions 28. The desired roughness of the bonding zones can be achieved by any suitable process such as, for example, mechanical abrading, chemical etching, shot peening, laser peening, and/or plasma spraying. Other processes for producing the desired roughness are contemplated by the present disclosure.

In various instances, the cartridge deck 46 may further include one or more attachment members 58. The attachment members 58 aid in securing the compressible adjunct 14 to the cartridge deck 46. In certain instances, the attachment members 58 comprise barbs that can maintain an initial alignment between the bonding zone 56 and the corresponding attachment regions 48 of the compressible adjunct 14 during the melting and/or resolidifying processes used to bond the compressible adjunct 14 to the cartridge deck 46.

The compressible adjunct 14 can be pressed against the cartridge deck 46 so that the attachment members 58 engage the face 26 of the compressible adjunct 14, and/or to establish an initial alignment between the bonding zones 56 and the attachment regions 28. The attachment regions 28 are then melted onto the bonding zones 56. Upon resolidifying, the attachment regions 58 secure the compressible adjunct 14 to the bonding zones 56.

Figure 8:
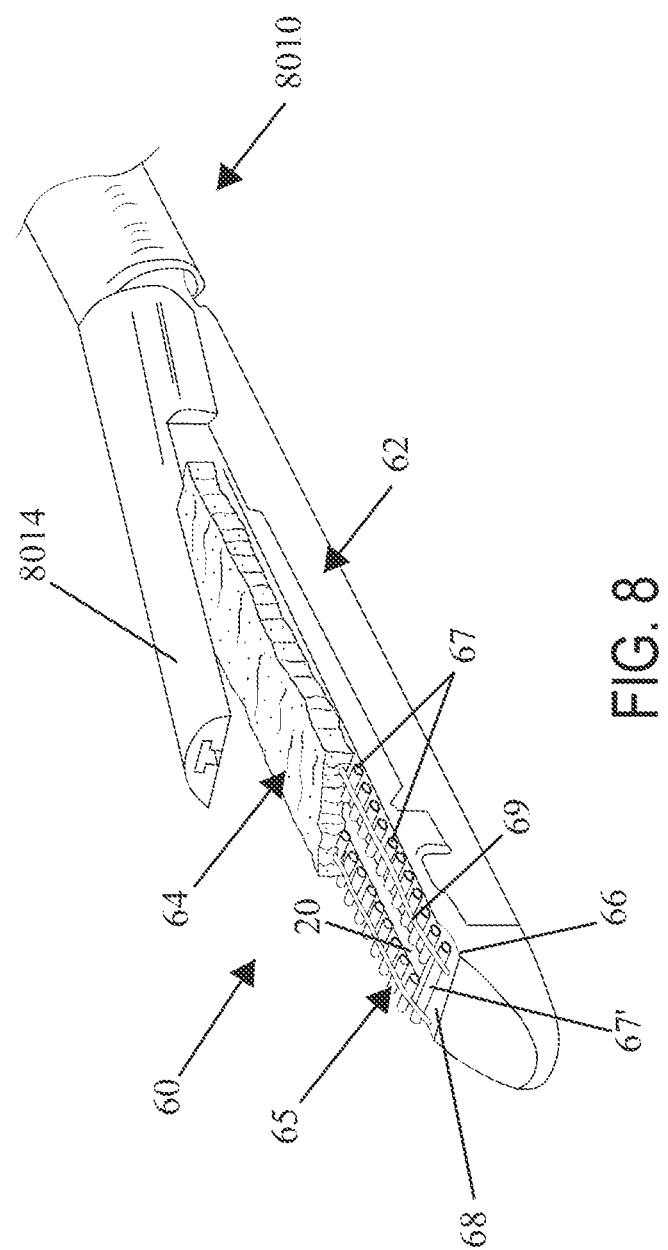
FIG. 8 is a partial perspective view of an end effector including a staple cartridge, a compressible layer, and a bonding layer, wherein a portion of the compressible layer has been removed for the purpose of illustration.

Referring now to FIG. 8, a staple cartridge assembly 60 is assembled with a surgical stapling and severing instrument such as, for example, the surgical stapling and severing instrument 8010. The staple cartridge assembly 60 includes a staple cartridge 62. The staple cartridge 62 is similar in many respects to the staple cartridges 12, 42, and 10000. The staple cartridge 62 includes a cartridge deck 66, which includes an outer surface such as, for example, an outer surface 68. The staple cartridge assembly 60 further includes a compressible layer 64 and a bonding layer 65. The bonding layer 65 can be comprised of a plurality of bonding islands 67, as illustrated in FIG. 8. The bonding islands 67 can be spaced apart from one another and disposed on the outer surface 68 of the cartridge deck 66 in a predetermined arrangement. The bonding islands 67 are arranged in a pattern surrounding, or at least partially surrounding, the knife slot 20. Said another way, the bonding islands 67 are arranged in a pattern along a periphery, or a perimeter, of the knife slot 20. Other arrangements of the bonding islands 67 onto the outer surface 68 are contemplated by the present disclosure.

In certain instances, one or more of the bonding islands 67 comprise a cylindrical shape, as illustrated in FIG. 8. Other shapes are also contemplated by the present disclosure. For example, one or more bonding islands 67 may comprise a dome shape. In the embodiment illustrated in FIG. 8, a bonding island 67' is disposed in the outer surface 68 at distal portion thereof, which is distal to the knife slot 20.

In various instances, the bonding islands 67 of the bonding layer 65 can be formed with the cartridge deck 66 during manufacturing. Alternatively, the bonding layer 65 can be attached to the cartridge deck 66 by the surgeon, for example. Any suitable attachment technique can be employed to secure the boding layer 65 to the cartridge deck 66. In at least one instance, the bonding layer 65 may include one or more connecting straps 69, for example. The connecting straps 69 also interconnect the bonding islands 67, and can be employed to secure the boding layer 65 to the cartridge deck 66, for example.

In any event, the compressible layer 64 can be secured to the cartridge deck 66 by pressing, or positioning, the compressible layer 64 against the melted, or at least partially melted, bonding islands 67, then allowing, or causing, the bonding islands 67 to resolidify. Said another way, the compressible layer 64 can be secured to the cartridge deck 66 by causing a temporary phase transition in the bonding islands 67 while the compressible layer 64 is pressed, or positioned, against the bonding islands 67.

In one embodiment, the compressible layer 64 is pressed, or positioned, against the bonding islands 67. Then, the bonding islands 67 are heated to a predetermined temperature which causes the bonding islands 67 to be melted, or at least partially melted. Finally, the bonding islands 67 are cooled, or allowed to cool, down below the predetermined temperature thereby causing the bonding islands 67 to resolidify and secure the compressible layer 64 to the cartridge deck 66. Alternatively, the bonding islands 67 can be heated to the predetermined temperature prior to pressing, or positioning, the compressible layer 64 against the bonding islands 67.

In certain instances, the bonding islands 67 are resolidified by removing or deactivating the heat source. In other instances, the bonding islands 67 are resolidified by active cooling in addition to removing or deactivating the heat source. For example, a fan or any other cooling system can be employed to cool the bonding islands 67 to a temperature below the predetermined temperature.

In at least one instance, the compressible layer 64 may be comprised of a first biocompatible material, and the bonding islands 67 may be comprised of a second biocompatible material which is different from the first biocompatible material. The second biocompatible material may have a lower melting temperature than the first biocompatible material. In such instances, heating the bonding islands 67 to the melting temperature of the second biocompatible material but lower than the melting temperature of the first biocompatible material, causes the bonding islands 67 to melt and flow into the compressible layer 64 and onto the outer surface 68. The compressible layer 64, however, will remain in a solid phase. Upon resolidifying, the bonding islands 67 secure the compressible layer 64 to the outer surface 68 of the cartridge deck 66.

In at least one instance, the compressible layer 64 is secured to the cartridge deck 66 by causing a temporary phase change or transition in the second biocompatible material of the bonding islands 67 while the compressible layer 64 is pressed, or positioned, against the cartridge deck 66. In certain instances, the temporary phase change in the second biocompatible material is not accompanied by a phase change in the first biocompatible material of the compressible layer 64.

In various instances, the compressible layer 64 and/or the bonding layer 67 may comprise bioabsorbable materials such as, for example, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, and/or polycaprolactone (PCL). In certain instances, the compressible layer 64 and/or the bonding layer 67 may comprise composite materials that include two or more polymers, the polymers selected from a group including PGA, PLA, PDS, PHA, PGCL and/or PCL, for example. In at least one instance, the second biocompatible material is comprised of PDS, for example.

The reader will appreciate that the compressible adjuncts and/or layers of the present disclosure can be attached to an anvil such as, for example, the anvil 8014 of the surgical stapling and severing instrument 8010 in the same manner the compressible adjuncts and/or layers are attached to the staple cartridges of the present disclosure, and vice versa. For example, the compressible adjunct 14 can be attached to the anvil 8014 by uniformly heating the anvil 8014 to a temperature sufficient to melt the fibers of the attachment regions 28 but not the fibers of the non-attachment regions 30. Upon resolidifying, the melted fibers of the attachment regions 28 secure the body 24 of the compressible adjunct 14 to the anvil 8014. Likewise the bonding layer 65 can be employed to secure the compressible layer 64 to the anvil 8014 in the same manner the bonding layer 65 secures the compressible layer 64 to the staple cartridge 62.

Figure 9:
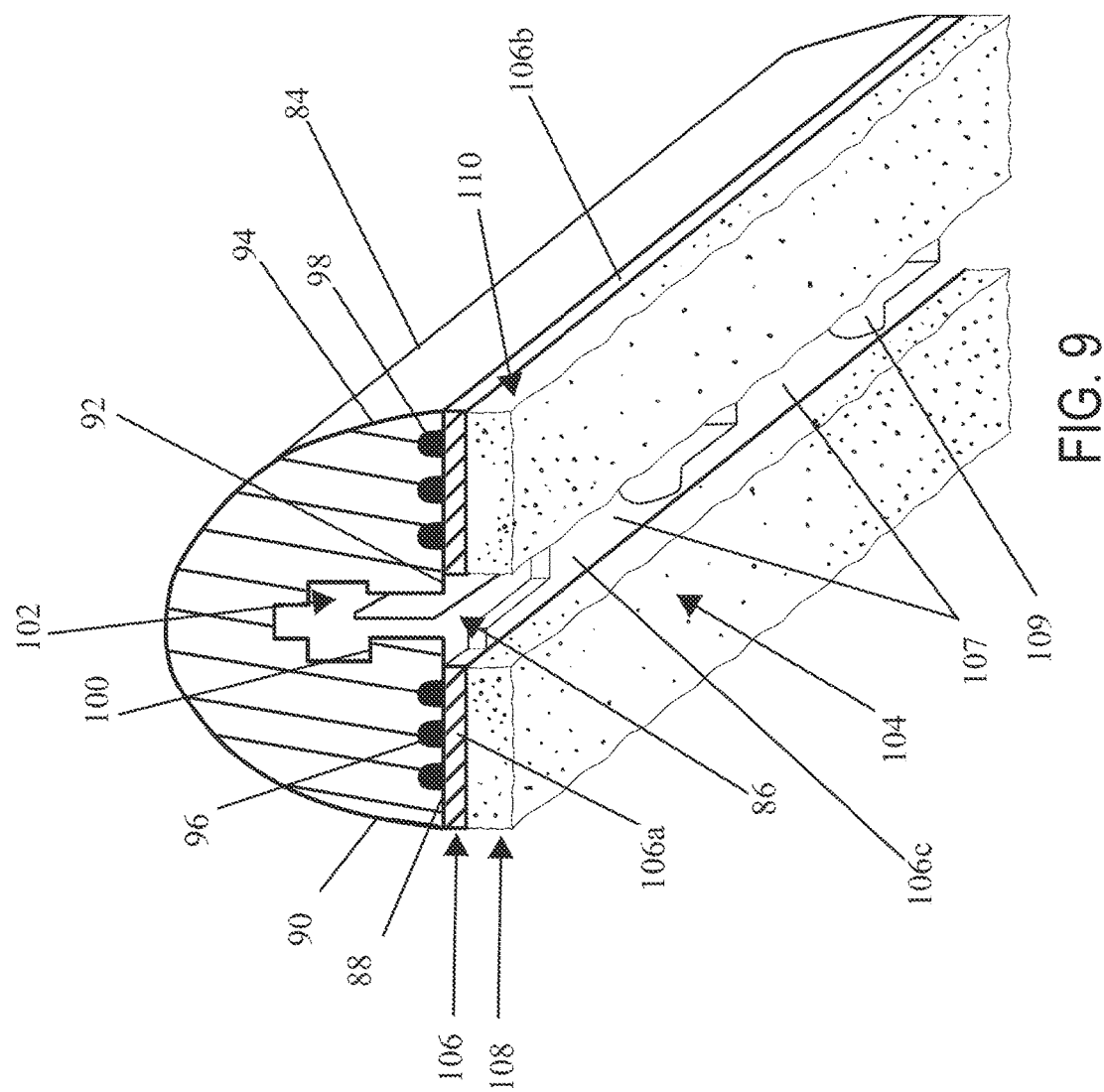
FIG. 9 is a transverse cross-sectional view of a compressible adjunct assembly attached to an anvil of a surgical instrument.

Referring primarily to FIGS. 1 and 9, a surgical stapling and severing instrument such as, for example, the surgical stapling and severing instrument 8010 may include a compressible adjunct assembly 104. The compressible adjunct assembly 80 can be attached to a jaw member of the surgical stapling and severing instrument 8010. In at least one instance, the compressible adjunct assembly 104 is attached to an anvil such as, for example, an anvil 84 (FIG. 9), which is similar in many respects to the anvil 8014 (FIG. 1).

Alternatively, the compressible adjunct assembly 104 can be attached to a staple cartridge such as, for example, the staple cartridge 10000. In certain instances, a first compressible adjunct assembly 104 is attached to an anvil and a second compressible adjunct assembly 104 is attached to a staple cartridge of the same surgical stapling and severing instrument. In such instances, tissue is captured between the first and second compressible adjunct assemblies 104 upon transitioning the surgical stapling and severing instrument to a closed configuration.

Like the anvil 8014, the anvil 84 includes an elongate slot 86 that extends through a length of the anvil 84 defining a first outer surface 88 extending on a first side 90 of the elongate slot 86, and a second outer surface 92 extending on a second side 94 of the elongate slot 86, as illustrated in FIG. 9. In certain instances, the anvil 84 is movable relative to a staple cartridge such as, for example, the staple cartridge 10000 to capture tissue therebetween. Alternatively, the staple cartridge 10000 can be moved relative to the anvil 84 to capture tissue therebetween. Alternatively, the anvil 84 and the staple cartridge 10000 can be moved toward one another to capture the tissue therebetween. A firing assembly such as, for example, the firing assembly 9090 (FIG. 3) can be utilized with the surgical stapling and severing instrument 8010 to deploy staples from the staple applying assembly 8012 (FIG. 1) into tissue captured between the anvil 84 and the staple cartridge 10000, as described in greater detail above.

Referring to FIG. 9, the first outer surface 88 includes a plurality of pockets 96. Likewise, the second outer surface 92 includes a plurality of pockets 98. The pockets 96 and 98 can be configured to receive and deform the staples as they are deployed from the staple cartridge 10000, for example. Furthermore, the elongate slot 86 can be configured to accommodate the cutting edge 9116 (FIG. 3) as it is advanced to cut tissue captured by the surgical stapling and severing instrument 8010.

Referring to FIGS. 3 and 9, the anvil 84 may include an internal surface 100 that defines an internal space 102 within the anvil 84. The pins 9110 (FIG. 3) of the firing assembly 9090 can ride against the internal surface 102, and can be motivated through the internal space 102 as the firing assembly 9090 is advanced to deploy the staples into the tissue captured by the staple applying assembly 8012.

Referring again to FIG. 9, the compressible adjunct assembly 104 includes an attachment layer 106, a first compressible adjunct 108, and a second compressible adjunct 110. The attachment layer 106 can be configured to couple the first compressible adjunct 108 and the second compressible adjunct 110 to the anvil 84, as described in greater detail below. A first section 106a of the attachment layer 106 is positionable on the first side 90 of the elongate slot 86, and a second section 106b is positionable on the second side 94 of the elongate slot 86. The elongate slot 86 separates the first section 106a from the second section 106b. An intermediary section 106c of the attachment layer 106 extends between the first section 106a and the second section 106b. The intermediary section 106c bridges the elongate slot 86. In certain instances, the intermediary section 106c only partially bridges the elongate slot 86

In certain instances, the intermediary section 106c completely bridges the elongate slot 86. In at least one instance, the intermediary section 106c may be comprised of a plurality of bridging portions 107, as illustrated in FIG. 9. Each bridging portion 107 extends between the first section 106a and the second section 106b. The bridging portions 107 are spaced apart from one another. Gaps 109 in the intermediary section 106b separate the bridging portions 107. The gaps 109 expose the elongate slot 86.

As illustrated in FIG. 9, the bridging portions 107 can be strategically arranged along the elongate slot 86 to maintain the integrity of the attachment layer 106 while minimizing the firing force needed to drive the cutting edge 9116 (FIG. 3) as it is advanced to cut the intermediate layer 106c and tissue captured between a staple cartridge and the anvil 84. The gaps 109 and the bridging portions 107 alternate in position along at least a portion of the elongate slot 86.

Various techniques for manufacturing a compressible adjunct assembly such as, for example, the compressible adjunct assembly 104 are described in U.S. patent application Ser. No. 14/187,383, entitled IMPLANTABLE LAYERS AND METHODS FOR ALTERING IMPLANTABLE LAYERS FOR USE WITH SURGICAL FASTENING INSTRUMENTS, and filed Feb. 24, 2014, now U.S. Patent Application Publication No. 2015/0238185, the entire disclosure of which is incorporated herein by reference. In at least one instance, the attachment layer 106 can be attached to the first compressible adjunct 108 and second compressible adjunct 110 during fabrication of the first compressible adjunct 108 and second compressible adjunct 110 using a lyophilization process, for example.

Alternatively, the attachment layer 106 can be attached to the first compressible adjunct 108 and second compressible adjunct 110 after fabrication of the first compressible adjunct 108 and second compressible adjunct 110. For example, as described in greater detail elsewhere herein, the first compressible adjunct 108 can be positioned, or pressed, against a partially melted first section 106a of the attachment layer 106. Upon resolidification, the first section 106a is attached to the first compressible adjunct 108. In a similar manner, the first section 106a can be attached to the first outer surface 88, the second section 106b can be attached to the outer surface 92, and the second section 106b can be attached to the second compressible adjunct 110, for example.

As illustrated in FIG. 9, the first section 106a of the attachment layer 106 extends between the first compressible adjunct 108 and the first outer surface 88. Likewise, the second section 106b of the attachment layer 106 may extend between the second compressible adjunct 110 and the outer surface 92. The first section 106a completely separates the first compressible adjunct 108 from the first outer surface 88. In addition, the second section 106b completely separates the second compressible adjunct 110 from the outer surface 92. Alternatively, a compressible adjunct assembly may comprise an attachment layer 206 that only partially separates one or more compressible adjuncts from an anvil. Said another way, the first section 106a may include one or more gaps configured to expose the first compressible adjunct 108 to the first outer surface 88. Likewise, the second section 106b may include one or more gaps configured to expose the second compressible adjunct 110 to the outer surface 92.

The attachment layer 106 comprises a height that is smaller than the height of the first compressible adjunct 108 and/or the height of the second compressible adjunct 110. Alternatively, the attachment layer 106 may comprise a height that is greater than or equal to the height of the first compressible adjunct 108 and/or the height of the second compressible adjunct 110. In at least one instance, the attachment layer 106 is comprised of a film, which can be attached to the first compressible adjunct 108 and/or the second compressible adjunct 108.

Figure 10:
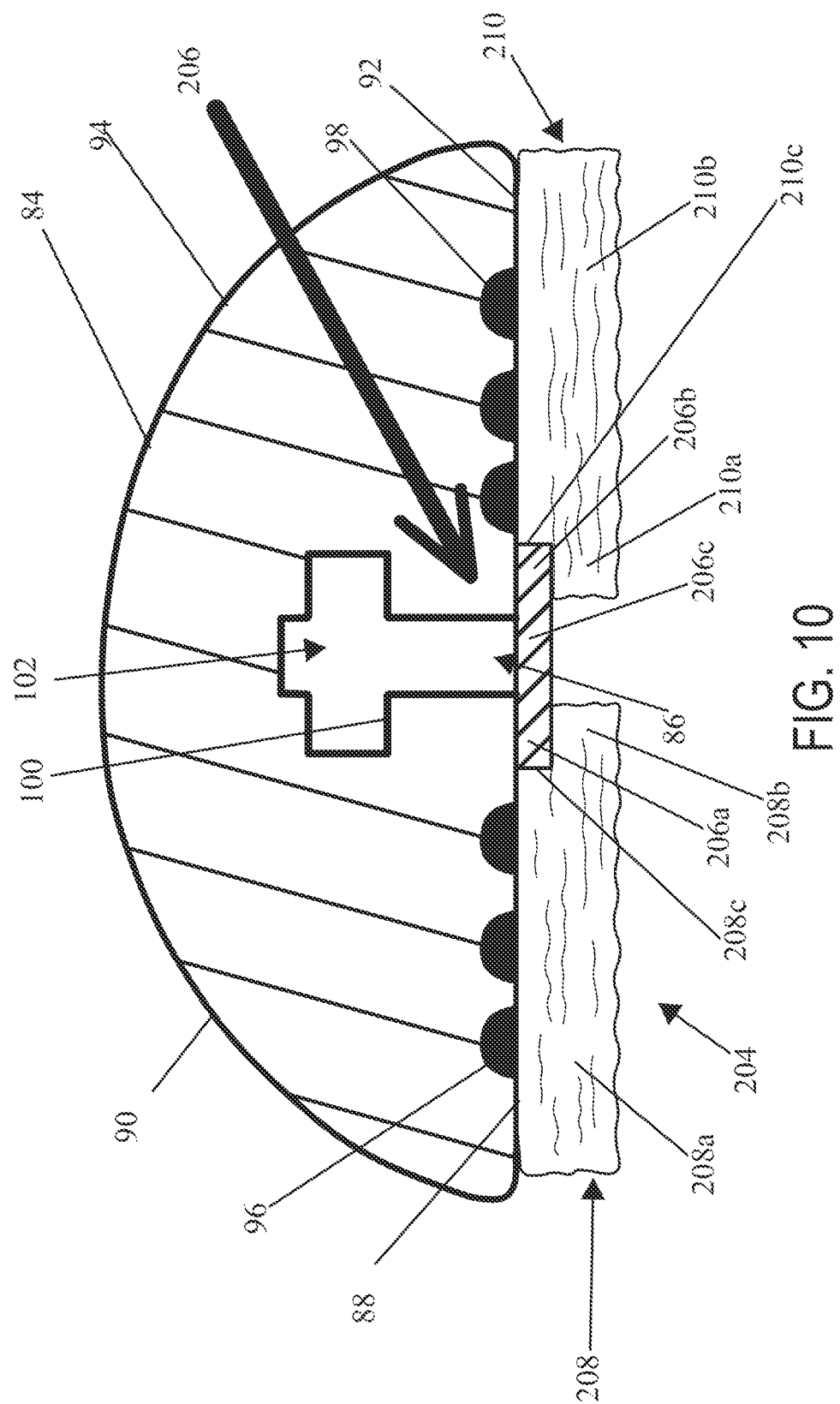
FIG. 10 is a transverse cross-sectional view of a compressible adjunct assembly attached to an anvil of a surgical instrument.

Referring to FIG. 10, a compressible adjunct assembly 204 may comprise an attachment layer 206 that partially separates a first compressible adjunct 208 from the first outer surface 88 and/or partially separates a second compressible adjunct 210 from the outer surface 92. The compressible adjunct assembly 204 is similar in many respects to the compressible adjunct assembly 104. The compressible adjunct assembly 204 can be assembled with the anvil 84.

The attachment layer 206 of the compressible adjunct assembly 204 includes a first section 206a positionable on the first side 90 of the elongate slot 86, and a second section 206b positionable on the second side 94 of the elongate slot 86. Also, an intermediary section 206c of the attachment layer 206 extends between the first section 206a and the second section 206b. The intermediary section bridges the elongate slot 86, as illustrated in FIG. 10. In certain instances, the intermediary section 206c only partially bridges the elongate slot 86.

The first compressible adjunct 208 of the compressible adjunct assembly 204 is attached to the first section 206a, and the second compressible adjunct 210 of the compressible adjunct assembly 204 is attached to the second section 206b. When the compressible adjunct assembly 204 is assembled with the anvil 84, as illustrated in FIG. 10, the first compressible adjunct 208 extends laterally beyond the first section 206a in a first direction away from the elongate slot 86. In addition, the first outer surface 88 also extends laterally beyond the first section 206a in the first direction. Likewise, the second compressible adjunct 210 extends laterally beyond the second section 206b in a second direction away from the elongate slot 86 and opposite the first direction. In addition, the outer surface 92 also extends laterally beyond the second section 206b in the second direction. In result, as illustrated in FIG. 10, an external portion 208a of the first compressible adjunct 208 is in direct contact with the outer surface 88 while a stepped internal portion 208b is separated from the outer surface 88 by the first section 206a of the attachment layer 206. Likewise, an external portion 210a of the second compressible adjunct 210 is in direct contact with the outer surface 92 while a stepped internal portion 210b is separated from the outer surface 92 by the second section 206b of the attachment layer 206.

The stepped internal portions 208b and 210b define first and second boundaries 208c and 210c, respectively. The attachment layer 206 extends laterally between the first boundary 208c and the second boundary 210c crossing the elongate slot 86 to interconnect the first compressible adjunct 208 and the second compressible adjunct 210. When the compressible adjunct assembly 204 is assembled with the anvil 84, as illustrated in FIG. 10, the attachment layer 206 is positioned against a central area of the anvil 84 extending between an inner row of the pockets 96 and an inner row of the pockets 98. In addition, the internal stepped portions 208b and 210b are separated from the anvil 84 by the attachment layer 206.

Further to the above, the first boundary 208c is interior to the inner row of the pockets 96, and the second boundary 210c is interior to the inner row of the pockets 98. The first section 206a of the attachment layer 206 is positioned against a portion of the outer surface 88 extending between the elongate slot 86 and the inner row of the pockets 96. In addition, the external portion 208a is directly positioned against the pockets 96 of the outer surface 88. Likewise, the second section 206b of the attachment layer 206 is positioned against a portion of the outer surface 92 extending between the elongate slot 86 and the inner row of the pockets 98. In addition, the external portion 210*a* is directly positioned against the pockets 98 of the outer surface 92. In certain instances, the boundaries 208*c* and 210*c* can be further spaced apart laterally to allow the attachment layer 206 to further encompass one or more of the rows of the pockets 96 and/or one or more of the rows of the pockets 98.

The attachment layer 206 comprises a height that is smaller than the height of the first compressible adjunct 208 and/or the height of the second compressible adjunct 210. Alternatively, the attachment layer 206 may comprise a height that is greater than or equal to the height of the first compressible adjunct 208 and/or the height of the second compressible adjunct 210. In at least one instance, the attachment layer 206 is comprised of a film, which can be attached to the internal stepped portion 208*b* of the first compressible adjunct 208 and/or to the internal stepped portion 210*b* of the second compressible adjunct 108.

Figure 11:
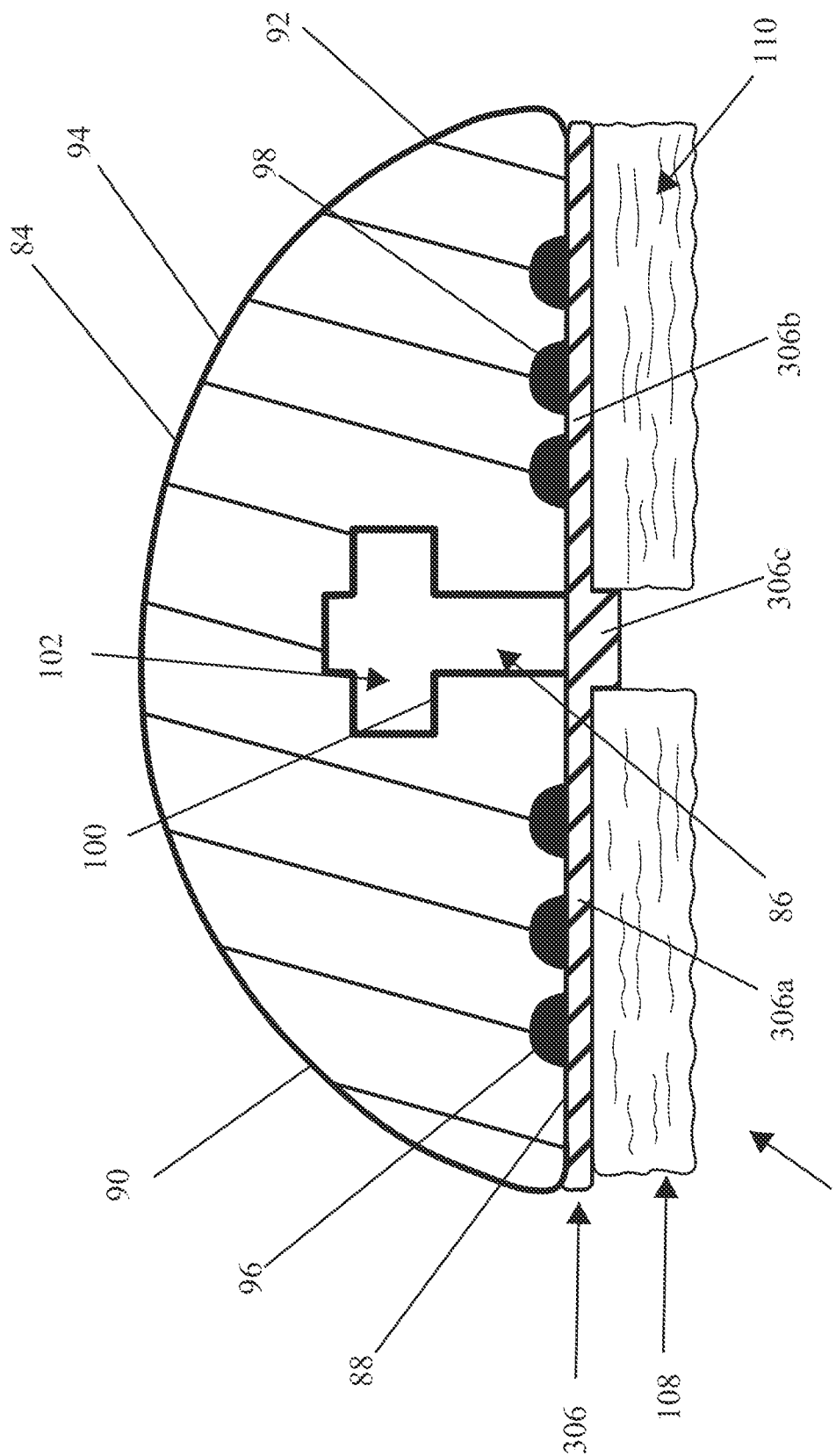
FIG. 11 is a transverse cross-sectional view of a compressible adjunct assembly attached to an anvil of a surgical instrument.

Referring to FIGS. 11-15, a compressible adjunct assembly 304 includes an attachment layer 306 that includes a raised, elevated, or stepped up intermediary section 306*c*. The compressible adjunct assembly 304 is similar in many respects to the compressible adjunct assembly 104. For example, the compressible adjunct assembly 304 can be assembled with the anvil 84, as illustrated in FIG. 11. Also, the first compressible adjunct 108 of the compressible adjunct assembly 304 can be attached to a first section 306*a* of the attachment layer 306, and the second compressible adjunct 110 of the compressible adjunct assembly 304 can be attached to a second section 306*b* of the attachment layer 306, for example.

Figure 12:
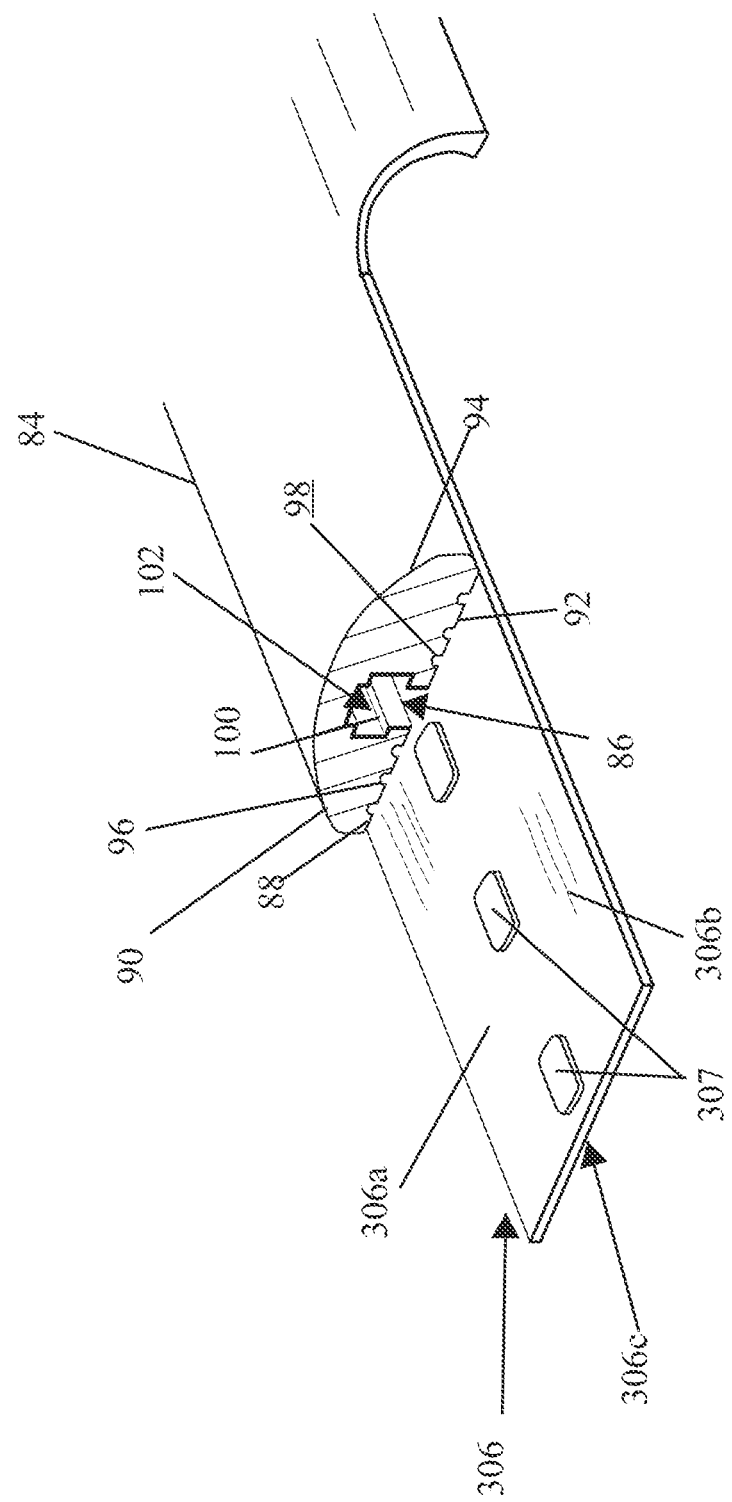
FIG. 12 a partial perspective view of an anvil assembled with an attachment layer, wherein a portion of the anvil has been removed for the purpose of illustration.

The intermediary section 306*c* is configured to protrude into a gap defined between the first compressible adjunct 108 and the second compressible adjunct 110. Alternatively, the intermediary section 306*c* can be configured to protrude into the elongate slot 86 when the compressible adjunct assembly 304 is assembled with the anvil 84, as illustrated in FIG. 12. In certain instances, the intermediary section 306*c* may include a first portion configured to protrude into the elongate slot 86 and a second portion configured to protrude into the gap defined between the first compressible adjunct 108 and the second compressible adjunct 110.

In certain instances, the intermediary section 306*c* serves as an alignment feature for aligning the first compressible adjunct 108 against the first section 306*a* of the attachment layer 306 and/or aligning the second compressible adjunct 110 against the second section 306*b* of the attachment layer 306. As illustrated in FIG. 11, the intermediary section 306*c* includes side walls 320 and 322. The first compressible adjunct 108 is configured to abut against the side wall 320, and the second compressible adjunct 108 is configured to abut against the side wall 322.

Figure 13:
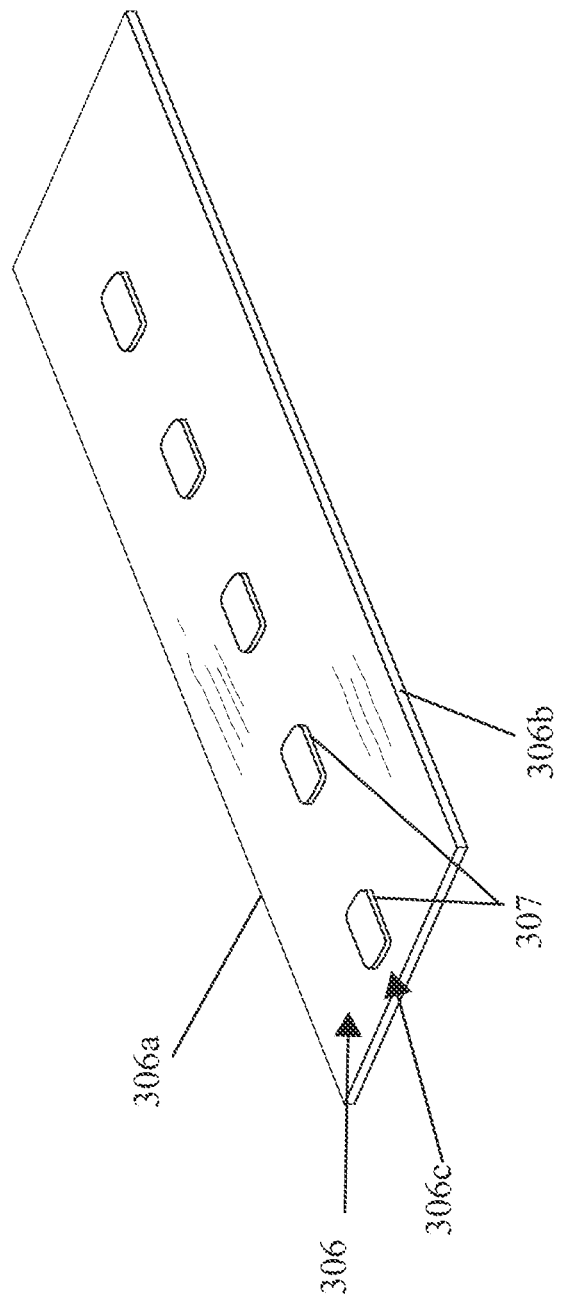
FIG. 13 is a perspective view of the attachment layer of FIG. 12.

In certain instances, the intermediary section 306*c* serves as an alignment feature for aligning the attachment layer 306 in position against the anvil 84. As illustrated in FIGS. 12 and 13, the intermediary section 306*c* includes include a plurality of projections 307 that are insertable into the elongate slot 86. The projections 307 are spaced apart from one another and arranged longitudinally in a row along a length of the intermediary section 306*c*. In at least one instance, the projections 307 can be equidistant from one another. Alternatively, the projections 307 can be arranged closer to each other in a first portion of the intermediary section 306*c* than a second portion of the intermediary section 306*c*. In at least one instance, one or more of the projections 307 comprises a top surface with a rectangular, or at least substantially rectangular, shape. Other shapes are contemplated by the present disclosure such as, for example, a circular shape or a dome shape.

Further to the above, the projections 307 are arranged longitudinally in a row along a length of the elongate slot 86, and are dimensioned to fit into the elongate slot 86. The projections 307 serve as alignment features for aligning the attachment layer 306 in position against the anvil 84. In certain instances, the projections 307 can be dimensioned to fit into the gap defined between the first compressible adjunct 108 and the second compressible adjunct 110. The projections 307 can serve as alignment features for aligning the first compressible adjunct 108 against the first section 306*a* of the attachment layer 306 and/or aligning the second compressible adjunct 110 against the second section 306*b* of the attachment layer 306.

In at least one instance, the opening of the elongate slot 86 is slightly greater than the widths the projections 307. Alternatively, the opening of the elongate slot 86 can be slightly smaller than the widths the projections 307, which may cause the projections 307 to be slightly deformed as they are pressed into the elongate slot 86. The deformed projections 307 may serve as anchoring features for securing the compressible adjunct assembly 304 to the anvil 84.

Figure 14:
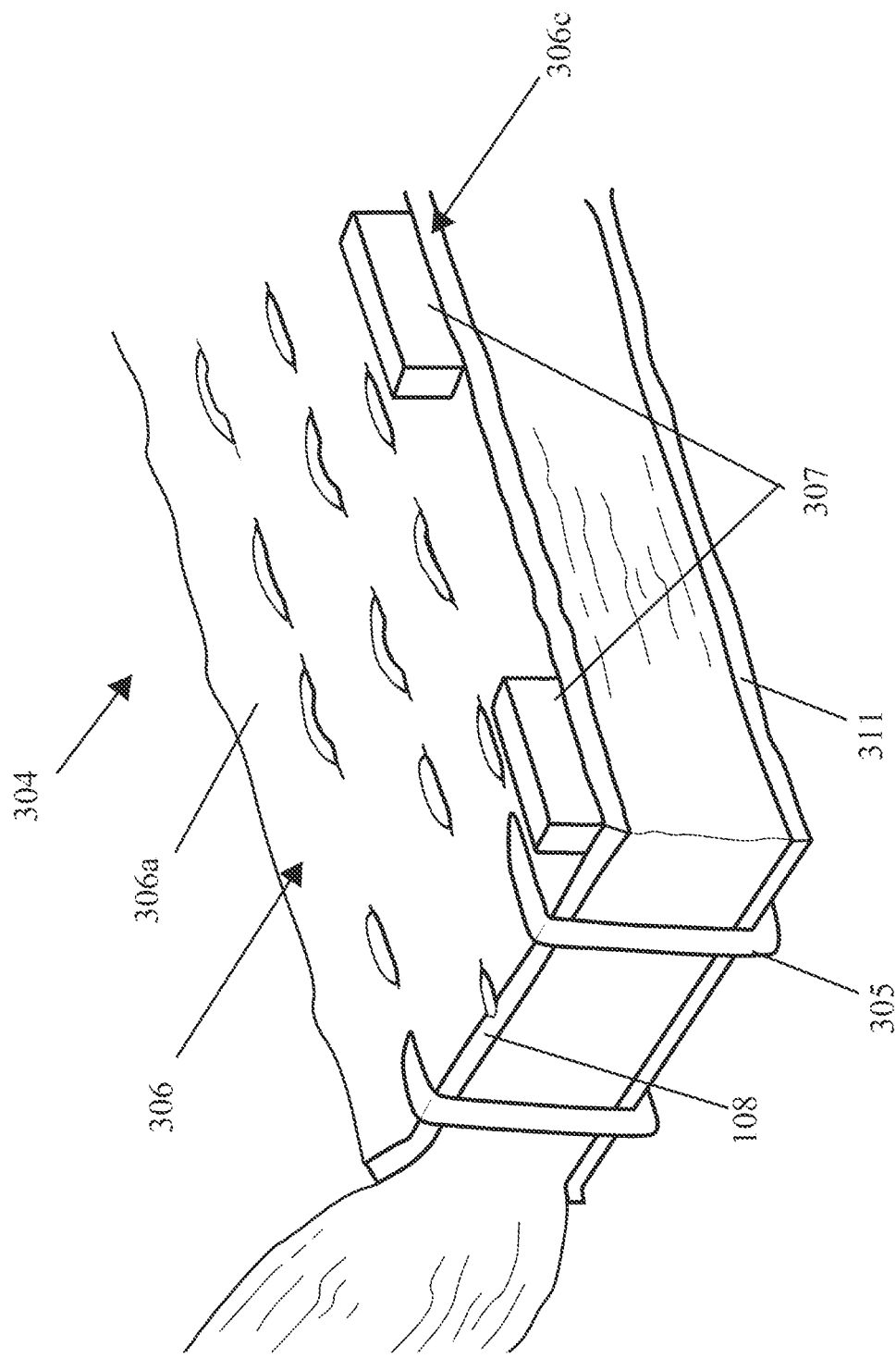
FIG. 14 is a partial perspective view of tissue sandwiched between two compressible adjunct assemblies, wherein the tissue is stapled and cut using a surgical stapling and severing instrument according to at least one embodiment disclosed herein.
Figure 15:
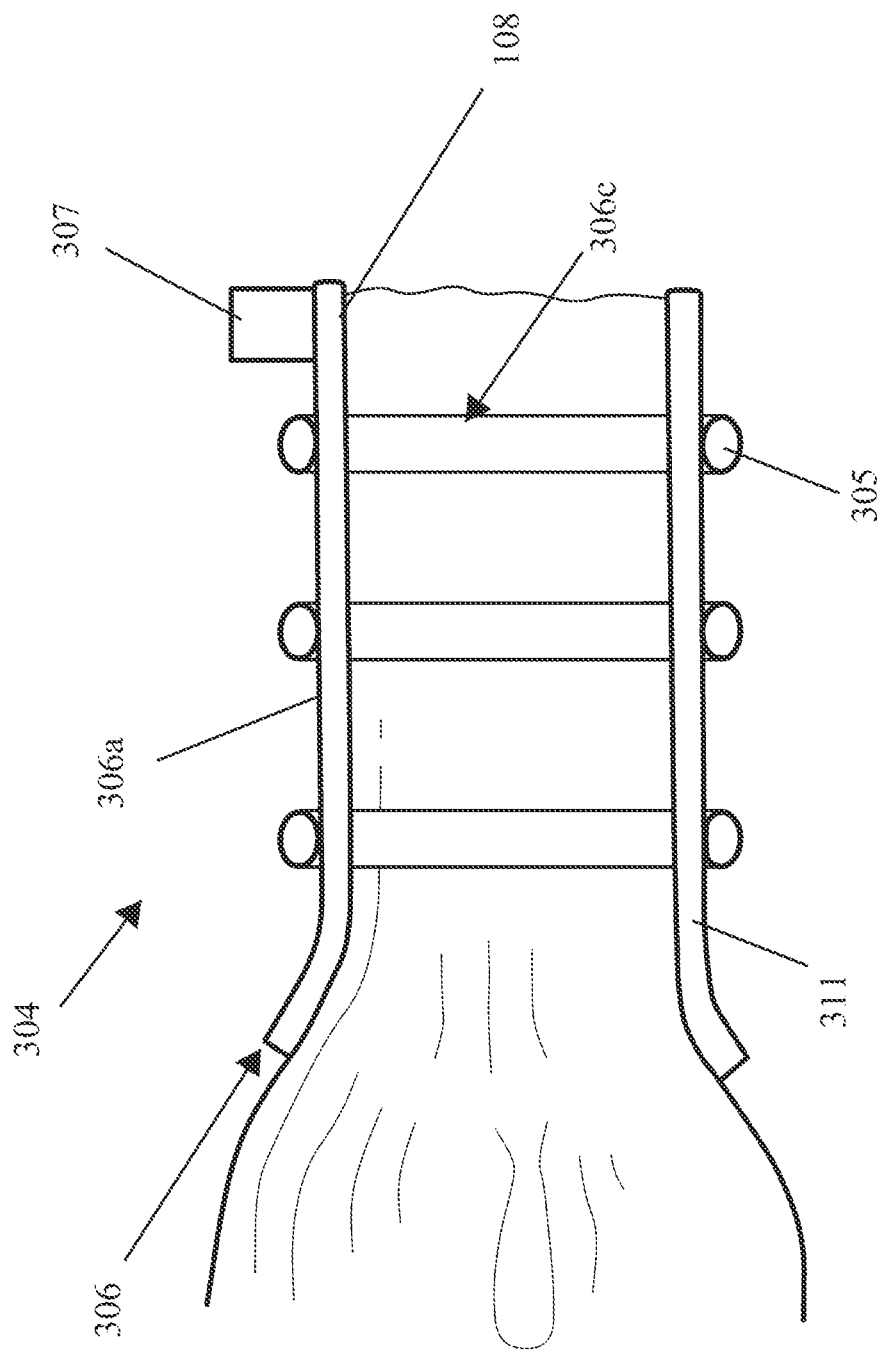
FIG. 15 is a transverse cross-sectional view of the tissue and compressible adjunct assemblies of FIG. 14.

Referring to FIGS. 14 and 15, tissue is sandwiched between the compressible adjunct assembly 304 and a compressible adjunct assembly 311. The tissue is stapled and cut using a surgical stapling and severing instrument such as, for example, the surgical stapling and severing instrument 8010. A plurality of staples 305 are deployed from a staple cartridge such as, for example, the staple cartridge 1000 (FIG. 17) to capture the tissue between the compressible adjunct assembly 304 and the compressible adjunct assembly 311. The captured tissue is severed along with the projections 307 of the attachment layer 306 as the cutting edge 9116 (FIG. 3) is advanced through the longitudinal slot 86. The compressible adjunct assembly 304, originally attached to the anvil 84, is now released from the anvil 84 and remains with the stapled tissue in the patient's body. Likewise, compressible adjunct assembly 311, originally attached to the staple cartridge 10000, is now released from the staple cartridge 10000 and remains with the stapled tissue in the patient's body.

Figure 16:
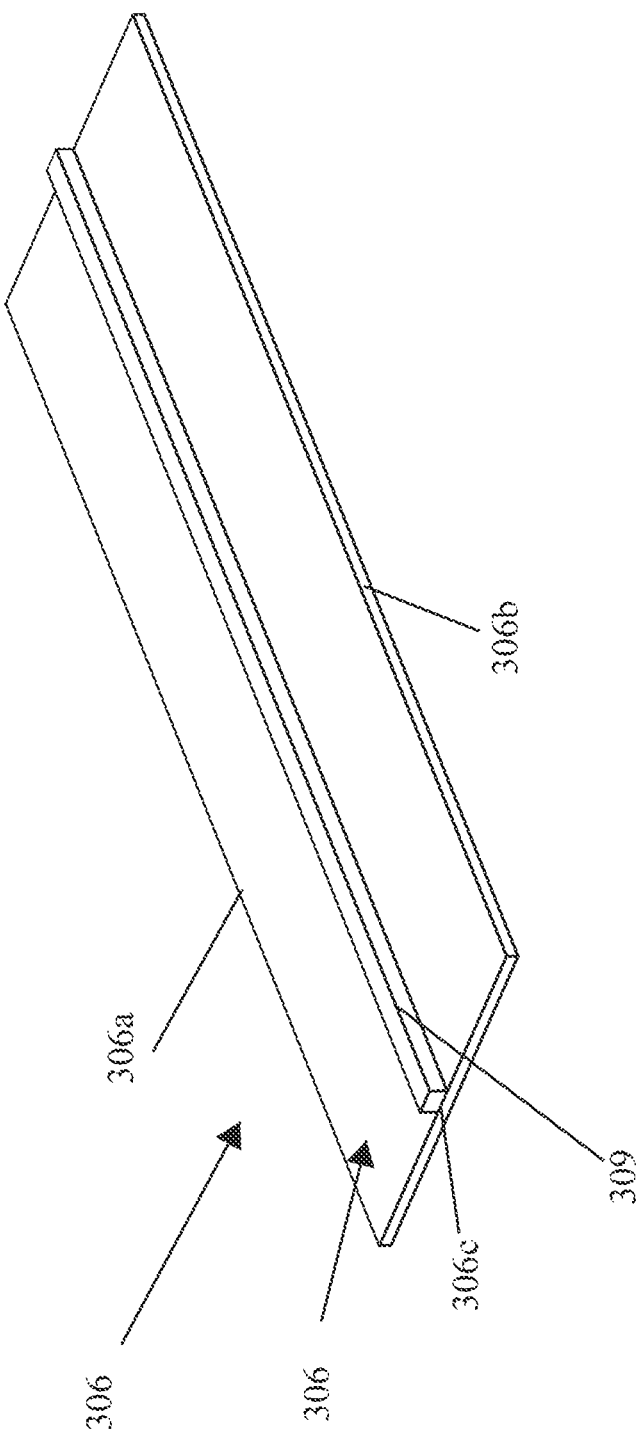
FIG. 16 is a perspective view of an attachment layer including an intermediate section having a bar extending therefrom.

In the embodiment illustrated in FIG. 16, the intermediary section 306*c* includes a bar 309 extending longitudinally along a length of the intermediary section 306*c*. The bar 309 comprises a top surface with a rectangular, or at least substantially rectangular, shape. Other shapes are contemplated by the present disclosure such as, for example, a dome shape or a curved shape. The bar 309 extends longitudinally along a length of the elongate slot 86, and is dimensioned to fit into the elongate slot 86. In at least one instance, the bar 309 is dimensioned to snuggly or tightly fit into the elongate slot 86. In at least one instance, the opening of the elongate slot 86 is slightly greater than the width of the bar 309. Alternatively, the opening of the elongate slot 86 can be slightly smaller than the width of the bar 309, which may cause of the bar 309 to be slightly deformed as it is pressed into the elongate slot 86. The deformed bar 309 may serve as an anchoring feature for securing the compressible adjunct assembly 304 to the anvil 84. In addition, the bar 309 can serve as an alignment feature for aligning the attachment layer 306 in position against the anvil 84.

Like the projections 307, the bar 309 can be dimensioned to fit into the gap defined between the first compressible adjunct 108 and the second compressible adjunct 110. The bar 309 can serve as an alignment feature for aligning the first compressible adjunct 108 against the first section 306a of the attachment layer 306 and/or aligning the second compressible adjunct 110 against the second section 306b of the attachment layer 306.

Figure 17:
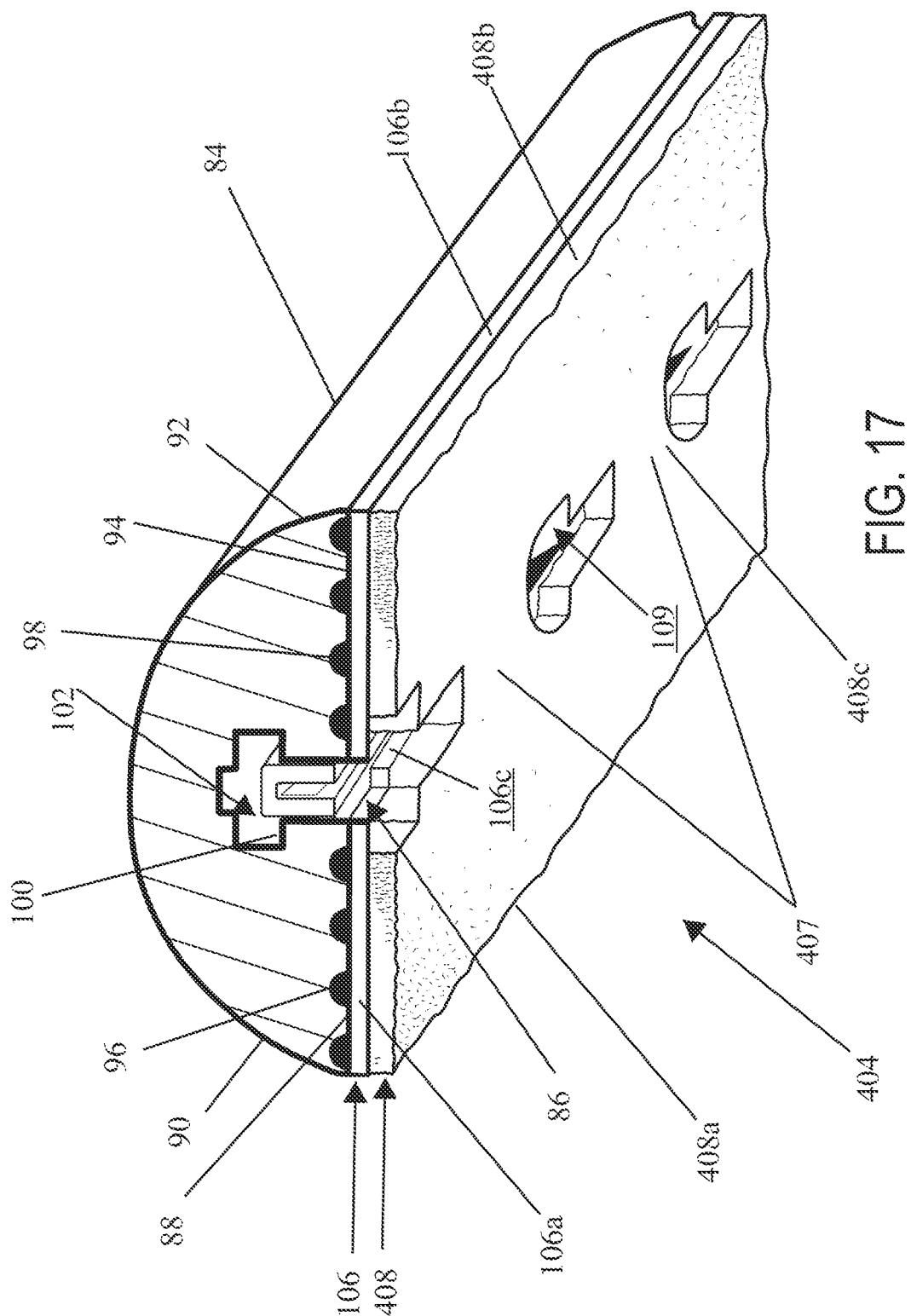
FIG. 17 is a transverse cross-sectional view of an anvil assembled with a compressible adjunct assembly including an attachment layer and a compressible layer.

Referring to FIG. 17, a compressible adjunct assembly 404 is assembled with the anvil 84. The compressible adjunct assembly 404 is similar in many respects to the compressible adjunct assembly 104. For example, the compressible adjunct assembly 404 includes the attachment layer 106. As described above in greater detail, the attachment layer 106 includes the bridging portions 107 that extend between the first section 106a and the second section 106b.

As illustrated in FIG. 17, the compressible adjunct assembly 404 also includes a compressible layer or adjunct 408, which is similar in many respects to the compressible adjuncts 108 and 110. In addition, the compressible adjunct 408 includes a first compressible portion 408a positionable on the first side 90 of the elongate slot 86, and a second compressible portion 408b positionable on the second side 94 of the elongate slot 86. In other words, the elongate slot 86 separates the first compressible portion 408a from the second compressible portion 408b when the compressible adjunct assembly 404 is assembled with the anvil 84. An intermediary compressible portion 408c of the compressible adjunct 408 extends between the first compressible portion 408a and the second compressible portion 408b. The intermediary compressible portion 408c bridges the elongate slot 86, as illustrated in FIG. 17. In certain instances, the intermediary compressible portion 408c only partially bridges the elongate slot 86. In certain instances, the intermediary compressible portion 408c completely covers the elongate slot 86.

Referring to FIG. 17, the intermediary compressible portion 408c includes of a plurality of bridging portions 407 extending between the first compressible portion 408a and the second compressible portion 408b. The bridging portions 407 are spaced apart from one another in the same, or at least substantially the same, manner the bridging portions 107 of the attachment layer 106 are spaced from one another. The gaps 109 defined between the bridging portions 107 also extend between corresponding bridging portions 407 which are aligned with the bridging portions 107 such that the elongate slot 86 is exposed through the Gaps 109. In certain instances, however, the bridging portions 107 and the bridging portions 407 can be out of alignment preventing or reducing thorough gaps.

The attachment layer 106 comprises a height that is smaller than the height of the compressible adjunct 408. Said another way, the attachment layer 106 can be thinner than the compressible adjunct 408. Alternatively, in certain instances, the attachment layer 106 may comprise a height that is greater than or equal to the height of the compressible adjunct 408. In at least one instance, the attachment layer 106 is comprised of a film, which can be attached to the compressible adjunct 408 such that the bridging portions 407 are aligned with the bridging portions 107, as illustrated in FIG. 17.

Figure 18:
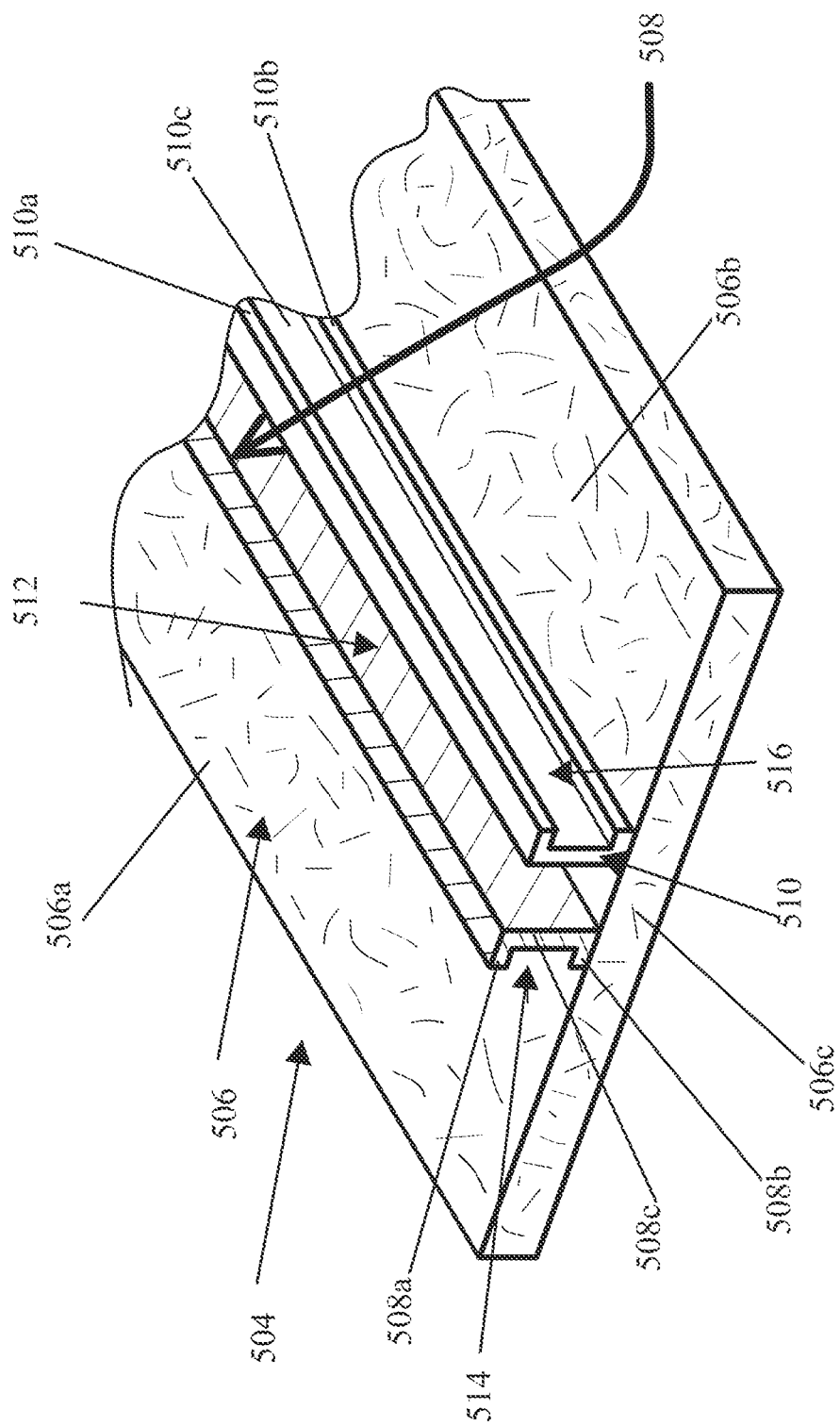
FIG. 18 is a partial perspective view of a compressible adjunct assembly including a compressible layer and two attachment members in accordance with at least one embodiment described herein.
Figure 19:
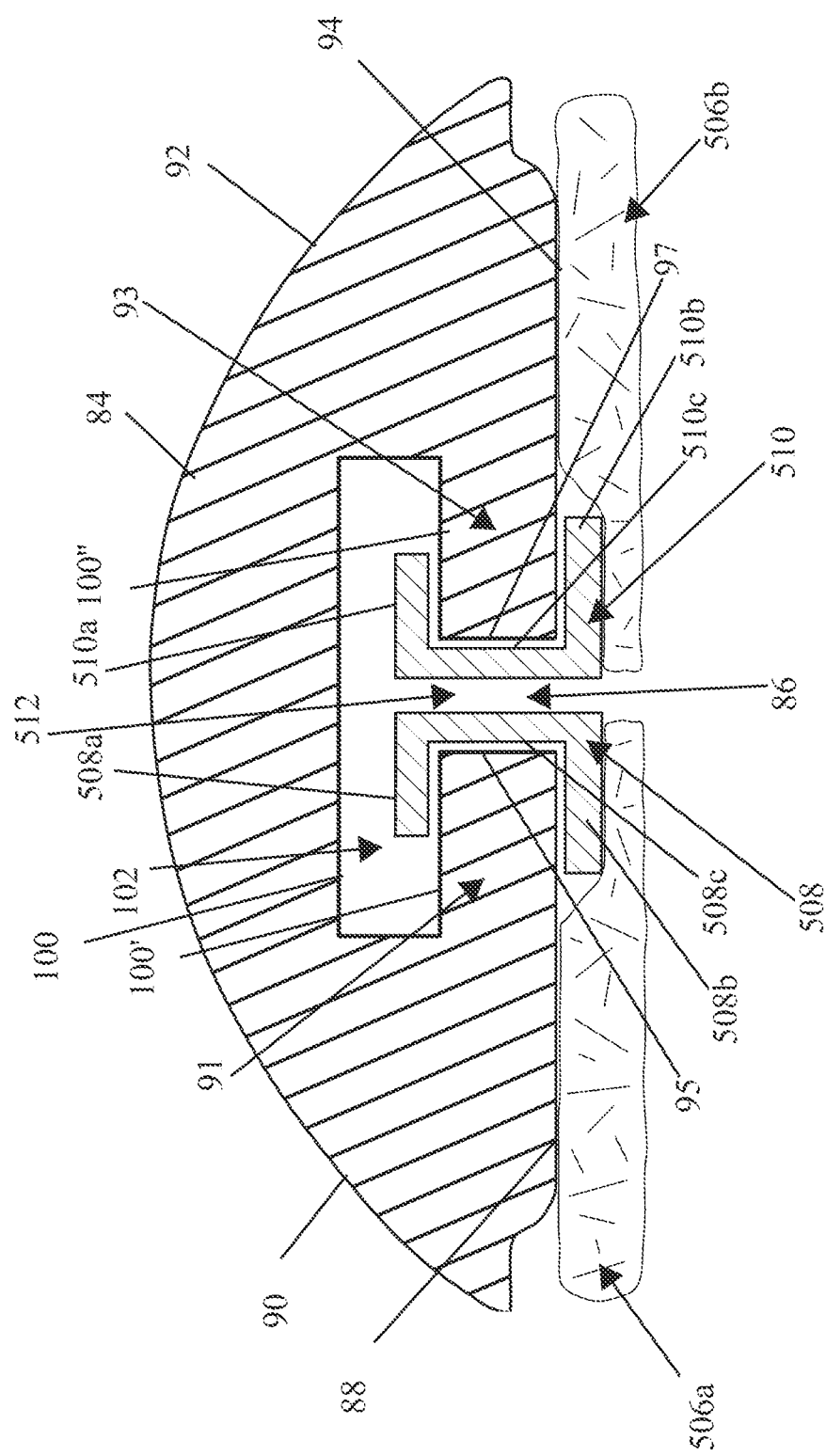
FIG. 19 is a cross-sectional view of an anvil assembled with the compressible adjunct assembly of FIG. 18 after the compressible adjunct assembly has been severed by a cutting edge.

Referring to FIGS. 18 and 16, a compressible adjunct assembly 504 includes a compressible layer 506, a first attachment member 508, and a second attachment member 510. It is envisioned that the compressible adjunct assembly 504 includes only one attachment member. Alternatively, the compressible adjunct assembly 504 may include three or more attachment members. As illustrated in FIG. 19, the compressible adjunct assembly 504 can be assembled with a jaw member of a surgical stapling and severing instrument such as, for example, the anvil 84 of the surgical stapling and severing instrument 8010. The attachment members 508 and 510 are configured to releasably attach the compressible layer 506 to the anvil 84.

Referring again to FIG. 19, the cutting edge 9116 has severed the compressible layer 506 of the compressible adjunct assembly 504 into a first compressible portion 506a on the first side 90 of the anvil 84 and a second compressible portion 506b on the second side 92 of the anvil 84. Tissue Captured by the surgical stapling and severing instrument 8010 can also be severed along with the compressible layer 506 by the cutting edge 9116 as the cutting edge 9116 is advanced through the elongate slot 86. A first portion of the severed tissue may be stapled was the first compressible portion 506a, and a second portion of the severed tissue may be stapled with the second compressible portion 506b.

In certain instances, the first compressible portion 506a and the second compressible portion 506b can be independent members that are separately attached to the anvil 84. In such instances, the cutting edge 9116 may not sever the compressible layer 506 while severing the captured tissue, as described above. Instead, the cutting edge 9116 may pass between the first compressible portion 506a and the second compressible portion 506b.

Referring again to FIGS. 18 and 16, the attachment members 508 and 510 are spaced apart from each other. A passage 512 extends between the attachment members 508 and 510 for accommodating the cutting edge 9116 as the cutting edge 9116 is advanced through the elongate slot 86. When the compressible adjunct assembly 504 is assembled with the anvil 84, the first attachment member 508 is matingly engaged with a first ledge 91 of the first side 90 of the anvil 84 and the second attachment member 510 is matingly engaged with a second ledge 93 of the second side 92 of the anvil 84. The attachment members 508 and 510 comprise "C" shaped profiles that are dimensioned and/or sufficiently resilient to snap fit around the ledges 93 and 95, respectively, to secure the compressible adjunct assembly to the anvil 84. Matting recesses 514 and 516 of the attachment members 508 and 510, respectively, are configured to receive the ledges 91 and 93, respectively.

Further to the above, the first attachment member 508 includes a first attachment portion 508a positionable against an internal portion 100' of the internal surface 100. The internal portion 100' may form a top surface of the first ledge 91. A second attachment portion 508b of the attachment member 508 is attached to an intermediate compressible portion 506c of the compressible layer 506. A coupling portion 508c interconnects the first attachment portion 508a and the second attachment portion 508b. The coupling portion 508c extends into the elongate slot 86, and is positioned against a side wall 95 of the ledge 91.

Like the first attachment member 508, the second attachment member 510 includes a first attachment portion 510a positionable against an internal portion 100" of the internal surface 100. The internal portion 100" may form a top surface of the second ledge 93. A second attachment portion 510b of the attachment member 510 is attached to the intermediate compressible portion 506c of the compressible layer 506. Like the coupling portion 508c, a coupling portion 510c interconnects the first attachment portion 510a and the second attachment portion 510b. The coupling portion 510c extends into the elongate slot 86, and is positioned against a side wall 97 of the ledge 97.

As illustrated in FIG. 18, the attachment members 508 and 510, when assembled with the compressible layer 506, are oriented such that second attachment member 510 is a mirror-image of the first attachment member 508. The attachment members 508 and 510 extend along the compressible layer 506 in parallel, or at least substantially in parallel, with each other. The space between the coupling portion 508c and the coupling portion 510c defines the passage 512 which is configured to accommodate the advancement of the cutting edge 9116, as described above. Furthermore, the pins 9110 (FIG. 3) of the firing assembly 9090 ride against the first attachment portions 508a and 510a as the firing assembly 9090 is advanced to deploy the staples into the tissue captured by the surgical stapling and severing instrument 8010.

Referring again to FIG. 18, the attachment members 508 and 510 extend along the entire length of the compressible layer 506. Alternatively, the attachment members 508 and 510 may extend along a portion of the length of the compressible layer 506. In at least one instance, the attachment members 508 and 510 may extend along a middle portion of the length of the compressible layer 506. In at least one instance, the first attachment member 508 extends along a first portion of the length of the compressible layer 506, while the second attachment member 510 extends along a second portion of the length of the compressible layer 506 that is different from the first portion.

In certain instances, one or both of the second attachment portions 508b and 510b can be embedded in the intermediate compressible portion 506c. In at least one instance, one or both of the second attachment portions 508b and 510b can be inserted, or partially inserted, into a solution that is lyophilized to produce the compressible layer 506. Alternatively, one or both of the second attachment portions 508b and 510b can be attached to the compressible layer 506 after fabrication of the compressible layer 506. Any suitable attachment technique can be employed in attaching the second attachment portions 508b and 510b to the compressible layer 506 such as, for example, a biocompatible adhesive.

Figure 20:
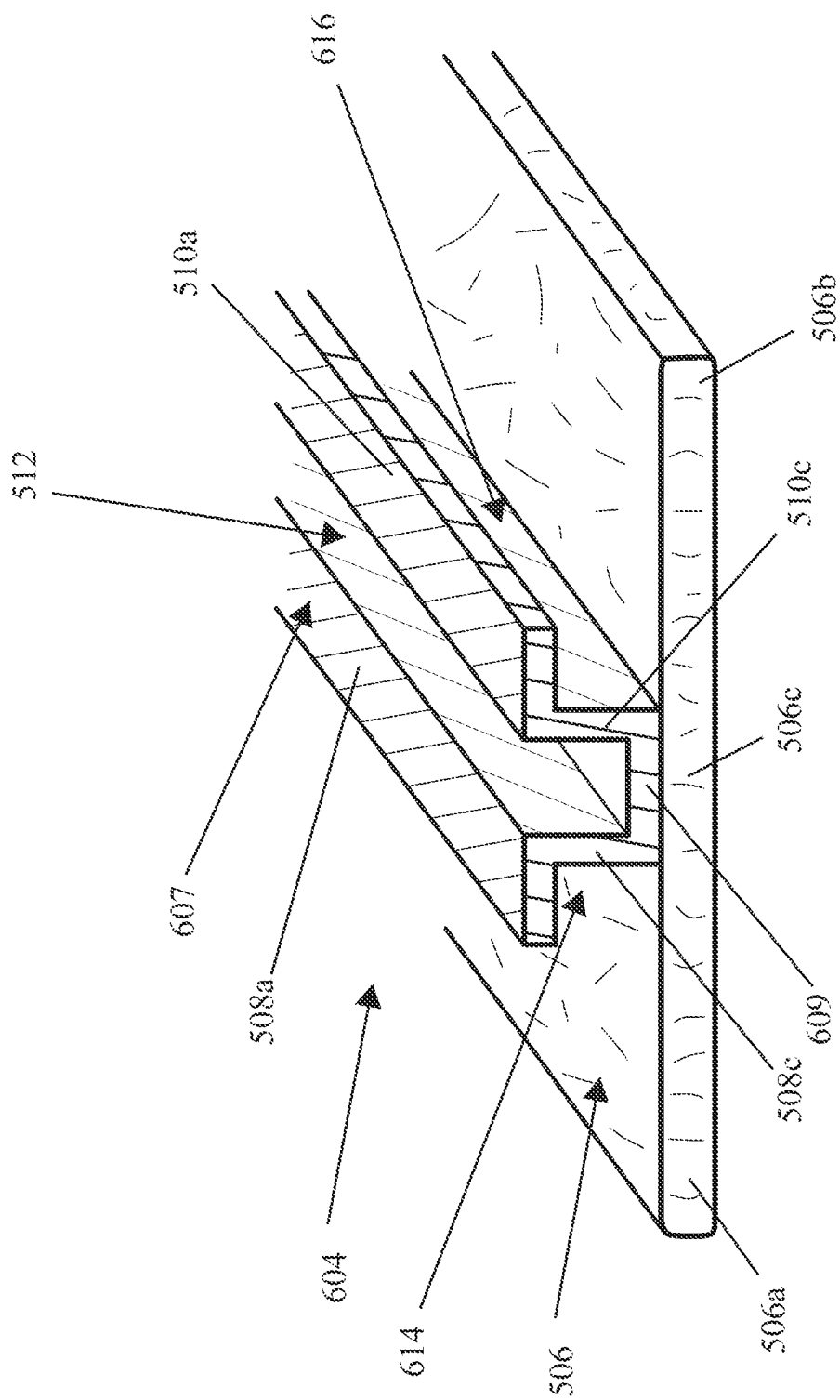
FIG. 20 is a partial perspective view of a compressible adjunct assembly including a compressible layer and two attachment members in accordance with at least one embodiment described herein.

Referring to FIG. 20, a compressible adjunct assembly 604 is depicted. The compressible adjunct assembly 604 is similar in many respects to the compressible adjunct assembly 504. For example, the compressible adjunct assembly 604 can be assembled with a jaw member of a surgical stapling and severing instrument such as, for example, the anvil 84 of the surgical stapling and severing instrument 8010. However, the compressible adjunct assembly 604 does not include spaced apart attachment members. Instead, the attachment members are united in the form of a single attachment layer 607 that is shaped to form the attachment portions 508a and 510a. The attachment layer 607 is configured to releasably attach the compressible adjunct assembly 604 to the anvil 84.

In at least one instance, the attachment layer 607 is formed as a flat, or at least substantially flat, layer or film which is modified to a desired shape that comprises the attachment portions 508a and 510a. Alternatively, the attachment layer 607 can take its desired shape during formation. For example, a mold comprising the desired shape can receive a melted biocompatible material, which is solidified inside the mold forming the desired shape of the attachment layer 607. Other techniques for manufacturing the attachment layer 607 are contemplated by the present disclosure.

Referring again to FIG. 20, the attachment layer 607 includes the second an intermediate attachment portion 609 which replaces the attachment portions 508b and 510b. The intermediate attachment portion 609 is attached to the intermediate compressible portion 506c. In at least one instance, the intermediate attachment portion 609 is embedded, or at least partially embedded, in the intermediate compressible portion 506c. Furthermore, coupling portions 508c and 510c protrude from opposite ends of the intermediate attachment portion 609, in a direction away from the intermediate compressible portion 506c of the compressible layer 506, to define the passage 512. The cutting edge 9116 is advanced through the passage 512 between the coupling portions 508c and 510c as it cuts through the intermediate attachment portion 609, the intermediate compressible portion 506c, and the captured tissue during the firing sequence.

Mating recesses 614 and 616 are defined between the attachment layer 607 and the compressible layer 506 on opposite sides from the passage 512, as illustrated in FIG. 20. The mating recesses 614 and 616 are configured to receive the ledges 91 and 93, respectively. When the compressible adjunct assembly 604 is assembled with the anvil 84, the ledge 91 is positioned between the first attachment portion 508a and the first compressible portion 506a of the compressible layer 506, and the ledge 93 is positioned between the first attachment portion 510a and the second compressible portion 506b of the compressible layer 506.

In certain instances, the attachment layer 607 and/or the compressible layer 506 may comprise variations in thickness and/or edge conditions to reduce the potential for tissue trauma in surrounding tissue and/or to help maintain the integrity of the compressible adjunct assembly 604 during attachment, manipulation, and/or release from the anvil 84. In at least one instance, the attachment layer 607 and/or the compressible layer 506 are reinforced with atraumatic and/or thicker edges.

Figure 21:
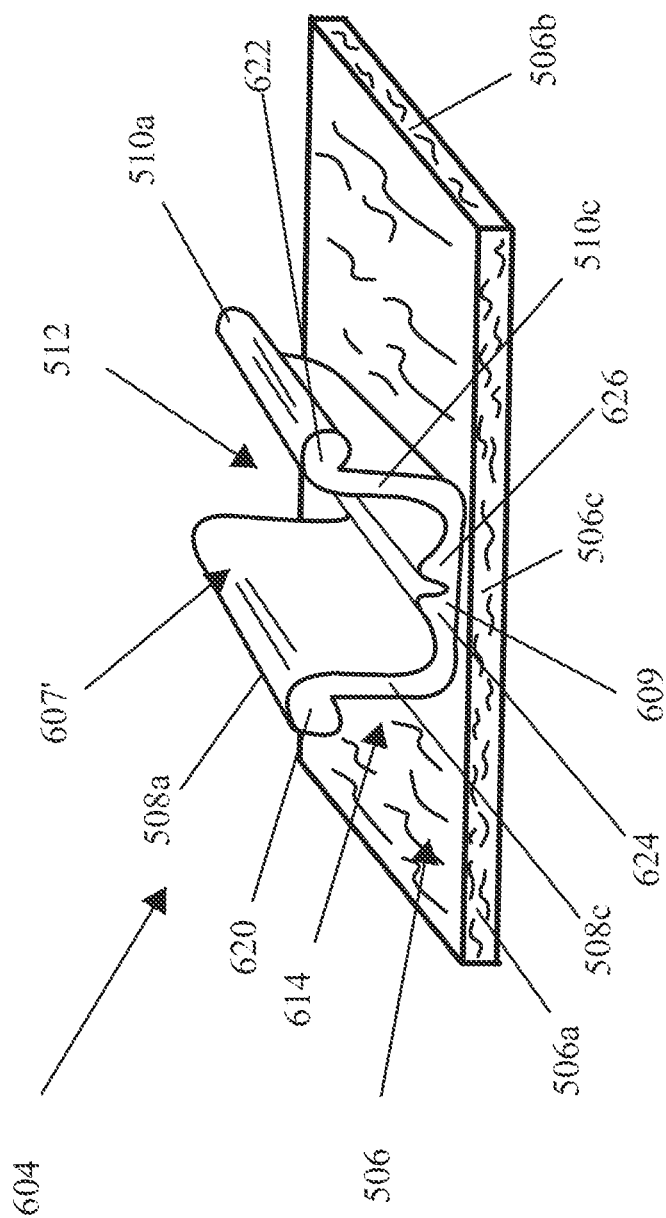
FIG. 21 is a perspective view of a compressible adjunct assembly including a compressible layer and two attachment members in accordance with at least one embodiment described herein.

Referring to FIG. 21, the attachment layer 607' includes rolled edges 620 and 622, which reduce the potential for tissue trauma in surrounding tissue. In addition, the attachment layer 607' is reinforced with relatively thicker regions 624 and 626 at the intermediate attachment portion 609 to improve the robustness of the compressible adjunct assembly 604 during attachment, manipulation, and/or release from the anvil 84. Other high stress areas in the compressible adjunct assembly 604 can also be reinforced in the same, or a similar, manner.

Figure 22:
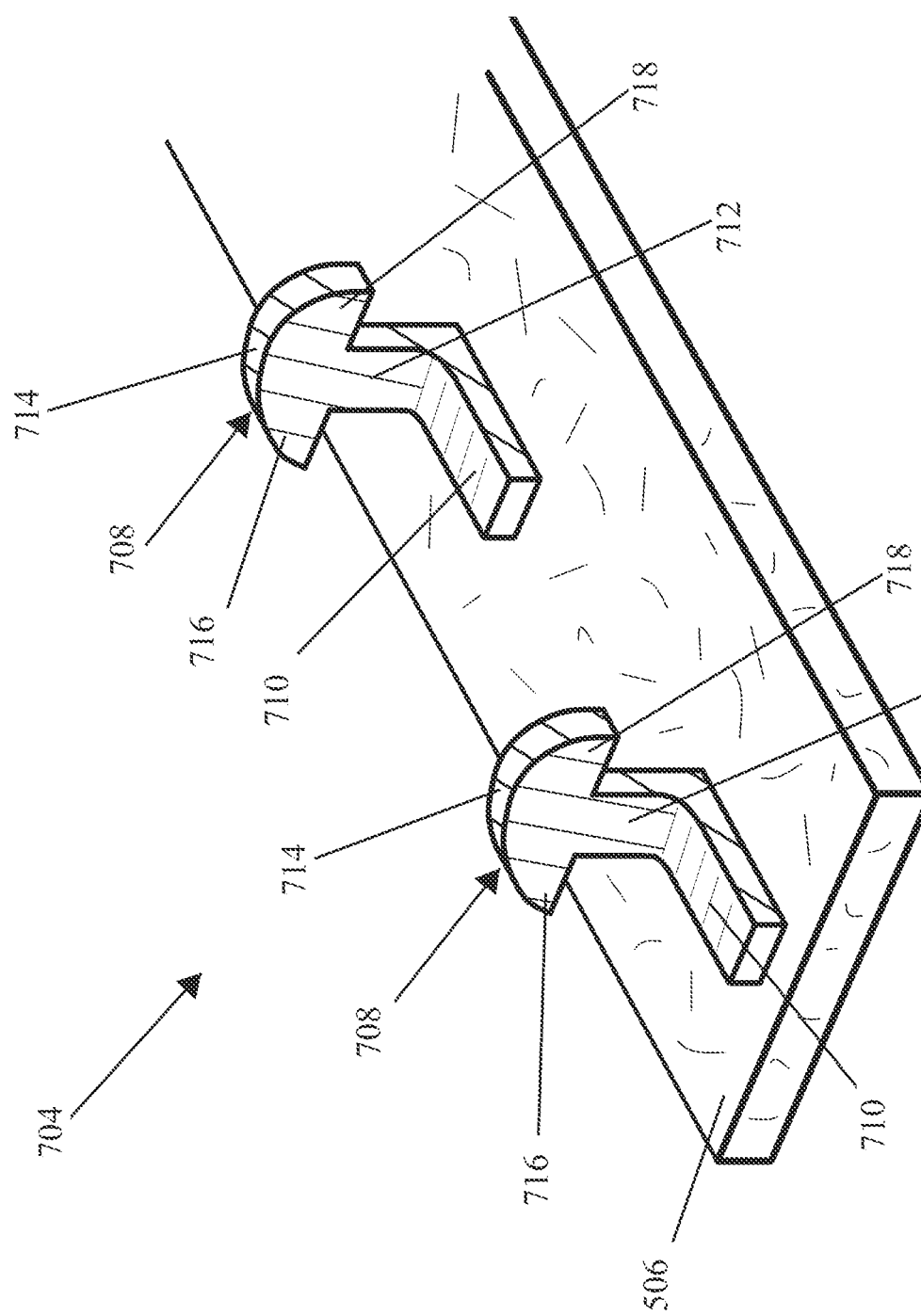
FIG. 22 is a partial perspective view of a compressible adjunct assembly including a compressible layer and a plurality of attachment members in accordance with at least one embodiment described herein.
Figure 31:
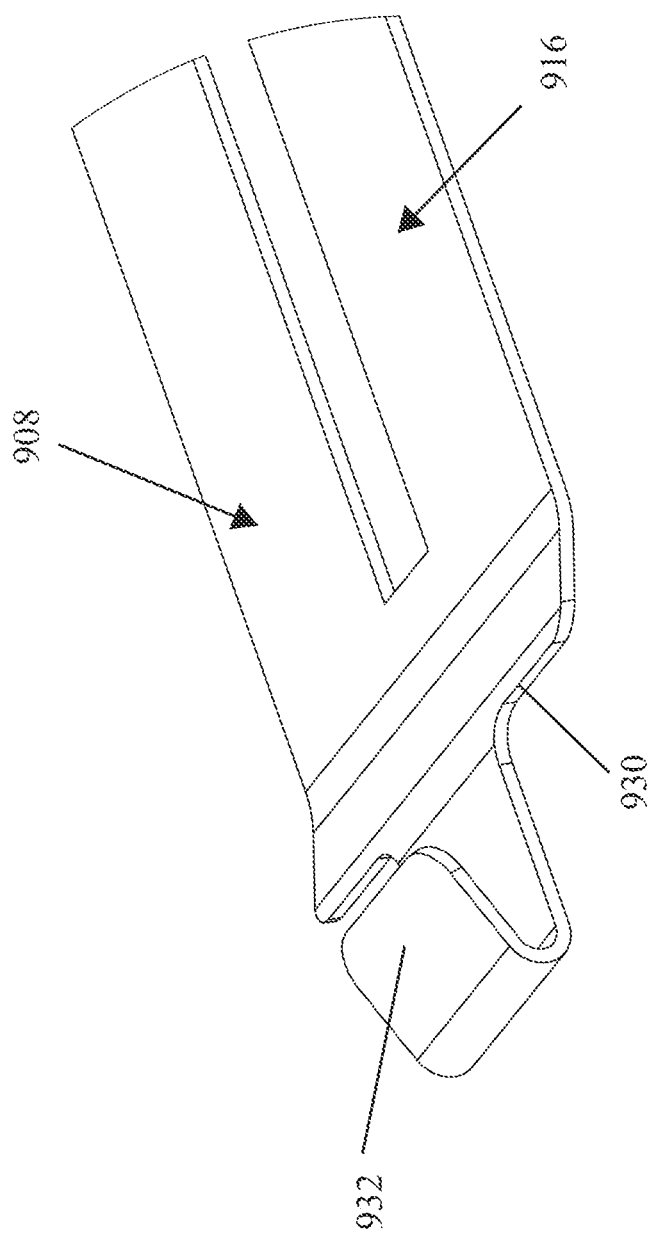
FIG. 31 is a partial perspective view of a distal portion of the attachment layers of FIG. 29.

Referring now to FIGS. 22-24, a compressible adjunct assembly 704 includes the compressible layer 506 and a plurality of attachment members 708 that are spaced apart from one another and arranged longitudinally in a row along a length of the compressible layer 506. In certain instances, the attachment members 708 are arranged along a central portion of the compressible layer 506. In certain instances, the attachment members 708 are arranged along a distal portion and/or a proximal portion of the compressible layer 506. Like the attachment members 508 and 510, the attachment members 708 are configured to releasably attach the compressible layer 506 to the anvil 84. However, unlike the attachment members 508 and 510, each attachment member 708 is capable of being positioned against the ledges 95 and 97 simultaneously. The attachment members 708 are severed by the cutting edge 9116 as the cutting edge 9116 is advanced through the elongate slot 86 to cut the compressible layer 506 and the captured tissue.

The attachment members 708 each comprise a base 710, a stem 712 extending from the base, and a head or crown 714 extending from the stem 712. When the compressible adjunct assembly 704 is assembled with the anvil 84, the stem 712 is positioned in the elongate slot 86, as illustrated in FIG. 23, and the head 714 resides in the internal space 102 within the anvil 84. The head 714 comprises a transverse cross-sectional area that resembles the shape of a dome which extends laterally beyond the stem 712 to simultaneously engage the internal surfaces 100' and 100" of the anvil 84, as illustrated in FIG. 23. Other shapes of the head 714 are contemplated by the present disclosure.

Lateral extensions 716 and 718 of the head 714 comprise flat surfaces 720 and 722, respectively, which rest against the internal surfaces 100' and 100", respectively. The surfaces 720 and 722 need not be completely flat. In certain instances, the surfaces 720 and 722 can be roughened to improve traction against the internal surfaces 100' and 100". Gripping features may be incorporated into the surfaces 720 and 722. In certain instances, a biocompatible adhesive may be employed to bond the surfaces 720 and 722 to the internal surfaces 100' and 100", for example.

Referring again to FIG. 22, the head 714 and/or the stem 712 are configured to bend in the distal direction as the E-beam 9102 is advanced distally against the head 714 during the firing sequence. The proximally projecting top guide 9118 may push against the head 714 causing the head 714 to bend forward and downward to allow room for the passage of the E-beam 9102. The pins 9110 may pass on top of the lateral extensions 716 and 718. As the lateral extensions 716 and 718 flatten against the internal surfaces 100' and 100", the head 714 may assist in blocking tissue ahead of the E-beam 9102 from entering the internal space 102 and disrupting the advancement of the pins 9110. This added functionality can improve the performance of the firing assembly 9090 and reduce potential trauma to the treated tissue by preventing the treated tissue from being entrapped within the anvil 84. As illustrated in FIG. 22, the head 714 and the stem 712 comprise a reduced transverse cross-sectional area. In other words the head 714 and the stem 712 are substantially flattened to improve bending and/or facilitate insertion of the head 714 into the internal space 102. Also, in various instances, the head 714 and/or the stem 712 are comprised, or at least partially comprised, of a resilient biocompatible material to improve bending and/or facilitate insertion of the head 714 into the internal space 102.

Referring to FIG. 24, the base 710 is embedded in the compressible layer 506. In certain instances, the base 710 is only partially embedded in the compressible layer 506. In certain instances, the base 710 is not embedded into the compressible layer 506, but instead is attached to an exterior surface thereof. For example, a biocompatible adhesive can be employed to attach the base 710 to the compressible layer 506. As illustrated in FIG. 24, the base 710 defines an axis A-A which intersects an axis B-B defined by the stem 712 at an angle α. The angle α is 90°. In certain instances, the angle α is greater than 90°. In other instances, the angle α is less than 90°.

As illustrated in FIG. 24, the stem 712 protrudes from a proximal end portion of the base 710. Alternatively, the stem 712 may protrude from a distal end portion of the base 710. Alternatively, the stem 712 may protrude from a central portion of the base 710. As illustrated in FIG. 22, the base 712 comprises a rectangular shape. The rectangular-shaped he bases 710 are aligned longitudinally along the longitudinal slot 86 when the compressible adjunct assembly 704 is assembled with the anvil 84. Other shapes, sizes, and arrangements of the bases 712 are contemplated by the present disclosure. In at least one instance, a base 712 may comprise a circular shape and a stem 714 may protrude from the center of the circular base 712.

Referring now to FIGS. 25-28, a compressible adjunct assembly 804 includes a compressible layer 806 that is attached to a plurality of attachment members 808. The compressible adjunct assembly 804 is similar in many respects to the compressible adjunct assemblies 504, 604, and 704. For example, the compressible adjunct assembly 804 can be assembled with a jaw member of a surgical stapling and severing instrument such as, for example, the anvil 84 of the surgical stapling and severing instrument 8010. As described in greater detail below, the attachment members 808 releasably attach the compressible layer 806 to the anvil 84.

The compressible layer 806 includes an intermediate compressible portion 806c extending longitudinally between a first compressible portion 806a and a second compressible portion 806b. A plurality of slots 809 are defined in the intermediate compressible portion 806c. The slots 809 are spaced apart from one another and arranged longitudinally in a row along a length of the compressible layer 806. In certain instances, the slots 809 are arranged along a central portion of the intermediate compressible portion 806c of the compressible layer 806. In certain instances, the slots 809 are arranged along a distal portion and/or a proximal portion of the intermediate compressible portion 806c. When the compressible adjunct assembly 804 is assembled with the anvil 84, the slots 809 are aligned with the elongate slot 86 such that the cutting edge 9116 passes through the slots 809 during distal advancement of the cutting edge 9116. This reduces friction against the cutting edge 9116 which prolongs the life of the cutting edge 9116 and/or reduces the force required to advance the firing assembly 9090.

Referring to FIG. 25, the attachment members 808 are spaced apart from one another and arranged longitudinally along a length of the intermediate compressible portion 806c such that the attachment members 808 alternate between two sides 814 and 816 of a plane define by the slots 809. Other positions and arrangements of the attachment members 808 with respect to the compressible layer 806 are contemplated by the present disclosure. Each attachment member 808 is positioned against a slot 809. Alternatively, an attachment member 808 can be positioned between two consecutive slots 809.

The attachment members 808 comprise a generally curved shape which can improve the stiffness of the attachment members 808. Other shapes are contemplated by the present disclosure. As illustrated in FIG. 25, the attachment members 808 comprise a partial cylindrical frame with a concave side 820 facing away from the slots 809 and a convex side 818 facing toward the slots 809. The attachment members 808 further comprise a coupling portion 808c extending between an attachment portion 808a and a base 808b. The attachment portion 808a comprise lateral extensions 810 that are configured to rest against the internal surface 100' or the internal surface 100" to secure the compressible adjunct assembly 804 to the anvil 84.

Further to the above, the base 808b includes tabs 824 configured to secure the attachment member 808 to the compressible layer 806. In at least one instance, as illustrated in FIG. 26, a base 808b includes a single tab 824 that is received in a bifurcated portion 826 of the compressible layer 806. In at least one instance, as illustrated in FIG. 27, a base 808b includes two tabs 824 that are configured to receive a portion 828 of the compressible layer 806 therebetween. In at least one instance, as illustrated in FIG. 28, a base 808a includes a tab 824 that comprises a slot 830. The portion 828 of the compressible layer 806 can be twisted and inserted into the slot 830 to secure the attachment member 808 to the compressible layer 806.

Referring now to FIG. 29, a compressible adjunct assembly 904 is assembled with an anvil 984. The anvil 984 is similar in many respects to the anvil 84 (FIG. 9) and the anvil 8014 (FIG. 1). For example, the anvil 984 includes the elongate slot 86 which defines a first outer surface 988 extending on the first side 90 of the elongate slot 86, and a second outer surface 992 extending on the second side 94 of the elongate slot 86. Also, the anvil 984 is movable relative to a staple cartridge such as, for example, the staple cartridge 10000 to capture tissue therebetween. The outer surfaces 988 and 992 of the anvil 984 are stepped, as illustrated in FIG. 29. In other embodiments, however, an anvil can include planar outer surfaces that are not stepped. In at least one instance, an anvil may include a central surface that is offset from two lateral surfaces. Other anvils with various shapes and surfaces are contemplated by the present disclosure.

In any event, the compressible adjunct assembly 904 includes a first attachment layer 908 positionable against the first outer surface 988 and a second attachment layer 910 positionable against the second outer surface 992. As illustrated in FIG. 29, the first attachment layer 908 is releasably attached to the second attachment layer 910. Attachment members 916 and 918 extend laterally from the attachment layers 908 and 916, respectively. The attachment members 916 and 918 include interlocking portions 912 and 920, respectively, and distal end portions 914 and 922, respectively. The distal end portions 914 and 922 are tucked under the ledges 91 and 93, respectively, to secure the compressible adjunct assembly 904 to the anvil 984, as illustrated in FIG. 29. Although one pair of the attachment members 916 and 918 is shown, it is understood that the first layer 908 may include a plurality of the attachment members 916 which can be interlocked with a plurality of the attachment members 918 extending from the second layer 910.

Referring to FIG. 30, the interlocking portions 912 and 920 may include interlocking slots 913 and 921, respectively, which can be configured for mating engagement with one another. In at least one instance, a biocompatible adhesive can be employed to reinforce the engagement between the slot 913 and 921.

Figure 32:
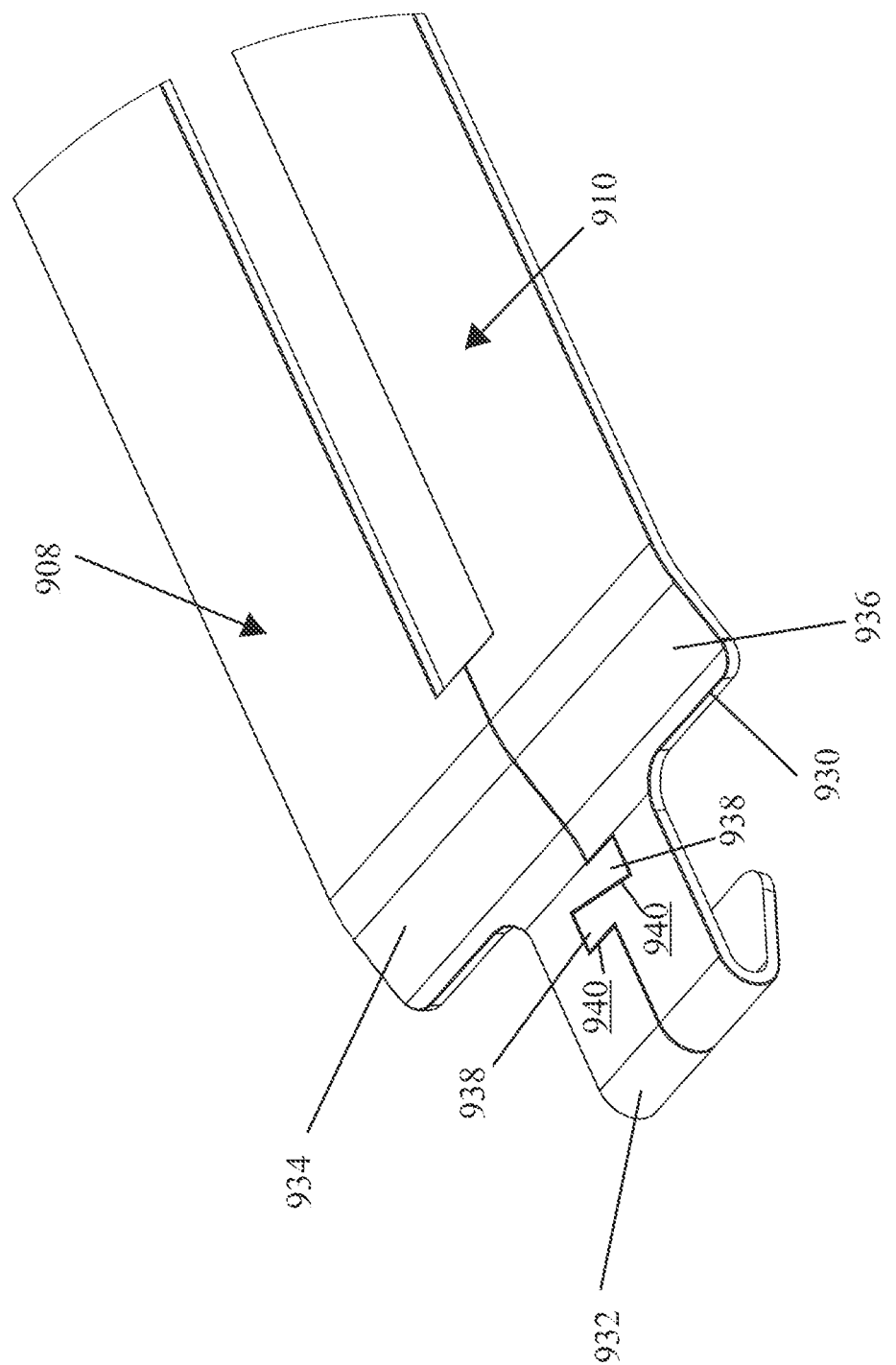
FIG. 32 is another partial perspective view of the distal portion of the attachment layers of FIG. 29.
Figure 33:
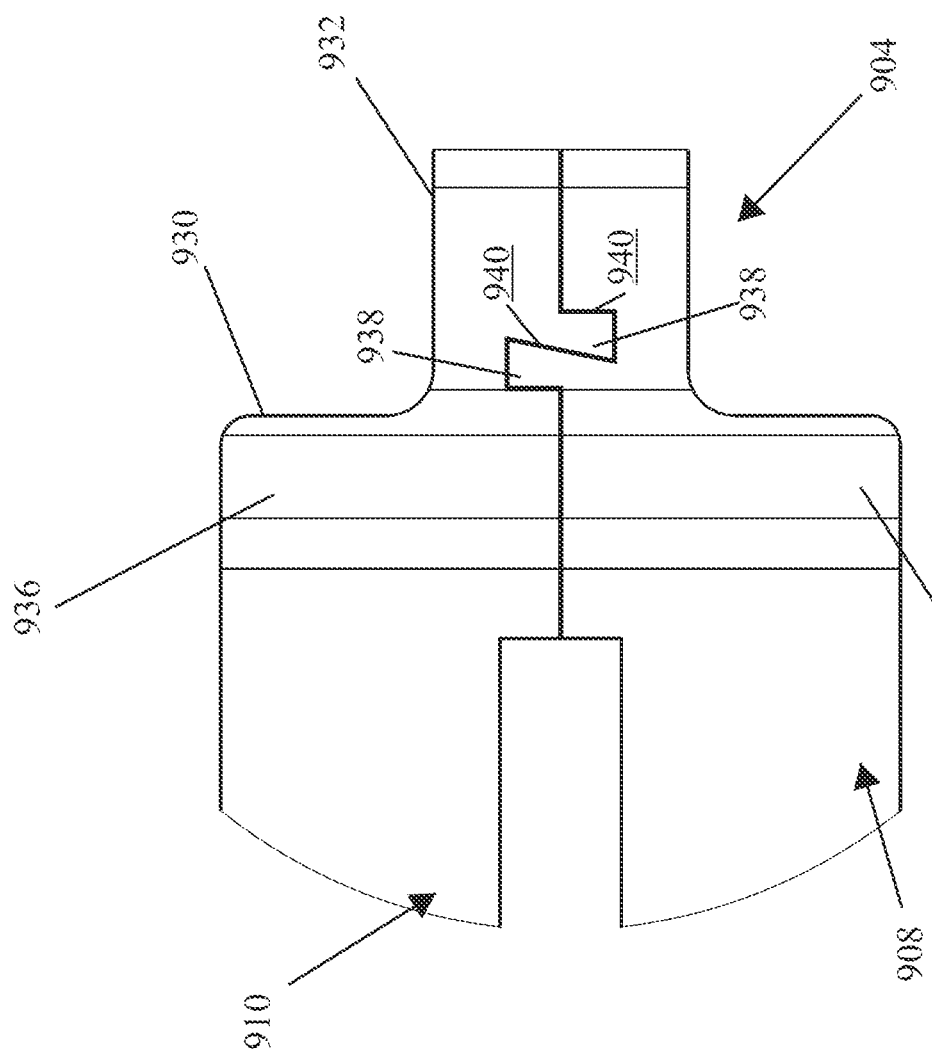
FIG. 33 is a partial longitudinal cross-sectional view of the attachment layers of FIG. 29.
Figure 34:
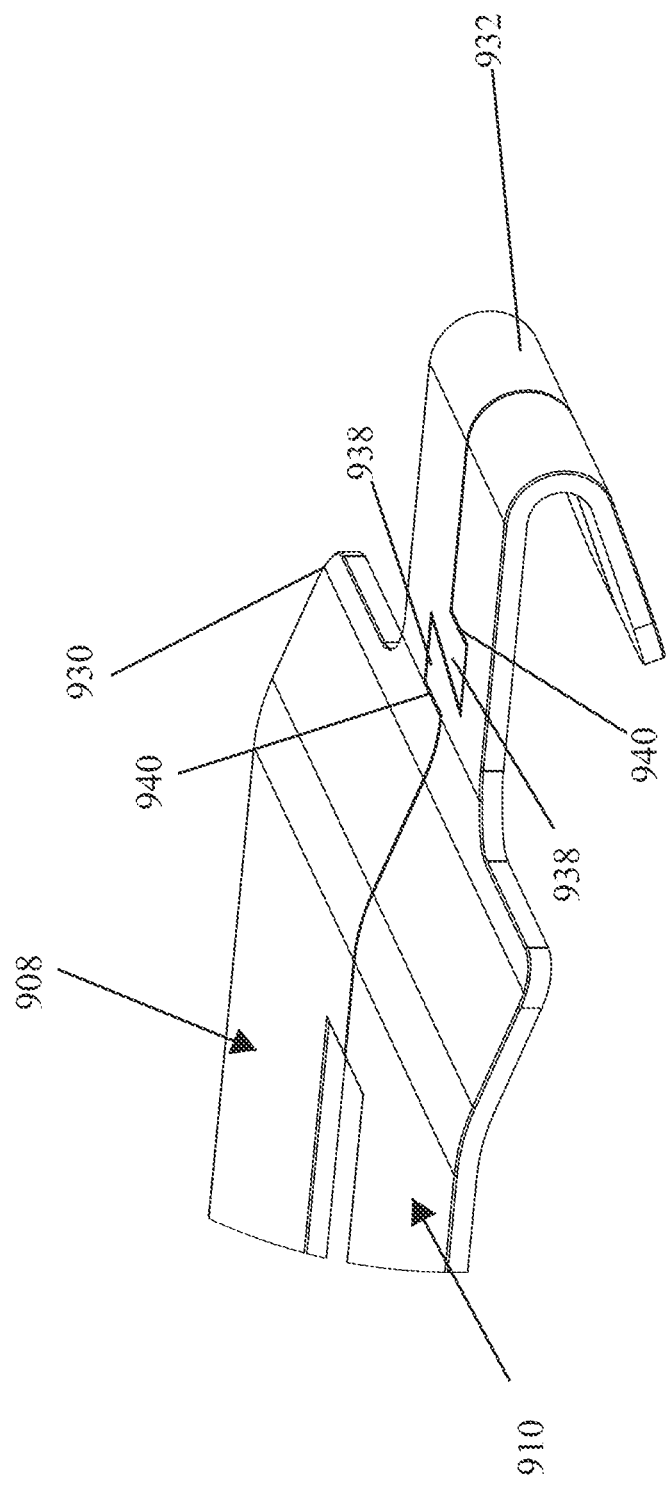
FIG. 34 is another partial perspective view of the distal portion of the attachment layers of FIG. 29.

Referring to FIGS. 31-34, the attachment layers 908 and 910 are further joined by a distal end portion 930 that includes a bent or rolled tab 932 which is tucked or inserted into a distal end of the anvil 984 to secure the compressible adjunct assembly 904 to the anvil 984. As illustrated in FIG. 32, the distal end portion 930 can be comprised of two separated end portions 934 and 936 extending from the layers 908 and 910, respectively. The end portions 934 and 936 are joined together to form the distal end portion 930. As illustrated in FIG. 33, the end portions 934 and 936 may comprise dovetail-shaped transverse joints 938 and corresponding dovetail-shaped transverse slots 940 for mating engagement with the dovetail-shaped transverse joints 938. Other coupling features for attaching the end portions 934 and 936 to form the distal end portion 930 are contemplated by the present disclosure.

Figure 35:
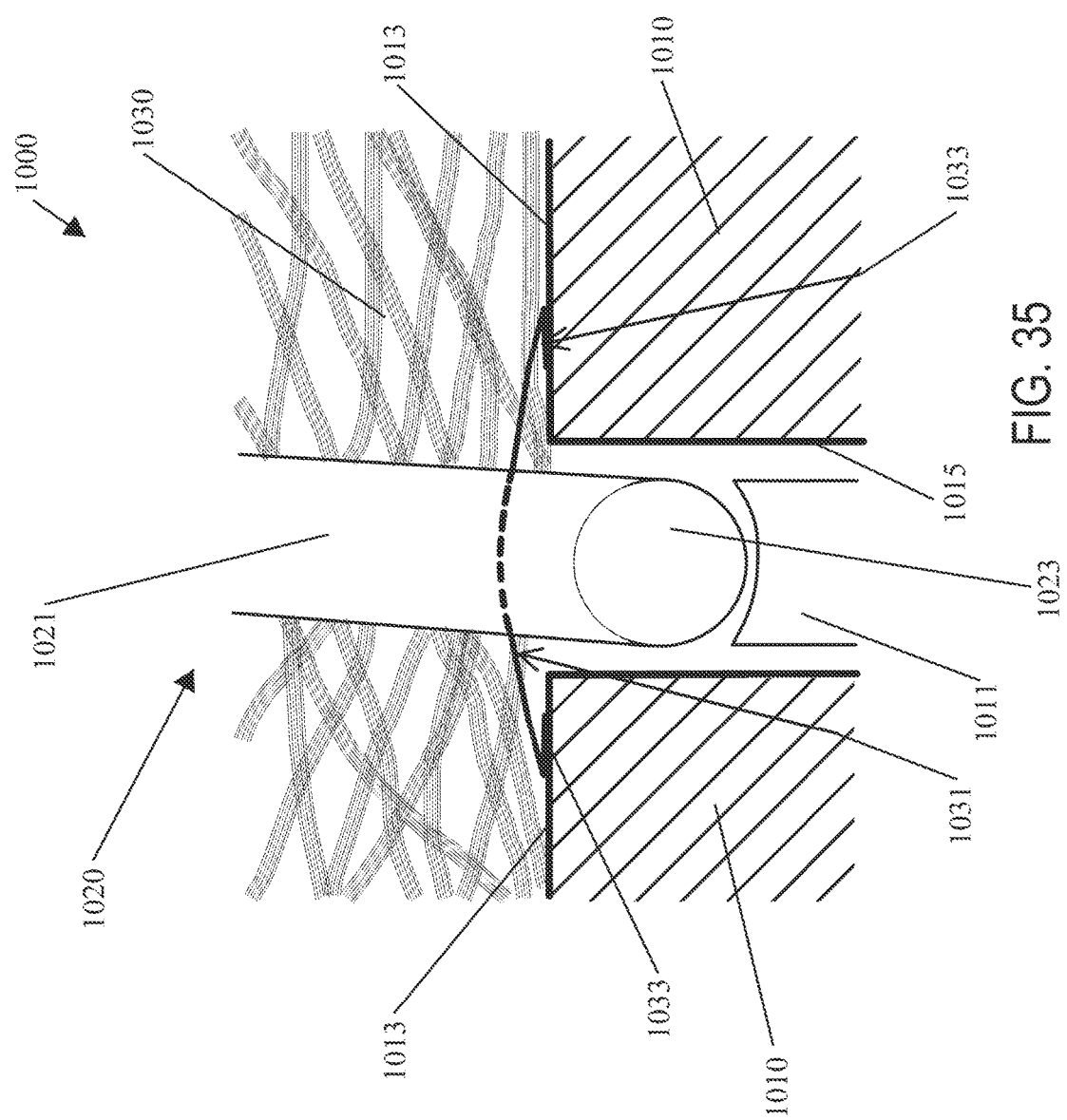
FIG. 35 is a partial cross-sectional view of a staple cartridge assembly comprising an implantable adjunct in an attached configuration in accordance with at least one embodiment.
Figure 36:
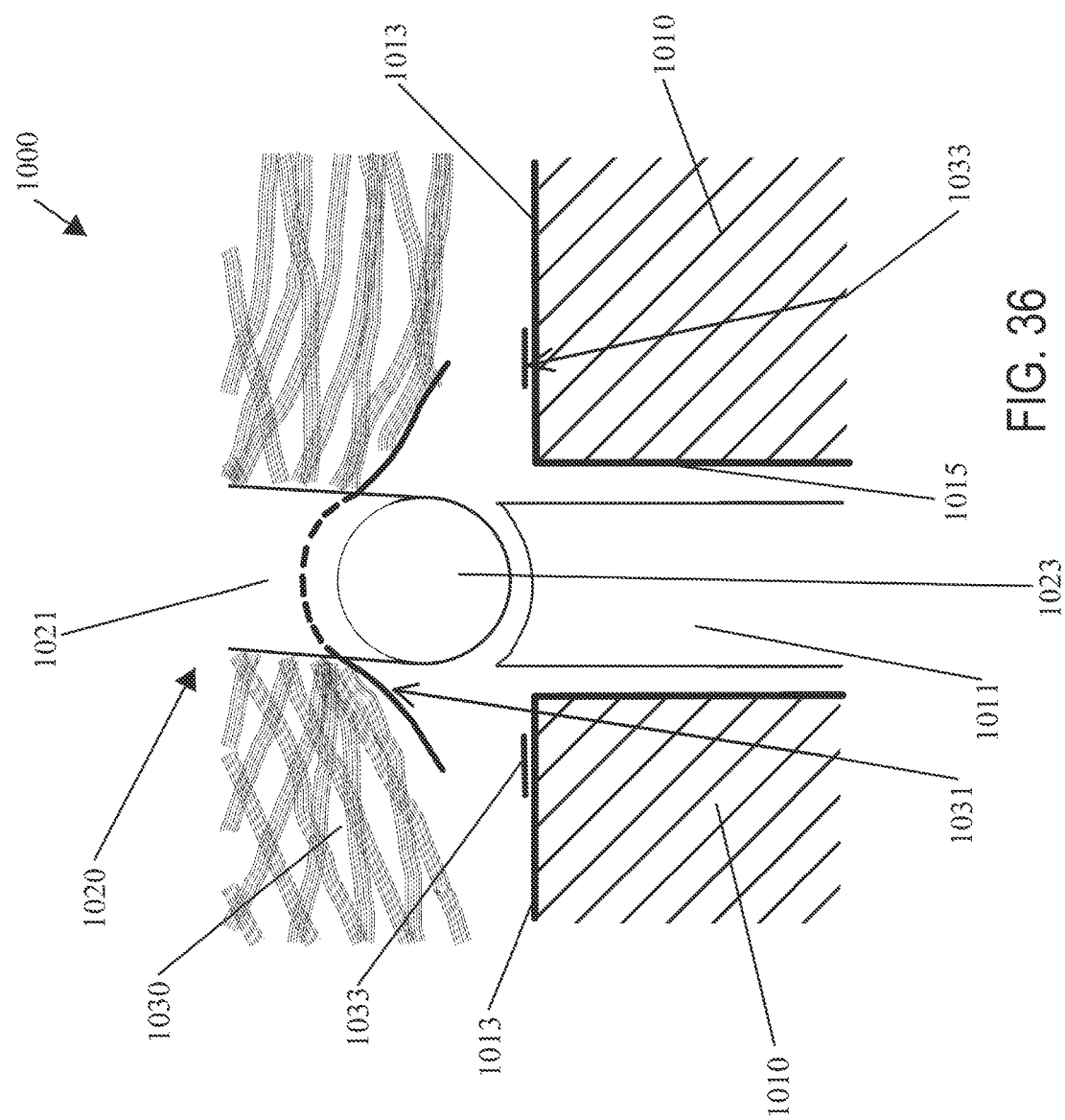
FIG. 36 is a partial cross-sectional view of the staple cartridge assembly of FIG. 35 where the implantable adjunct is in a detached configuration.

A staple cartridge assembly 1000 comprising a cartridge body 1010 and an implantable adjunct 1030 is depicted in FIGS. 35 and 36. The cartridge body 1010 comprises a cartridge deck, or adjunct facing surface, 1013 and a plurality of staple cavities 1015 defined in the deck 1013. The staple cartridge assembly 1000 further comprises a plurality of staples 1020 positioned in the staple cavities 1015 and a plurality of staple drivers 1011 configured to drive the staples 1020 out of the staple cavities 1015. Each staple 1020 comprises staple legs 1021 and a staple base 1023 from which the staple legs 1021 extend. In an unfired state, the staples 1020 are stored within the cartridge body 1010 such that the staple legs 1021 partially extend out of the staple cavity 1015 beyond, or above, the cartridge deck 1013. The staple legs 1021 can at least partially extend into the implantable adjunct 1030 when the staples 1020 are in their unfired state. Embodiments are envisioned in which the staple legs do not extend above the cartridge deck 1013 when the staples are in their unfired state.

The implantable adjunct 1030 comprises at least one attachment feature 1031 comprising deck-attachment portions 1033. Each attachment feature 1031 comprises a unitary structure, for example, and is configured to releasably hold, or attach, the implantable adjunct 1030 to the cartridge deck 1013. Each attachment feature 1031 traverses a staple cavity 1015 such that, when the staple 1020 in the staple cavity 1015 is deployed from the staple cavity 1015, the attachment feature 1031 is engaged, broken, and/or torn, by the staple base 1023 of the staple 1020 to release a portion of the implantable adjunct 1030 from the cartridge deck 1013. The attachment feature 1031 may traverse the cavity 1015 in a direction which is perpendicular to, or at an angle with respect to, the staple cavity 1015. As illustrated in FIGS. 35 and 36, the attachment features 1031 extend laterally across the staple cavities 1015. Various alternative embodiments are envisioned where multiple attachment features traverse each staple cavity 1015 such that the staple bases 1023 of the staples 1020 must engage and overcome multiple attachment features to release the adjunct 1030 from the cartridge deck 1013. Other embodiments are envisioned where one attachment portion spans multiple staple cavities requiring more than one staple to contact and dislodge the attachment portion.

The attachments features 1031 are attached to the adjunct 1030 in any suitable manner. In at least one instance, the attachments features 1031 comprise fibers which are woven into the adjunct 1030, for example. In at least one such instance, the adjunct 1030 is comprised of interwoven fibers and the attachment features 1031 are interwoven into the adjunct 1030. In certain instances, the attachment features 1031 are adhered to the adjunct 1030 utilizing at least one adhesive. In at least one such instance, the adjunct 1030 comprises a film and the attachment features 1031 are bonded to the film. In any event, the deck-attachment portions 1033 of the attachment features 1031 can be attached to the deck 1013 in any suitable manner. In at least one instance, the attachment portions 1033 can be adhered to the deck 1013 utilizing at least one adhesive. In certain instances, the attachment features 1031 of the adjunct 1030 can be heated and then pressed against the deck 1013 in order to attach the deck-attachment portions 1033 to the deck 1013.

Attaching the adjunct to the cartridge in the above-described manner permits segments of the adjunct to stay attached to the cartridge deck until the staples which capture such segments of the adjunct are deployed. Attaching the adjunct to the cartridge in this manner also provides multiple, distinct attachment locations which are progressively released as the firing assembly incises and staples tissue. For example, as the firing assembly travels from a proximal end of the staple cartridge assembly to a distal end of the staple cartridge assembly, the proximal-most staples are deployed from the staple cartridge before the distal-most staples are deployed which, as a result, releases the proximal end of the adjunct before the distal end of the adjunct. Stated another way, the attachment features that have not yet been engaged by their respective staples remain attached to the cartridge deck during the firing progression until the firing assembly reaches those staples.

Further to the above, FIG. 36 depicts a staple base 1023 of a staple 1020 after it has engaged and released an attachment feature 1031 of the adjunct 1030 from the cartridge deck 1013. The attachment feature 1031 comprises break-away portions which are configured to fail once a force is applied to the attachment feature 1031 by the staple base 1023 that exceeds a threshold force. Upon reaching the threshold force, the attachment feature 1031 is configured to break, rip, and/or tear in order to release the adjunct 1030 from the cartridge deck 1013. The deck-attachment portions 1033 are configured to remain attached to the cartridge deck 1013 when the attachment feature 1031 breaks. Other embodiments are envisioned where the detachment of the attachment portions 1033 from the cartridge deck 1013 are responsible for the release of the adjunct 1030 from the cartridge deck 1013. In such embodiments, the attachment feature 1031 disengages from the cartridge deck 1013 entirely.

In addition to or in lieu of the above, the deck 1013 can be treated and/or cleaned before the adjunct 1030 is attached to the deck 1013. Such treatment and/or cleaning can improve the bond between the adjunct 1030 and the deck 1013. In at least one instance, surfactants, soaps, and/or lubricants are used to facilitate the loading, or insertion, of the staples into the staple cavities and, in such instances, the deck 1013, or at least portions of the deck 1013, can be screened to prevent or inhibit surfactants, soaps, and/or lubricants from flowing onto the deck 1013. One such soap comprises sodium stearate, for example. In certain instances, lasers, plasma and/or IR heating can be utilized to clean the deck 1013, or at least portions of the deck 1013, in order to improve the adhesion between the attachment features 1031 and the deck 1013.

Figure 37:
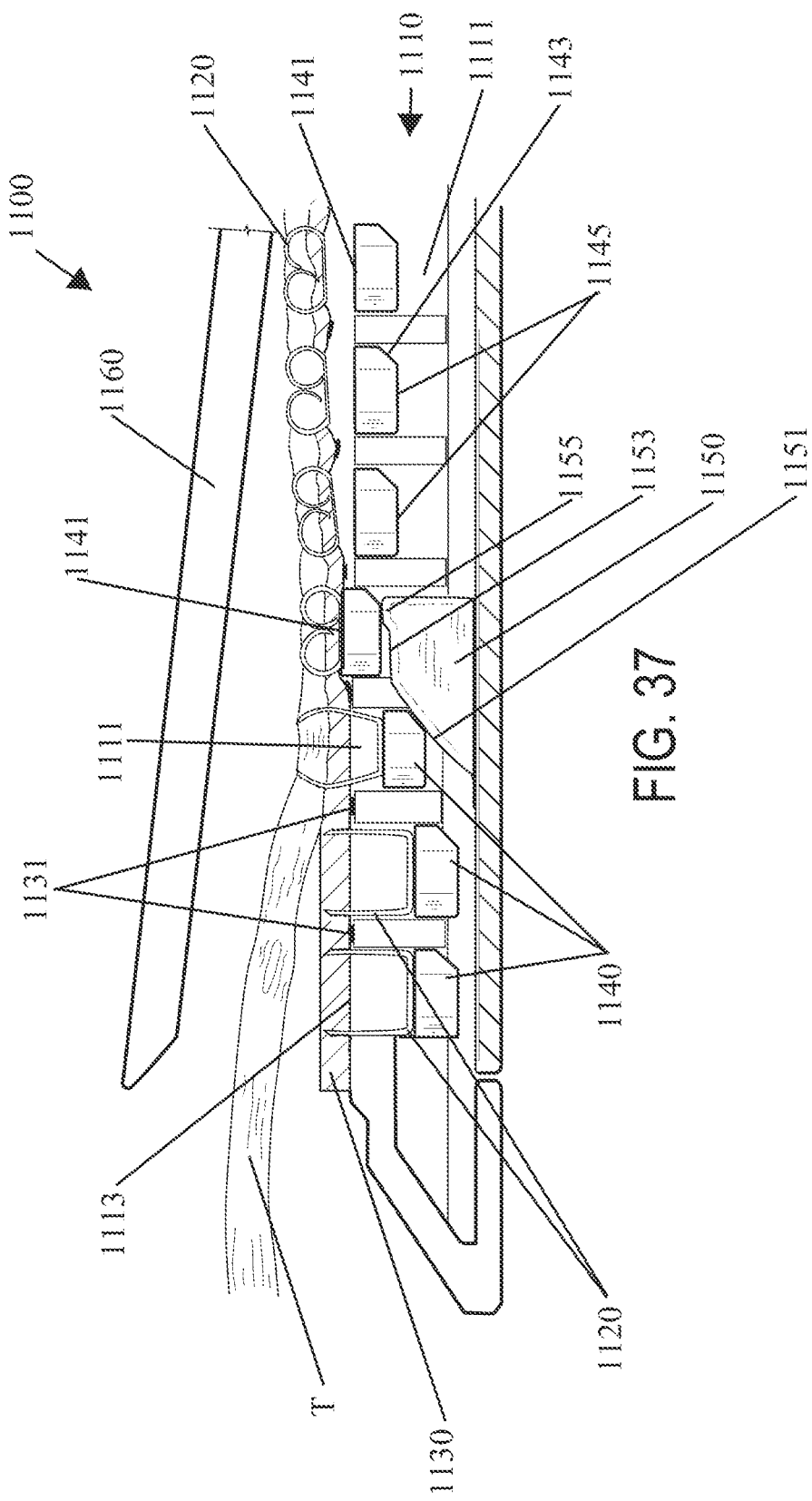
FIG. 37 is a partial side view of a surgical stapling assembly comprising a staple cartridge, a plurality of staples, and an implantable adjunct where the surgical stapling assembly has been partially fired and a portion of the implantable adjunct has been separated from the staple cartridge.
Figure 38:
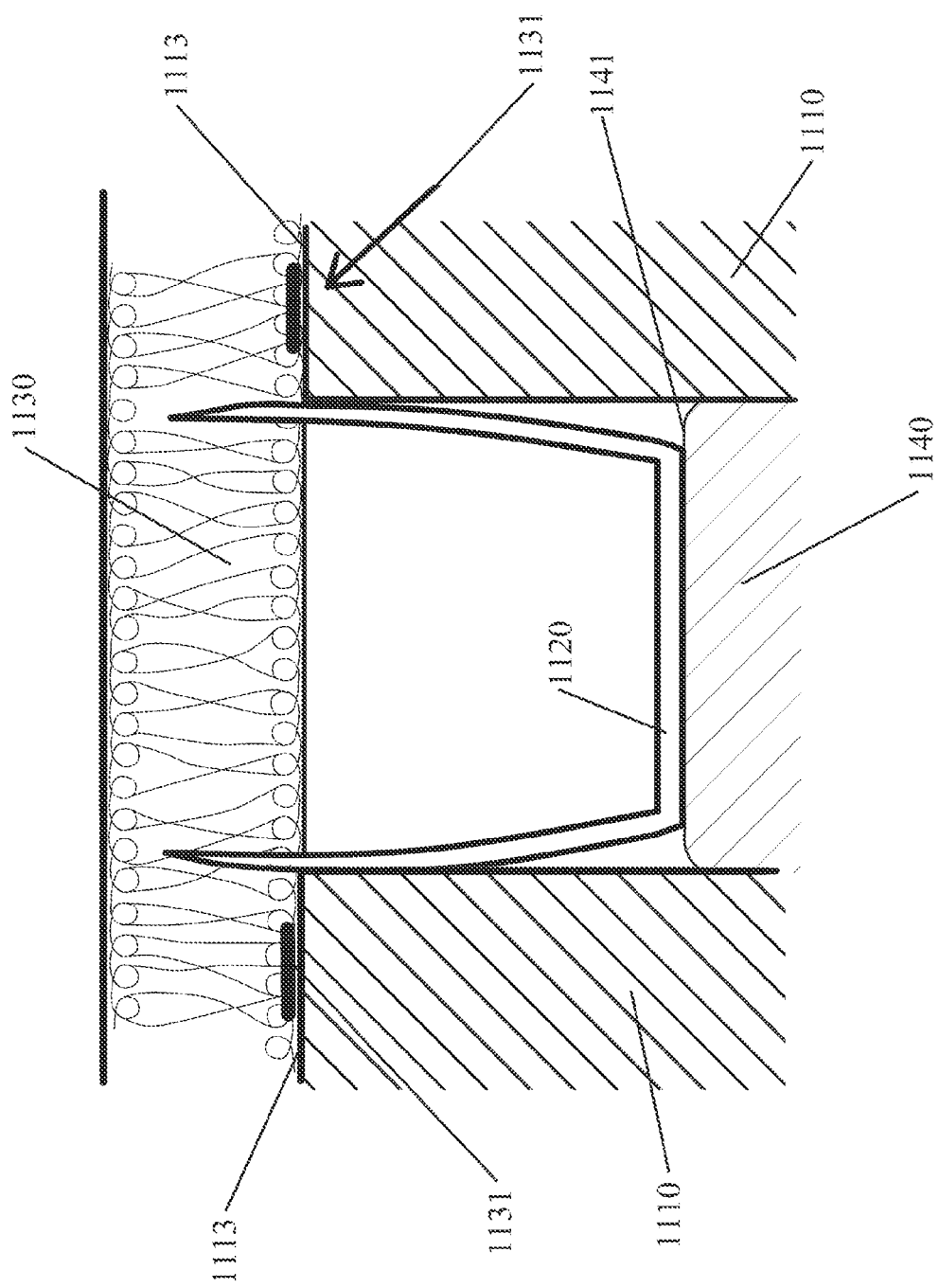
FIG. 38 is a partial cross-sectional view of the surgical stapling assembly of FIG. 37 illustrating a staple that has not been deployed from the staple cartridge.

A surgical stapling assembly 1100 is depicted in FIG. 37 and FIG. 38. The surgical stapling assembly 1100 comprises an anvil 1160, a staple cartridge assembly 1110, and an implantable adjunct 1130. The staple cartridge assembly 1110 comprises a cartridge body comprising a plurality of staple cavities 1111 and a deck surface 1113, a plurality of staples 1120 removably stored within the staple cavities 1111, and a plurality of staple drivers 1140 configured to drive the staples 1120 out of the staple cavities 1111 toward the anvil 1160 of the surgical stapling assembly 1100. The staple cartridge assembly 1110 also comprises a sled 1150 configured to convert the linear motion of a firing assembly into vertical motion of the staple drivers 1140 to drive the staples 1120 out of the staple cavities 1111. The sled 1150 comprises an initial contact ramp 1151, an intermediate contact surface 1153, and a final contact ramp 1155 all configured to contact the staple drivers 1140 as the firing assembly drives the sled 1150 from a proximal end of the cartridge assembly 1110 to a distal end of the cartridge assembly 1110.

Each staple driver 1140 comprises three or more portions—an initial lift portion 1143 configured to be engaged by the initial contact ramp 1151 of the sled 1150 as the sled 1150 travels distally through the cartridge body—a bottom surface 1145 configured to be engaged by the intermediate contact surface 1153 and the final contact ramp 1155 of the sled 1150—and a top, or staple support, surface 1141. After the initial lift portion 1143 is engaged by the contact ramp 1151 of the sled 1150, the staple drivers 1140 are contacted by the intermediate contact surface 1153 and then the final contact ramp 1155 of the sled 1150. The final contact ramp 1155 of the sled 1150 is configured to drive the staple drivers 1140 such that the top surface 1141 is driven above the cartridge deck surface 1113. Lifting the top surface 1141 of the staple drivers 1140 beyond the cartridge deck 1113 permits the staple drivers 1140 to lift the adjunct 1130 and/or tissue T away from the cartridge deck surface 1113. More specifically, lifting the top surface 1141 of the staple drivers 1140 beyond the cartridge deck 1113 encourages the detachment of attachment portions 1131 of the adjunct 1130 from the cartridge deck 1113.

Further to the above, the attachment portions 1131 are attached to the cartridge deck 1113 intermediate the staple cavities 1111 defined in the deck 1113. During the longitudinal progression of the firing assembly, the adjunct 1130 is disengaged from the cartridge body at the attachment portions 1131. The attachment portions 1131 are configured to progressively release corresponding portions of the adjunct 1130 from the cartridge body one attachment portion 1131 at a time. More specifically, as a driver 1140 is lifted above the cartridge deck 1113 through a staple cavity opening, as discussed above, the attachment portions 1131 adjacent the staple cavity opening are released thereby releasing a corresponding portion of the adjunct 1130 from the cartridge deck 1113 while the attachment portions 1131 positioned distal to the detached attachment portions 1131 retain the adjunct 1130 against the cartridge deck 1113 until the subsequent drivers 1140 are lifted above the cartridge deck 1113.

In many instances, all of the staples stored in a staple cartridge are deployed from the staple cartridge. In such instances, the adjunct 1130 is entirely released from the deck 1113 by the staples during the firing process. In other instances, however, a surgeon may elect to not fire all of the staples from the staple cartridge. In such instances, the remaining adjunct that has not been stapled to the tissue remains attached to the cartridge deck 1113. The portion of the adjunct that has not been stapled to the tissue can be easily torn, or separated, from the portion of the adjunct that has been stapled to the tissue. The portion of the adjunct that has not been stapled to the tissue remains attached to the cartridge to limit, or eliminate, the amount of unstapled adjunct left in the patient. In various instances, the adjunct 1130 tears proximal of the last driver lifted above the cartridge deck 1113. In various other instances, the adjunct 1130 tears distal of the last driver lifted above the cartridge 1113.

Further to the above, the attachment portions 1131 can be created utilizing any suitable method. In at least one instance, a laser melting process can be utilized to create the attachment portions 1131. In certain instances, a heat staking process can be utilized to create the attachment portions 1131. In at least one instance, portions of a woven fiber adjunct can be pre-processed with discrete laser melting such that the fibers become sticky in the attachment portions 1131. Regardless of the manner used to create the attachment portions 1131, the adjunct 1130 can be held tightly over the staple cavities such that sufficient tension, shear, and/or pealing forces are applied to the attachment portions 1131 to detach the adjunct 1130 from the deck 1113.

Figure 39:
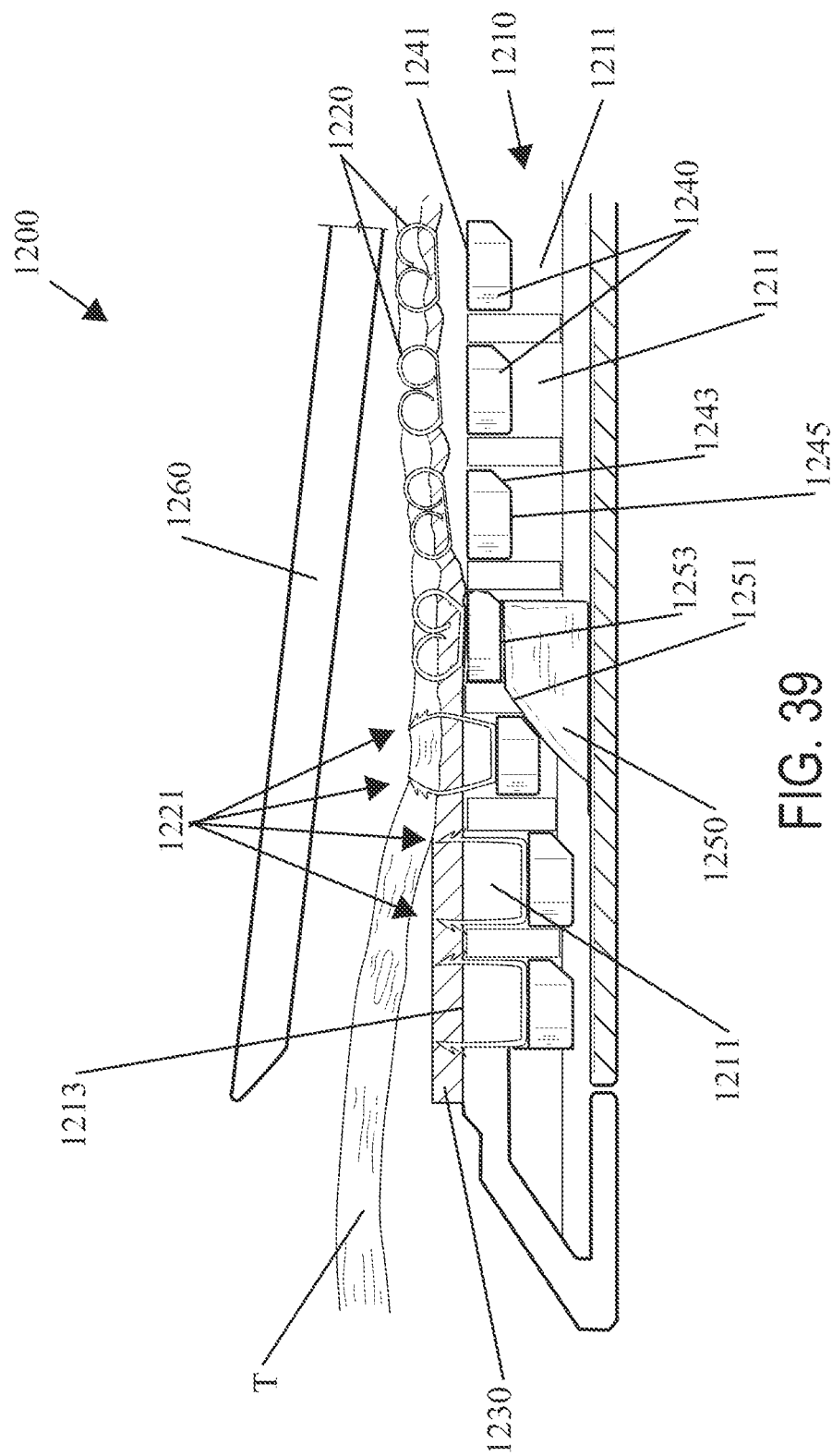
FIG. 39 is a partial side view of a surgical stapling assembly comprising a staple cartridge, a plurality of barbed staples, and an implantable adjunct where the surgical stapling assembly has been partially fired and a portion of the implantable adjunct has been separated from the staple cartridge.
Figure 40:
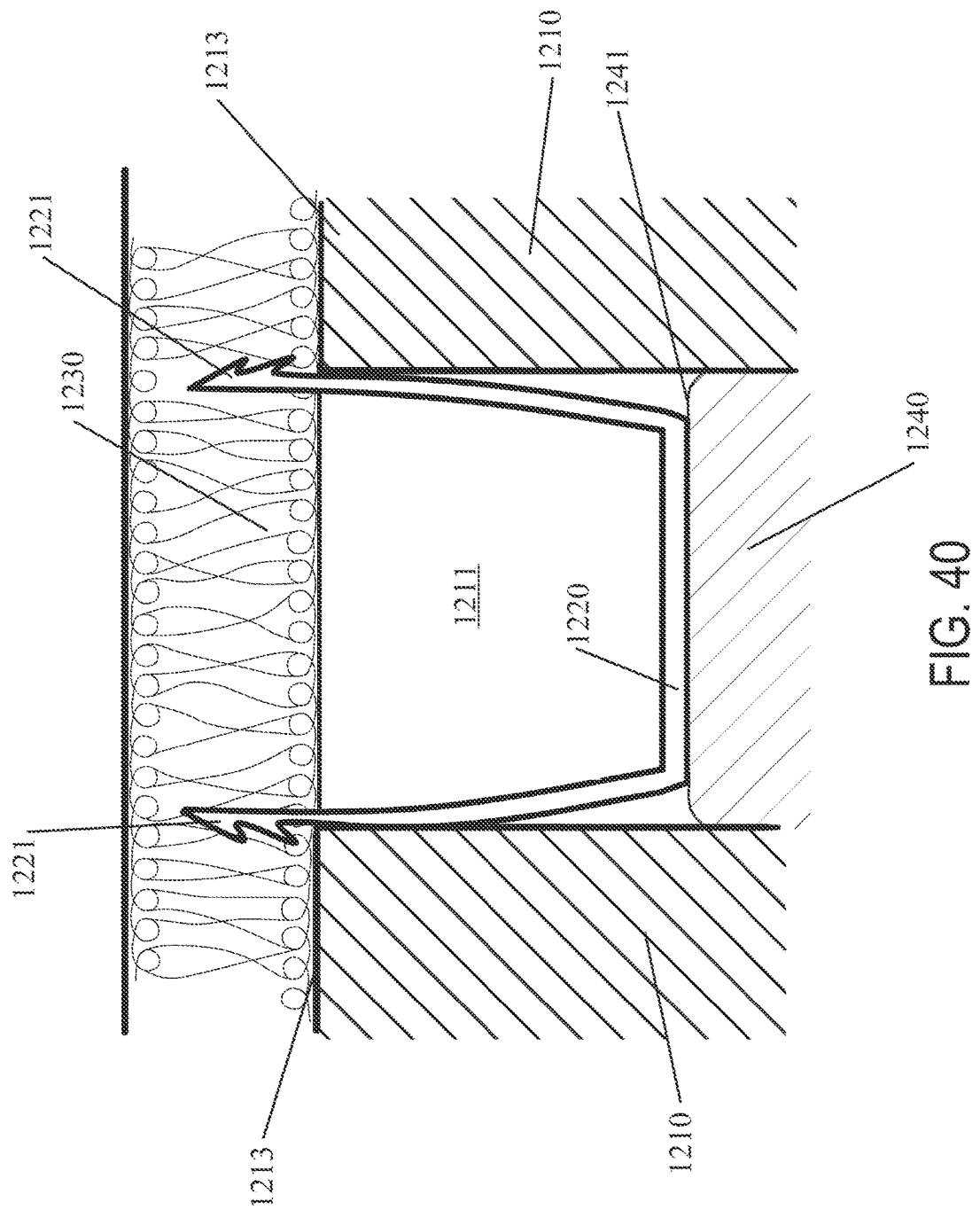
FIG. 40 is a partial cross-sectional view of the surgical stapling assembly of FIG. 39 illustrating a staple that has not been deployed from the staple cartridge.

A surgical stapling assembly 1200 is depicted in FIGS. 39 and 40. The surgical stapling assembly 1200 comprises an anvil 1260, a staple cartridge assembly 1210, and an implantable adjunct 1230. The staple cartridge assembly 1210 comprises a cartridge body comprising a plurality of staple cavities 1211 and a deck surface 1213, a plurality of staples 1220 removably stored within the staple cavities 1211, and a plurality of staple drivers 1240 configured to drive the staples 1220 out of the staple cavities 1211 and toward the anvil 1260 of the surgical stapling assembly 1200. The staple cartridge assembly 1210 also comprises a sled 1250 configured to convert the linear motion of the firing assembly into vertical motion of the staple drivers 1240 to drive the staples 1220 out of the staple cavities 1211. The sled 1250 comprises an initial contact ramp 1251 and a final contact ramp 1253 configured to contact the staple drivers 1240 as the firing assembly drives the sled 1250 from a proximal end of the cartridge assembly 1210 to a distal end of the cartridge assembly 1210.

The staple drivers 1240 comprise, one, initial lift portions 1243 configured to be engaged by the initial contact ramp 1251 of the sled 1250 as the sled 1250 travels distally through the cartridge body to initiate lifting of the drivers 1243, two, bottom surfaces 1245 configured to be engaged by the final contact ramp 1253 of the sled 1250 and, three, a top, or staple support, surface 1241. The legs of the staples 1220 are biased against the sidewalls of the staple cavities 1211 to hold the staples 1220 in the staple cavities 1211. The legs of the staples 1220 comprise staple tips 1221 having a barbed configuration configured to releasably retain, or hold, the adjunct 1230 to the cartridge body. As a result, the adjunct 1230 is held to the cartridge deck 1213 by the staple tips 1221 of a staple 1220 until the staple 1220 is driven out of the staple cavity 1211. As the staple 1220 is driven out of the staple cavity 1211, and owing to the interaction between the barbs, the adjunct 1230 is able to travel with the staple 1220 as the staple tips 1221 are moved toward the anvil 1260. The barbed configuration of the staple tips 1221 permit a progressive release of the adjunct 1230 from the cartridge deck 1213.

The staple tips 1221 are configured to progressively release the adjunct 1230 from the cartridge deck 1213 in a manner similar to those discussed above. As a proximal staple 1220 is ejected from the cartridge body, a distal staple 1220 retains the adjunct 1230 against the cartridge deck 1213. In the event that a clinician decides to remove the surgical stapling instrument from the stapling site after only partially firing the staple cartridge, the remaining adjunct that has not been stapled to the tissue remains attached to the cartridge deck 1213. The portion of the adjunct that has not been stapled to the tissue can be torn, or separated, from the portion of the adjunct that has been stapled to the tissue. The portion of the adjunct that has not been stapled to the tissue remains attached to the cartridge to limit, or eliminate, the amount of unstapled adjunct left in the patient. In various instances, the adjunct 1230 can comprise perforations, or discontinuities, for example, configured to permit tearing of the adjunct 1230 without difficulty. The perforations can be positioned between each staple cavity 1211, for example.

Further to the above, a staple leg of a staple 1220, for example, can have a first set of barbs configured to engage the adjunct 1230 when the staple 1220 is in its unfired position. As the staple 1220 is being fired, the first set of barbs can exit the adjunct 1230. As the first set of barbs exit the adjunct 1230, a second set of barbs can enter into the adjunct 1230. The second set of barbs can be engaged with the adjunct 1230 when the staple 1220 is in its fired position. In at least one instance, the first set of barbs can comprise two barbs while the second set of barbs can comprise two barbs, for example. Regardless of the number of barbs that are used, the first set of barbs can be positioned above the deck 1213 of the cartridge body when the staples 1220 are in their unfired position while the second set of barbs can be positioned below the top surface of the deck 1213 when the staples 1220 are in their unfired position.

As illustrated in FIG. 40, the barbs extend laterally outwardly; however, the barbs can extend in any suitable direction, such as laterally inwardly, for example. In addition to or in lieu of the above, a staple leg can comprise tip portions which extend inwardly to grip an adjunct.

Figure 41:
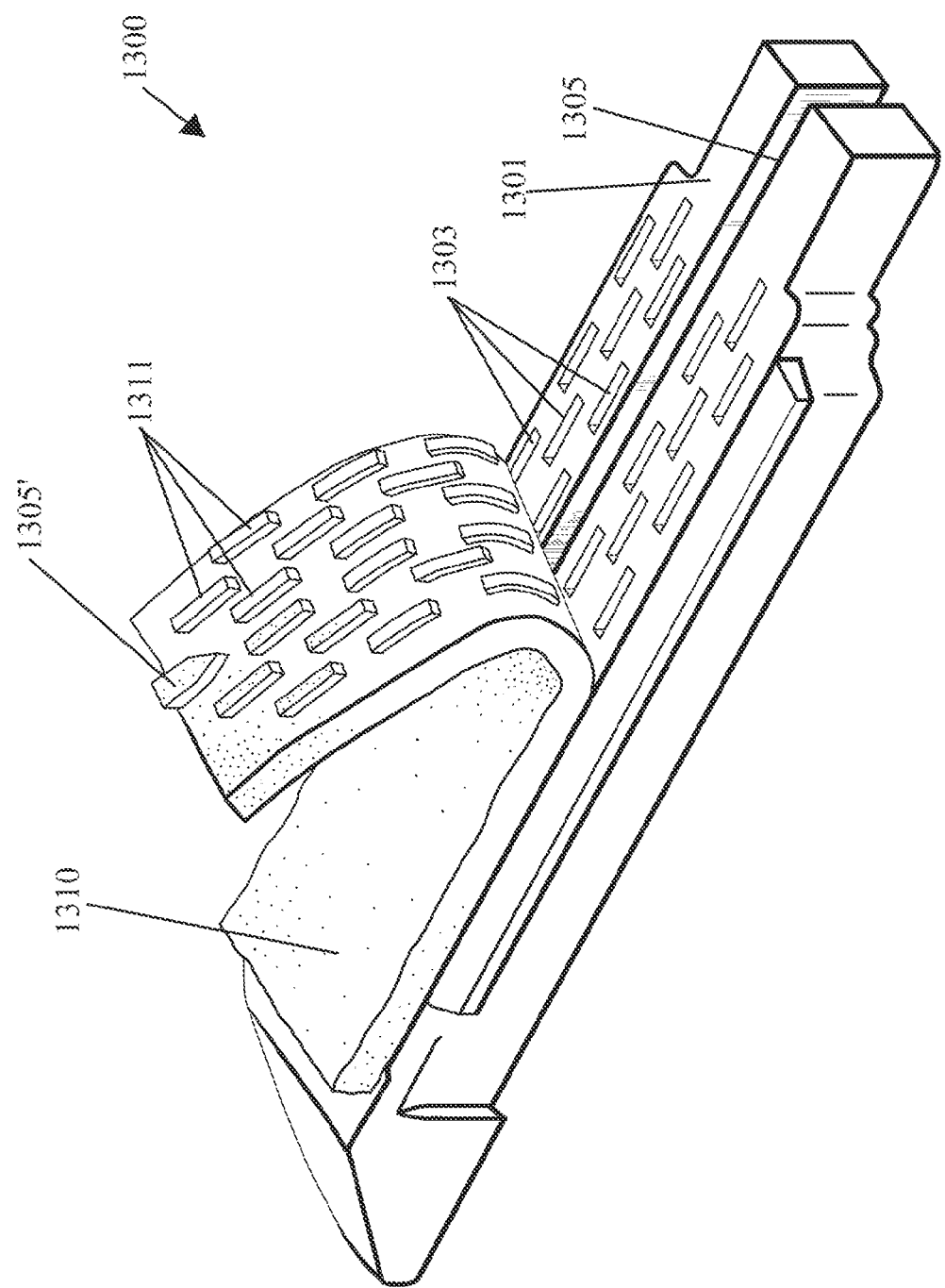
FIG. 41 is partial perspective view of a staple cartridge assembly comprising a staple cartridge and an implantable adjunct residing at least partially within the staple cartridge in accordance with at least one embodiment.

A staple cartridge assembly 1300 is depicted in FIG. 41. The staple cartridge assembly 1300, configured for use with a surgical stapling instrument, comprises an implantable adjunct, or material, 1310 and a staple cartridge body 1301. The staple cartridge comprises a plurality of deck features such as staple cavities 1303 configured to removably store a plurality of staples therein and, in addition, a slot 1305 configured to receive a firing assembly therethrough. The implantable adjunct 1310 is attached, secured, and/or affixed to the cartridge body 1301 by thermoforming. For example, the cartridge body 1301 is heated to a specific temperature and then the implantable adjunct 1310 is pressed onto, into, and/or against the cartridge body 1301. Upon engagement with the cartridge body 1301, the implantable adjunct 1310 forms, or molds, into the deck features of the cartridge body 1301 providing attachment features 1311 configured to permit the progressive release of the adjunct 1310 from the cartridge body 1301. Similarly, a portion 1315 of the adjunct 1310 can conform to the configuration of the slot 1305. The portion 1315 can extend along the entirety of the slot 1305 or a portion of the slot 1305. In at least one instance, the portion 1315 is only positioned at the proximal end of the slot 1305, for example. One advantage of the staple cartridge assembly 1300 may include having an implantable adjunct with a more complex shape which custom fits with a corresponding staple cartridge while sustaining a simpler manufacturing process, for example.

In at least one embodiment, further to the above, the staples can be loaded into the cartridge body 1301 to form a sub-assembly which is then heated to a temperature above, at, or close to the glass transition temperature of the material, or materials, comprising the adjunct 1310. In at least one instance, the sub-assembly is heated to about 105 degrees Celsius, for example. The adjunct 1310 is then placed over the cartridge body 1301. At this point, the adjunct 1310 is unheated, or at room temperature; however, it is contemplated that the adjunct 1310 could be pre-heated. The adjunct 1310 is then pushed downwardly onto the cartridge body 1301 and, as a result, the cartridge body 1301 heats the adjunct 1310 to a temperature which is above, at, or close to the glass transition temperature of the material, or materials, comprising the adjunct 1310. In at least one instance, the adjunct 1310 is a foam comprised of PGA and/or PLA, for example. Owing to the fact that the foam is heated to a temperature above, at, or slightly below the glass transition temperature of the PGA and/or PLA, the foam can take a new permanent shape around the features of the cartridge body 1301 and/or the staples positioned therein. For instance, the cartridge body 1301 can include projections extending from the deck and, when the adjunct 1310 is pushed onto the heated deck projections, the adjunct 1310 can be permanently deformed around the deck projections. In such instances, the adjunct 1310 tightly grips the deck projections until the adjunct 1310 is pushed off of the projections by the staples. Similarly, the adjunct 1310 can permanently deform around and tightly grip the heated staple legs. In at least one instance, the diameter of the newly-formed holes can be about 10% smaller than the diameter of the staple legs, for example. In any event, the pressure applied to the adjunct 1310 can be removed at any suitable time. In at least one instance, the pressure is applied to the adjunct 1310 until the temperature of the cartridge body 1301, the staples, and the adjunct 1310 is well below, or at least below, the glass transition temperature of the materials comprising the adjunct 1310. Alternatively, the pressure can be removed when the temperature of the staple cartridge assembly 1300 is at or above the glass transition temperature of the materials comprising the adjunct 1310.

Figure 42:
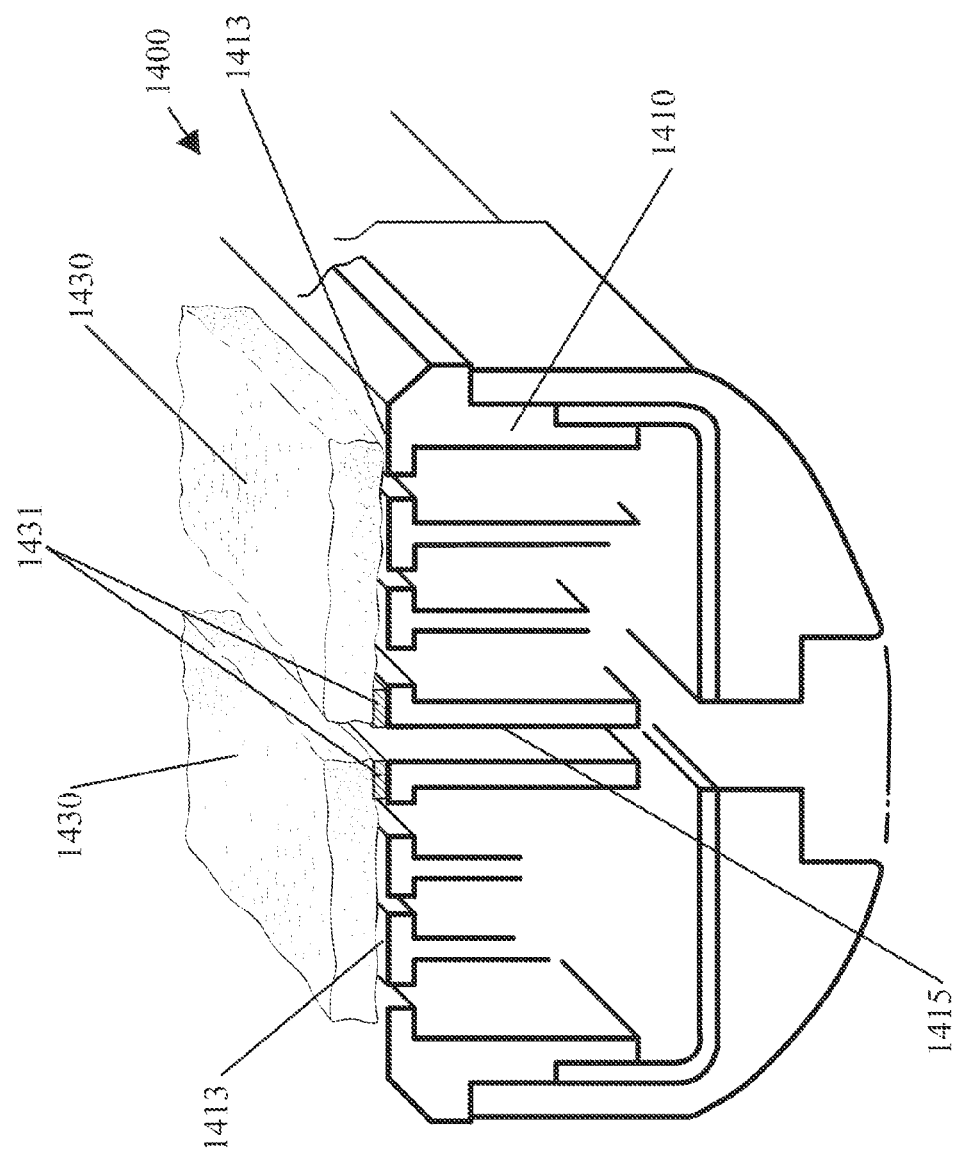
FIG. 42 is a partial, end perspective view of a staple cartridge assembly comprising a staple cartridge and an implantable adjunct comprising a body portion and a plurality of attachment portions in accordance with at least one embodiment.
Figure 43:
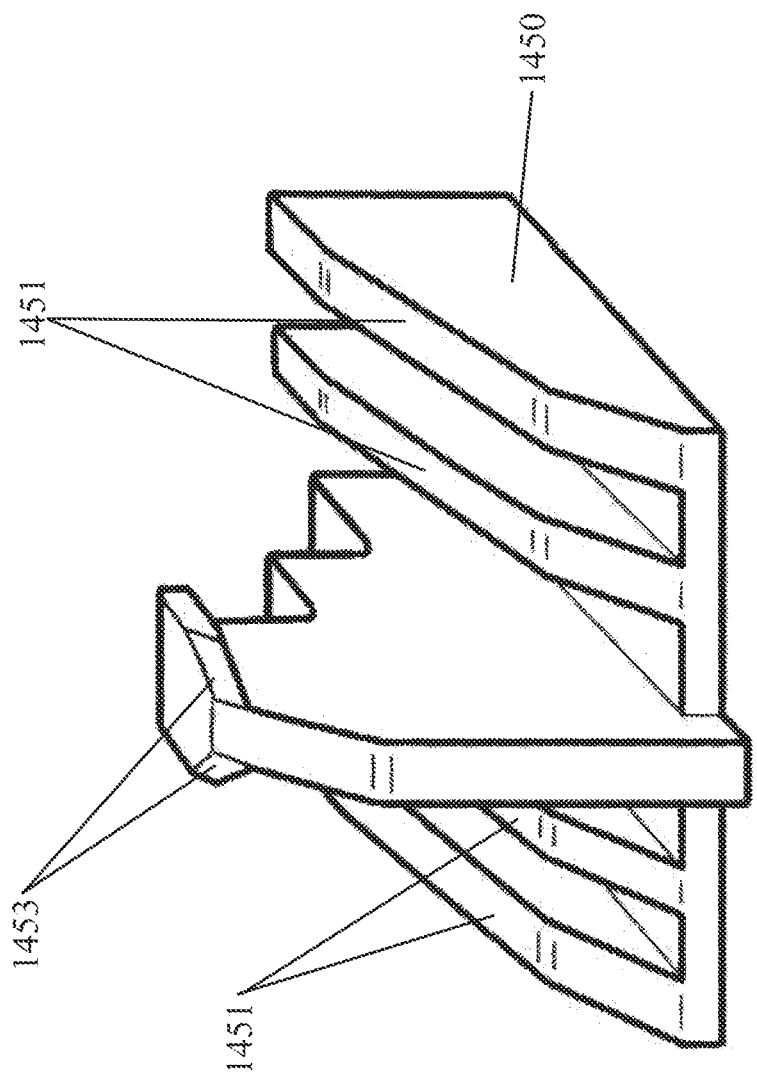
FIG. 43 is a perspective view of a sled of a firing assembly in accordance with at least one embodiment.
Figure 44:
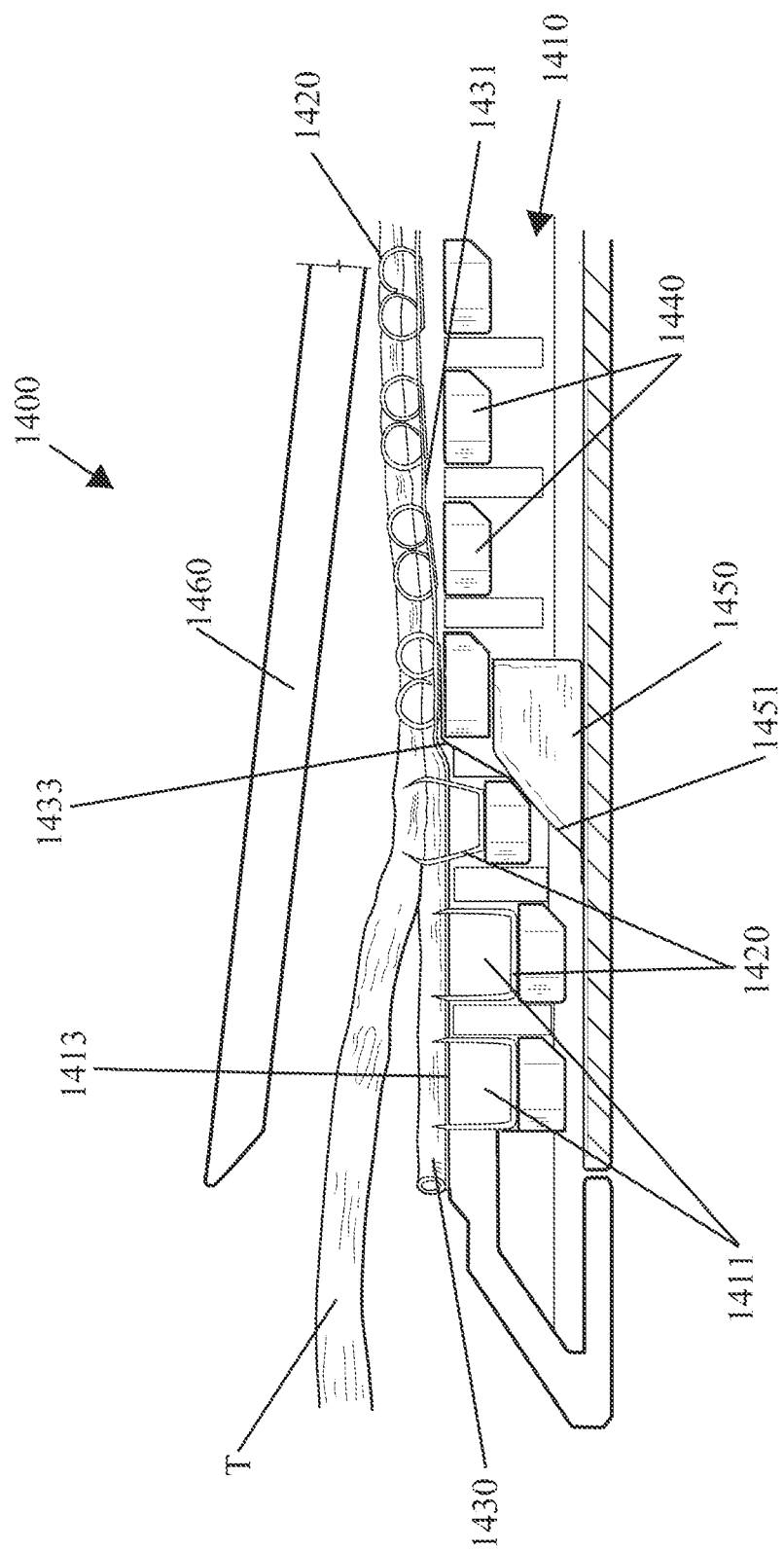
FIG. 44 is a partial side view of a surgical stapling assembly comprising the staple cartridge assembly of FIG. 42 which includes a staple cartridge and an implantable adjunct and a firing assembly comprising the sled of FIG. 43 where the surgical stapling assembly has been partially fired and a portion of the implantable adjunct has been detached from the staple cartridge.

FIGS. 42-44 depict yet another surgical stapling assembly 1400. The surgical stapling assembly 1400 comprises an anvil 1460, a staple cartridge assembly 1410, and an implantable adjunct 1430. The staple cartridge assembly 1410 comprises a cartridge body comprising a plurality of staple cavities 1411, a deck surface 1413, and a slot 1415. The staple cartridge assembly 1410 further comprises a plurality of staples 1420 removably stored within the staple cavities 1411, and a plurality of staple drivers 1440 configured to drive the staples 1420 out of the staple cavities 1411 toward the anvil 1460 of the surgical stapling assembly 1400. The staple cartridge assembly 1410 also comprises a sled 1450 configured to convert the linear motion of a firing assembly into vertical motion of the staple drivers 1440 to drive the staples 1420 out of the staple cavities 1411. The sled 1450 comprises driver ramps 1451 configured to contact and drive the staple drivers 1440 toward the anvil 1460 and, in addition, a release portion 1453 configured to detach the adjunct 1430 from the deck 1413.

The release portion 1453 comprises lateral flanges which extend over a portion of the deck surface 1413. More specifically, the lateral flanges extend over the deck surface 1413 between the slot 1415 and the inner rows of staple cavities 1411. The adjunct 1430 comprises attachment portions 1431 configured to releasably hold the adjunct 1430 to the cartridge deck 1413 until the release portion 1453 of the sled 1450 engages the attachment portions 1431. As the firing assembly progresses through the staple cartridge assembly 1410, the release portion 1453 can act as a plow, for example, configured to plow, cut, incise, and/or slice the attachment portions 1431 as the release portion 1453 engages the attachment portions 1431. The attachment portions 1431 are engaged progressively as the firing assembly traverses the cartridge body from its proximal end toward its distal end.

Figure 45:
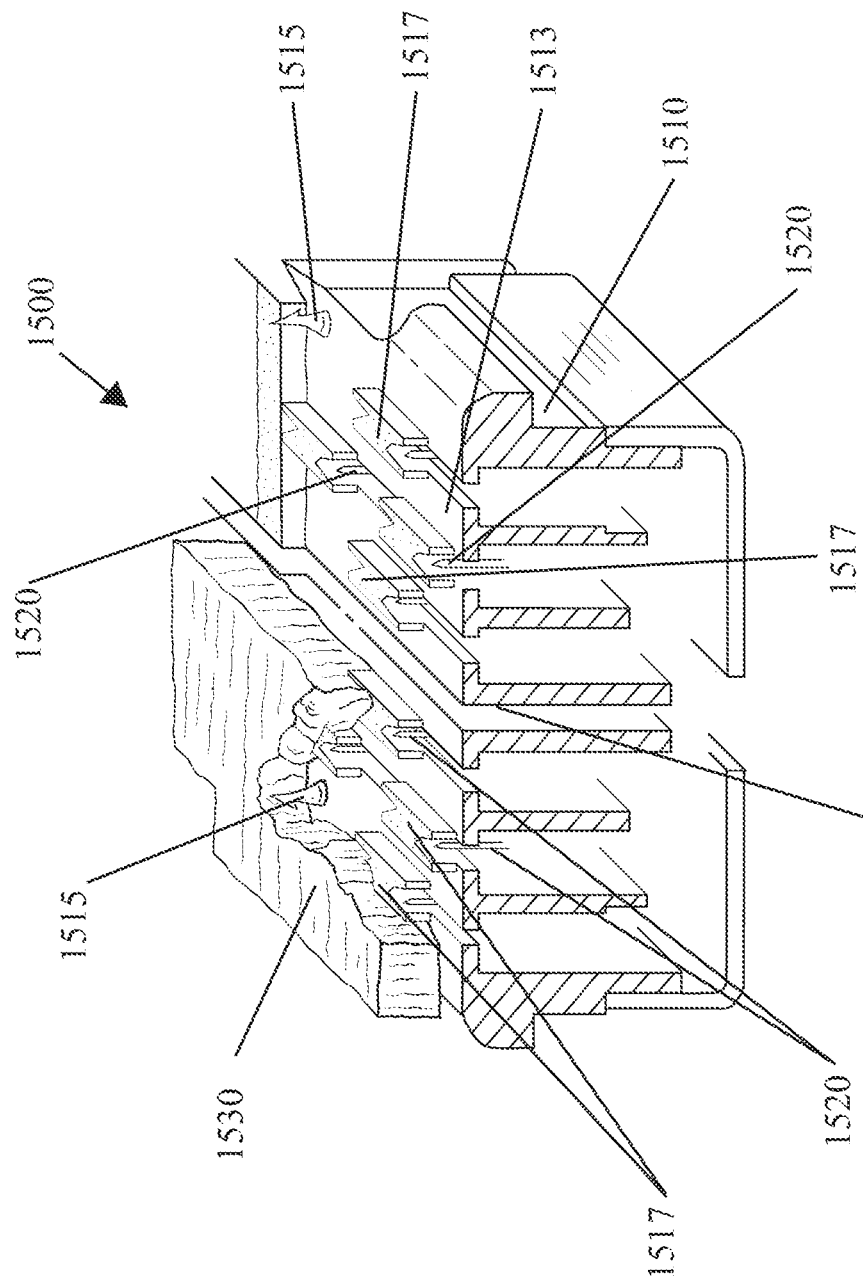
FIG. 45 is a partial, end perspective view of a staple cartridge assembly comprising deck retaining features in accordance with at least one embodiment.

Turning now to FIG. 45, a staple cartridge assembly 1500 is depicted. The staple cartridge assembly 1500 comprises a cartridge body 1510 comprising a cartridge deck 1513, attachment features 1515, deck features 1517, and a slot 1519. The staple cartridge assembly 1500 further comprises a plurality of staples 1520 and an implantable adjunct 1530 releasably held to the cartridge deck 1513 by the attachment features 1515. The deck features 1517 guide the staples 1520 as the staples 1520 are ejected from the staple cartridge 1510. The deck features 1517 also limit movement of the adjunct 1530 during clamping and/or cutting of the tissue captured by the surgical instrument employing the staple cartridge assembly 1500.

The attachment features 1515 comprise barbs, for example. Each barb 1515 comprises a sharp tip configured to puncture the adjunct 1530 and a retention shoulder configured to inhibit the barb 1515 from backing out of the adjunct 1530. The barbs 1515 can extend from the deck 1513 at any suitable location. For instance, the barbs 1515 can be arranged in longitudinal rows on opposite sides of the cartridge body 1510. In such instances, the adjunct 1530 can be held between the longitudinal rows of barbs 1515. The adjunct 1530 can be held taut, tensioned, or stretched between the rows of barbs 1515 which can facilitate the transection of the adjunct 1530 by a cutting member of a firing assembly passing through the longitudinal slot 1519. As the cutting member transects the adjunct 1530, the tension within the adjunct 1530 is released. Moreover, the transected portions of the adjunct 1530 may move, or migrate, laterally outwardly away from the longitudinal slot 1519 in response to the release of the tension within the adjunct 1530. Such movement of the transected adjunct portions may cause the transected adjunct portions to at least partially detach from the barbs 1515. In at least one instance, the retention shoulders of the barbs 1515 face laterally outwardly such that the lateral outward movement of the adjunct portions tends to release the adjunct portions from the barbs 1515.

Figure 46:
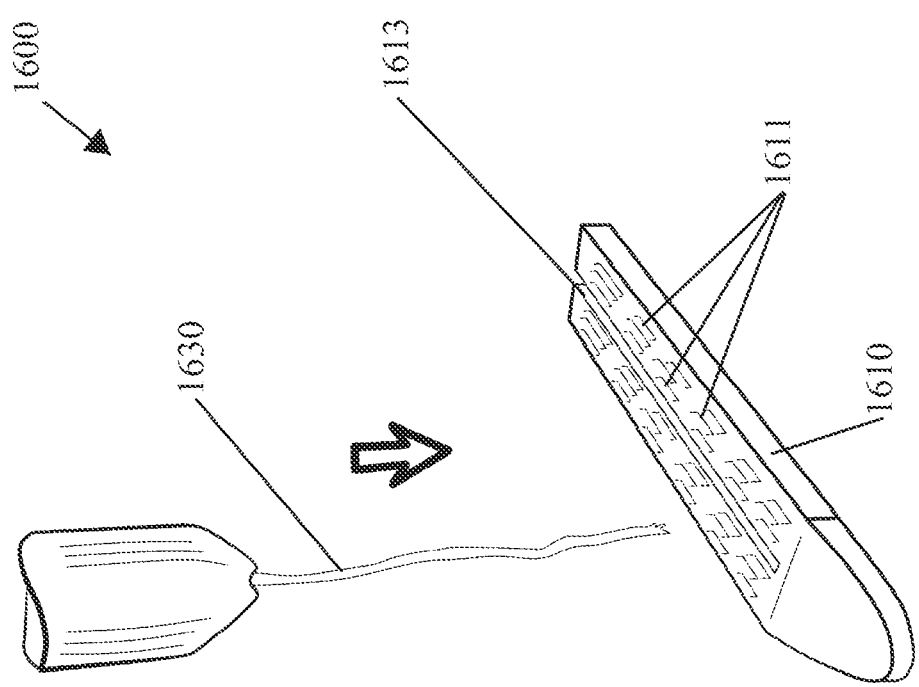
FIG. 46 illustrates an initial step of a method for assembling an implantable adjunct onto a staple cartridge.
Figure 47:
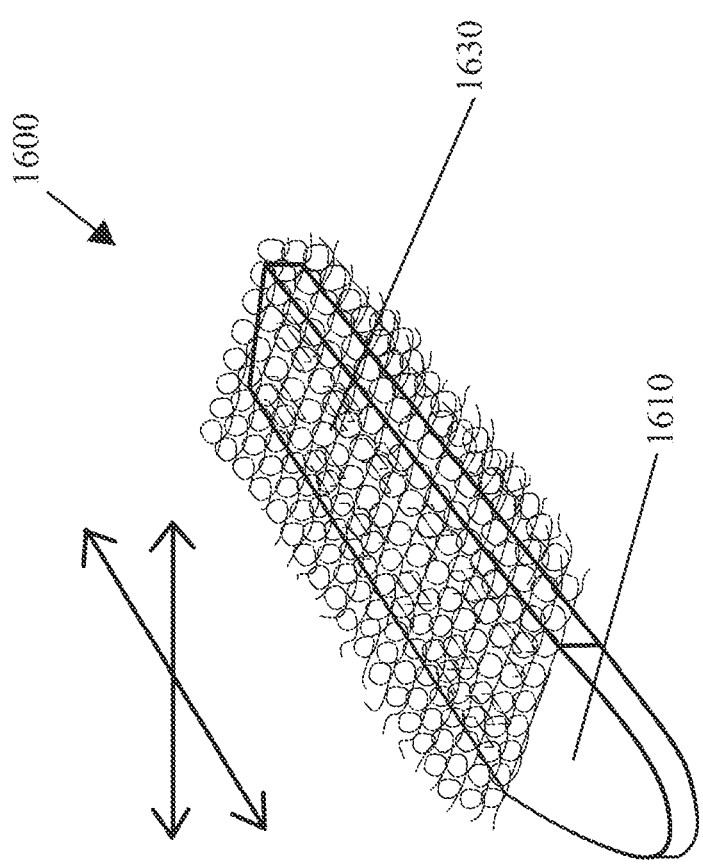
FIG. 47 illustrates another step in the method depicted in FIG. 46.
Figure 48:
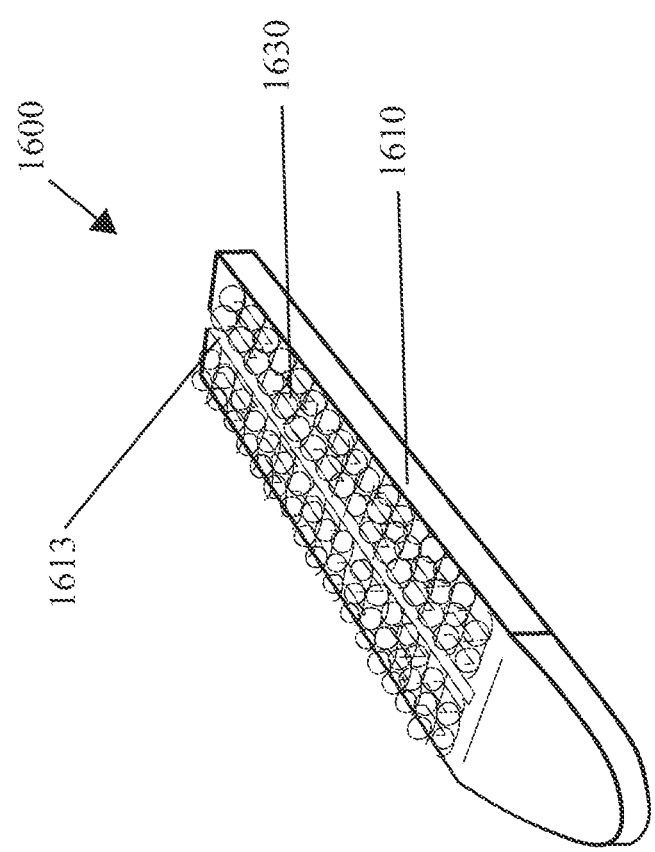
FIG. 48 illustrates a subsequent step in the method depicted in FIGS. 46 and 47.

As discussed above, an adjunct can be manufactured and then assembled to a staple cartridge. Turning now to FIGS. 46-48, a staple cartridge assembly 1600 comprises a cartridge body 1610 including staple cavities 1611 and a longitudinal slot 1613 defined therein. The staple cartridge assembly 1600 further comprises an implantable adjunct which is manufactured directly on the cartridge body 1610. As illustrated in FIG. 46, an implantable material 1630 can be dispensed on the deck of the cartridge body 1610. In various instances, the implantable material can comprise melt-blown non-woven material, for example. Such an instance is depicted in FIG. 47, for example. In at least one embodiment, electro-spinning is utilized to melt and blow a polymeric material onto the cartridge body 1610. In at least one such embodiment, the polymeric material is heated to a temperature which exceeds the glass transition temperature of the polymeric material, for example. In certain embodiments, the polymeric material is part of a solution. In either event, the polymeric material is flowable and is accelerated toward the cartridge body 1610. The polymeric material is accelerated by a mechanical spinning member, such as a spinneret, for example, and/or accelerated by applying a voltage differential between the polymeric material and a target. In various instances, the polymeric material is electrically charged. In at least one instance, the polymeric material comprises one or more magnetic materials embedded therein. The target can comprise the cartridge body 1610 and/or a metal plate positioned behind the cartridge body 1610, for example.

In some instances, further to the above, the melt-blown non-woven material extends over the edges of the cartridge body 1610 after it has been dispensed on the cartridge body 1610. Such excess material, referring to FIG. 48, can be trimmed such that the edges of the material 1630 are aligned with, or substantially aligned with, the edges of the cartridge body 1610. Such trimming can occur once the temperature of the melt-blown non-woven material has sufficiently cooled.

Further to the above, melt-blown non-woven material can be used to manufacture an implantable adjunct which is not formed directly on a cartridge body. In at least one such instance, a polymeric material is heated and blown into a cavity, or mold, to form an implantable adjunct. After the polymeric material has sufficiently cooled, the polymeric material can be trimmed to a suitable size. In addition to or in lieu of the above, a melt-blown non-woven material can be applied to a cartridge body to adhere an implantable adjunct to the cartridge body. In such instances, the adjunct can be pressed onto the melt-blown non-woven material while the material is still at least partially melted, for example.

Figure 49:
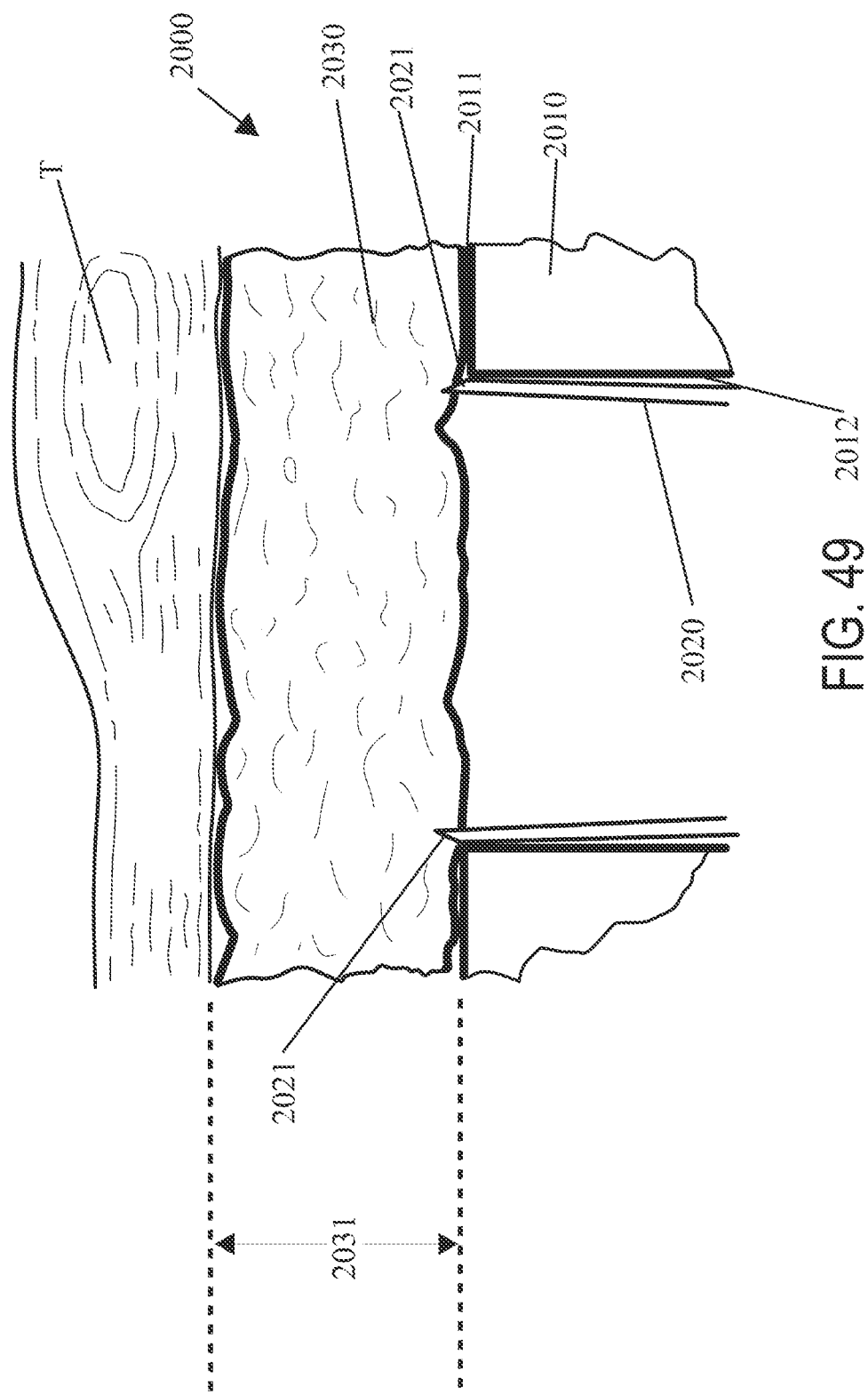
FIG. 49 is a detail view of a staple cartridge assembly in accordance with at least one embodiment comprising an implantable layer.
Figure 50:
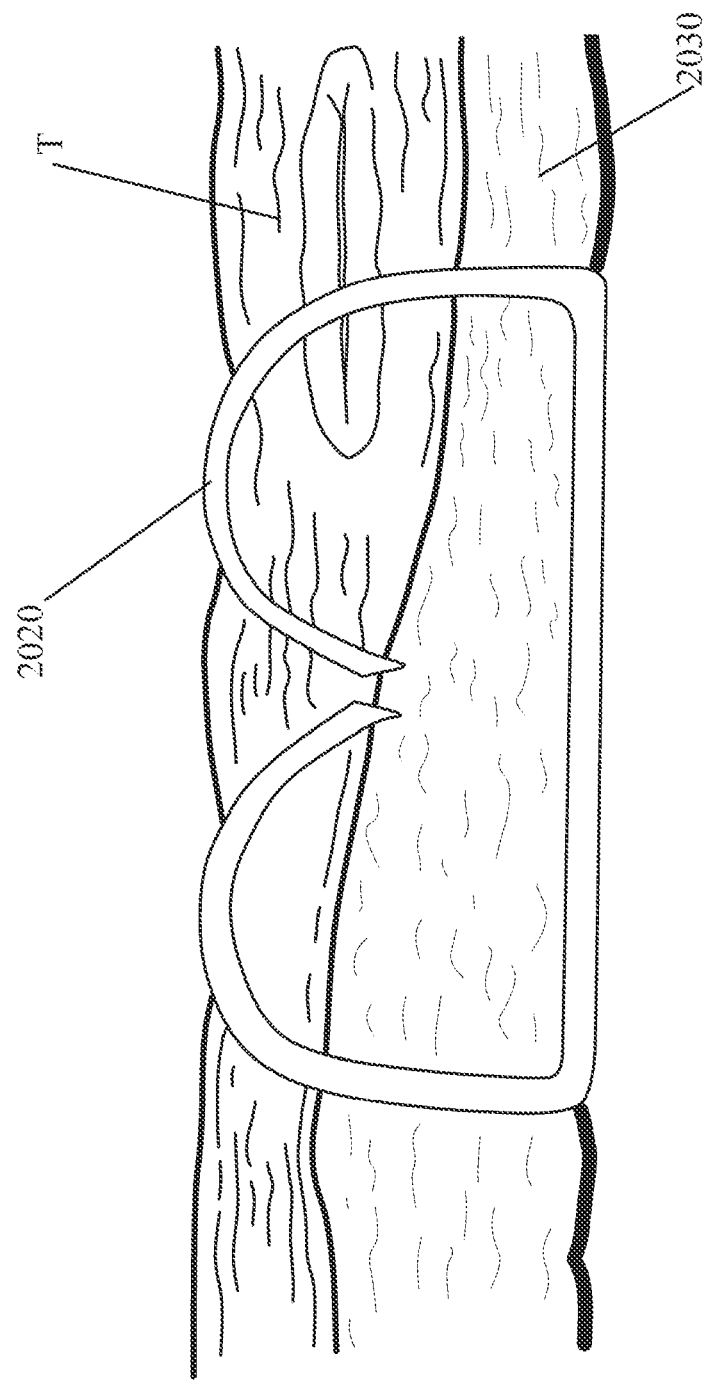
FIG. 50 is a detail view of the layer of FIG. 49 implanted against the tissue of a patient.

Turning now to FIG. 49, a staple cartridge assembly 2000 comprises a cartridge body 2010 and an implantable layer 2030. The cartridge body 2010 comprises a deck 2011 and a plurality of staple cavities 2012 defined in the deck 2011. The layer 2030 is adjacent the deck 2011 and extends over the staple cavities 2012. A staple 2020 is removably positioned in each staple cavity 2012. Each staple 2020 is movable from an unfired position to a fired position by a firing member and/or staple driver system. As illustrated in FIG. 49, the tips 2021 of the staples 2020 extend above the deck 2011 and are partially embedded in the layer 2030 when the staples 2020 are in their unfired position; however, other embodiments are envisioned in which the tips 2021 do not extend above the deck 2011 and are not embedded in the layer 2030. When the staples 2020 are ejected from the staple cavities 2012, the staples 2020 capture portions of the layer 2030 therein and implant the layer 2030 against the patient tissue T, as illustrated in FIG. 50.

The layer 2030 is comprised of a plurality of first fibers and a plurality of second fibers. The first fibers are comprised of a first material and the second fibers are comprised of a second material which is different than the first material. The first material has a first thermal transition temperature in which the first material changes states. The second material has a second thermal transition temperature in which the second material changes states. In at least one instance, the first material has a first glass transition temperature and the second material has a second glass transition temperature which is different than the first glass transition temperature. When the first material exceeds its glass transition temperature, the first fibers will contract. Similarly, the second fibers will contract when the second material exceeds its glass transition temperature. A contraction of a fiber comprises a shortening of its longest length. More specifically, a fiber often comprises a strand which has a curved and/or twisted shape and, when the strand is heated above its glass transition temperature, the shape of the strand will tend to become more curved and/or twisted which shortens its longest length eventhough the overall length of the strand has not changed. In such instances, the configuration of the fibers will become less organized.

The first fibers and the second fibers of the layer 2030 can be mixed utilizing any suitable process. In at least one process, the first fibers and the second fibers can be interwoven, for example. For instance, the first fibers can be woven into a mesh and the second fibers can be interwoven into the mesh. After the fibers have been suitably mixed, the fibers can be exposed to heat. The fibers are heated to a temperature above the first thermal transition temperature but below the second thermal transition temperature. As a result, the first fibers contract and the second fibers do not contract, or at least they do not substantially contract. Nonetheless, the contraction of the first fibers will constrict the second fibers and change the overall shape of the layer 2030. More specifically, the contracting first fibers will pull the edges of the layer 2030 inwardly. Such inward movement of the edges can increase the thickness 2031 of the layer 2030. In certain instances, the layer will become puffy and/or bunch up. In any event, the heating processes described herein can allow a layer 2030 to assume a configuration which can compensate for variations of the tissue thickness captured in the staples.

The first and second materials of the layer 2030 can comprise any suitable materials. For example, the first material is a first polymer and the second material is a second polymer. For instance, the first material is polydioxanone (PDS) and the second material is polyglycolic acid (PGA), such as VICRYL manufactured by Ethicon, Inc., for example. The layer 2030 comprises more of the second material having a higher thermal transition temperature than the first material having a lower thermal transition temperature. In at least one example, the ratio of VICRYL, i.e., the second material, to PDS, i.e., the first material, is approximately 7:1. In at least one other example, the ratio of VICRYL, i.e., the second material, to PDS, i.e., the first material, is approximately 5:1. Other ratios and materials are possible.

Further to the above, various alternative embodiments are envisioned in which the layer 2030 is heated to a processing temperature such that the first fibers are heated above their thermal transition temperature and the second fibers are also heated above their thermal transition temperature. In at least one such instance where the first thermal transition temperature is below the second thermal transition temperature, the first fibers will contract more than the second fibers.

After the layer 2030 has been heated to achieve its desirable properties as described herein, the layer 2030 is cooled and/or permitted to cool below the first thermal transition temperature and the second thermal transition temperature. The layer 2030 is cooled below the first and second thermal transition temperatures before being assembled to the cartridge body 2010.

Figure 57:
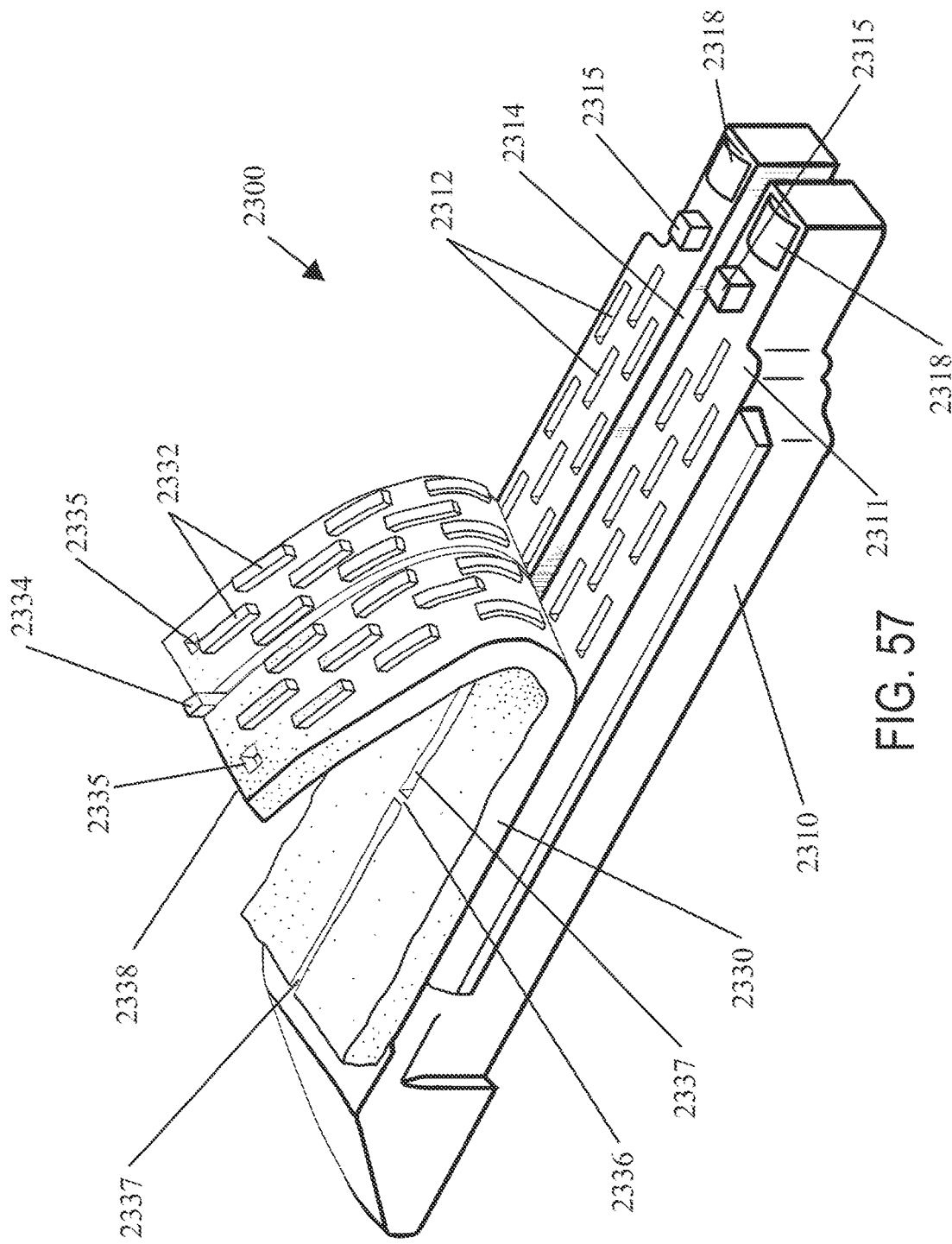
FIG. 57 is a perspective view of a staple cartridge assembly in accordance with at least one embodiment comprising an implantable layer.

In various alternative embodiments, turning now to FIG. 57, a layer 2330 of a staple cartridge assembly 2300 is heated to a temperature that is above at least one of the first thermal transition temperature and the second thermal transition temperature and then positioned and/or pressed against a cartridge body 2310 of the cartridge assembly 2300. The layer 2330 is then cooled and/or permitted to cool.

Further to the above, the cartridge body 2310 comprises a deck 2311 and staple cavities 2312 defined in the deck 2311. The cartridge body 2310 further comprises posts 2315 extending upwardly from the deck 2311. When the heated layer 2330 is pressed against the deck 2311, the layer 2330 can conform to the features of the cartridge body 2310. For instance, portions of the layer 2330 can be wedged into the staple cavities 2312 and can assume the shape of the staple cavities 2312 to form projections 2332. Similarly, portions of the layer 2330 can form around the posts 2315 and assume the shape of the posts 2315 to form apertures 2335. Also, similarly, portions of the layer 2330 can be wedged into a longitudinal knife slot 2314 of the cartridge body 2310 to form tabs 2334.

Further to the above, the initial alignment between the heated layer 2330 and the cartridge body 2310 will determine how the features are formed on the bottom of the layer 2330. The cartridge body 2310 comprises one or more datums which can assist in the proper alignment between the layer 2330 and the cartridge body 2310. The cartridge body 2310 comprises alignment stops 2318 extending upwardly from the proximal end of the cartridge body 2310 which can be utilized to align the proximal end 2338 of the layer 2330 with the proximal end of the cartridge body 2310.

Figure 52:
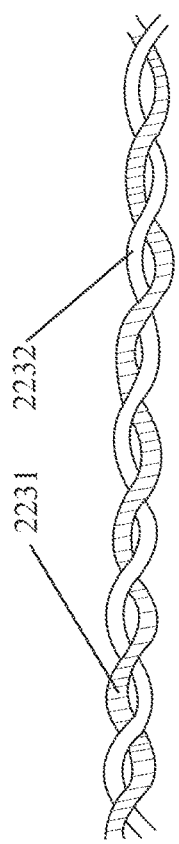
FIG. 52 illustrates a fiber assembly including a first fiber comprised of a first material intertwined with a second fiber comprised of a second material.
Figure 53:
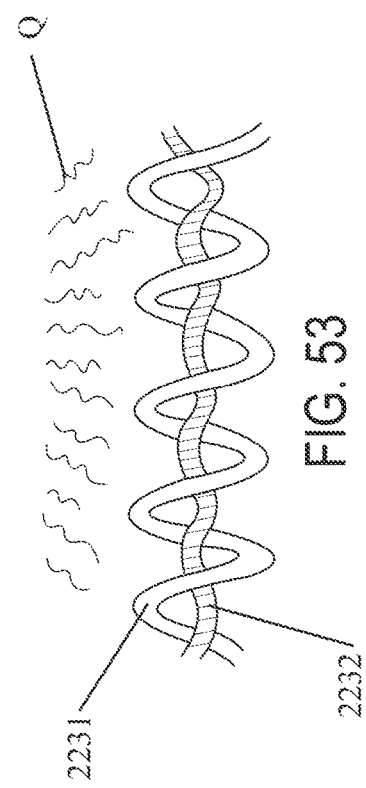
FIG. 53 illustrates the fiber assembly of FIG. 52 being exposed to heat.
Figure 54:
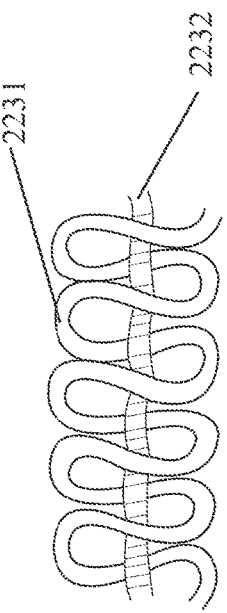
FIG. 54 illustrates the fiber assembly of FIG. 52 in a contracted state after being exposed to the heat.

Turning now to FIG. 52, a first fiber 2231 and a second fiber 2232 are intertwined or interwoven. When the fibers 2231 and 2232 are exposed to heat, Q, the first fiber 2231 becomes less disorganized and begins to contract along its longest dimension, as illustrated in FIG. 52. As also illustrated in FIG. 52, the first fiber 2231 contracts relative to the second fiber 2232. While the first fiber 2231 contracts in its longest dimension, referring to FIG. 53, the first fiber 2231 expands in a lateral direction. As a result, the assembly of fibers 2231, 2232 can become resilient and can change shape under load.

Figure 55:
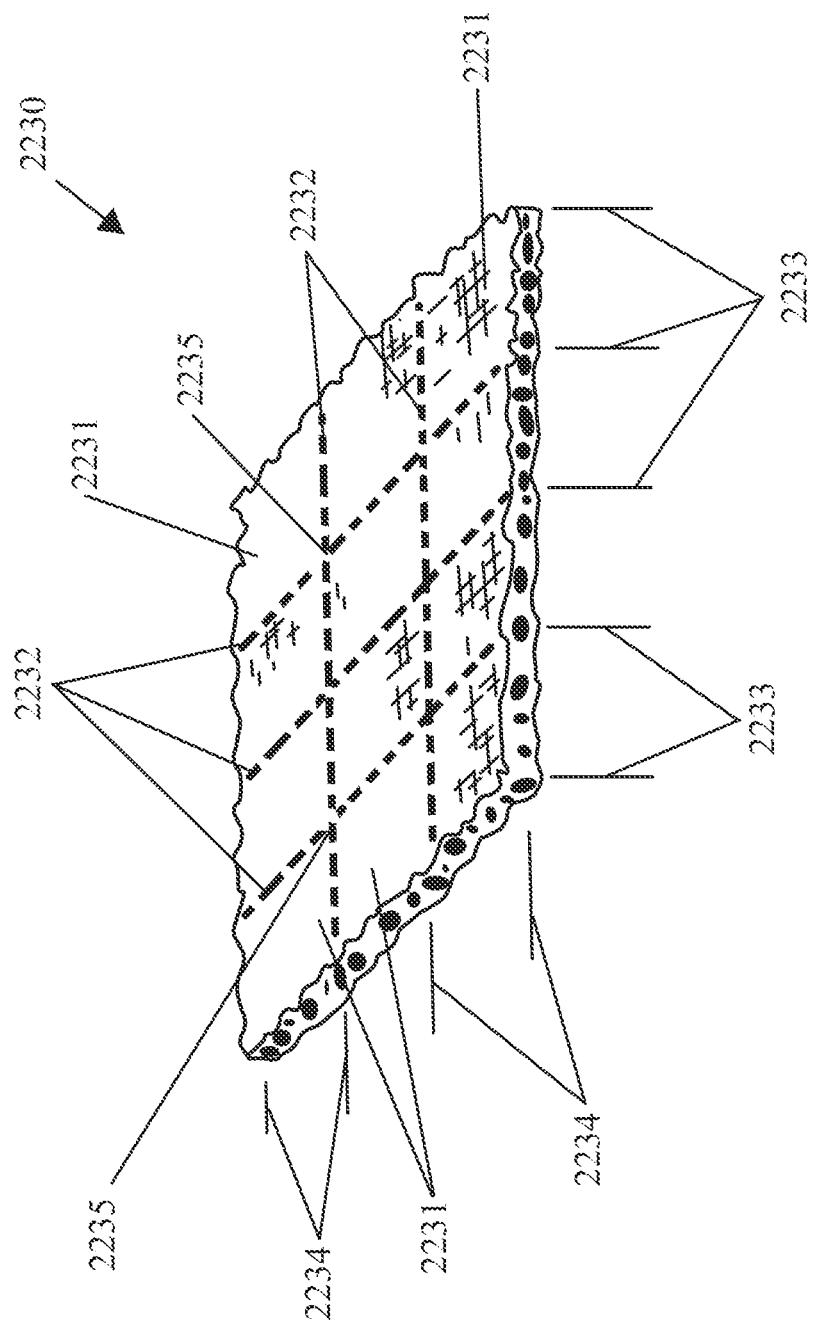
FIG. 55 is a perspective view of an implantable layer in accordance with at least one embodiment.
Figure 56:
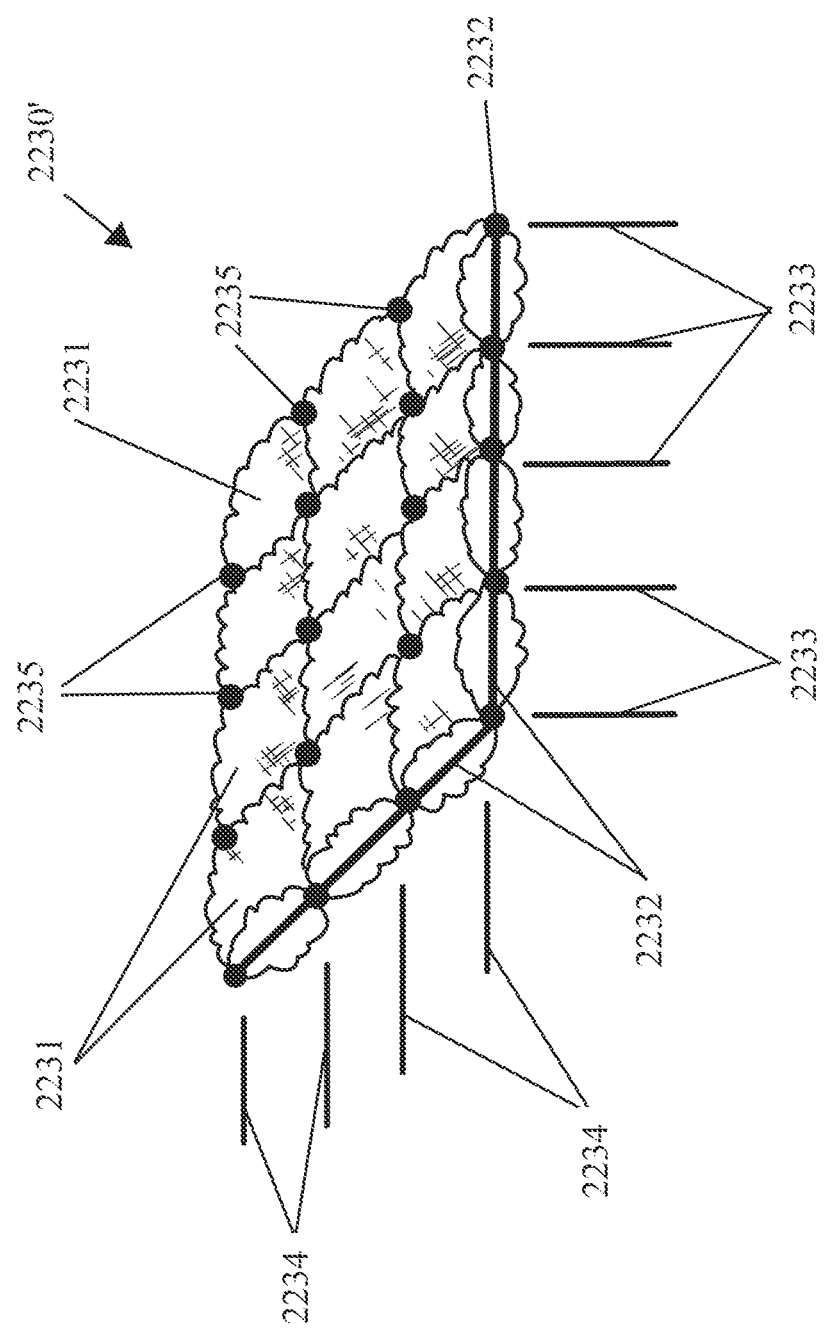
FIG. 56 is a perspective view of the layer of FIG. 55 in a contracted state after being exposed to heat.

The arrangement of the fibers 2231 and 2232 within a layer can be random. In certain instances, the arrangement of the fibers 2231 and 2232 within a layer can be at least partially organized. Turning now to FIG. 55, a layer 2230 comprises a mesh of second fibers 2232. The second fibers 2232 are attached, or interwoven, to one another at nodes 2235; however, various embodiments are envisioned in which the second fibers 2232 are not attached to each other. The second fibers 2232 are arranged in a lattice, or network, which extends along longitudinal axes 2233 and lateral axes 2234. The axes 2233 and 2234 are orthogonal, or substantially orthogonal, to each other; however, other embodiments are envisioned in which the lattice of second fibers 2232 are not arranged along an organized array of axes. The first fibers 2231 are interwoven into the mesh of the second fibers 2232. When the layer 2230 is exposed to a temperature which exceeds the first thermal transition temperature of the first material, the first fibers 2231 contract, as illustrated in FIG. 56. As a result, the layer 2230 assumes a laterally expanded configuration, referenced as layer 2230'.

Figure 51:
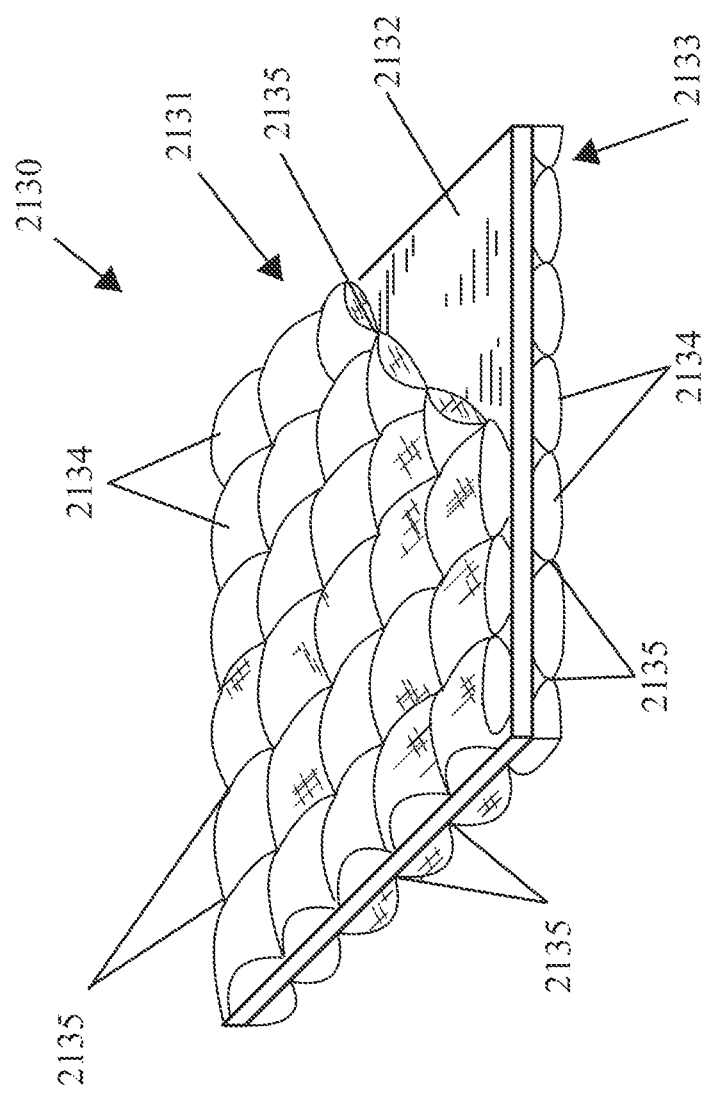
FIG. 51 is a perspective view of an implantable layer assembly in accordance with at least one embodiment.

Turning now to FIG. 51, a layer assembly 2130 comprises a first layer 2131, a second layer 2132, and a third layer 2133. The first layer 2131 comprises a plurality of first fibers 2134 interwoven with a plurality of second fibers 2135. Similarly, the third layer 2133 comprises a plurality of first fibers 2134 interwoven with a plurality of second fibers 2135. Similar to the above, the first fibers 2134 are comprised of a first material having a first thermal transition temperature and the second fibers 2135 are comprised of a second material having a second thermal transition temperature which is different than the first thermal transition temperature. The second layer 2132 is positioned intermediate the first layer 2131 and the third layer 2133. The second layer 2132 is comprised of a film; however, any suitable material could be utilized. The first layer 2131 and the third layer 2133 can be attached to the second layer 2132 utilizing one or more adhesives, for example. The second layer 2132 separates the first layer 2131 from the third layer 2133. In various instances, the second layer 2132 can permit the first layer 2131 and the third layer 2133 to be constricted independently of one another.

In various instances, further to the above, portions of a layer can be removed and/or modified utilizing any suitable process. Referring again to FIG. 57, one or more longitudinal slits 2337 can be created in the layer 2330 utilizing a laser cutting process, for example. Bridges 2336 are defined intermediate the slits 2337 and hold the two lateral halves of the layer 2330 together.

Figure 58:
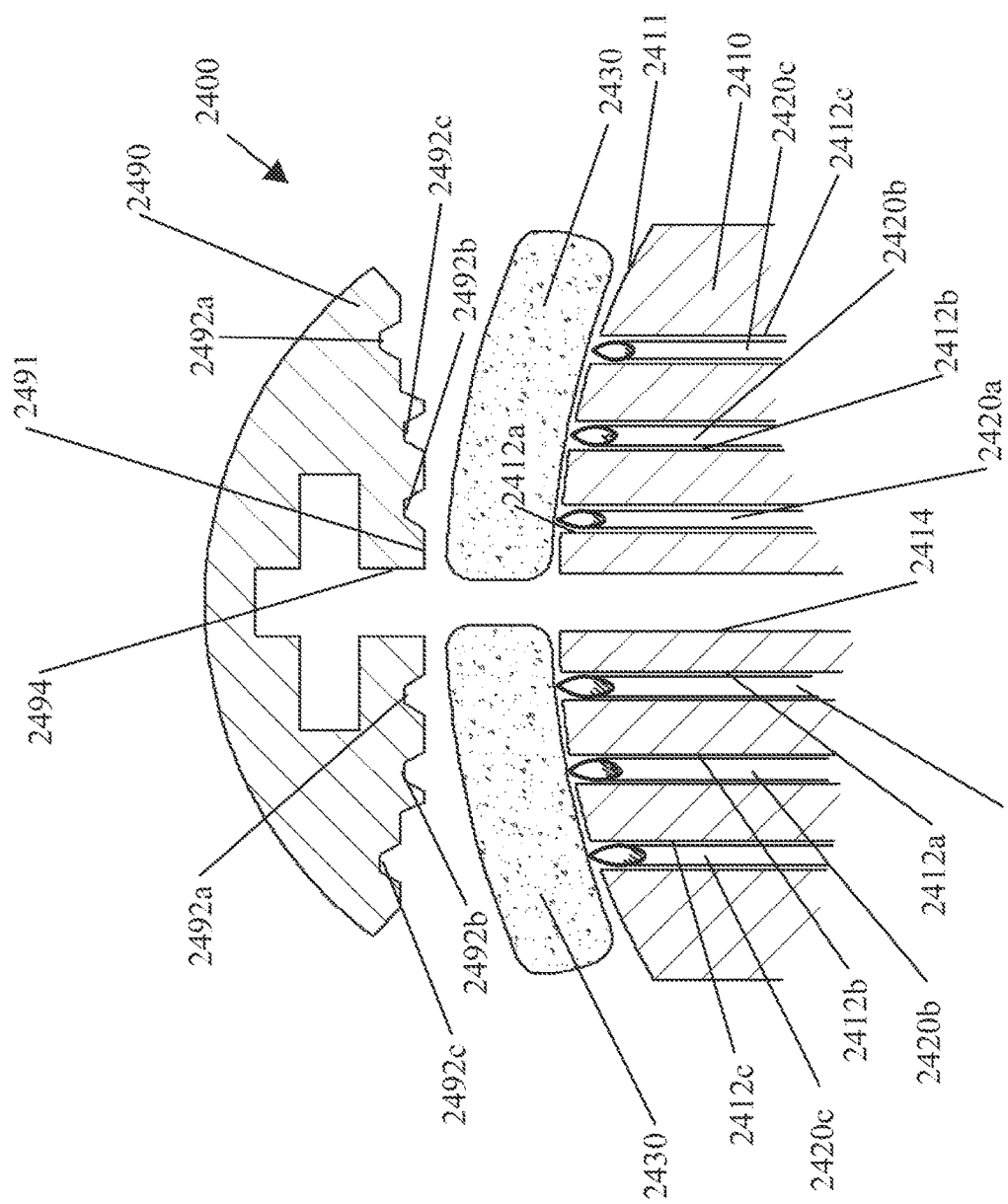
FIG. 58 is a cross-sectional view of a staple cartridge assembly in accordance with at least one embodiment comprising staples having different unformed heights.

Turning now to FIG. 58, an end effector assembly 2400 comprises a staple cartridge body 2410 and an anvil 2490. The cartridge body 2410 comprises a deck 2411, a longitudinal knife slot 2414, and longitudinal rows of staple cavities defined on opposite sides of the slot 2414. More particularly, a first longitudinal row of staple cavities 2412a is disposed on each side of the longitudinal slot 2414, a second longitudinal row of staple cavities 2412b is disposed laterally relative to each first row of staple cavities 2412a, and a third longitudinal row of staple cavities 2412c is disposed laterally relative to each second row of staple cavities 2412b. A first staple 2020a is removably stored in each first staple cavity 2412a, a second staple 2020b is removably stored in each second staple cavity 2412b, and a third staple 2020c is removably stored in each third staple cavity 2412c.

Further to the above, the first staples 2020a each have a first unformed height, the second staples 2020b each have a second unformed height, and the third staples 2020c each have a third unformed height. The first unformed height is shorter than the second unformed height and the second unformed height is shorter than the third unformed height. Other embodiments are envisioned in which the first staples 2020a, the second staples 2020b, and/or the third staples 2020c have the same unformed height. U.S. Pat. No. 8,317,070, entitled SURGICAL STAPLING DEVICES THAT PRODUCE FORMED STAPLES HAVING DIFFERENT LENGTHS, which issued on Nov. 27, 2012, is incorporated herein by reference in its entirety. The anvil 2490 comprises a first longitudinal row of forming pockets 2492a aligned with the staple cavities 2412a, a second longitudinal row of forming pockets 2492b aligned with the staple cavities 2412b, and a third longitudinal row of forming pockets 2492c aligned with the staple cavities 2412c. The staples 2020a, 2020b, and 2020c are ejected from the staple cavities 2412a, 2412b, and 2412c by a plurality of staple drivers positioned in the cartridge body 2410 which lift the staples 2020a, 2020b, and 2020c into contact with the forming pockets 2492a, 2492b, and 2492c, respectively.

Figure 59:
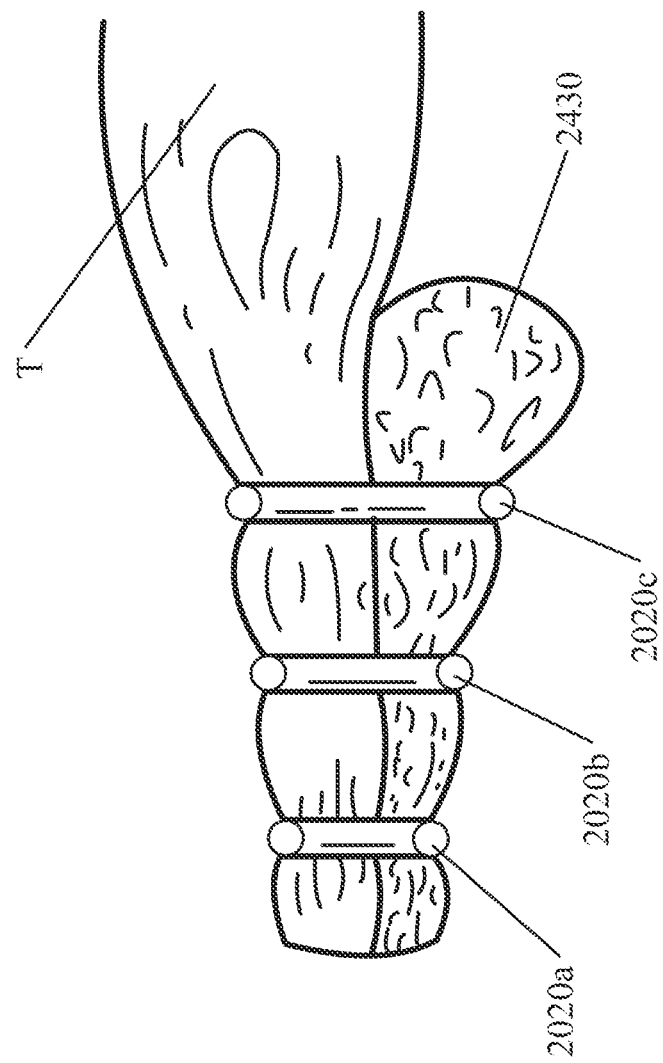
FIG. 59 illustrates the staples of FIG. 58 formed to different formed heights.

Further to the above, the staple drivers positioned in the cartridge body 2410 and the forming pockets 2492a, 2492b, and 2492c of the anvil 2490 are configured to deform the staples 2020a, 2020b, and 2020c to different formed heights. More specifically, the first staples 2020a are deformed to a first formed height, the second staples 2020b are deformed to a second formed height which is taller than the first formed height, and the third staples 2020c are deformed to a third formed height which is taller than the second formed height. FIG. 59 illustrates such an arrangement. Other embodiments are envisioned in which the third formed height is the same as the second formed height.

Further to the above, referring again to FIG. 58, the deck 2411 of the cartridge body 2410 comprises a sloped support surface. The portion of the deck 2411 extending along the first longitudinal row of staple cavities 2412a is higher than the portion of the deck 2411 extending along the second longitudinal row of staple cavities 2412b. Similarly, the portion of the deck 2411 extending along the second longitudinal row of staple cavities 2412b is higher than the portion of the deck 2411 extending along the third longitudinal row of staple cavities 2412c. The deck 2411 comprises an arcuate surface. In various instances, the sloped support surface of the deck 2411 can include discrete stepped surfaces. For instance, the deck 2411 can include a first longitudinal step which extends along the first row of staple cavities 2412a, a second longitudinal step which extends along the second row of staple cavities 2412b, and/or a third longitudinal step which extends along the third row of staple cavities 2412c. The deck 2411 can further include sloped surfaces intermediate the first step and the second step and/or intermediate the second step and the third step.

Further to the above, the anvil 2490 includes a stepped tissue compression surface. For instance, the third longitudinal rows of forming pockets 2492c are defined in longitudinal steps. In alternative embodiments, the anvil 2490 comprises a flat tissue compression surface. In either event, tissue positioned between the cartridge body 2410 and the anvil 2490 is compressed to a suitable pressure therebetween when the end effector 2400 is in a clamped configuration, as illustrated in FIG. 58. Such tissue compression, however, is not uniform within the end effector 2400. For instance, the tissue adjacent the first row of staple cavities 2412a is compressed to a first pressure, the tissue adjacent the second row of staple cavities 2412b is compressed to a second pressure which is less than the first pressure, and the tissue adjacent the third row of staple cavities is compressed to a third pressure which is less than the second pressure. Other arrangements are contemplated.

The end effector 2400 further comprises implantable layers 2430 positioned over the deck 2411. For instance, a first layer 2430 is positioned on a first side of the longitudinal slot 2414 and a second layer 2430 is positioned on a second side of the longitudinal slot 2414. The layers 2430 define a longitudinal slot therebetween which is aligned, or at least substantially aligned, with the slot 2414 defined in the cartridge body 2410 and a longitudinal slot 2494 defined in the anvil 2490. The cartridge slot 2414, the layer slot, and the anvil slot 2494 are configured to permit a firing member to move longitudinally through the end effector 2400. In alternative embodiments, a layer positioned on the deck 2411 does not comprise a layer slot and a cutting portion of the firing member transects the layer as the firing member is moved distally.

Figure 60:
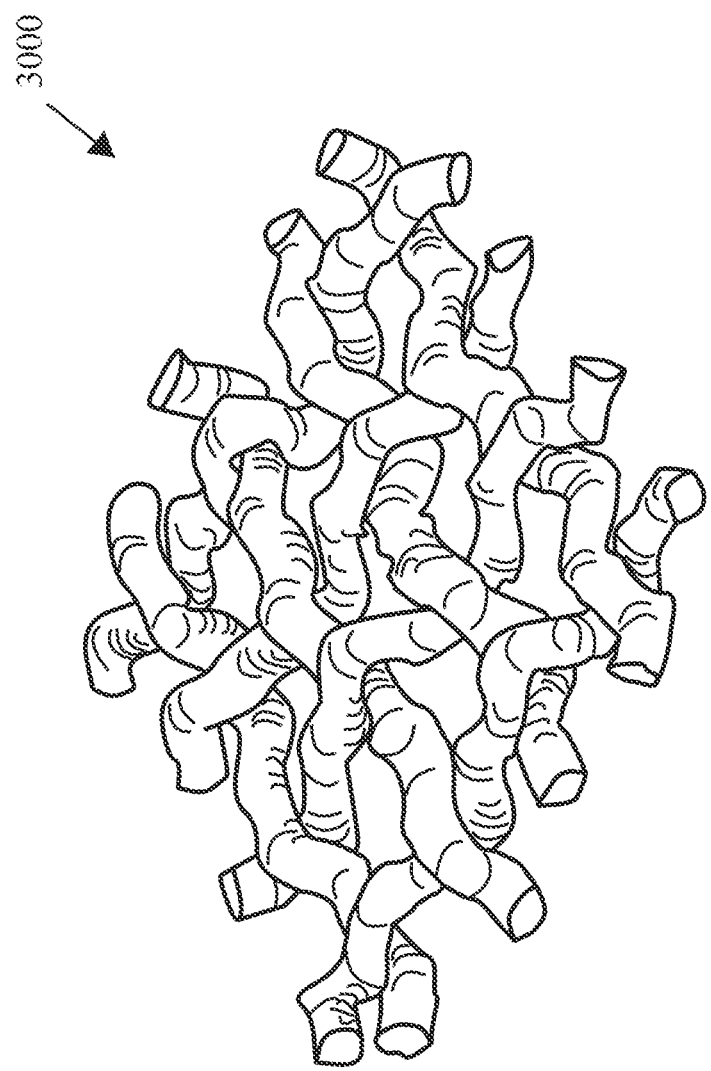
FIG. 60 illustrates a plurality of kinked fibers in accordance with at least one embodiment.
Figure 61:
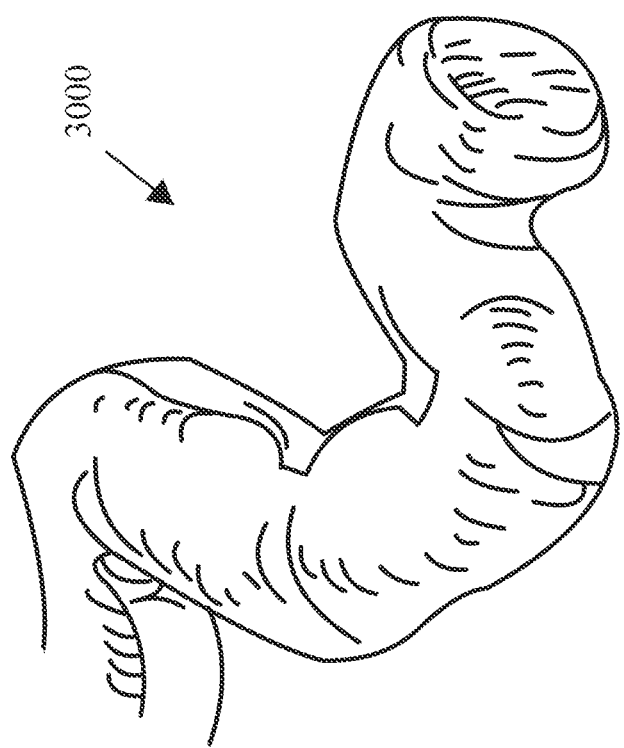
FIG. 61 is a perspective view of a kinked fiber of FIG. 60.
Figure 62:
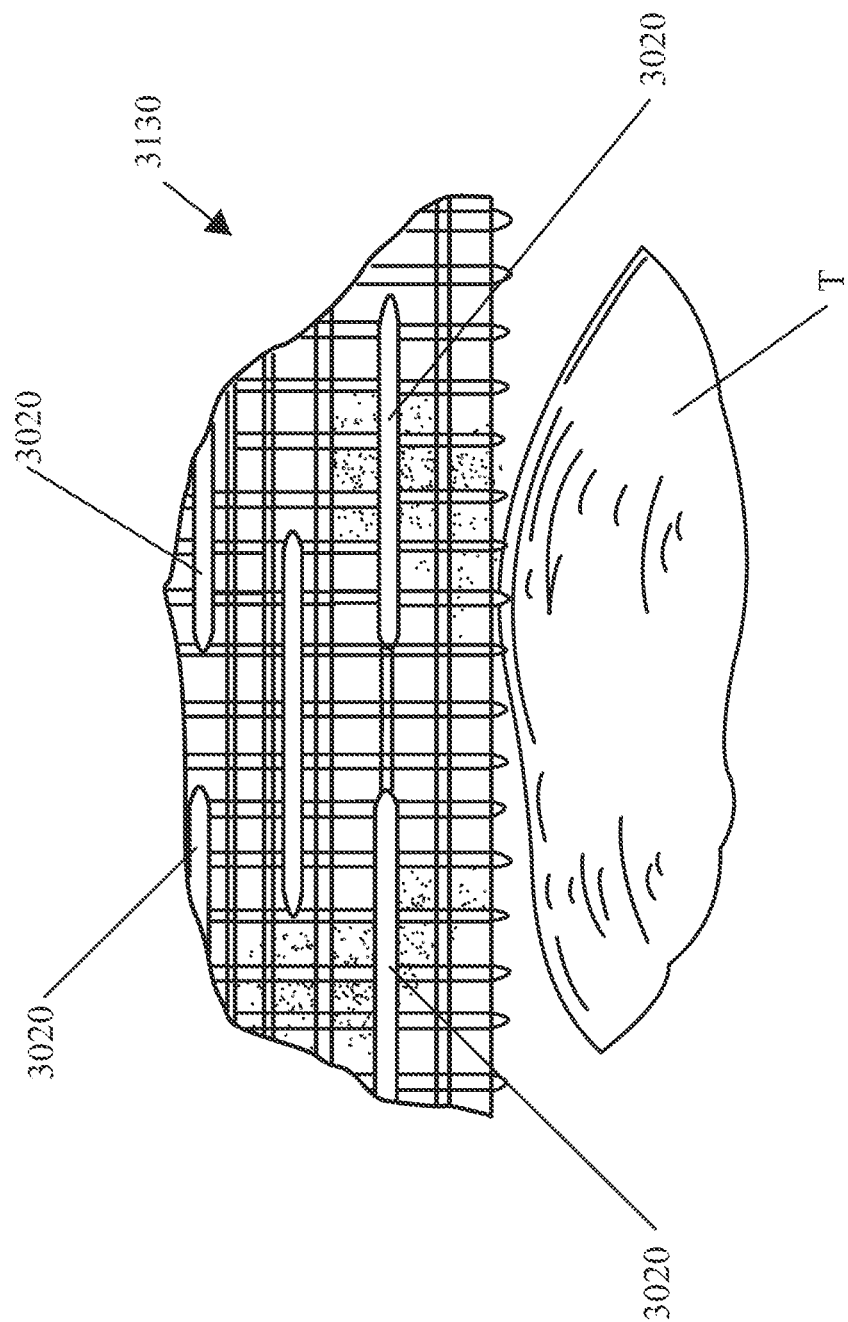
FIG. 62 is a partial perspective view of an implantable layer that does not comprise kinked fibers.
Figure 63:
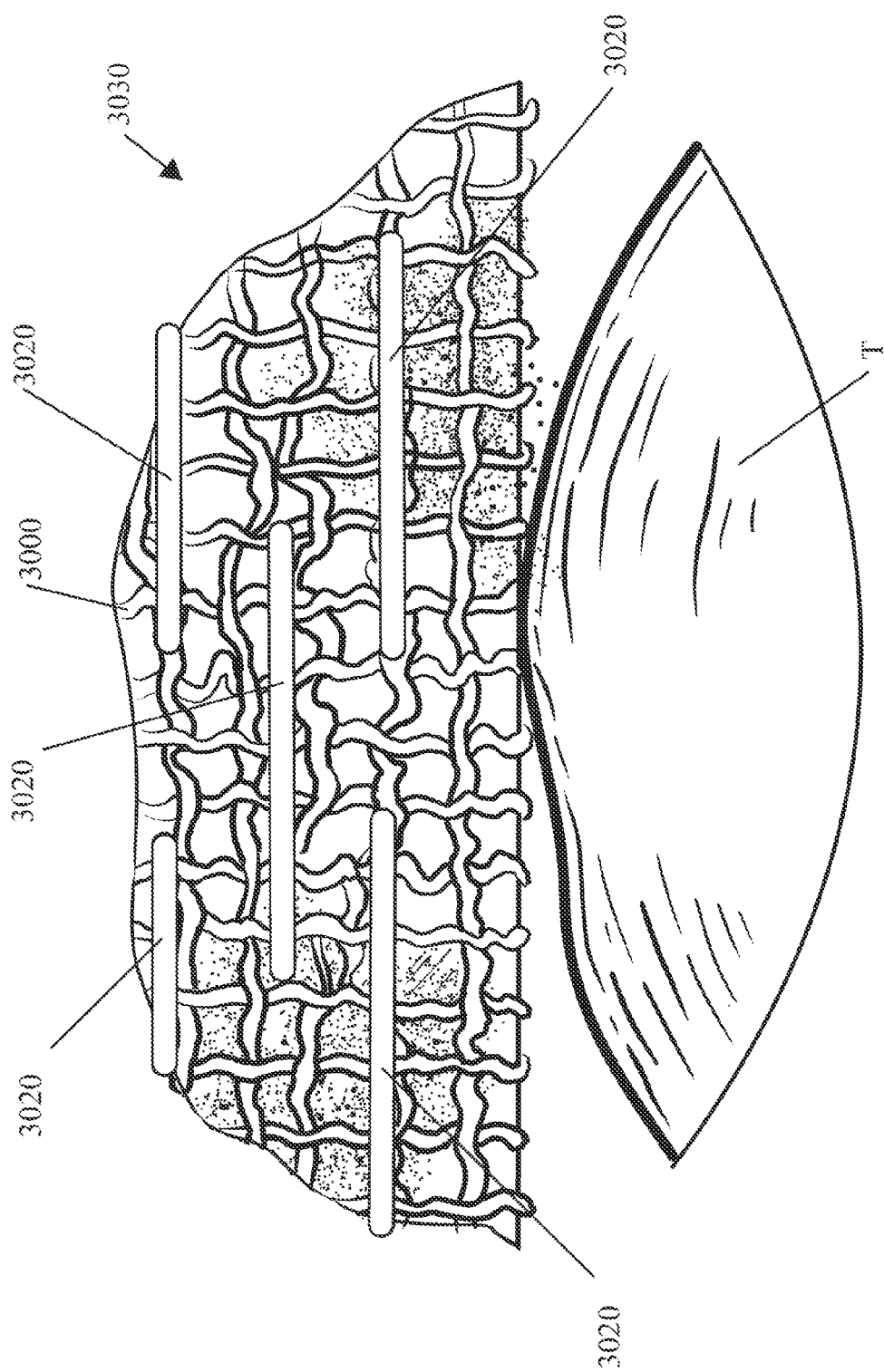
FIG. 63 is a partial perspective view of an implantable layer in accordance with at least one embodiment that comprises the kinked fibers of FIG. 60.

The implantable layers described herein can be comprised of fibers which are interwoven together. Fibers 3000, for example, are illustrated in FIGS. 60 and 61. Each fiber 3000 comprises a strand which has been plastically deformed and includes one or more kinks defined therein. An implantable layer, such as layer 3030 illustrated in FIG. 63, for example, that comprises fibers 3000 is resilient and can compensate for variations in tissue thickness captured within staples 3020. The fibers 3000 are woven together to form an implantable layer which can act as a collective spring. Moreover, the fibers 3000 of the layer 3030 are soft as a result of their kinked configuration and are less likely to abrade tissue T as compared to previous implantable layers that do not include the fibers 3000, such as the layer 3130 depicted in FIG. 62, for example.

Figure 65:
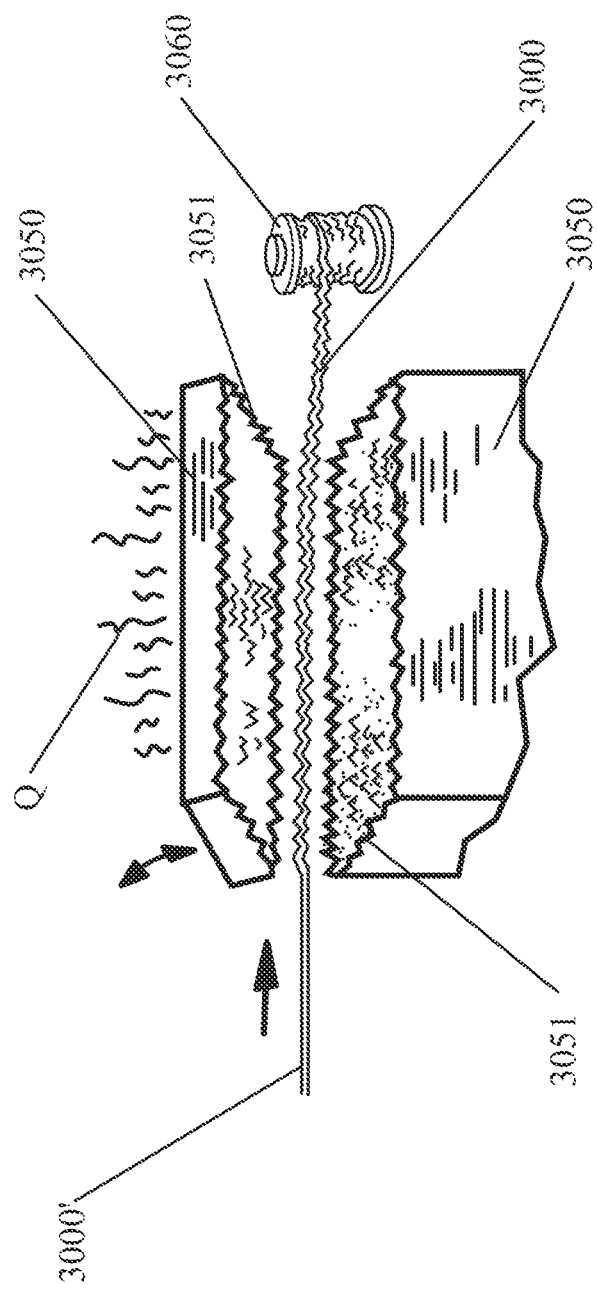
FIG. 65 illustrates a process for creating the kinked fibers of FIG. 60.

The fibers 3000 can be manufactured in any suitable manner. In various instances, a manufacturing process can utilize any suitable means for mechanically and/or thermally creating kinks in the fibers 3000 and/or otherwise plastically deforming the fibers 3000. Turning now to FIG. 65, a heated die can be utilized to plastically deform a strand 3000' to form a continuous fiber 3000. The heated die comprises first and second sides 3050 wherein at least one of the sides is movable relative to the other side between an open position and a closed position. FIG. 65 illustrates the heated die in an open configuration. When the die is in its open configuration, a portion of the unformed strand 3000' is positioned in the die between the open sides 3050. In at least one instance, the manufacturing process includes a spool 3060 configured to pull the strand 3000' into the die. Each side 3050 of the die includes a heated surface 3051. The heated surfaces 3051 include a plurality of projections which are configured to contact the strand 3000' and, through mechanical pressure and/or heating, plastically deform the strand 3000'. At such point, the continuous strand 3000' becomes a continuous fiber 3000 which is wrapped around the spool 3060. The continuous fiber 3000 can be transected during a subsequent step in the manufacturing process, if desired.

Figure 66:
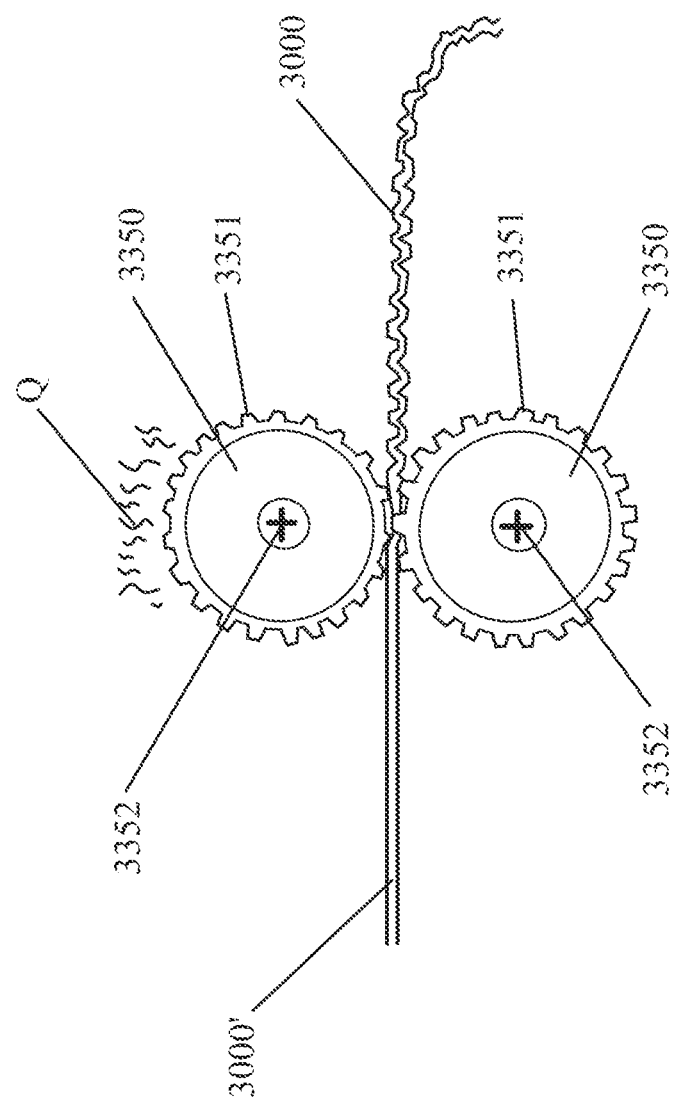
FIG. 66 illustrates a process for creating the kinked fibers of FIG. 60.
Figure 67:
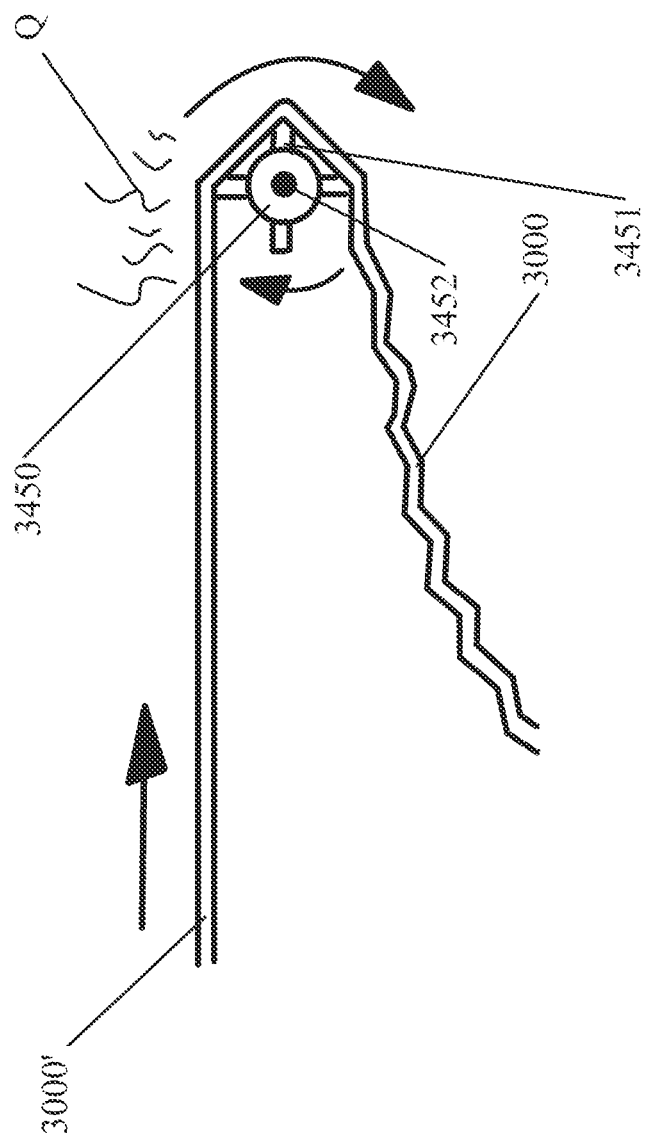
FIG. 67 illustrates a process for creating the kinked fibers of FIG. 60.

Further to the above, turning now to FIG. 66, a manufacturing process includes one or more rotatable dies 3350. Each die 3350 is rotatable about an axis 3352 and includes a plurality of teeth 3351 extending around the die 3350. The teeth 3351 of the rotatable dies 3350 are intermeshed and deform the continuous strand 3000' into the continuous fiber 3000 when the strand 3000' passes through the intermeshed teeth 3351. Similar to the above, the dies 3350 are heated and apply heat (Q) to the strand 3000'. Turning now to FIG. 67, a manufacturing process includes a rotatable die 3450. The die 3450 is rotatable about an axis 3452 and includes teeth 3451 extending therefrom. A continuous strand 3000' is wrapped around the perimeter of the die 3450 and is engaged with the teeth 3451. The teeth 3451 are heated and, when the teeth 3451 contact the strand 3000', the strand 3000' becomes a continuous kinked fiber 3000. A tensile force can be applied to the fiber 3000 to pull the fiber 3000 around the die 3450.

In addition to or in lieu of the above, the fibers 3000 can be deformed, or kinked, in any suitable manner. In various instances, air texturing and/or any other suitable form of texturing could be used, for example. Moreover, the intervals between the deformations, or kinks, in the fibers 3000 can be utilized to control the properties of the fibers 3000. Fibers 3000 having shorter intervals between the deformations, or kinks, will be less stiff than fibers 3000 having longer intervals between the deformations, or kinks Regardless of the manner of deformation used to deform the fibers 3000, the fibers 3000 can comprise any suitable cross-section. In at least one instance, the strands 3000' can comprise a circular, or an at least substantially circular, cross-section which is at least partially flattened after the strands 3000' have been deformed, or kinked to form the fibers 3000. In various instances, the fibers 3000 have an oblate cross-section where they have been deformed, for example.

Further to the above, the fibers 3000 can undergo a deformation, or kinking process, during one or more steps of a manufacturing process to form an implantable layer. In at least one process, the fibers 3000 are deformed, or kinked, before they are weaved together in a preliminary weaving process. Such a deformation process can utilize pressure and/or heat, for example. Alternatively, the fibers do not undergo a deformation process before the preliminary weaving process. In either event, once the fibers 3000 have been woven together, they are unwoven. The process of weaving and then unweaving the fibers 3000 deforms, or kinks, the fibers 3000. After the fibers 3000 have been unwoven, they may or may not undergo a deformation, or kinking, process. Such a deformation process can utilize pressure and/or heat, for example. After the fibers 3000 have undergone a suitable number of pre-kinking processes, the fibers 3000 are then re-woven into an implantable layer.

In various instances, further to the above, only the pre-kinked fibers 3000 are utilized to weave an implantable layer while, in other instances, the pre-kinked fibers 3000 are mixed with other fibers, such as unkinked fibers, for example. In at least one instance, a woven implantable layer comprises a first group of pre-kinked fibers 3000 comprised of a material and a second group of unkinked fibers comprised of the same material. In another instance, a woven implantable layer comprises a first group of pre-kinked fibers 3000 comprised of a first material and a second group of unkinked fibers comprised of a second material which is different than the first material. In yet another instance, a woven implantable layer comprises a first group of pre-kinked fibers 3000 which are kinked at a first interval and a second group of pre-kinked fibers which are kinked at a second interval which is different than the first interval. Implantable layers comprised of a first group of fibers having a higher stiffness interwoven with a second group of fibers having a higher stiffness, such as those described herein, for example, can provide the implantable layer with a desired modulus of elasticity.

Figure 68:
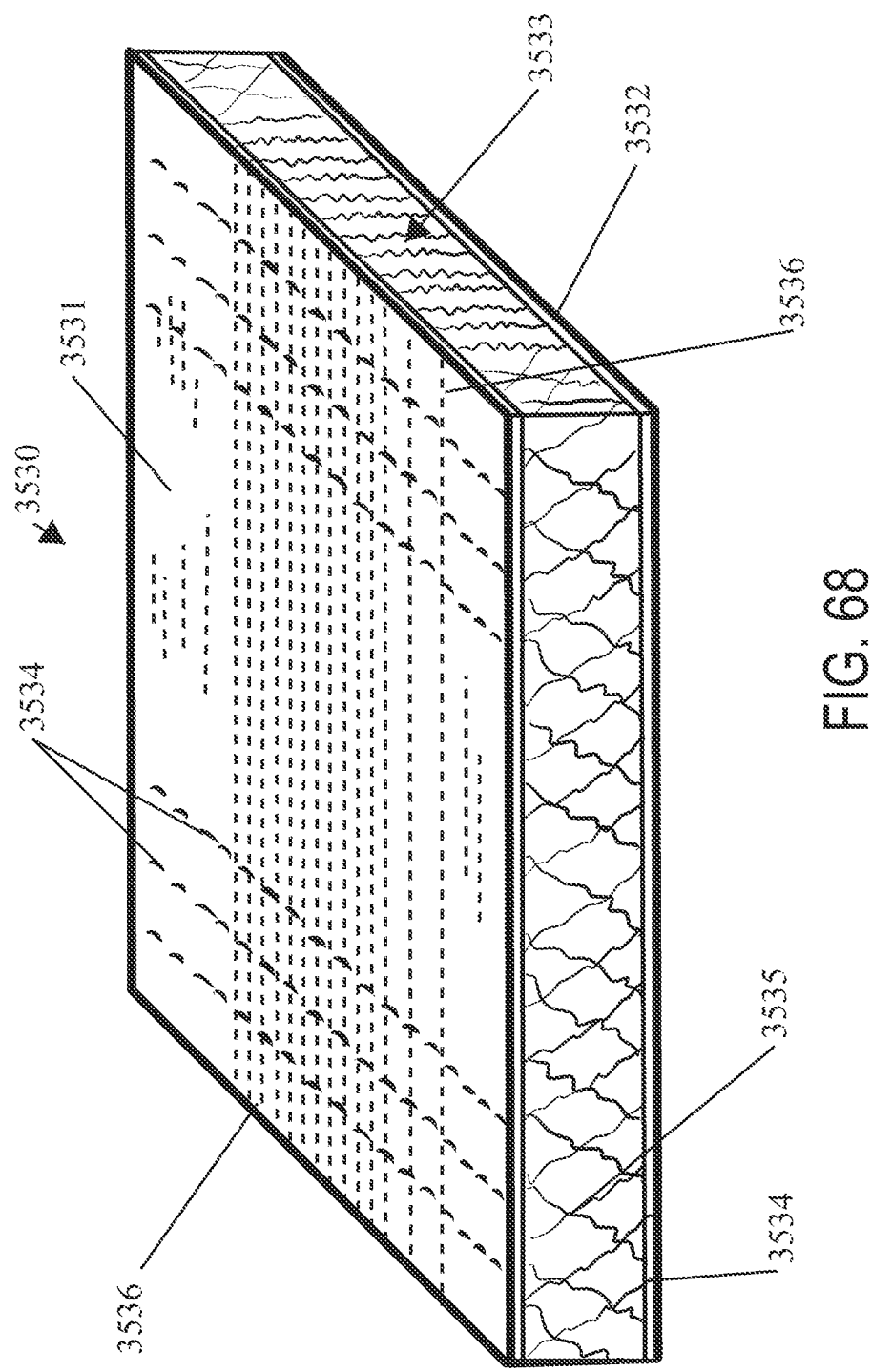
FIG. 68 is a perspective view of an implantable layer in accordance with at least one embodiment comprising the kinked fibers of FIG. 60 interwoven with another group of fibers.
Figure 69:
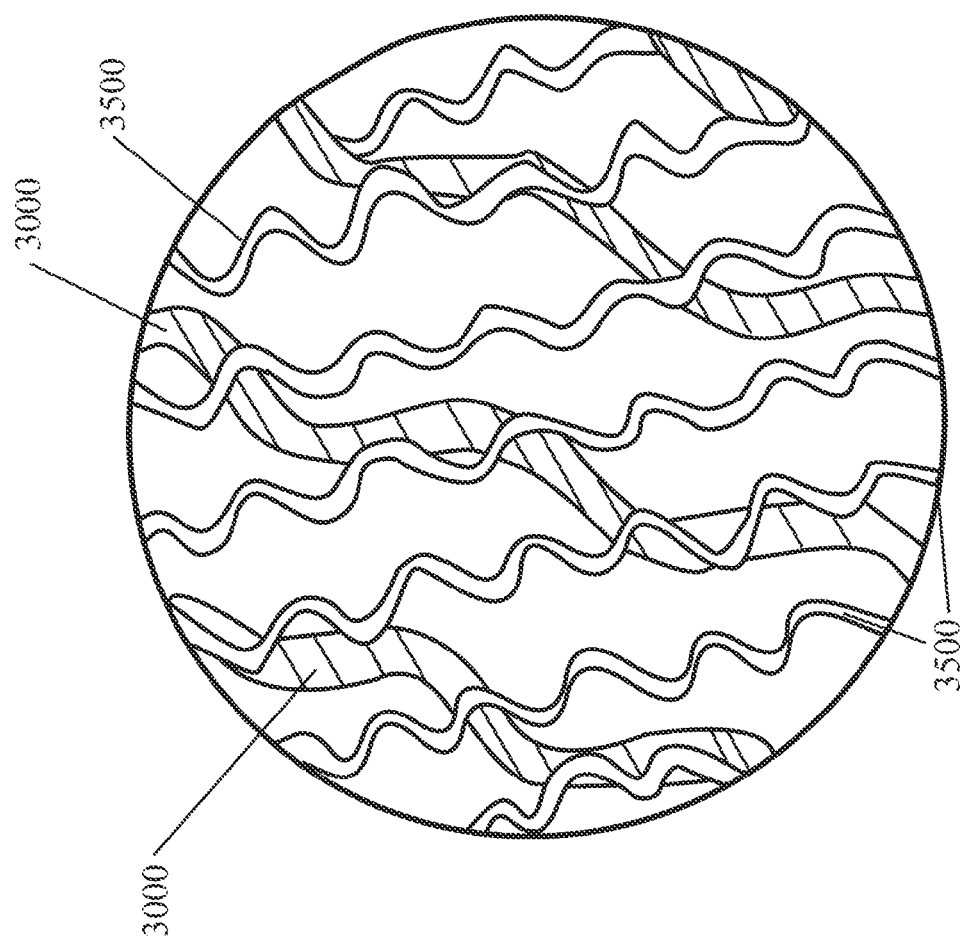
FIG. 69 is a detail view of the implantable layer of FIG. 68.
Figure 70:
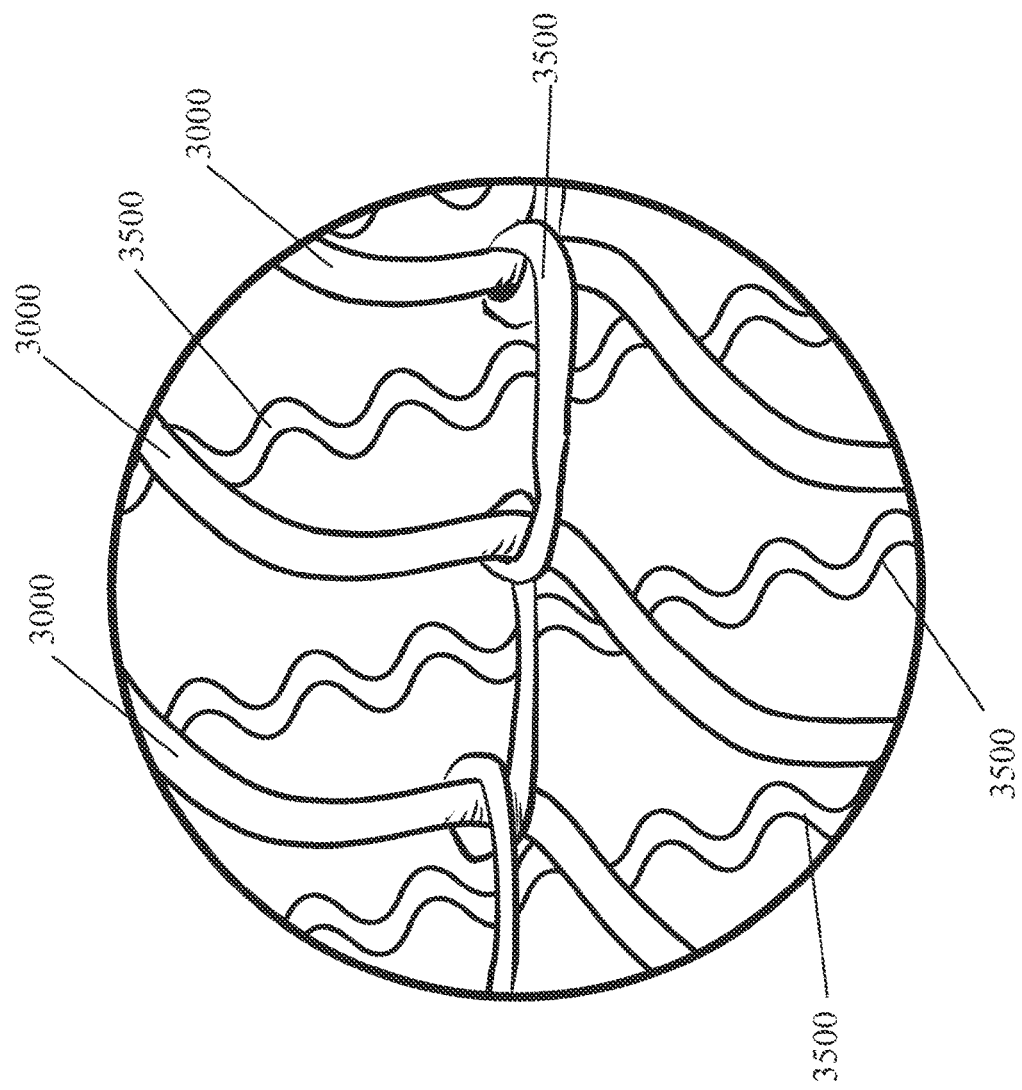
FIG. 70 is another detail view of the implantable layer of FIG. 68.

The deformed, or kinked, fibers described herein can be woven into an implantable layer in any suitable manner. In various instances, an implantable layer can be woven such that it does not comprise seams. Turning now to FIG. 68, an implantable layer 3530 can be woven, or knitted, such that it comprises seams. The implantable layer 3530 comprises a top surface 3531, a bottom surface 3532, and interwoven fibers which are connected to each other along lateral seams 3533, longitudinal seams 3534, and internal seams 3535. Referring to FIG. 69, the layer 3530 is comprised of fibers 3000 and, in addition, fibers 3500. Referring to FIG. 70, the fibers 3000 and 3500 are interwoven to form the seams 3533, 3534, and 3535.

The seams 3533, 3534, and 3535 can be interwoven at a desired density to achieve a desired result. For instance, the density of the longitudinal seams 3534 is higher on the lateral sides of the layer 3530 than in the middle of the layer 3530. The middle of the layer 3530 is aligned with a cutting member of the stapling instrument when the layer 3530 is positioned on a staple cartridge and inserted into the stapling instrument. Owing to the lower density in the middle of the layer 3530 being aligned with the cutting member, the layer 3530 can be more easily transected by the cutting member while permitting the layer 3530 to have a different density in the regions which are captured by the staples. Also, for instance, the density of the lateral seams 3533 is higher in the middle of the layer 3530 than at the proximal and distal ends of the layer 3530. Owing to the lower density at the proximal end of the layer 3530, the cutting member can more easily begin its transection of the layer 3530. Similarly, the lower density at the distal end of the layer 3530 can assist the cutting member in finishing its cut as the cutting member slows down at the end of its stroke.

Figure 64:
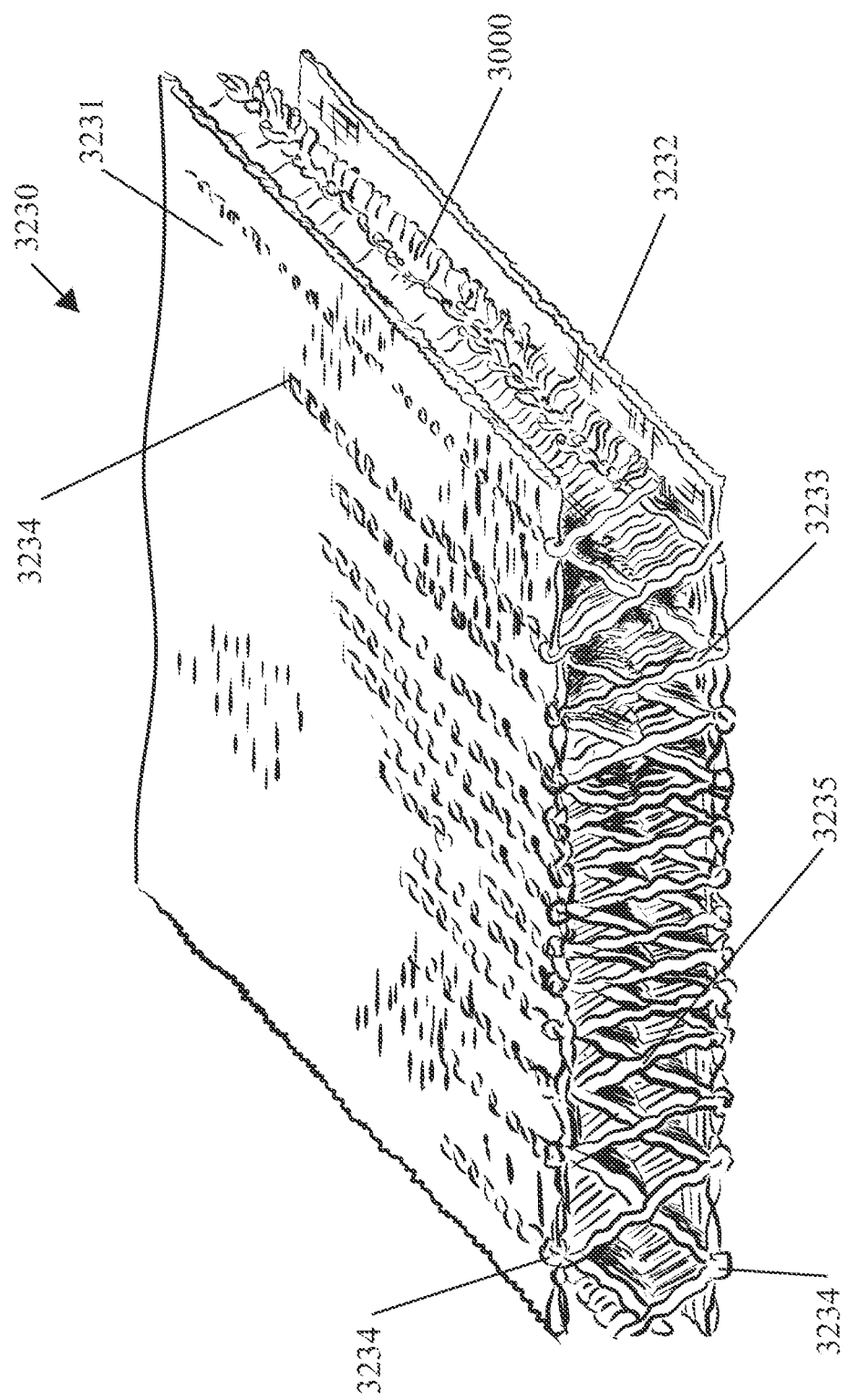
FIG. 64 is a perspective view of an implantable layer in accordance with at least one embodiment that comprises the kinked fibers of FIG. 60.

A layer 3230 is illustrated in FIG. 64. The layer 3230 comprises a top portion 3231, a bottom portion 3232, and an intermediate portion 3233 connecting the top portion 3231 and the bottom portion 3232. The intermediate portion 3233 spaces and positions the top portion 3231 relative to the bottom portion 3232. The portions 3231, 3232, and 3233 are comprised of kinked fibers 3000. The fibers 3000 are organized, or weaved, into lateral seams 3233 and longitudinal seams 3234. The density of the longitudinal seams 3234 is higher in the medial portion of the layer 3230 as compared to the lateral portions of the layer 3230.

Figure 71:
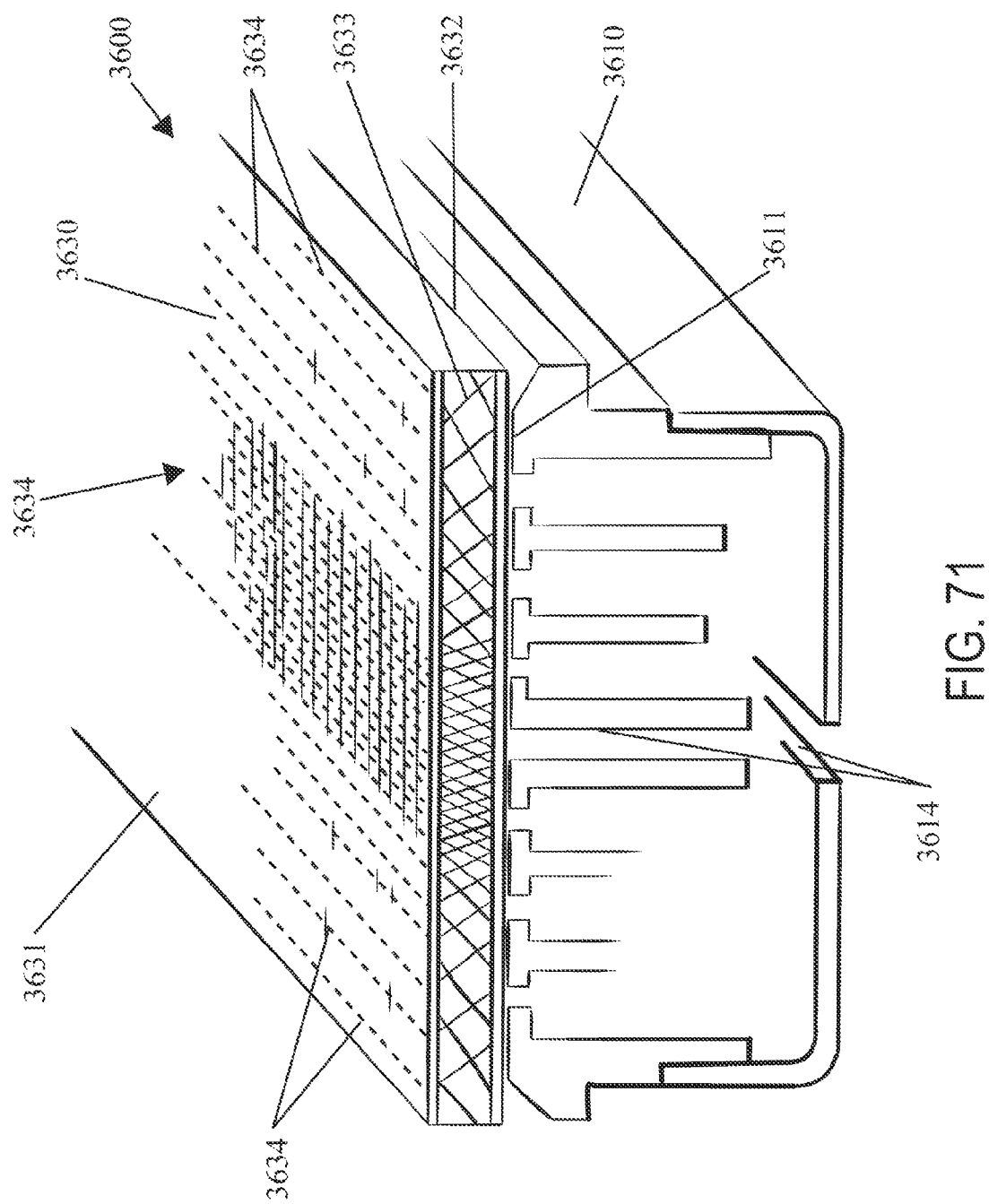
FIG. 71 is a cross-sectional view of a staple cartridge assembly in accordance with at least one embodiment including an implantable layer.
Figure 72:
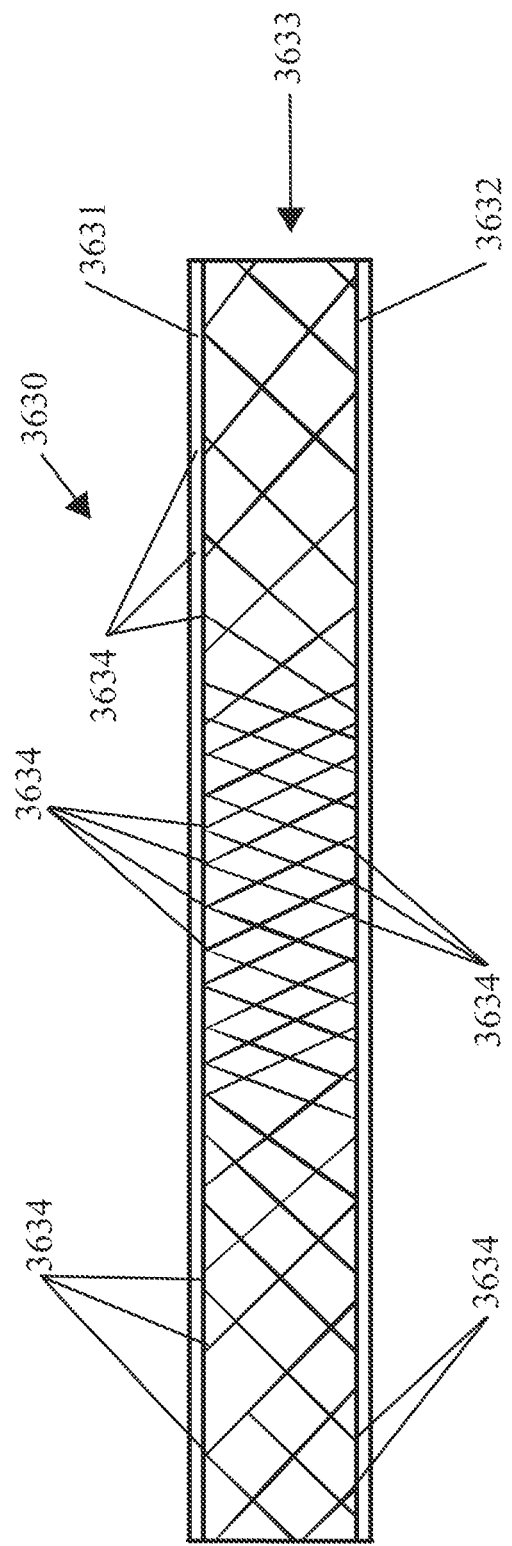
FIG. 72 is a cross-sectional view of the implantable layer of FIG. 71.

Further to the above, turning now to FIGS. 71 and 72, a staple cartridge 3600 includes a cartridge body 3610 and an implantable layer 3630. The cartridge body 3610 comprises a deck 3611 configured to support the layer 3630. The layer 3630 comprises a top surface 3631, a bottom surface 3632, and is comprised of fibers 3633. The density 3634 of the fibers 3633 is higher in the middle of the layer 3630 than the lateral sides of the layer 3630. In fact, the higher density 3634 of the fibers 3633 is aligned with a longitudinal slot 3614 defined in the cartridge body 3610 which is configured to receive a cutting portion of the firing member. The higher density 3634 of the fibers 3633 in the middle of the layer 3630 can reduce buckling or movement of the layer 3630 relative to the cartridge body 3610.

Figure 73:
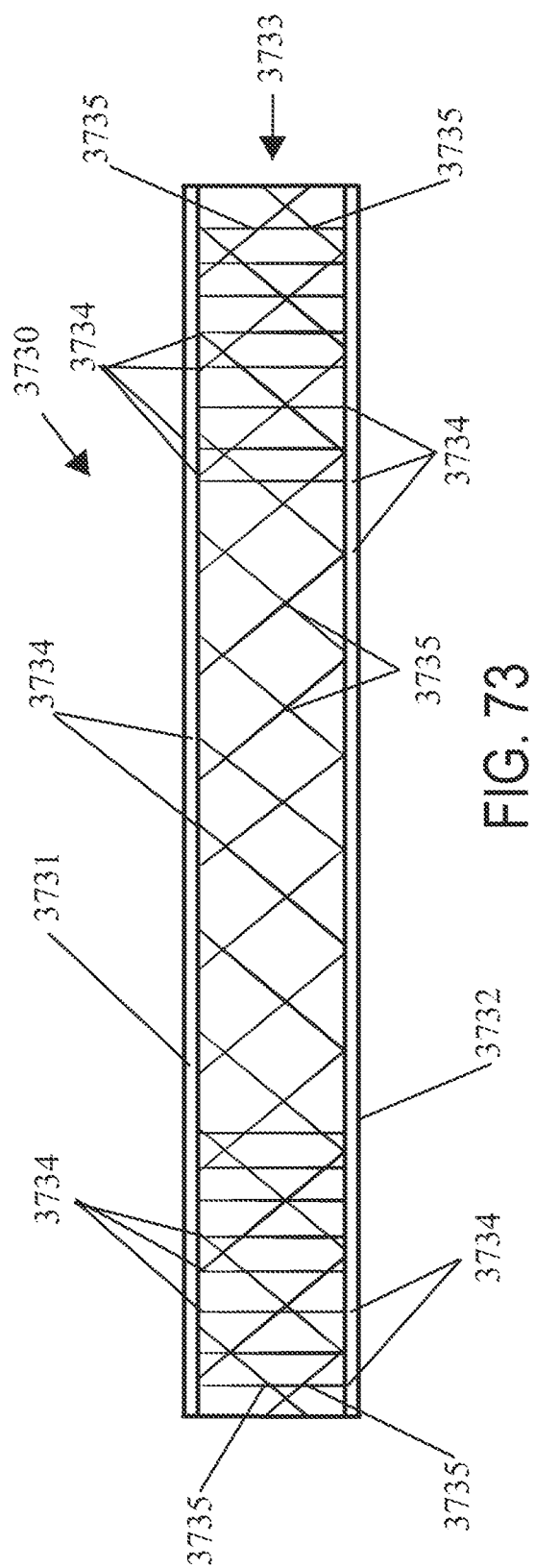
FIG. 73 is a cross-sectional view of an implantable layer in accordance with at least one alternative embodiment.

Turning now to FIG. 73, an implantable layer 3730 comprises a top surface 3731, a bottom surface 3732, and a body comprised of interwoven fibers. The fibers are interwoven into lateral seams 3733 and longitudinal seams 3734. The fibers are interconnected to one another at weave points 3735. The weave points 3735 connect fibers that extend laterally and/or longitudinally within the implantable layer 3730. The weave points 3735 can connect the fibers within a lateral seam 3733. The weave points 3735 can connect fibers within a longitudinal seam 3734. The weave points 3735 can connect the lateral seams 3733 with the longitudinal seams 3734. The density of the weave points 3735 in the implantable layer 3730 can control the resiliency or elasticity of the implantable layer 3730. The portions of the layer 3730 having a higher weave point density may be less resilient than the portions of the layer 3730 having a lower weave point density. With regard to the embodiment depicted in FIG. 73, the lateral portions of the layer 3730 have a high weave point density while the medial portion of the layer 3730 has a low weave point density; however, any suitable arrangement of weave point densities could be utilized.

Figure 74:
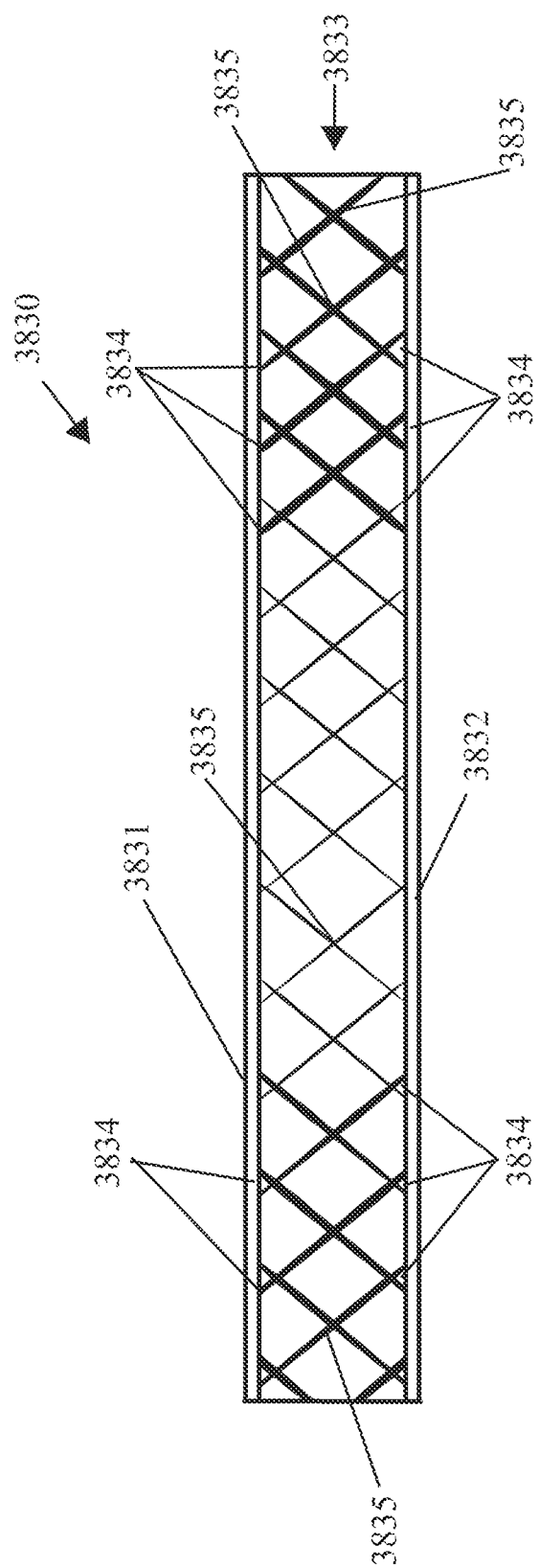
FIG. 74 is a cross-sectional view of an implantable layer in accordance with at least one alternative embodiment.

Turning now to FIG. 74, an implantable layer 3830 comprises a top surface 3831, a bottom surface 3832, and a body comprised of interwoven fibers. The fibers are interwoven into lateral seams 3833 and longitudinal seams 3834. The fibers are interconnected to one another at weave points 3835. The weave points 3835 connect fibers that extend laterally and/or longitudinally within the implantable layer 3830. The weave points 3835 can connect the fibers within a lateral seam 3833. The weave points 3835 can connect fibers within a longitudinal seam 3834. The weave points 3835 can connect the lateral seams 3833 with the longitudinal seams 3834.

In various instances, further to the above, the fibers that are interwoven into an implantable layer can have the same diameter and/or length. In other instances, the fibers can have different diameters and/or lengths. Referring again to FIG. 74, certain fibers of the implantable layer 3830 have a first diameter, or thickness, and other fibers have a second diameter, or thickness, which is larger than the first diameter. The thinner fibers are in the center of the implantable layer 3830 and the thicker fibers are in the lateral sides of the implantable layer 3830. When the cutting member of the surgical stapling instrument passes through the center of the implantable layer 3830, the thinner fibers can facilitate the cutting of the implantable layer 3830. Alternatively, the thicker fibers are in the center of the implantable layer 3830 which can inhibit the layer 3830 from buckling.

Figure 75:
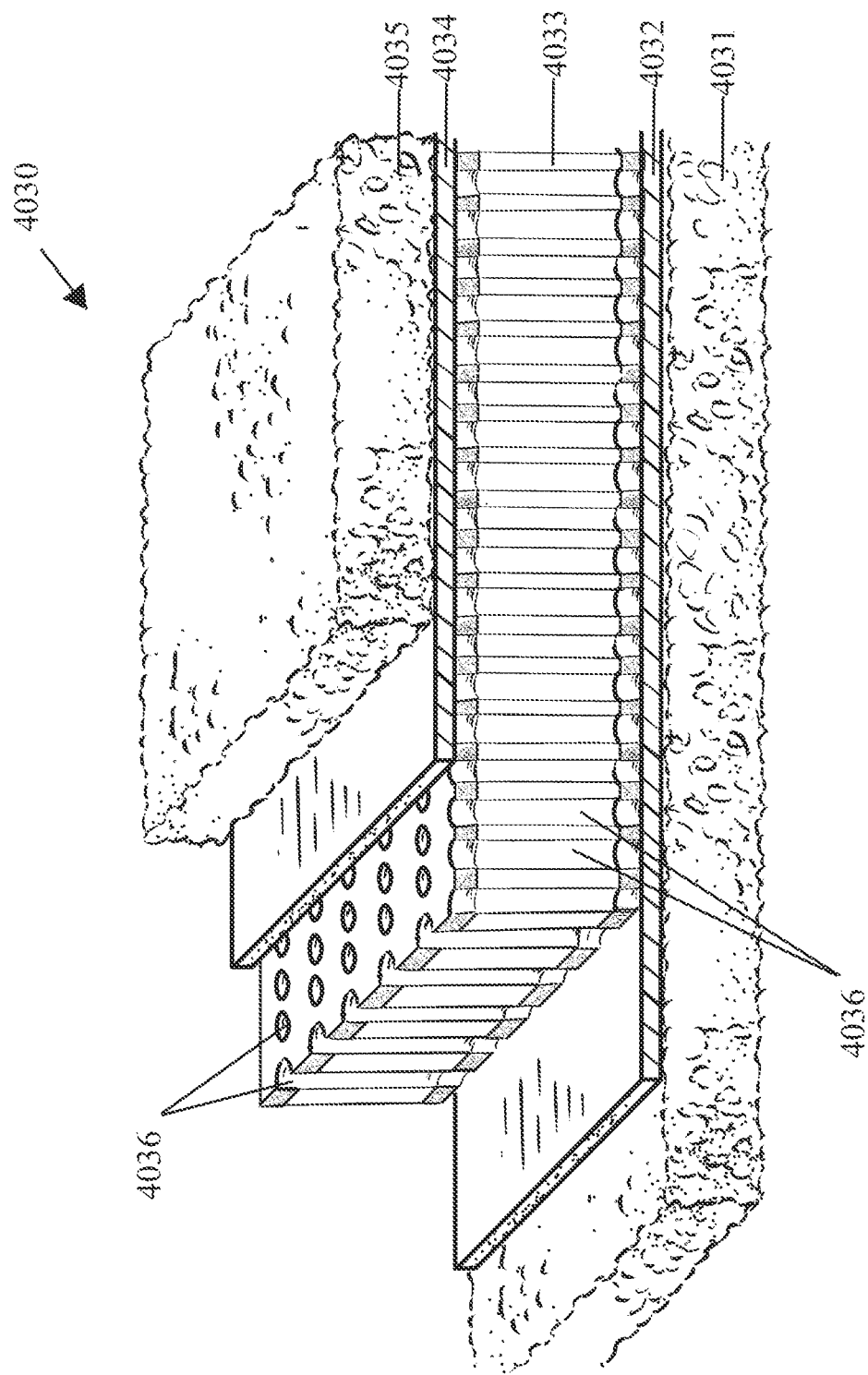
FIG. 75 is a cross-sectional view of an implantable layer in accordance with at least one embodiment.
Figure 76:
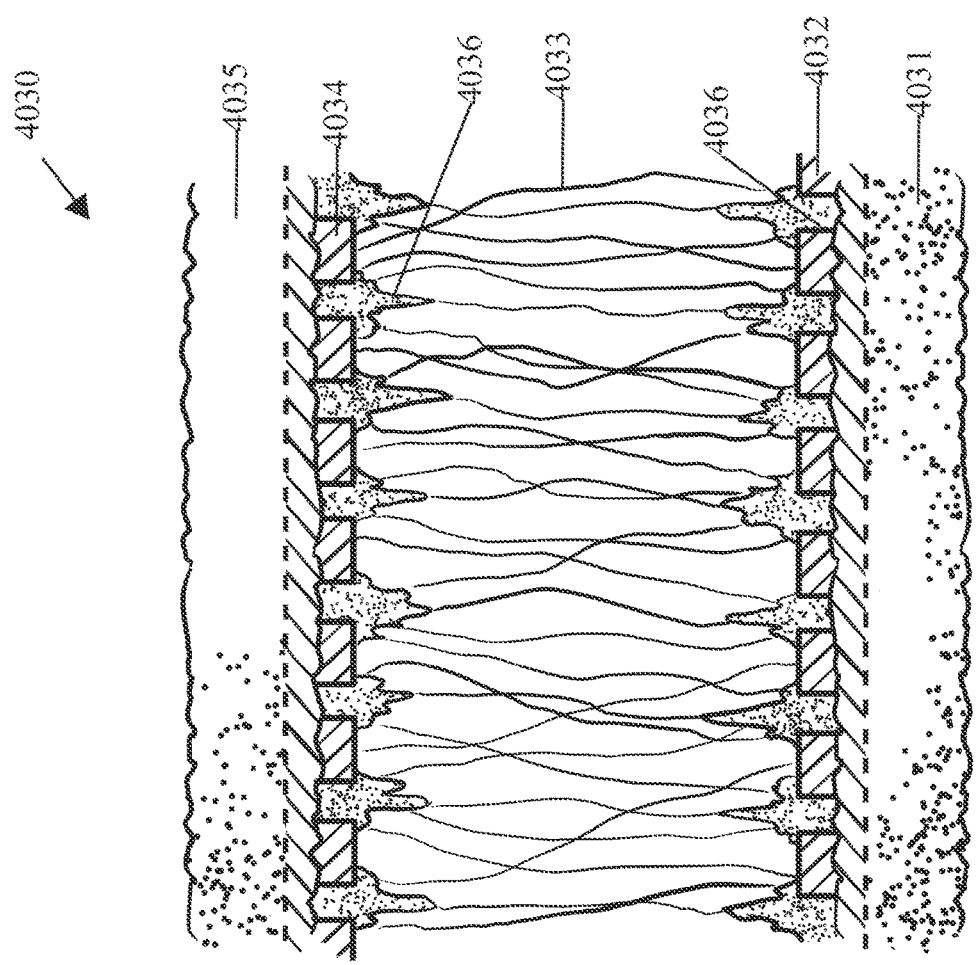
FIG. 76 is a cross-sectional view of the implantable layer of FIG. 75.

Turning now to FIGS. 75 and 76, an implantable adjunct 4030 comprises a plurality of layers. The adjunct 4030 comprises a first outside layer 4031 and a second outside layer 4035. The first outside layer 4031 is comprised of interwoven fibers. Similarly, the second outside layer 4035 is comprised of interwoven fibers. The fibers of the outside layers 4031, 4035 can be comprised of any suitable material, such as VICRYL and/or any of the materials described in the present application, for example. The adjunct 4030 further comprises a middle, or intermediate, layer 4033. The middle layer 4033 is also comprised of interwoven fibers. The middle layer 4033 can be comprised of the same materials as the outside layers 4031, 4035 and/or different materials.

Referring again to FIGS. 75 and 76, the adjunct 4030 further comprises a first bonding layer 4032 and a second bonding layer 4034. The first bonding layer 4032 is positioned intermediate the first outside layer 4031 and the middle layer 4033. The second bonding layer 4034 is positioned intermediate the second outside layer 4035 and the middle layer 4033. The first bonding layer 4032 is comprised of a material that has a lower melt temperature than the materials comprising the layers 4031, 4033, and 4035. Similarly, the second bonding layer 4034 is comprised of a material that has a lower melt temperature than the materials comprising the layers 4031, 4033, and 4035.

Further to the above, the layers 4031, 4032, 4033, 4034, and 4035 of the adjunct 4030 are stacked in the manner depicted in FIG. 75. The adjunct 4030 is then heated. The adjunct 4030 is heated such that the temperature of the bonding layers 4032 and 4034 equals or exceeds the melt temperature of the material comprising the bonding layers 4032 and 4034. When the bonding layers 4032 and 4034 are comprised of the same material, the bonding layers 4032 and 4034 will melt at the same temperature. This temperature can be referred to as the threshold melt temperature. When the first bonding layer 4032 is comprised of a first material having a first melt temperature and the second bonding layer 4034 is comprised of a second material having a second, or different, melt temperature, one of the layers 4032, 4034 will begin to melt before the other. In such instances, the threshold melt temperature comprises the higher of the first and second melt temperatures.

Figure 77:
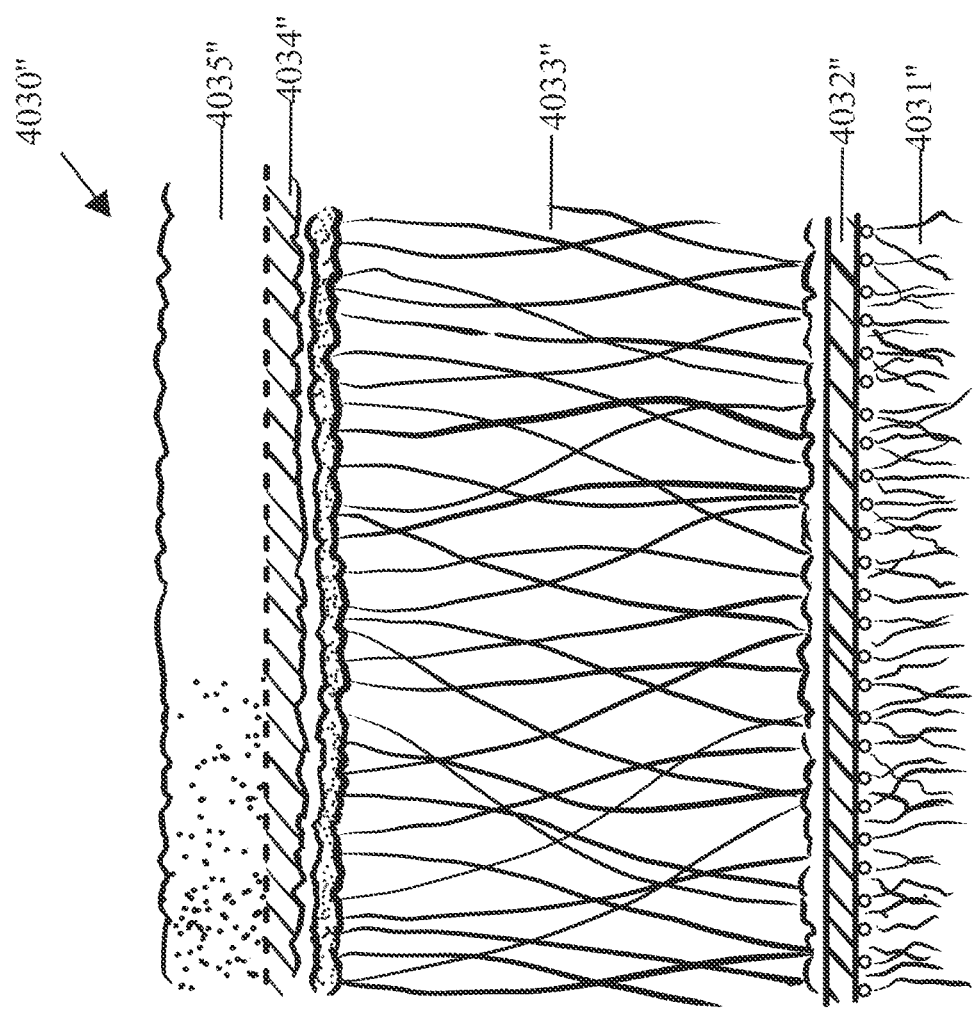
FIG. 77 is a cross-sectional view of an implantable layer in accordance with at least one embodiment.

As the bonding layers 4032, 4034 are melting, the melted material penetrates the first outside layer 4031, the middle layer 4033, and/or the second layer 4035. The amount in which the melted layers 4032, 4034 penetrate into the layers 4031, 4033, 4035 can be dependent on several factors. For example, the layers 4031, 4033, and/or 4035 can be comprised of interwoven fibers and the amount in which the melted layers 4032, 4034 penetrate the fiber weaves can depend on the openness of the fiber weaves. For instance, the melted layers 4032, 4034 can penetrate deeper into a more open, or looser, weave than a more closed, or tighter, weave. Stated another way, the melted layers 4032, 4034 may not penetrate extensively into a tightly knit weave. The first outside layer 4031 and the second outside layer 4035 have the same, or at least substantially the same, weave density. In various alternative embodiments, the first outside layer 4031 and the second outside layer 4035 have different weave densities. In at least one such embodiment, turning now to FIG. 77, the second outside layer 4035" of an alternative adjunct 4030" has a tighter weave than the first outside layer 4031". The first bonding layer 4032" may penetrate deeper, or more extensively, into the first outside layer 4031" than the second bonding layer 4034" may penetrate into the second outside layer 4035".

Referring again to FIG. 75, the middle layer 4033 of the adjunct layer 4030 comprises apertures 4036 defined therein. The apertures 4036 comprise throughholes. The melted bonding layers 4032, 4034 can enter into the apertures 4036 to improve, or increase, the bond between the bonding layers 4032, 4034 and the middle layer 4033. In alternative embodiments, the apertures 4036 may not extend entirely through the middle layer 4033. That said, such apertures 4036 may be sufficiently deep to receive a sufficient quantity of melted material to form an adequate bond with the bonding layers 4032, 4034. The first outside layer 4031 and/or the second outside layer 4035 may include apertures defined therein to improve, or increase, their bond with the first bonding layer 4032 and the second bonding layer 4034, respectively.

As discussed above, the adjunct 4030 is heated to melt, or at least partially melt, the bonding layers 4032, 4034. As also discussed above, the melted portions of the bonding layer 4032, 4034 flow into the layers 4031, 4033, and/or 4035. After the adjunct has been sufficiently heated, the adjunct 4030 is cooled and/or is permitted to cool. The adjunct 4030 can be placed in a refrigeration unit, set out in the open air, and/or exposed to a flow of air, for example. When the adjunct 4030 cools below the threshold melt temperature, the melted bonding layers 4032, 4034 can begin to solidify, thereby locking the layers 4031, 4032, 4033, 4034, and 4035 together. In various instances, the melted bonding layers 4032 and 4034 can assume a mechanically interlocked configuration with the layers 4031, 4033, and 4035, as illustrated in FIG. 76.

Further to the above, the layers 4031, 4033, and 4035 of the adjunct 4030 are comprised of materials having a melt temperature which is greater than the threshold melt temperature of the bonding layers 4032 and 4034. Moreover, the layers 4031, 4033, and 4035 are comprised of materials having a melt temperature which is greater than the highest processing temperature in which the adjunct 4030 is exposed to. As a result, the layers 4031, 4033, and 4035 will not melt while the bonding layers 4032 and 4034 are being melted. In at least one instance, the layers 4031, 4033, and 4035 are comprised of VICRYL, for example, and the bonding layers 4032 and 4034 are comprised of PDS, for example. In at least one instance, the bonding layers 4032 and 4034 are comprised of a PDS film, for example.

In various embodiments, further to the above, each bonding layer 4032, 4034 can be comprised of two or more materials. In certain instances, each material comprising the bonding layers 4032, 4034 has a melt temperature which is equal to or below the maximum processing temperature of the adjunct 4030. In other instances, some of the materials comprising the bonding layers 4032, 4034 have a melt temperature equal to or below the maximum processing temperature while others have a melt temperature above the maximum processing temperature. In such embodiments, some portions of the layers 4032 and 4034 will melt and penetrate the adjacent layers 4032, 4033, and 4035 while other portions of the layers 4032 and 4034 will maintain their structural integrity.

Further to the above, each layer 4031, 4033, and 4035 can be comprised of two or more materials. In certain instances, each material comprising the layers 4031, 4033, 4035 has a melt temperature which is above the maximum processing temperature of the adjunct 4030. In other instances, some of the materials comprising the layers 4031, 4033, 4035 have a melt temperature above the maximum processing temperature while others have a melt temperature equal to or below the maximum processing temperature. In such embodiments, some portions of the layers 4031, 4033, 4035 will melt and mix with the melted portions of the adjacent bonding layers 4032, 4034 thereby improving the bond between the layers 4031, 4032, 4033, 4034, and 4035 once the temperature of the adjunct 4030 has cooled below the melt temperature of each of the materials comprising the adjunct 4030.

The adjunct 4030 is not pressed when it is exposed to heat. The melted materials of the adjunct 4030 flow in response to the natural forces, such as gravitational and/or capillary forces, for example, acting on the melted materials; however, embodiments are envisioned in which the adjunct 4030 is pressed when it is exposed to heat. Such pressure can improve the flow of the melted materials within the adjunct 4030 and improve the bond between the layers 4031, 4032, 4033, 4034, and 4035. The pressure can be removed from the adjunct 4030 while the melted portions are still flowable. Alternatively, the pressure can be removed after the melted portions have re-solidified.

The adjunct 4030 comprises five layers; however, an adjunct employing the principles disclosed herein may comprise any suitable number of layers. For example, an adjunct can comprise three layers including the first outer layer 4031, the second outer layer 4035, and a bonding layer positioned intermediate the first outer layer 4031 and the second outer layer 4035.

In various alternative embodiments, an adjunct may not utilize a bonding layer. For example, an adjunct can utilize the first outer layer 4031 and the second outer layer 4035 wherein one or both of the layers 4031, 4035 is comprised of a material which is melted to flow and directly bond the layers 4031, 4035 together. Similarly, an adjunct can utilize the outer layers 4031, 4035 and the middle layer 4033 positioned intermediate the outer layers 4031, 4035 wherein one or more of the layers 4031, 4033, 4035 is comprised of a material which is melted to flow and directly bond the layers 4031, 4035 to the middle layer 4033.

As discussed above, the layers 4031, 4033, and 4035 of adjunct 4030 are comprised of interwoven fibers. In certain instances, the layers 4031, 4033, and 4035 can have the same, or at least substantially the same, weave density. In other instances, at least one of the layers 4031, 4033, and 4035 can have a weave density which is different than the other layers. Referring again to FIG. 77, the adjunct 4030" comprises a first outer layer 4031", a first bonding layer 4032", a spacer layer 4033", a second bonding layer 4034", and a second outer layer 4035". The weave density of the second outer layer 4035" is greater than the weave density of the first outer layer 4031" Similarly, the weave density of the first outer layer 4031" is greater than the weave density of the spacer layer 4033".

As discussed above, the bonding layers 4032 and 4034 of the adjunct 4030, when melted, can penetrate the adjacent layers 4031, 4033, and 4035. The penetration of the bonding layers 4032 and 4034 into the layers 4031, 4033, and 4035 can change the stiffness of the layers 4031, 4033, and 4035. More specifically, the penetration of the bonding layers 4032, 4034 into the layers 4031, 4033, 4035 can increase the stiffness of the layers 4031, 4033, 4035, depending on the degree in which the bonding layers 4032, 4034 penetrate the layers 4031, 4033, 4035. In various instances, the bonding layers 4032, 4034 can strengthen, fixate, and/or support the fibers of the adjacent layers 4031, 4033, 4035.

Figure 91:
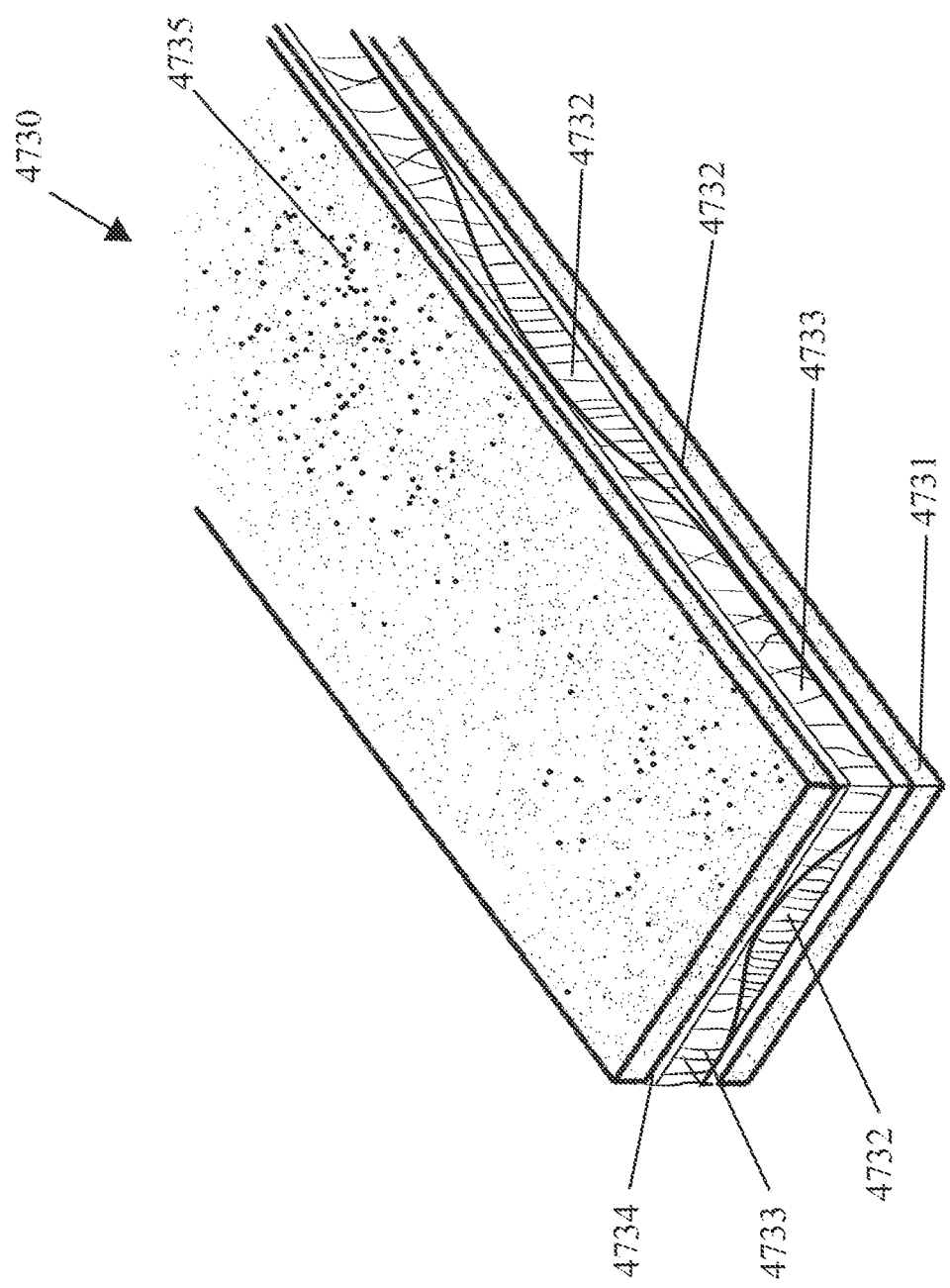
FIG. 91 is a partial perspective view of an implantable layer in accordance with at least one embodiment.
Figure 92:
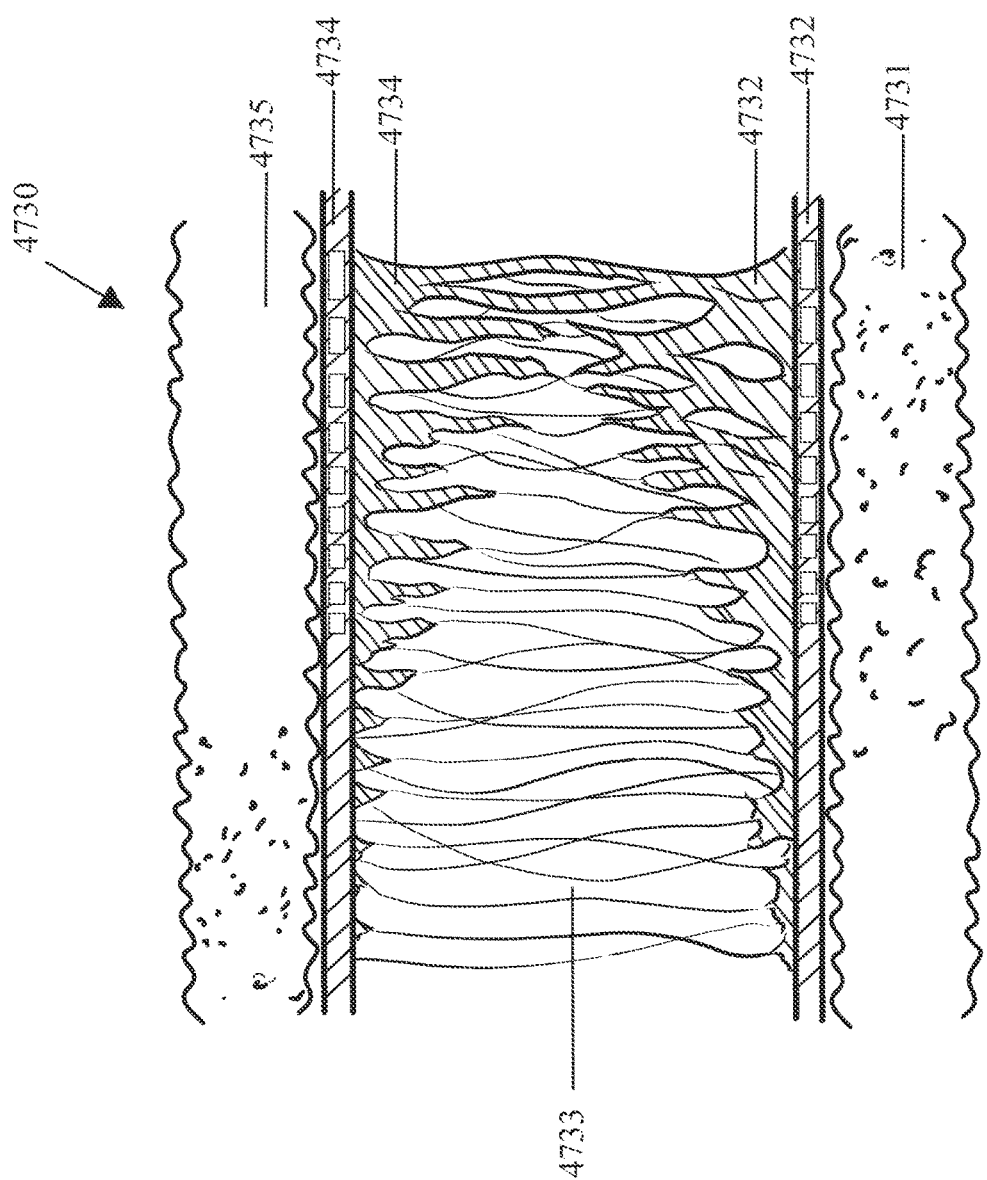
FIG. 92 is a partial cross-sectional view of the implantable layer of FIG. 91.

Further to the above, the weave densities of the layers 4031, 4033, and/or 4035 can be selected so as to control the penetration of the layers 4032, 4034 therein. Referring now to FIGS. 91 and 92, an adjunct 4730 comprises a first outer layer 4731, an intermediate layer 4733, a first bonding layer 4732 positioned intermediate the first outer layer 4731 and the intermediate layer 4733, a second outer layer 4735, and a second bonding layer 4734 positioned intermediate the second outer layer 4735 and the intermediate layer 4733. Certain portions of the intermediate layer 4733 have a low, or loose, weave density while other portions of the intermediate layer 4733 have a high, or tight, weave density. When the adjunct 4730 is heated to a temperature that at least equals the melt temperature of the first bonding layer 4732, the first bonding layer 4732 penetrates deeper into the portions of the intermediate layer 4733 having a loose weave density than the portions of the intermediate layer 4733 having a tight weave density. In addition to or in lieu of the above, the weave densities of the first outside layer 4731 and/or the second outside layer 4735 can be adapted to control the penetration of the bonding layers 4732 and 4734 into the outside layers 4731 and 4735, respectively.

Further to the above, referring again to FIG. 75, the density, size, and/or depth of the apertures 4036 can be selected to control the depth in which the layers 4032 and 4034 penetrate into the spacer layer 4033. As a result of the above, the stiffness of the adjunct 4030 can be controlled. For instance, the adjunct 4030 can comprise a longitudinal path defined therein which has a lower stiffness than the other portions of the adjunct 4030. In such instances, a knife transecting the adjunct 4030 can transect the adjunct 4030 along a path having a low stiffness. In at least one instance, the proximal and distal ends of the adjunct 4030 can have a lower stiffness than the other portions of the adjunct 4030. In such instances, the adjunct 4030 may provide less resistance to the cutting and stapling thereof at the beginning and the end of the firing stroke.

Figure 90:
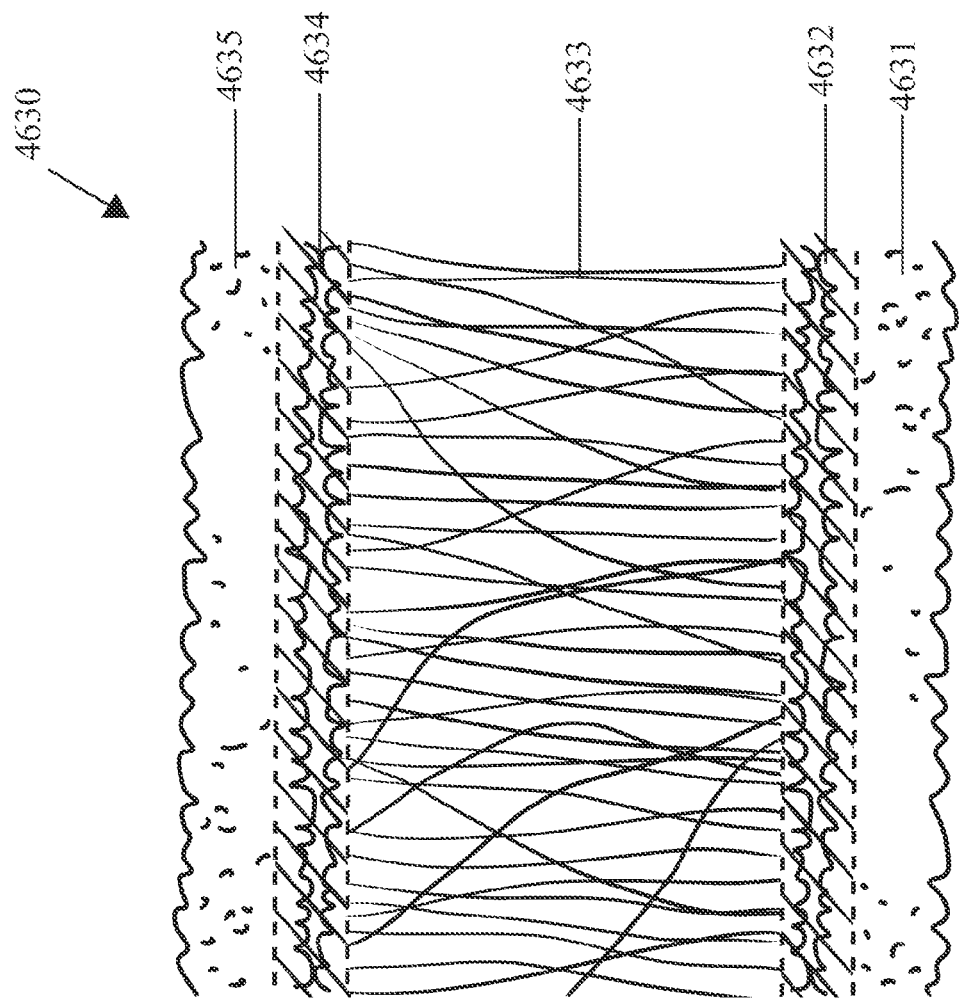
FIG. 90 is a partial cross-sectional view of an implantable layer in accordance with at least one embodiment.

In various alternative embodiments, an adjunct can comprise a bonding layer which does not penetrate, or at least substantially penetrate, the adjacent layers of the adjunct. In such embodiments, the bonding layer can join adjacent layers without substantially affecting the stiffness of the adjacent layers. Turning now to FIG. 90, an adjunct 4630 comprises a bonding layer 4632 which holds a first outer layer 4631 and an intermediate layer 4633 together without penetrating the first outer layer 4631 and/or the intermediate layer 4633. Similarly, the adjunct 4630 comprises a bonding layer 4634 which holds a second outer layer 4635 and the intermediate layer 4633 together without penetrating the second outer layer 4635 and/or the intermediate layer 4633.

Figure 80:
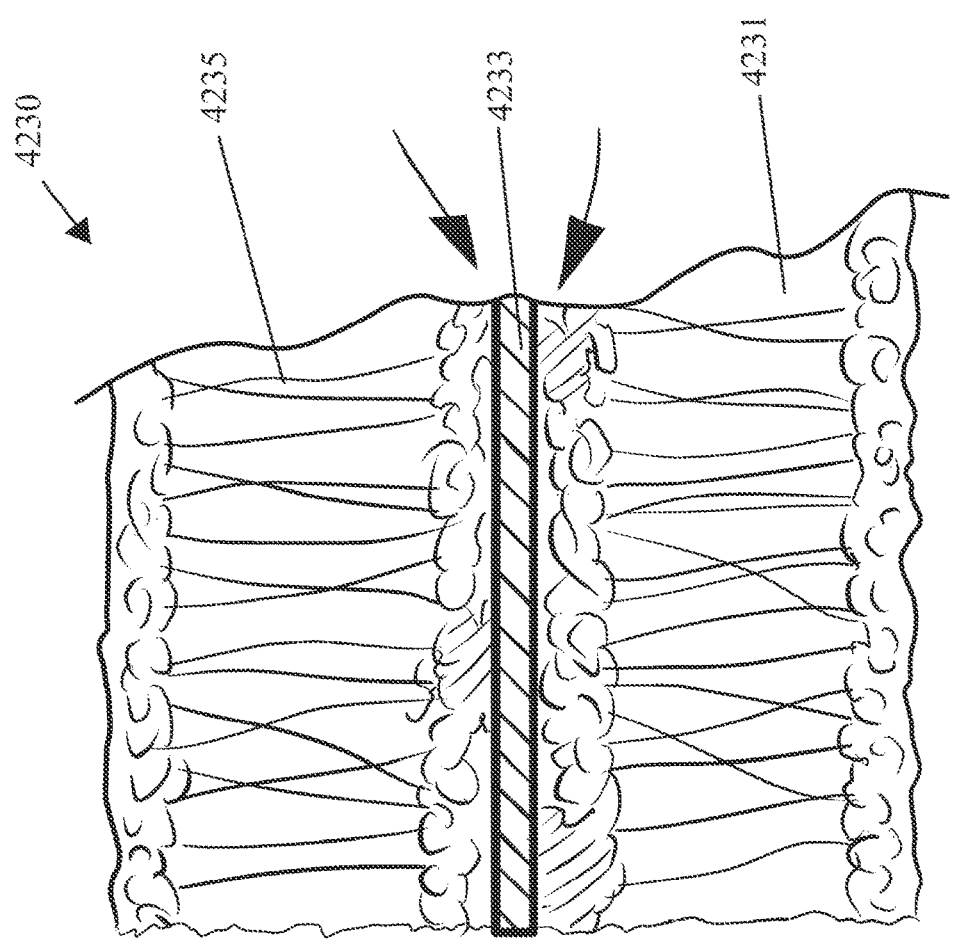
FIG. 80 is a partial cross-sectional view of an implantable layer in accordance with at least one embodiment.
Figure 81:
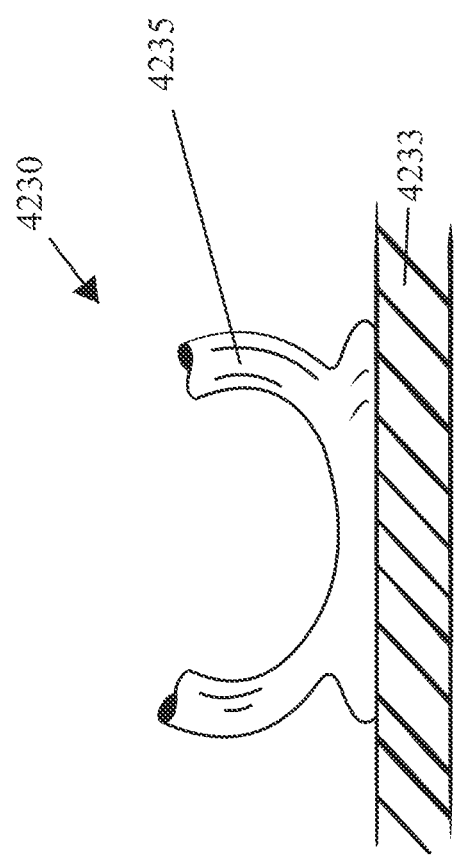
FIG. 81 is a detail view of a portion of the implantable layer of FIG. 80.

As described above, an adjunct can comprise a bonding layer positioned intermediate first and second outer layers. Turning now to FIGS. 80 and 81, an adjunct 4230 comprises a first outer layer 4231, a second outer layer 4235, and an intermediate layer 4233 positioned intermediate the first outer layer 4231 and the second outer layer 4235. In this embodiment, the outer layers 4231 and 4235 are comprised of one or more materials having a lower melt temperature than the melt temperature of the materials comprising the intermediate layer 4233. As a result, the melt temperatures of the outside layers 4231 and 4235 define the threshold melt temperature of the adjunct 4230. The adjunct 4230 is exposed to a processing temperature which at least partially melts the outside layers 4231 and 4235 but does not melt the intermediate layer 4233.

Figure 78:
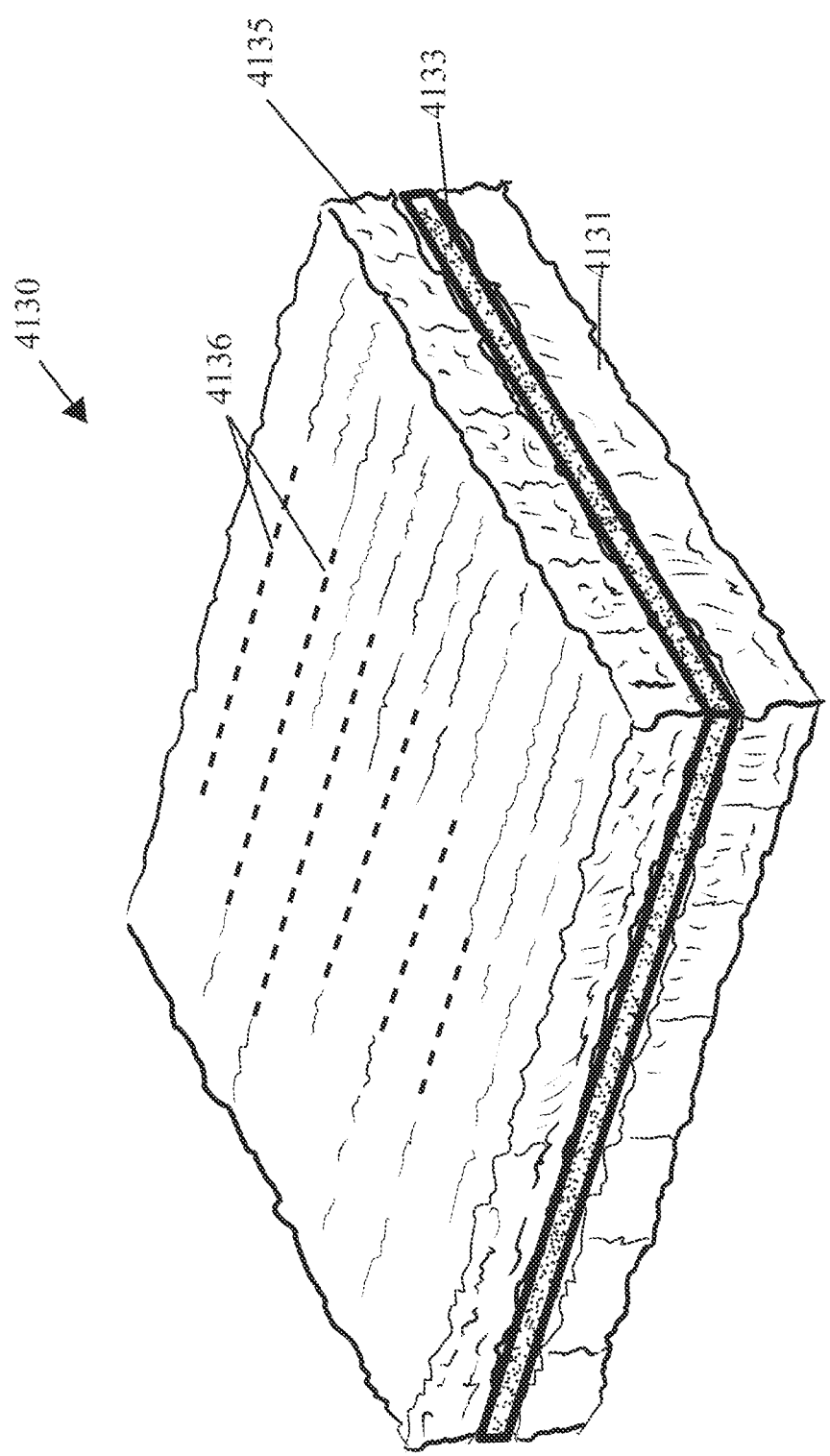
FIG. 78 is a perspective view of an implantable layer assembly in accordance with at least one embodiment.
Figure 79:
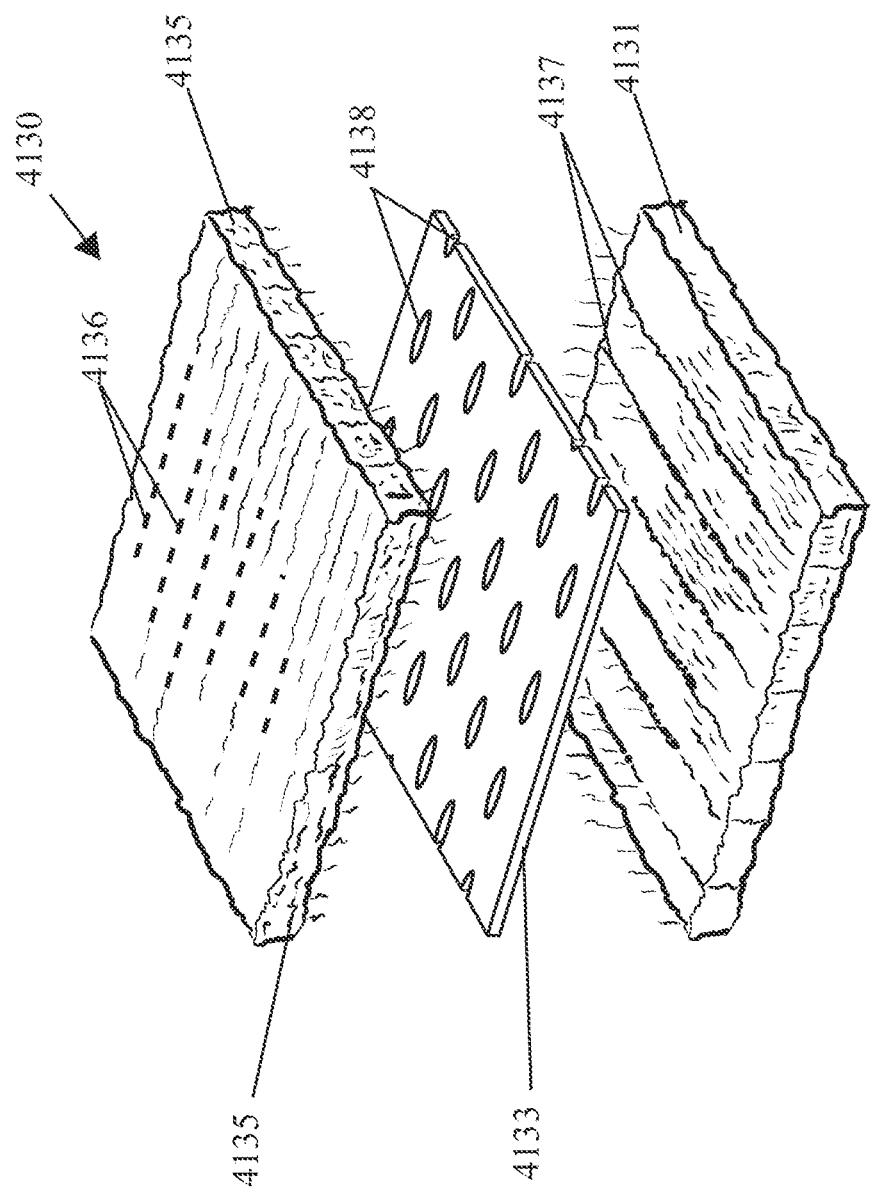
FIG. 79 is an exploded view of the implantable layer assembly of FIG. 78.
Figure 82:
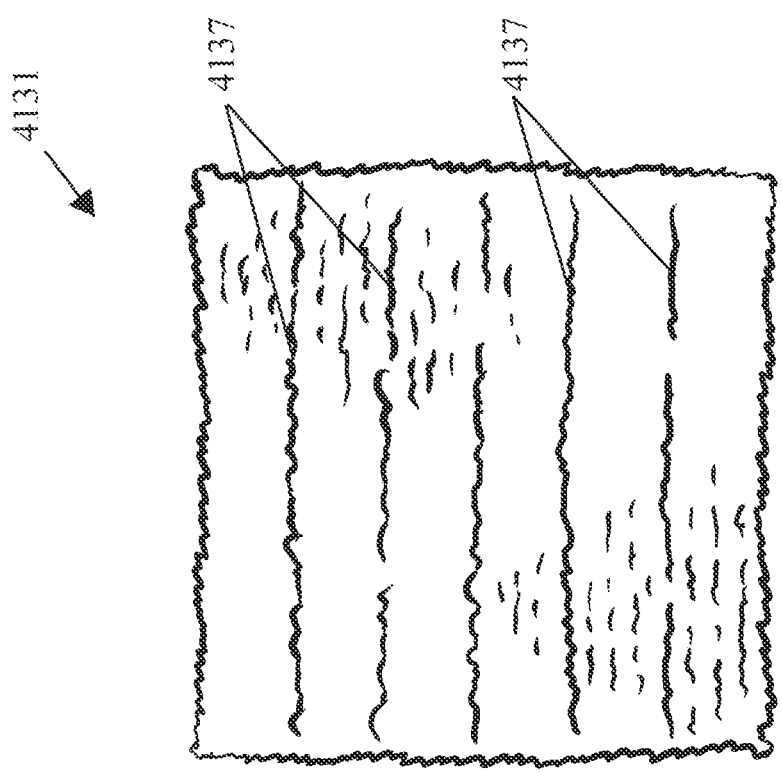
FIG. 82 is a plan view of a portion of the implantable layer assembly of FIG. 78.
Figure 83:
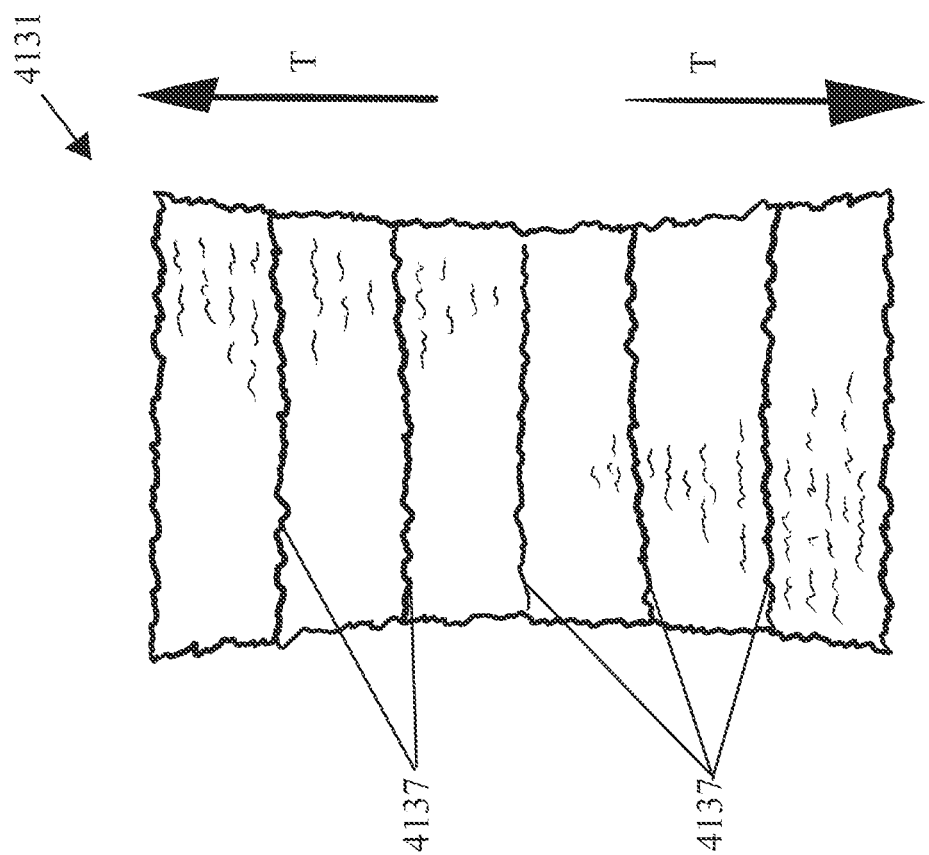
FIG. 83 illustrates the implantable layer portion of FIG. 82 in a stretched condition.

In addition to or in lieu of the above, one or more layers of an implantable adjunct can include relief, or stretch, joints. Moreover, one or more layers of an implantable adjunct can include relief, or stretch, slots defined therein. Turning now to FIG. 78, an implantable adjunct 4130 comprises a first outside layer 4131, a second outside layer 4135, and a bonding layer 4133 positioned intermediate the first outside layer 4131 and the second outside layer 4135. Turning now to FIGS. 79 and 82, the first outside layer 4131 comprises relief joints 4137 which extend laterally through the layer 4131. As illustrated in FIG. 83, the lateral relief joints 4137 decrease the longitudinal stiffness of the layer 4131, and the adjunct 4130, and facilitate the longitudinal expansion of the layer 4131, and the adjunct 4130. The relief joints 4137 have the same length; however, alternative embodiments are envisioned in which one or more of the relief joints 4137 have lengths which are different than the lengths of the other relief joints 4137.

Referring again to FIG. 79, the second outside layer 4135 comprises relief joints 4136 which extend longitudinally through the layer 4135. The longitudinal joints 4136 extend between a proximal end and a distal end of the adjunct 4130. The longitudinal relief joints 4136 decrease the lateral stiffness of the layer 4131, and the adjunct 4130, and facilitate the lateral expansion of the layer 4131, and the adjunct 4130. The relief joints 4136 have the same length; however, alternative embodiments are envisioned in which one or more relief joints 4136 have lengths which are different than the lengths of the other relief joints 4136.

Figure 84:
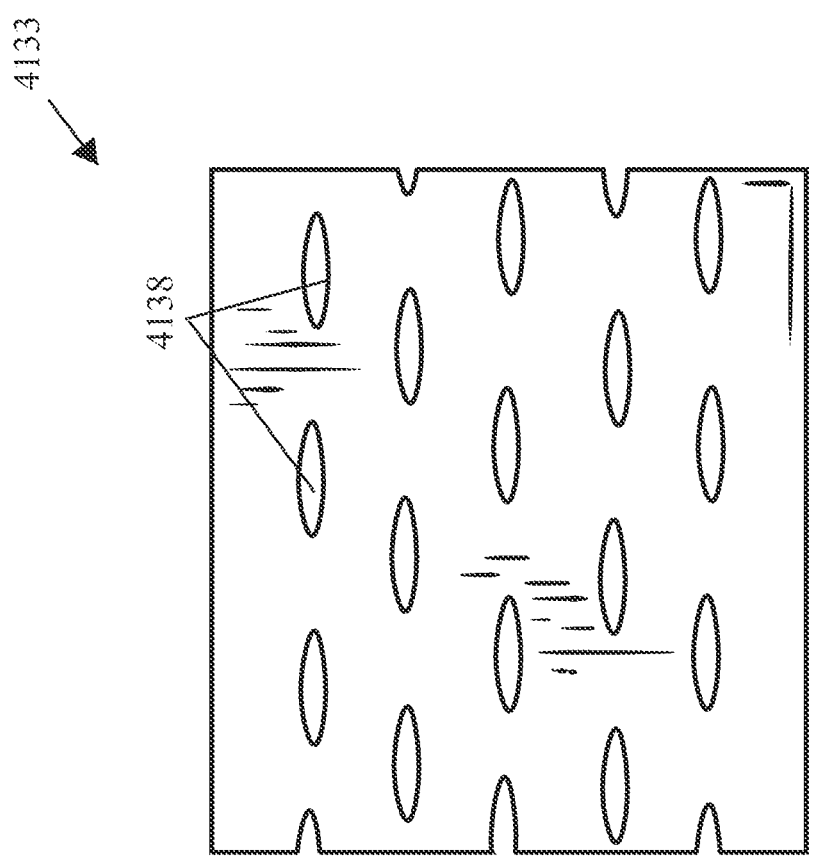
FIG. 84 is a plan view of a portion of the implantable layer assembly of FIG. 78.

Referring to FIGS. 79 and 84, the bonding layer 4133 comprises an array of slits 4138 defined therein. The slits 4138 are arranged in longitudinal rows which extend along longitudinal axes. Each slit 4138 comprises an elongate configuration wherein the longest dimension of each slit 4138 is aligned with an axis of a longitudinal row. As illustrated in FIG. 85, the slits 4138 facilitate the longitudinal and/or lateral expansion of the layer 4133 and the adjunct 4130. The slits 4138 have the same configuration; however, alternative embodiments are envisioned in which one or more slits 4138 have configurations which are different than the configurations of the other slits 4138. In various instances, any suitable layer of an adjunct can include the slits 4138.

Figure 88:
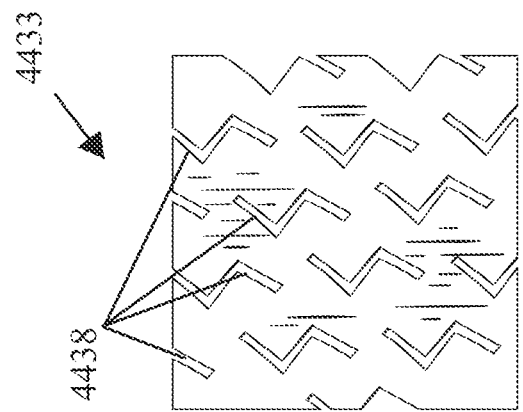
FIG. 88 is a plan view of an implantable layer in accordance with at least one alternative embodiment.
Figure 87:
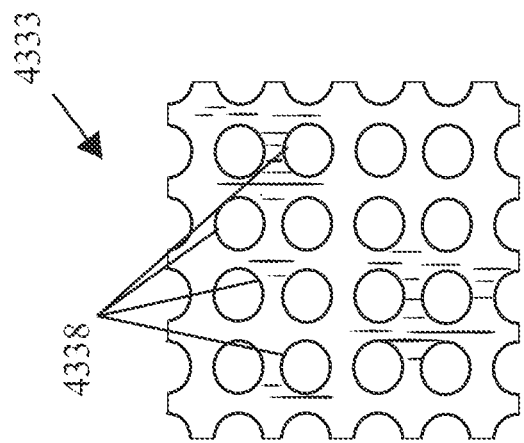
FIG. 87 is a plan view of an implantable layer in accordance with at least one alternative embodiment.
Figure 86:
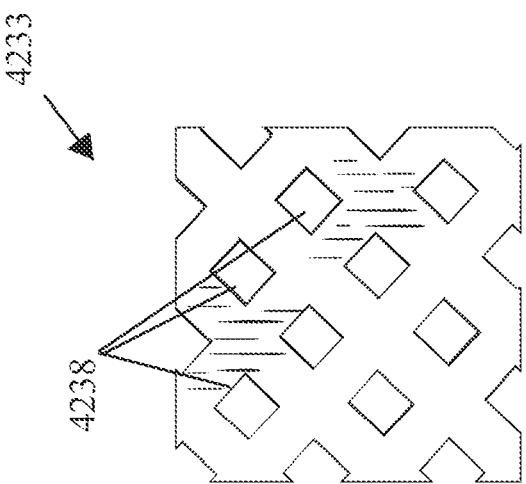
FIG. 86 is a plan view of an implantable layer in accordance with at least one alternative embodiment.

Turning now to FIG. 86, a layer 4233 of an adjunct comprises apertures 4238 defined therein which are configured to facilitate the longitudinal and/or lateral stretch of the layer 4233. Each aperture 4238 comprises a diamond configuration. The apertures 4238 defined in one row are offset laterally and longitudinally with respect to the apertures 4238 defined in an adjacent row. Turning now to FIG. 87, a layer 4333 of an adjunct comprises apertures 4338 defined therein which are configured to facilitate the longitudinal and/or lateral stretch of the layer 4333. Each aperture 4338 comprises a circular configuration. The apertures 4338 defined in one row are aligned with the apertures 4338 defined in an adjacent row. Turning now to FIG. 88, a layer 4433 of an adjunct comprises apertures 4438 defined therein which are configured to facilitate the longitudinal and/or lateral stretch of the layer 4433. Each aperture 4438 comprises a zig-zag slit that extends laterally and longitudinally. The apertures 4438 in one row are offset laterally and longitudinally with respect to the apertures 4438 in an adjacent row.

Figure 89C:
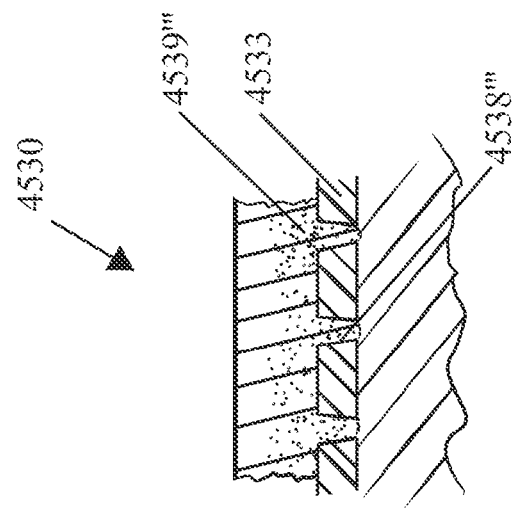
FIGS. 89A-89C illustrate manufacturing processes for creating openings in an implantable layer in accordance with at least one embodiment.
Figure 89B:
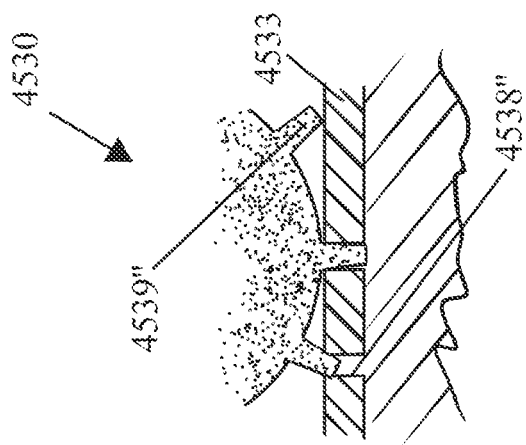
Figure 89A:
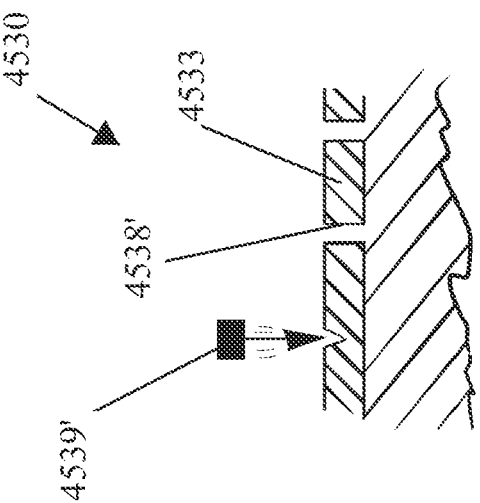

The apertures described herein can be created in a layer utilizing any suitable process. Turning now to FIG. 89A, a layer 4533 of an adjunct 4530 comprises a plurality of apertures 4538' defined therein. The apertures 4538' are burned in the layer 4533 utilizing a laser 4539'. Turning now to FIG. 89B, a rotatable die 4539" is utilized to punch apertures 4538" into the layer 4533. Turning now to FIG. 89C, a stamping die 4539''' is utilized to punch apertures 4538''' into the layer 4533.

Figure 93:
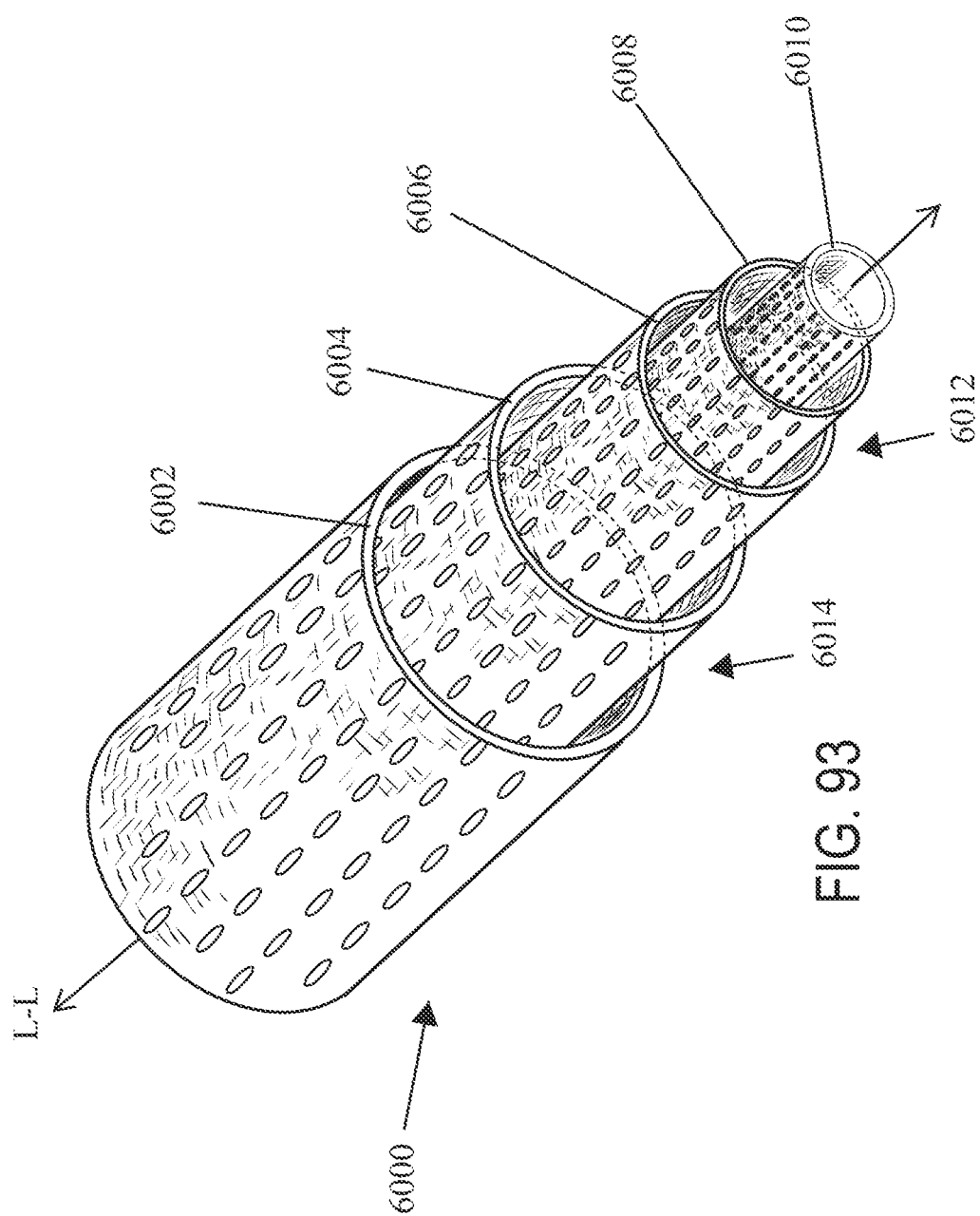
FIG. 93 is a perspective view of a partially-assembled compressible adjunct assembly including a plurality of fibrous tubular members.

Referring to FIG. 93, a compressible adjunct assembly 6000 includes an outer fibrous tubular member 6002, an inner fibrous tubular member 6010, a first intermediate fibrous tubular member 6004, a second intermediate fibrous tubular member 6006, and a third intermediate fibrous tubular member 6008. In certain instances, the compressible adjunct assembly 6000 may only include the inner and outer fibrous tubular members. Alternatively, the compressible adjunct assembly 6000 may include the inner and outer fibrous tubular members and only one of the intermediate fibrous tubular members. Alternatively, the compressible adjunct assembly 6000 may include the inner and outer fibrous tubular members and only two of the intermediate fibrous tubular members. Alternatively, the compressible adjunct assembly 6000 may include the inner and outer fibrous tubular members and more than three intermediate fibrous tubular members.

In certain instances, the inner fibrous tubular member 6010 can be switched with a core fibrous construct that is not hollow. In certain instances, the compressible adjunct assembly 6000 may be comprised of a plurality of hollow fibrous members that are not tubular or cylindrical in shape. In certain instances, the plurality of hollow fibrous members of the compressible adjunct assembly 6000 may comprise a square-shaped or rectangular transverse cross-sectional area. Other shapes are contemplated by the present disclosure.

Like other compressible adjunct assemblies of the present disclosure, the compressible adjunct assembly 6000 can be assembled with a jaw member of a surgical stapling and severing instrument such as, for example, the anvil 8014 and/or the staple cartridge 10000 of the surgical stapling and severing instrument 8010. In certain instances, a first compressible adjunct assembly 6000 can be assembled with the anvil 8014 and a second compressible adjunct assembly 6000 can be assembled with the staple cartridge 10000 such that tissue is captured between the first and second compressible adjunct assemblies 6000 when the surgical stapling and severing instrument 8010 is in a closed configuration. In either event, a plurality of staples can be deployed into a compressible adjunct assembly 6000 to fasten tissue captured by the surgical stapling and severing instrument 8010.

The fibrous tubular members of the compressible adjunct assembly 6000 are concentrically aligned along a longitudinal axis L-L and disposed around, or at least partially around, one another, as illustrated in FIG. 93. The second intermediate fibrous tubular member 6006 is disposed between the first and third intermediate fibrous tubular members 6004 and 6008. For the sake of brevity, the following discussion of the compressible adjunct assembly 6000 will focus on the second intermediate fibrous tubular member 6006 in addition to the outer and inner fibrous tubular members 6002 and 6010. The reader, however, will appreciate that the following discussion is equally applicable to the first and third intermediate fibrous tubular members 6004 and 6008.

Referring to FIG. 93, the inner fibrous tubular member 6010 is sized to fit, or at least partially fit, within the intermediate fibrous tubular member 6006 to define a cylindrical space or gap 6012 therebetween. Likewise, the intermediate fibrous tubular member 6006 is sized to fit, or at least partially fit, within the outer fibrous tubular member 6002 to define a cylindrical space or gap 6014 therebetween. As illustrated in FIG. 93, the inner fibrous tubular member 6010 extends, or at least partially extends, through the intermediate fibrous tubular member 6006 which extends, or at least partially extends, through the outer fibrous tubular member 6002.

Referring to FIG. 93, the fibrous tubular members of the compressible adjunct assembly 6000 are woven. In certain instances, one or more of the fibrous tubular members of the compressible adjunct assembly 6000 can be non-woven constructs. In at least one instance, the inner fibrous tubular member 6010 can be comprised of a non-woven fibrous construct that is not hollow. In any event, the fibers of the adjacent fibrous tubular members of the compressible adjunct assembly 6000 are intertwined, interrelated, and/or capable of interaction with one another.

One or more of the fibrous tubular members and/or fibrous constructs of the compressible adjunct assembly 6000 includes at least one fiber that is constricted or shrunk in response to a thermal treatment of the compressible adjunct assembly 6000.

The at least one fiber is comprised of at least one biocompatible material that experiences a reduction in size when heated to the predetermined temperature. In at least one instance, the at least one biocompatible material is an elastomer. In certain instances, the at least one biocompatible material has a glass transition temperature below ambient temperature.

In certain instances, the thermal treatment comprises heating the compressible adjunct assembly 6000 to a predetermined temperature. For example, the compressible adjunct assembly 6000 can be inserted into an oven, which can be heated to the predetermined temperature. Other techniques for delivering the thermal treatment to the compressible adjunct assembly 6000 are contemplated by the present disclosure.

Further to the above, one or more of the fibrous tubular members and/or fibrous constructs of the compressible adjunct assembly 6000 includes at least one fiber that has experienced a transition from a more ordered phase to a less ordered phase in response to the thermal treatment of the compressible adjunct assembly 6000. In at least one instance, the compressible adjunct assembly 6000 includes at least one fiber that has experienced an increase in entropy in response to the thermal treatment.

Figure 94:
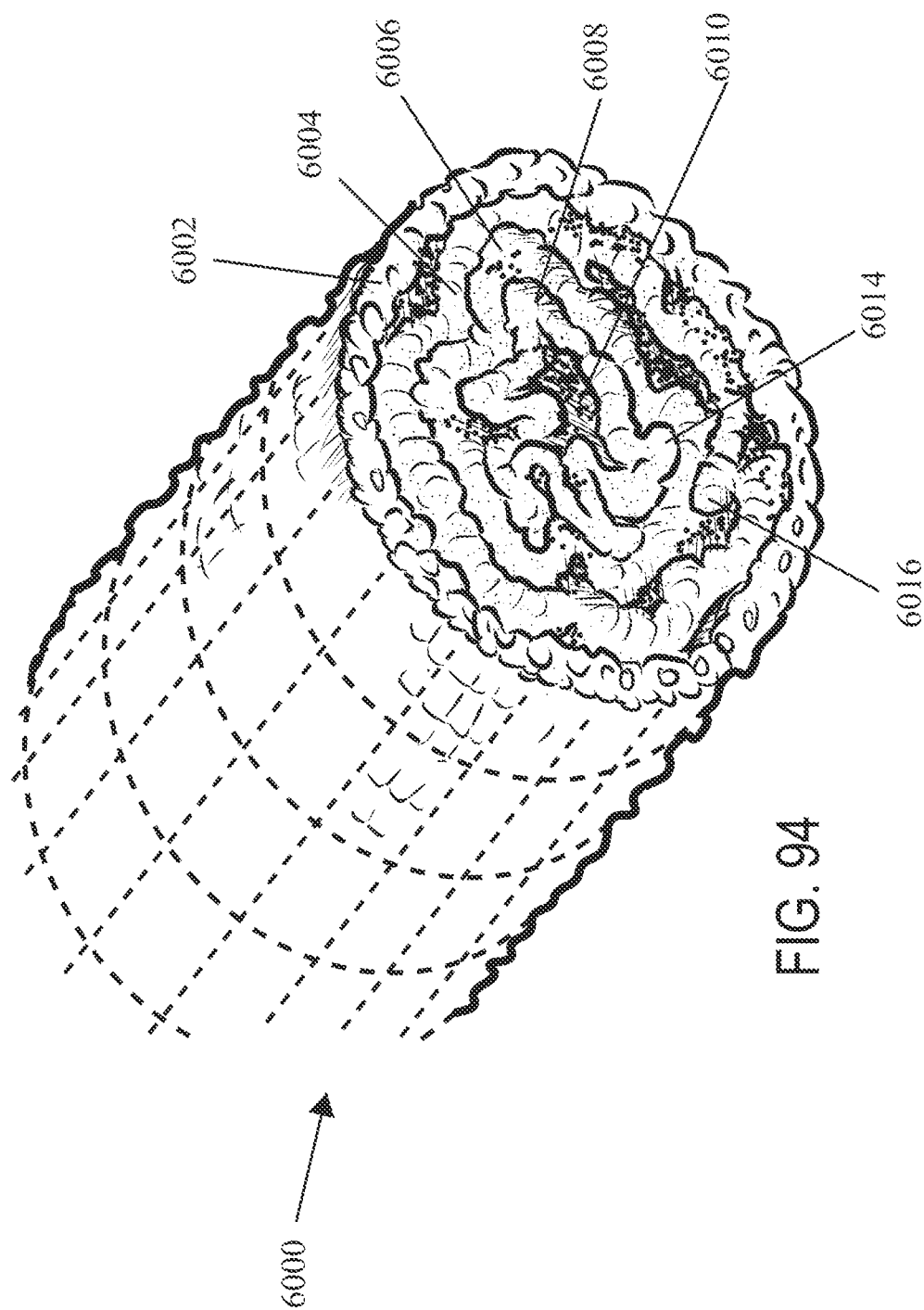
FIG. 94 is a partial perspective view of the compressible adjunct assembly of FIG. 93 assembled and thermally treated in accordance with at least one embodiment described herein.

Referring to FIG. 94, the shrinkage or constriction of the at least one fiber reinforces the compressible adjunct assembly 6000 by causing the individual fibrous tubular members of the compressible adjunct assembly 6000 to be brought closer to one another thereby reducing the empty space therebetween. The shrinkage of the at least one fiber can densify the compressible adjunct assembly 6000 by causing the fibers of the fibrous tubular members to bunch up or cluster into more compact semi-organized or disorganized tubular structures. In result, as illustrated in FIG. 94, the individual fibrous tubular members may lose their uniform tubular frames and instead adopt irregular shapes with bulges and depressions that improve the structural integrity of the compressible adjunct assembly 6000.

Referring to FIG. 94, one or more of the fibrous tubular members and/or fibrous constructs of the compressible adjunct assembly 6000 may comprise bioabsorbable materials such as, for example, polyglycolic acid (PGA) which is marketed under the trade name VICRYL, polylactic acid (PLA or PLLA), polydioxanone (PDS), polyhydroxyalkanoate (PHA), poliglecaprone 25 (PGCL) which is marketed under the trade name MONOCRYL, and/or polycaprolactone (PCL). One or more of the fibrous tubular members and/or fibrous constructs of the compressible adjunct assembly 6000 may comprise one or more composite materials that include two or more polymers, the polymers selected from a group including PGA, PLA, PDS, PHA, PGCL and/or PCL, for example.

Referring again to FIG. 93, one or more of the fibrous tubular members and/or fibrous constructs of the compressible adjunct assembly 6000 includes a first plurality of fibers comprised of a first biocompatible material such as, for example, VICRYL, and a second plurality of fibers comprised of a second biocompatible material, different from the first biocompatible material, such as, for example PDS. The compressible adjunct assembly 6000 comprises more of the first biocompatible material than the second biocompatible material. In at least one instance, the ratio of the first biocompatible material of the first plurality of fibers to the second biocompatible material of the second plurality of fibers can be any value selected from a range of about 3:1 to about 10:1, for example. In at least one instance, the ratio of the first biocompatible material to the second biocompatible material can be any value selected from a range of about 4:1 to about 9:1, for example. In at least one instance, the ratio of the first biocompatible material to the second biocompatible material can be any value selected from a range of about 5:1 to about 8:1, for example. In at least one instance, the ratio of the first biocompatible material to the second biocompatible material is 7:1. In at least one instance, the ratio of the first biocompatible material to the second biocompatible material is about 5:1, for example. Other ratios of the first biocompatible material to the second biocompatible material are contemplated by the present disclosure.

In at least one instance, all the fibrous tubular members and/or fibrous constructs of the compressible adjunct assembly 6000 may comprise the same, or at least substantially the same, ratio of the first biocompatible material to the second biocompatible material. Alternatively, the fibrous tubular members and/or fibrous constructs of the compressible adjunct assembly 6000 may comprise different ratios of the first biocompatible material to the second biocompatible material.

The compressible adjunct assembly 6000 is heated to a predetermined temperature at which the second plurality of fibers experiences a reduction in size corresponding to an increase in Entropy in response to the thermal treatment. In certain instances, the first plurality of fibers and the second plurality of fibers are entangled such that the shrinkage of the second plurality of fibers causes some or all of the first plurality of fibers to be pulled together, which densities the compressible adjunct assembly 6000. In certain instances, the second plurality of fibers are in an outer fibrous tubular member of the compressible adjunct assembly 6000 while the first plurality of fibers are in an inner fibrous tubular member of the compressible adjunct assembly 6000. In such instances, the second plurality of fibers, while shrinking, may cause the outer fibrous tubular member to constrict the inner fibrous tubular member.

Figure 95:
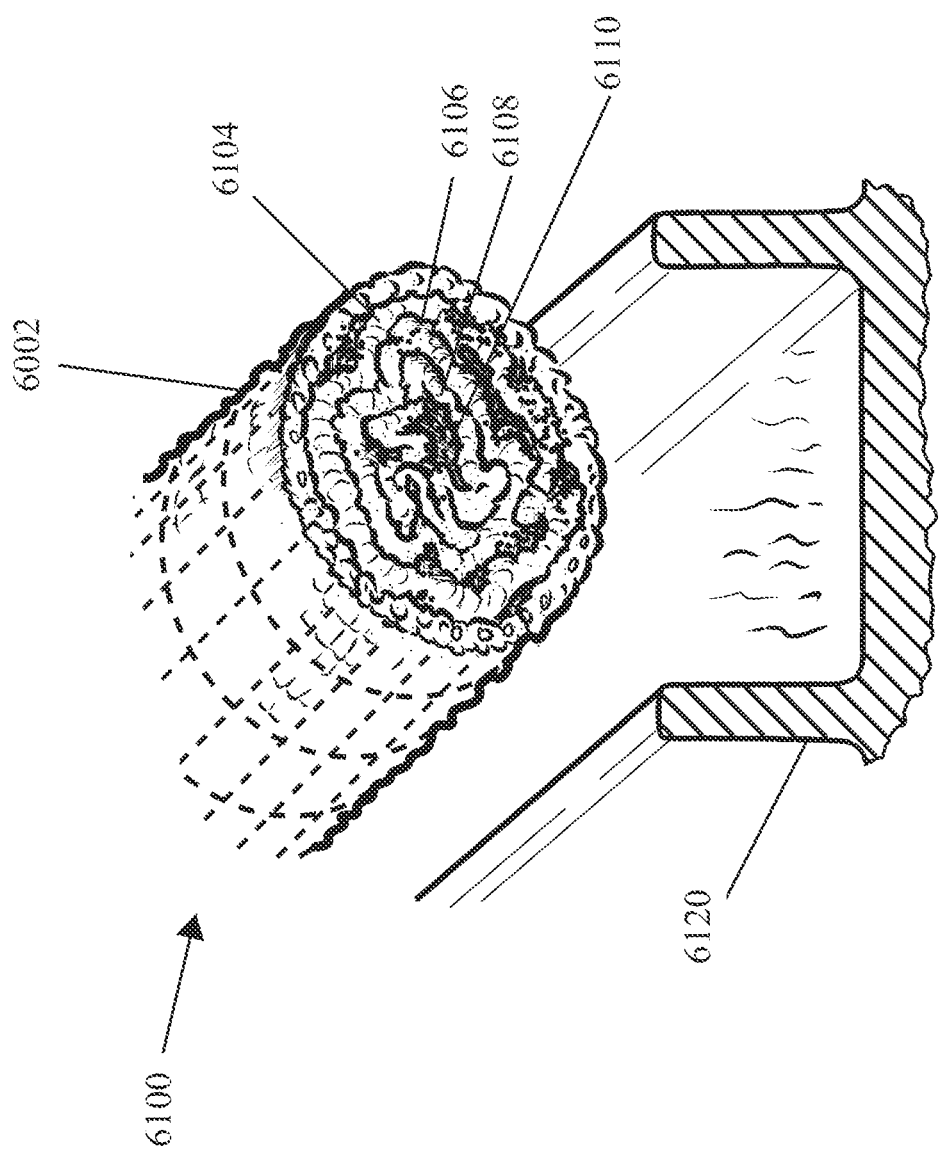
FIG. 95 is a partial perspective view of a compressible adjunct assembly being inserted into a heated mold in accordance with at least one embodiment described herein.
Figure 96:
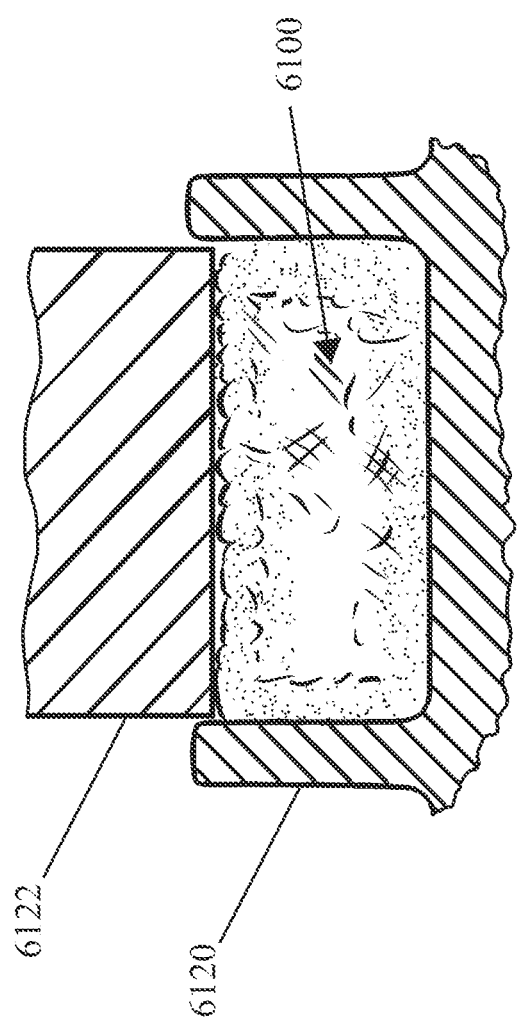
FIG. 96 is a cross-sectional view of the compressible adjunct assembly of FIG. 95 being subjected to a thermal pressing treatment in accordance with at least one embodiment described herein.
Figure 97:
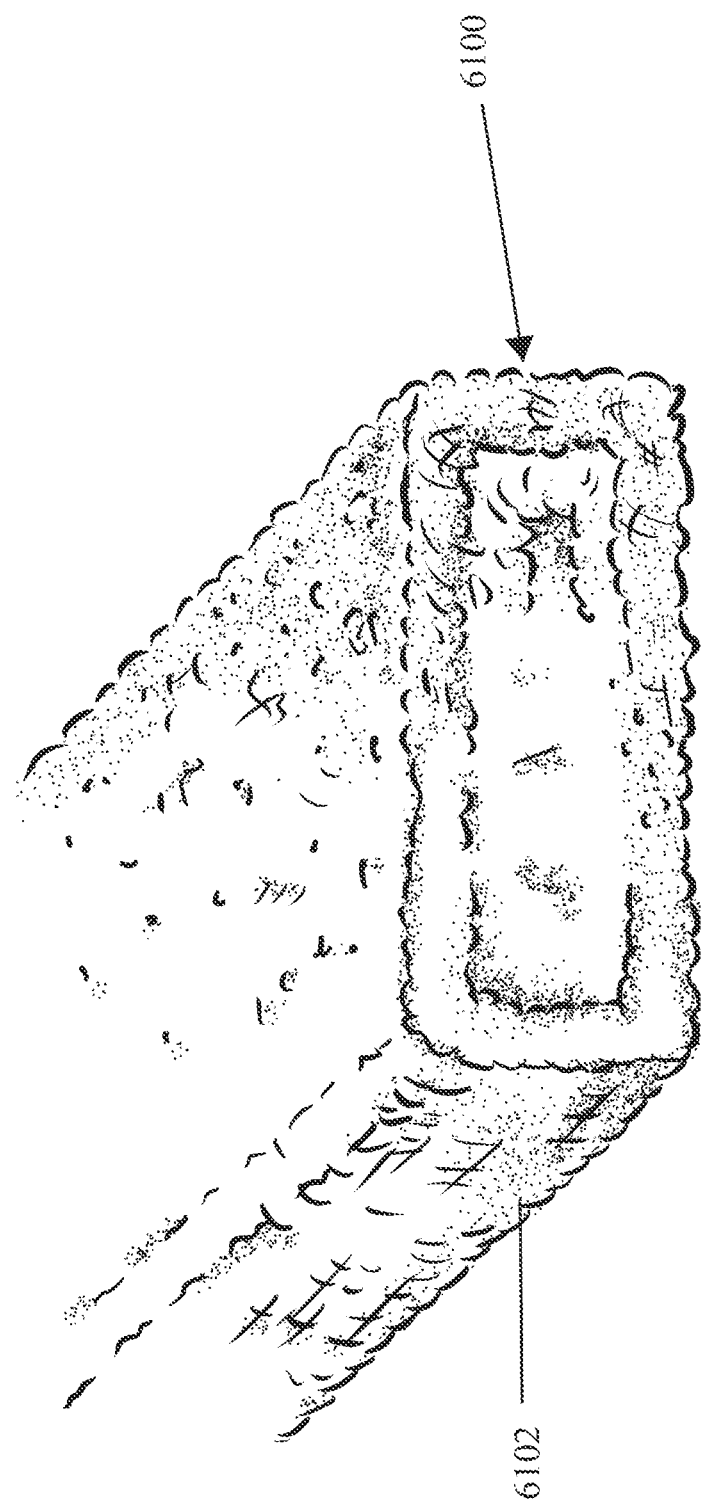
FIG. 97 is a partial perspective view of the compressible adjunct assembly of FIG. 95 after the thermal treatment is completed and after removal from the mold.

Referring now to FIGS. 95-97, a compressible adjunct assembly 6100 is similar in many respects to the compressible adjunct assembly 6000. For example, the compressible adjunct assembly 6100 comprises a plurality of fibrous tubular members 6102-6110 that are aligned concentrically and disposed around, or at least partially around, one another. Also, the compressible adjunct assembly 6100 can be assembled with a jaw member of a surgical stapling and severing instrument such as, for example, the anvil 8014 and/or the staple cartridge 10000 of the surgical stapling and severing instrument 8010. As discussed in greater detail below, the compressible adjunct assembly 6100 is modified into a desired shape by a thermal pressing process to be used with the surgical stapling and severing instrument 8010, for example.

As illustrated in FIG. 95, the compressible adjunct assembly 6100 is inserted into a mold 6020, which can be heated to a predetermined temperature. A predetermined external pressure is applied to the compressible adjunct assembly 6100 to modify the shape of the compressible adjunct assembly 6100 to the desired shape, as illustrated in FIG. 96. The compressible adjunct assembly 6100 is maintained under the predetermined conditions of temperature and pressure for a predetermined time period after which the compressible adjunct assembly 6100 is allowed to cool or is actively cooled below the predetermined temperature while the external pressure is maintained. Finally, the external pressure is removed, as illustrated in FIG. 96. Additional details of a thermal pressing process are described in U.S. patent application Ser. No. 14/187,383, entitled IMPLANTABLE LAYERS AND METHODS FOR ALTERING IMPLANTABLE LAYERS FOR USE WITH SURGICAL FASTENING INSTRUMENTS, and filed Feb. 24, 2014, now U.S. Patent Application Publication No. 2015/0238185, the entire disclosure of which is incorporated herein by reference.

Referring again to FIGS. 95-97, one or more of the fibrous tubular members 6102-6110 of the compressible adjunct assembly 6100 has a plurality of fibers that comprises a biocompatible material with a glass transition temperature "Tg". The predetermined temperature of the process described above is set to be greater than or equal to the glass transition temperature "Tg" but lower than the melting temperature of the biocompatible material. As illustrated in FIG. 96, a modifying member 6122 is employed to apply the predetermined external pressure to the compressible adjunct assembly 6100. The predetermined external pressure is set to a pressure sufficient to modify the compressible adjunct assembly 6100 to the desired shape. The value of the predetermined external pressure depends in part on the size of the mold 6120, the original size and/or shape of the compressible adjunct assembly 6100, and/or the desired size and/or shape of the compressible adjunct assembly 6100, for example.

In at least one instance, the predetermined pressure is maintained for approximately 10 minutes at the predetermined temperature and/or for approximately 10 minutes at a temperature below the predetermined temperature, for example. In certain instances, the predetermined pressure can be maintained for a period of time from about 30 seconds to about 8 hours, for example, at the predetermined temperature and/or for a period of time from about 30 seconds to about 8 hours, for example, at a temperature below the predetermined temperature. Other time periods for maintaining the predetermined temperature and/or pressure are contemplated by the present disclosure.

In certain instances, only the outer fibrous tubular member 6102 includes a biocompatible material comprising a glass transition temperature "Tg" below the predetermined temperature. Nonetheless, the modification to the outer fibrous tubular member 6102 by the thermal pressing process can be sufficient to cause the outer fibrous tubular member 6102 to hold the remaining fibrous tubular members 6104-6110, disposed within the outer fibrous tubular member 6102, in the desired shape.

In certain instances, the desired shape of the compressible adjunct assembly 6100 may comprise square-shaped or a rectangular transverse cross-sectional area. Other shapes are contemplated by the present disclosure. In at least one instance, the compressible adjunct assembly 6100 comprises a transverse cross-sectional area in the shape of a rectangular prism with edges and ends tapered flat or smashed flat for attachment to and/or alignment with an anvil such as, for example, the anvil 8014, and/or a staple cartridge such as, for example, the staple cartridge 10000.

Figure 98:
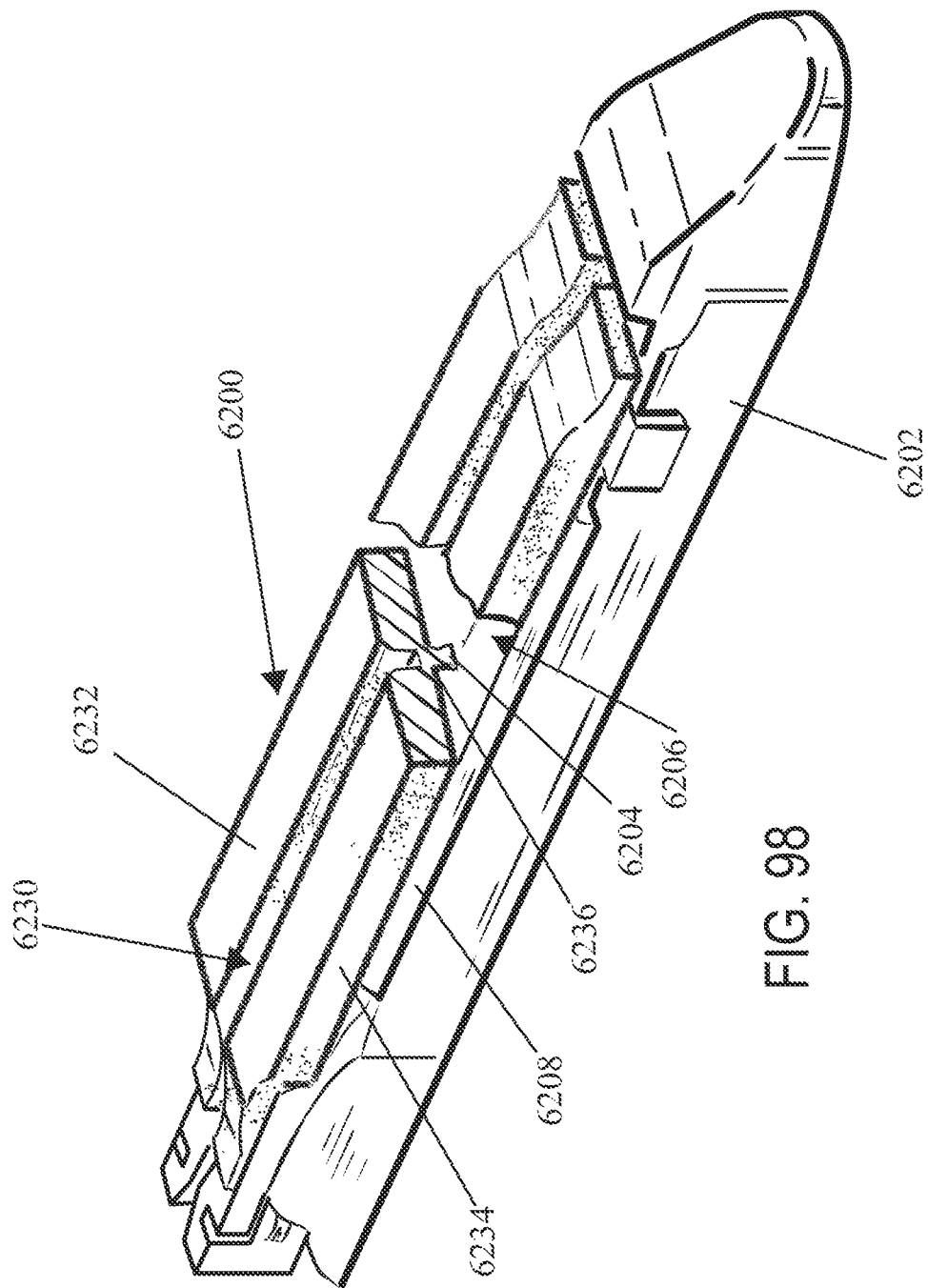
FIG. 98 is perspective view of a compressible adjunct assembly assembled with a staple cartridge in accordance with at least one embodiment described herein.
Figure 99:
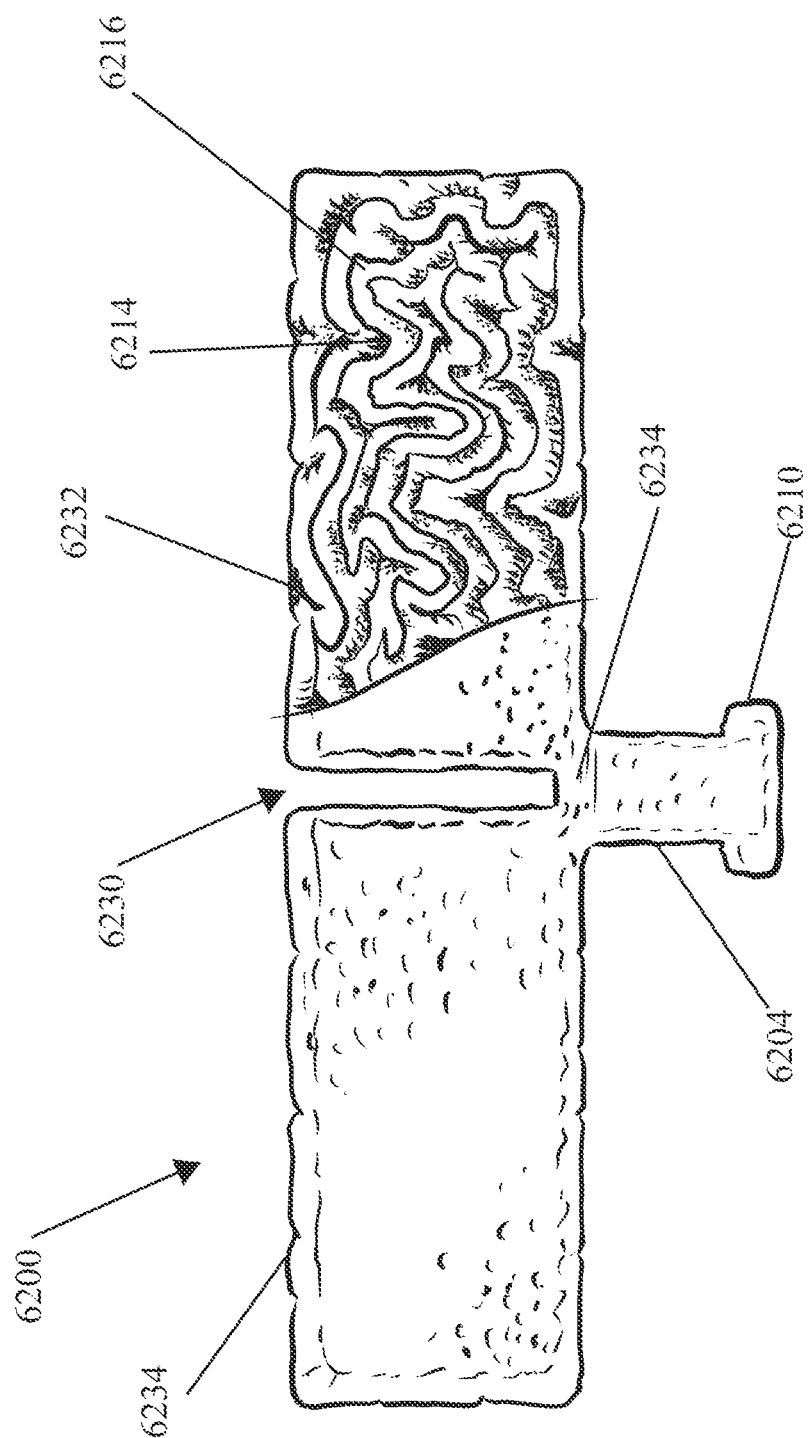
FIG. 99 is front view of the compressible adjunct assembly of FIG. 98, wherein a portion of the compressible adjunct assembly has been removed for the purpose of illustration.
Figure 100:
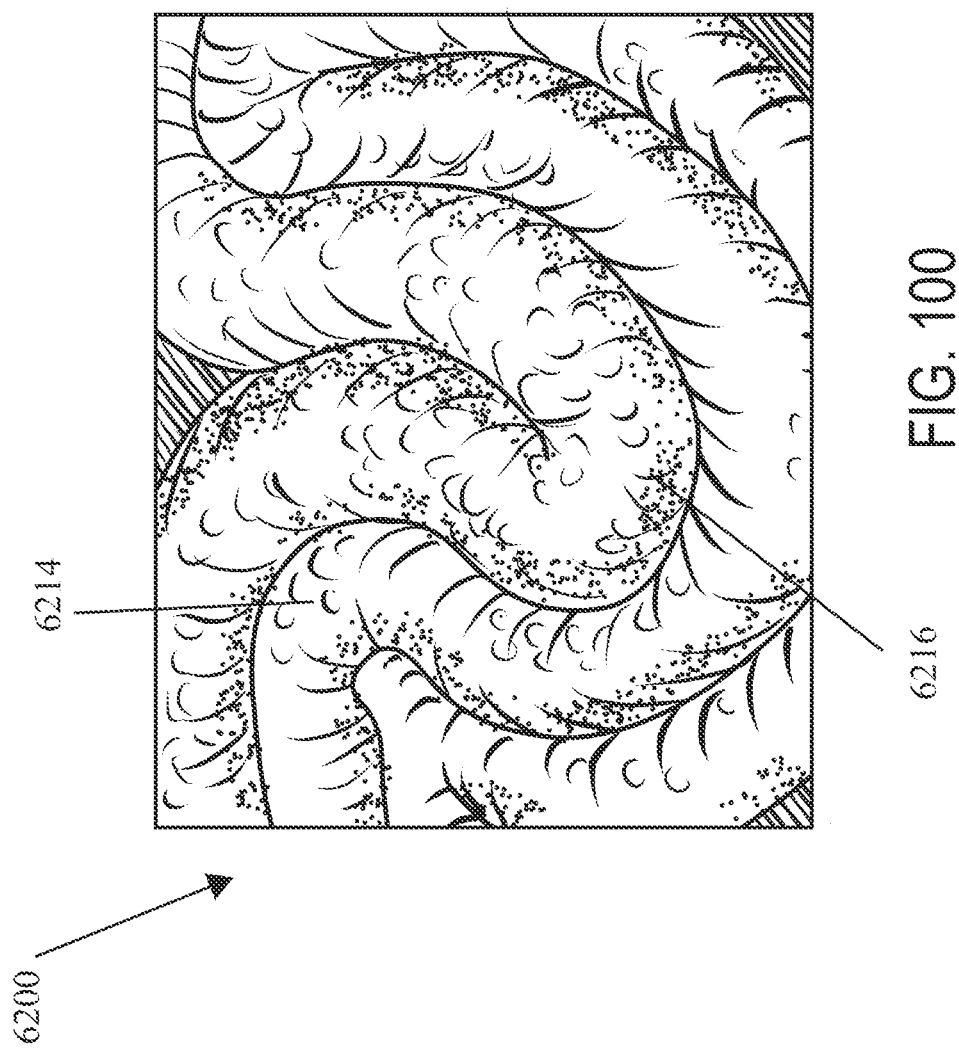
FIG. 100 is a close-up of an internal portion of the compressible adjunct assembly of FIG. 99.

Referring now to FIGS. 98-100, a compressible adjunct assembly 6200 is similar in many respects to the compressible adjunct assemblies 6000 and 6100. For example, the compressible adjunct assembly 6200 comprises a plurality of fibrous tubular members that are aligned concentrically and disposed around, or at least partially around, one another. Also, the compressible adjunct assembly 6200 is shrunk or constricted into a compact semi-organized or disorganized structure causing the individual fibrous tubular members to lose their uniform tubular frames and instead adopt irregular shapes with bulges 6214 and depressions 6216, as illustrated in FIG. 100, that improve the structural integrity of the compressible adjunct assembly 6200. Also, like the compressible adjunct assembly 6100, the compressible adjunct assembly 6200 has been transformed from an initial generally tubular shape to a desired shape, as illustrated in FIG. 99, during a thermal pressing process. The assembly 6200 is suitable for assembly with a jaw member of a surgical stapling and severing instrument such as, for example, the anvil 8014 and/or the staple cartridge 10000 of the surgical stapling and severing instrument 8010.

Referring to FIG. 98, the compressible adjunct assembly 6200 is assembled with a staple cartridge 6202 by inserting an attachment portion 6204 of the compressible adjunct assembly 6200 into an elongate slot 6206 of the staple cartridge 6202. The attachment portion 6204 is slightly larger than the elongate slot 6206. Accordingly, the attachment portion 6204 is deformed as it is inserted into the elongate slot 6206 and the friction built between the deformed attachment portion 6204 and the walls of the elongate slot 6206 holds the compressible adjunct assembly 6200 against and/or adjacent to a cartridge deck 6208 of the staple cartridge 6202. The attachment portion 6204 includes a laterally-extended apex portion 6210, as illustrated in FIG. 99, which improves the attachment of the compressible adjunct assembly 6200 to the staple cartridge 6202. In certain instances, additional or alternative attachment techniques can be employed to releasably attach the compressible adjunct assembly 6200 to the staple cartridge 6202. In at least one instance, a biocompatible glue can replace the attachment portion 6204 or can be used in addition to the attachment portion 6204. In the latter instance, the biocompatible glue can be applied to the attachment portion 6204 prior to its insertion into the elongate slot 6206, for example.

Further to the above, the compressible adjunct assembly 6200 includes a first compressible portion 6232 and a second compressible portion 6234. An elongate slot or a channel 6230 is defined between the first compressible portion 6232 and the second compressible portion 6234. The elongate slot 6230 extends, or at least partially extends, along a length of the elongate slot 6206 of the staple cartridge 6202 when the compressible adjunct assembly is assembled with the staple cartridge 6202. The attachment portion 6204 protrudes from a base 6236 defined at the bottom of the elongate slot 6230, as illustrated in FIG. 99. As the firing assembly 9090 (FIG. 3) is advanced to deploy the staples into the compressible adjunct assembly 6200 and the tissue captured by the surgical stapling and severing instrument 8010, the cutting edge 9116 (FIG. 3) is driven through the elongate slot 6230. In addition, the cutting edge 9116 may cut through the attachment portion 6204.

In certain instances, the attachment portion 6204 is torn from the base 6236 to release the compressible adjunct assembly 6200 from the staple cartridge 6202. Alternatively, the attachment portion 6204 is pulled out of the elongate slot 6206 of the staple cartridge 6202 as the compressible adjunct assembly 6200 is released from the staple cartridge 6202. In certain instances, the base 6236 remains intact, or at least partially intact, after the compressible adjunct assembly 6200 is released from the staple cartridge 6202. In such instances, the base 6236 continues to connect the first compressible portion 6232 and second compressible portion 6234 after the release is completed. Alternatively, the base 6236 can be severed or torn, which causes the first compressible portion 6232 and second compressible portion 6234 to be separated from one another.

The attachment portion 6204 continuously extends along a length of the elongate slot 6230. In certain instances, the attachment portion 6204 is divided into a plurality of attachment members that are spaced apart from one another and arranged longitudinally along a length of the elongate slot 6230. In at least one instance, the plurality of attachment members are equidistant from one another. Alternatively, the plurality of attachment members can be arranged closer to each other in a first portion of the elongate slot 6230 than a second portion of the elongate slot 6230. In certain instances, the attachment members can be concentrated at a proximal portion, a distal portion, and/or a central portion of the elongate slot 6230, for example.

In at least one instance, one or more of the plurality of attachment members may comprise a top surface with a rectangular, or an at least substantially rectangular, shape. Other shapes are contemplated by the present disclosure such as, for example, a circular shape or a dome shape. Like the attachment portion 6204, one or more of the attachment members may include a laterally extending end.

Figure 101:
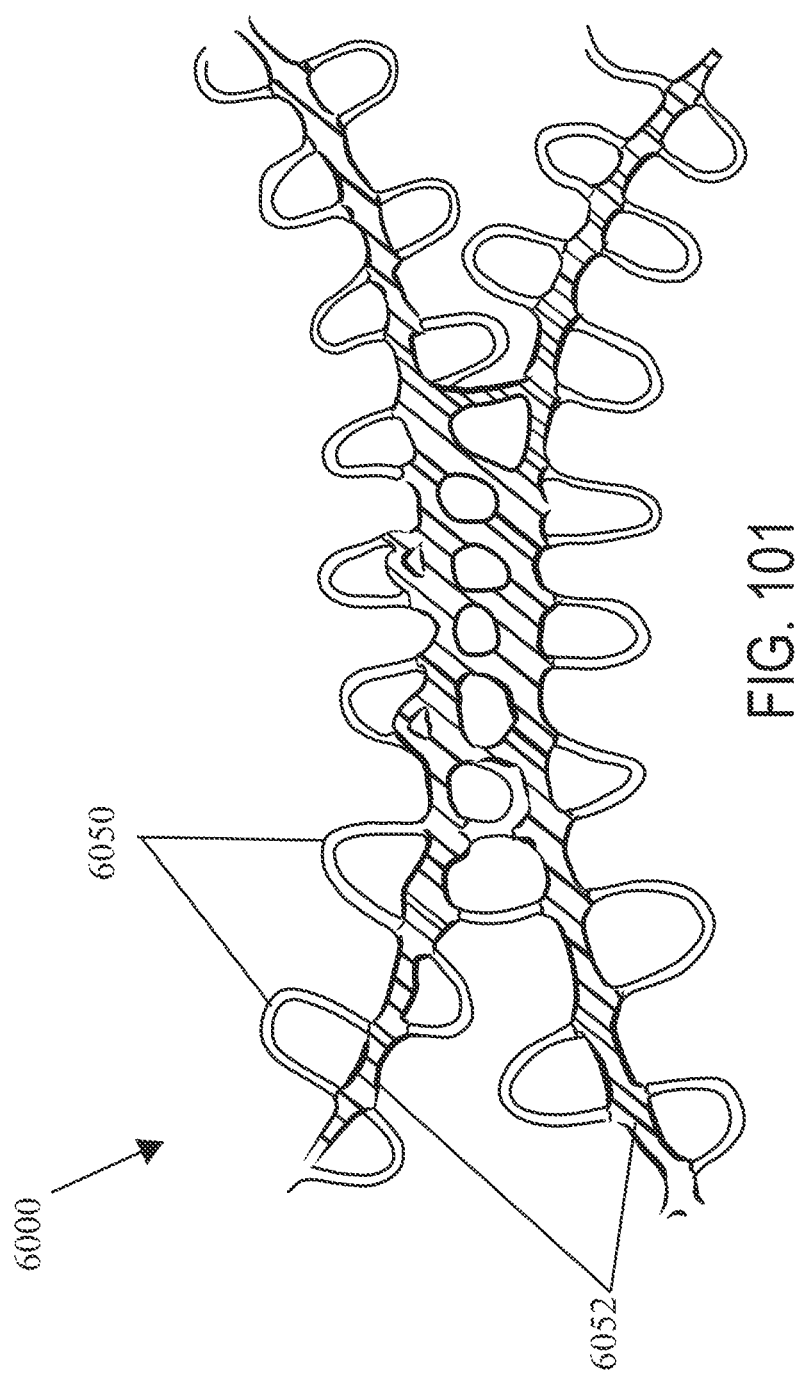
FIG. 101 is an illustration of a first plurality fibers and a second plurality of fibers, wherein the second plurality of fibers is melted and resolidified in accordance with at least one embodiment described herein.

Referring to FIG. 101, one or more of the fibrous tubular members and/or fibrous constructs of the compressible adjunct assembly 6000 includes a first plurality of fibers 6050 comprised of a first biocompatible material, such as VICRYL, for example, and a second plurality of fibers 6052 comprised of a second biocompatible material that is different from the first biocompatible material, such as PDS, for example. As illustrated in FIG. 101, the plurality of second fibers 6052 can be melted and resolidified to bond and reinforce the plurality of first fibers 6050.

In certain instances, the compressible adjunct assembly 6000 can be heated to a predetermined temperature that is equal to or greater than the melting temperature of the second biocompatible material but less than the melting temperature of the first biocompatible material. In such instances, the plurality of second fibers 6052 are melted. The melted material flow along, onto, and/or between the plurality of first fibers 6050. Upon cooling, the melted fibers 6052 bond to the fibers 6050 and interconnect adjacent fibers thereby reinforcing the structure of the compressible adjunct assembly 6000, as illustrated in FIG. 101.

Figure 102:
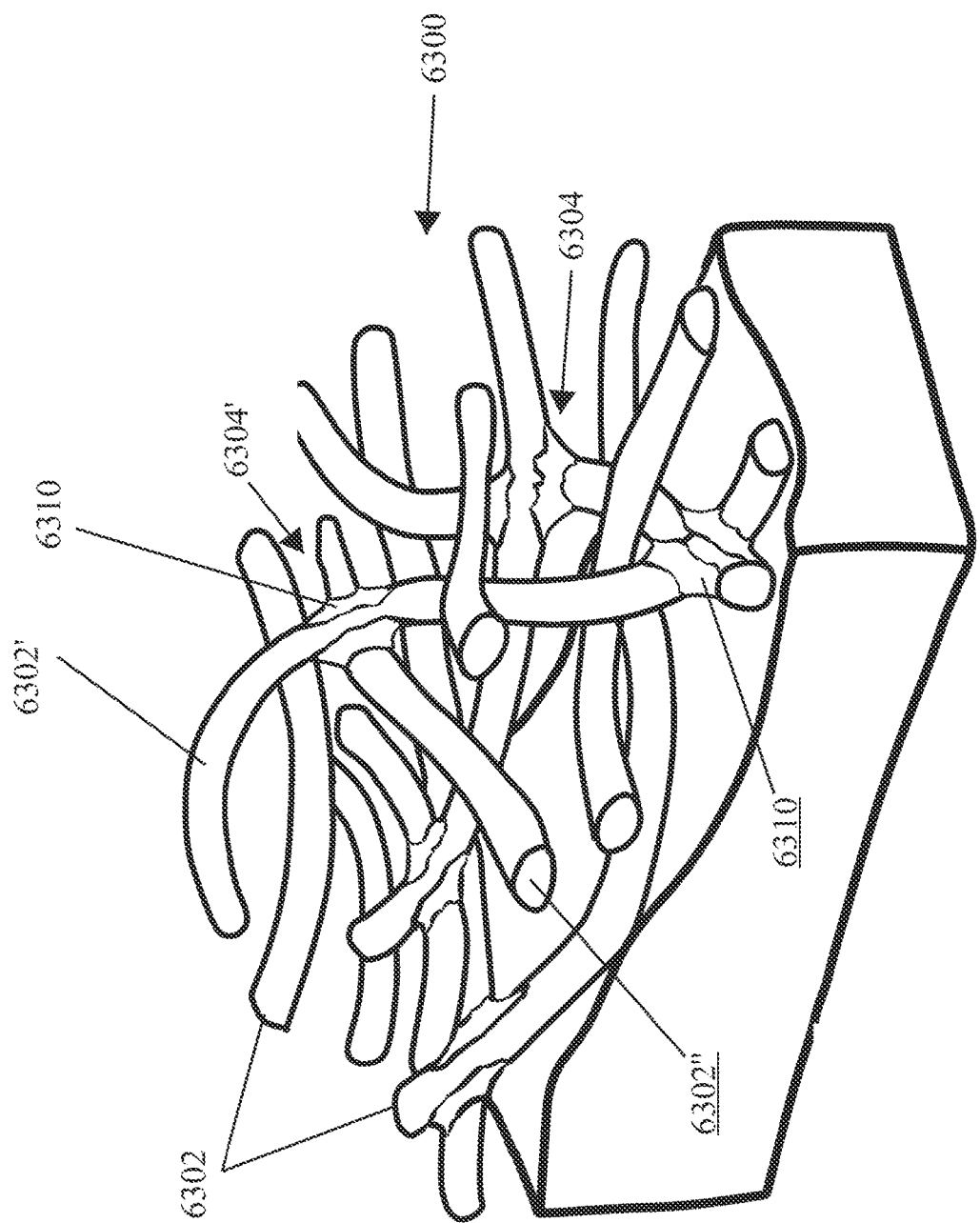
FIG. 102 is an illustration of a compressible adjunct assembly in accordance with at least one embodiment described herein.

Referring to FIG. 102, a compressible adjunct assembly 6200 includes biocompatible fibers 6302 that are entangled to form a three-dimensional structure. In addition, the compressible adjunct assembly 6200 includes a bonding medium 6310 that defines nexus points or bonding nodes 6304 that reinforce the three-dimensional structure of the compressible adjunct assembly 6200. The bonding nodes 6304 include adjacent portions of the fibers 6302 that are surrounded, or at least partially surrounded, by the bonding medium 6310 which affixes such adjacent portions of the fibers 6302.

Referring again to FIG. 102, a first fiber 6302' extends over a second fiber 6302", while the bonding medium 6310 extends between adjacent portions of the fibers 6302' and 6302". The bonding medium 6310 is attached to the adjacent portions of the fibers 6302' and 6302" defining a bonding node 6304'. Other arrangements of the fibers 6302 and the bonding nodes 6304 are contemplated by the present disclosure. In at least one instance, the bonding medium 6310 may join an end portion of one fiber with an intermediate portion of another fiber to define a bonding node, for example.

The bonding nodes 6304 define load bearing zones within the compressible adjunct assembly 6200, which are characterized by an increased density and/or a greater stiffness compared to surrounding zones which lack the bonding nodes 6304. The load bearing zones can be employed as attachment regions for securing the compressible adjunct assembly 6200 to a jaw member of a surgical stapling and severing instrument such as, for example, the anvil 8014 and/or the staple cartridge 10000 of the surgical stapling and severing instrument 8010.

In certain instances, a first compressible adjunct assembly 6200 can be assembled with the anvil 8014 and a second compressible adjunct assembly 6200 can be assembled with the staple cartridge 10000 such that tissue is captured between the first and second compressible adjunct assemblies 6300 when the surgical stapling and severing instrument 8010 is in a closed configuration. Also, a plurality of staples can be deployed into the compressible adjunct assembly 6200 to fasten tissue captured by the surgical stapling and severing instrument 8010, as described in greater detail elsewhere in the present disclosure.

Referring again to FIG. 10A, the compressible adjunct assembly 6200 is fabricated from a plurality of the fibers 6302 and a plurality of bonding fibers that are reshaped or altered to form the bonding medium 6310. The fibers 6302 and the bonding fibers are entangled into a three-dimensional structure that ultimately forms the compressible adjunct assembly 6200. The fibers 6302 are fabricated, or at least partially fabricated, from a first biocompatible material with a first melting point, while the bonding fibers are fabricated, or at least partially fabricated, from a second biocompatible material with a second melting point that is less than the first melting point of the first biocompatible material. Furthermore, the fibers 6302 lack or exclude the second biocompatible material of the bonding fibers; however, small amounts of the second biocompatible material can be present in the fiber 6302 in certain embodiments.

In certain instances, the fibers 6302 can be fabricated from a plurality of biocompatible materials with melting points that are greater than the melting point(s) of the biocompatible material(s) of the bonding fibers. Similarly, the bonding fibers can be fabricated from a plurality of biocompatible material with melting points that are less than the melting point(s) of the biocompatible material(s) of the fibers 6302.

Further to the above, the three-dimensional structure of the entangled fibers 6302 and bonding fibers can be subjected to one or more thermal pressing treatments. Predetermined pressures and/or temperatures are applied to a three-dimensional structure of the entangled fibers 6302 and bonding fibers resulting in the formation of the compressible adjunct assembly 6200. In certain instances, the pressure can be removed and the three-dimensional structure is only subjected to the predetermined temperature. In other instances, the pressure can be substituted with tension that may stretch the three-dimensional structure. In certain instances, various combinations of pressure and tension can be employed to mold the three-dimensional structure into a desired shape.

Figure 103:
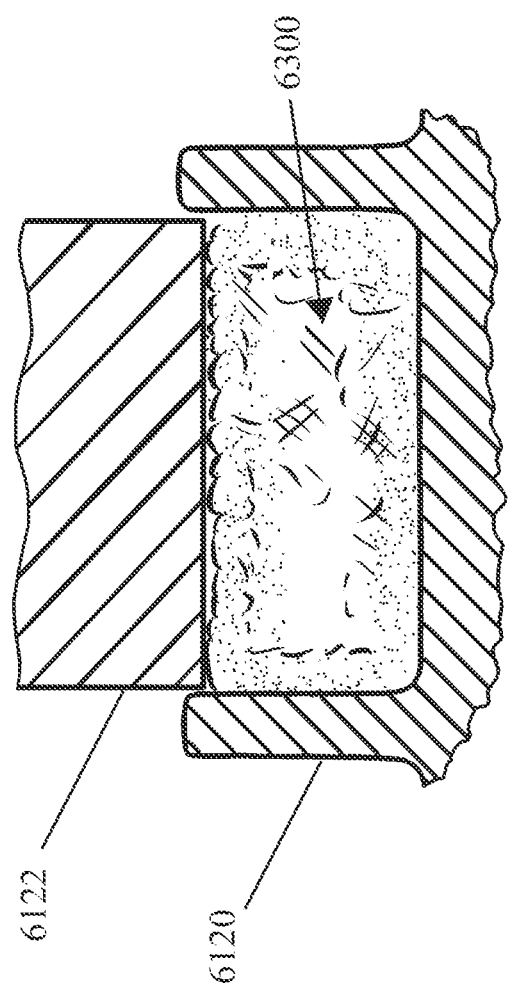
FIG. 103 is a cross-sectional view of the compressible adjunct assembly of FIG. 102 being subjected to a thermal pressing treatment in accordance with at least one embodiment described herein.

Referring to FIG. 103, the mold 6120 and the modifying member 6122 are employed to implement the thermal pressing treatment. The three-dimensional structure, which ultimately becomes, the compressible adjunct assembly 6200, is inserted into the mold 6120. The modifying member 6122 is then operated to apply a predetermined pressure to the three-dimensional structure to bring the three-dimensional structure to a desired shape. The applied pressure brings adjacent portions of the fibers 6302 and the bonding fibers into a closer proximity in preparation for the transition of the bonding fibers into the bonding medium 6310.

While the predetermined pressure is maintained, the mold is heated to bring the three-dimensional structure to the predetermined temperature. The predetermined temperature is a temperature, or range of temperatures, capable of melting the bonding fibers but not the fibers 6302. Said another way, the predetermined temperature is any temperature, or range of temperatures, greater than or equal to the melting point of the second biocompatible material but less than the melting point of the first biocompatible material. The melted bonding fibers flow along, onto, and/or between the fibers 6302.

Figure 104:
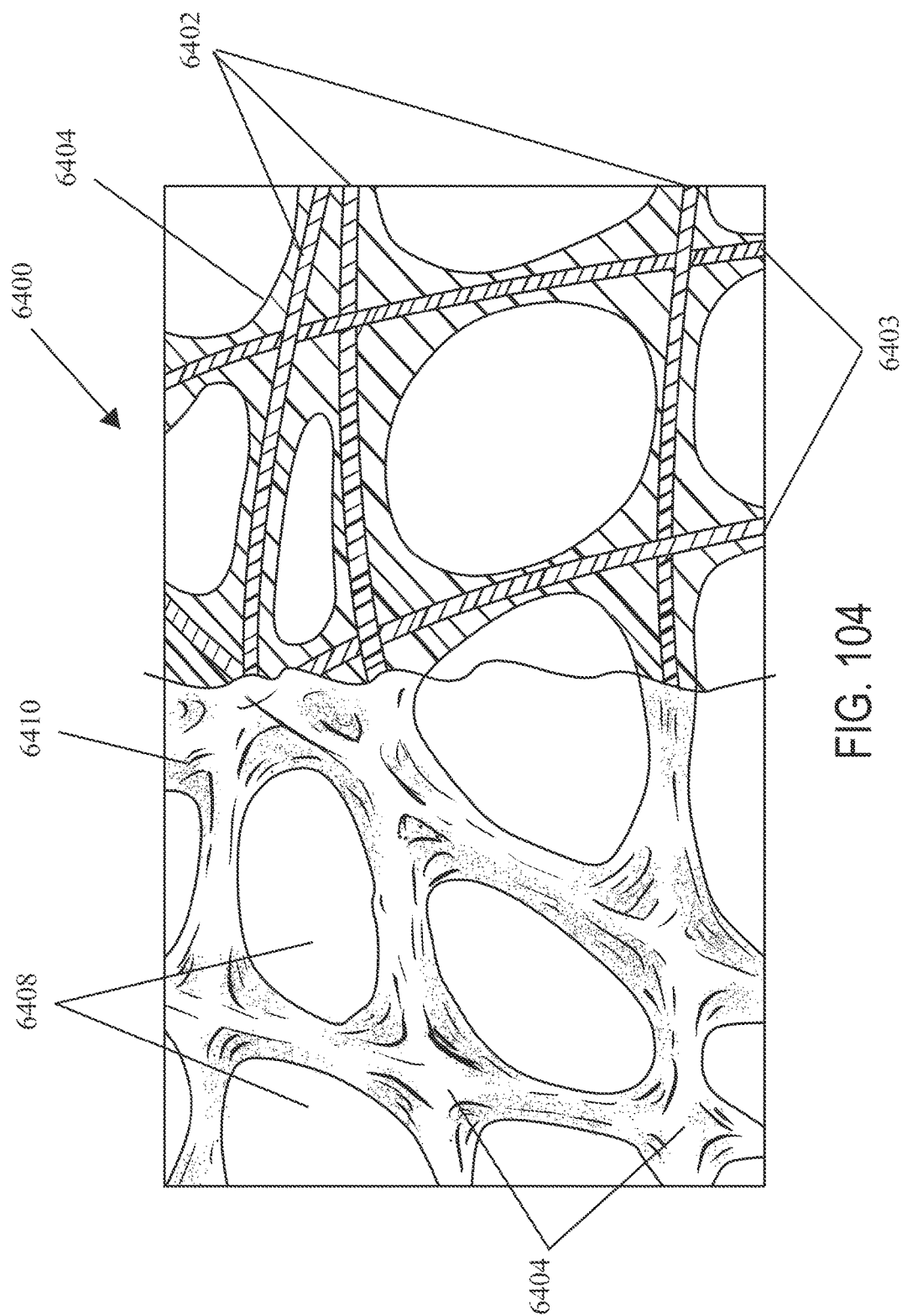
FIG. 104 is a partial cross-sectional view of a compressible adjunct assembly, wherein a portion of the compressible adjunct assembly has been removed for the purpose of illustration.

As the system is actively cooled or allowed to cool to a temperature lower than the predetermined temperature, the bonding medium 6310 is resolidified causing the formation of the bonding nodes 6304 between adjacent portions of the fibers 6302. Furthermore, the bonding medium 6310 may coat, or at least partially coat, at least portions of the fibers 6302 along their lengths, as illustrated in FIG. 104. The predetermined pressure can be maintained during cooling. The predetermined pressure can also be maintained for a predetermined period of time after the cooling is completed. When the pressure is removed, the newly formed bonding nodes 6304 maintain, or at least partially maintain, the new shape of the compressible adjunct assembly 6200.

In certain instances, the predetermined pressure causes the three-dimensional structure to decrease in height. In at least one instance, the reduction in height is selected from a range of values of about 1% to about 200%, for example. Other values for the reduction in height that is caused by the application of the predetermined pressure are contemplated by the present disclosure. Similar reductions in length and/or width are also contemplated by the present disclosure. In instances where tension is applied, one or more of the dimensions of three-dimensional structure may experience an increase in value. In any event, as illustrated in FIG. 103, the resulting compressible adjunct assembly 6200 comprises a shape suitable for assembly with a jaw member of a surgical stapling and severing instrument such as, for example, the anvil 8014 and/or the staple cartridge 10000 of the surgical stapling and severing instrument 8010.

In at least one instance, the predetermined pressure is maintained for approximately 10 minutes before heating, approximately 10 minutes at the predetermined temperature, and/or approximately 10 minutes at a temperature below the predetermined temperature, for example. In certain instances, the predetermined pressure can be maintained for a period of time from about 30 seconds to about 8 hours, for example, before heating, for a period of time from about 30 seconds to about 8 hours, for example, at the predetermined temperature, and/or for a period of time from about 30 seconds to about 8 hours, for example, at a temperature below the predetermined temperature. Other time periods for maintaining the predetermined temperature and/or pressure are contemplated by the present disclosure.

As illustrated in FIG. 102, the fibers 6302 of the compressible adjunct assembly 6200 are disorganized and randomly entangled. Accordingly, the bonding nodes 6304 of the compressible adjunct assembly 6200 are also disorganized and randomly positioned within the compressible adjunct assembly 6200. Alternatively, it may be desirable to produce compressible adjunct assemblies with bonding nodes that are organized into a planned framework. To do so, the fibers of the three-dimensional structure are systematically organized in a planned pattern. In at least one instance, the fibers are knitted or woven into a matrix or network with intersection points that are designed to give rise to bonding nodes.

Referring to FIG. 104, a compressible adjunct assembly 6400 is similar in many respects to the compressible adjunct assembly 6200. For example, the compressible adjunct assembly 6400 can be releasably attached to a jaw member of a surgical stapling and severing instrument such as, for example, the anvil 8014 and/or the staple cartridge 10000 of the surgical stapling and severing instrument 8010. In addition, the compressible adjunct assembly 6400 includes first fibers 6402 spaced apart from one another and generally arranged in a first direction, and second fibers 6403 which are also spaced apart from one another and generally arranged in a second direction intersecting the first direction. The first fibers 6402 and the second fibers 6403 are intertwined forming a matrix or network of fibers with a plurality of intersection points.

The compressible adjunct assembly 6400 also includes bonding fibers that are melted and resolidified to form a bonding medium 6410 that defines bonding nodes 6404 at the intersection points between the first fibers 6402 and the second fibers 6403. A bonding node 6404 may include portions of one or more fibers 6402 and portions of one or more fibers 6403. The bonding fibers can be strategically arranged adjacent to the fibers 6402 and/or 6403 to allow the bonding medium 6410 to flow along, onto, and/or between the fibers 6402 and/or 6403.

Referring again to FIG. 104, the framework defined by the first fibers 6402 and the second fibers 6403 is embedded, or at least partially embedded, in the bonding medium 6410. In certain instances, a bonding node 6404 is formed at an intersection point between a fiber 6402 and a fiber 6403. In certain instances, a bonding node 6404 is formed at an intersection point between three fibers including one fiber 6402 and two fibers 6403, or two fibers 6402 and one fiber 6403. Other bonding nodes 6404 may comprise various other combinations of the fibers 6402 and 6403.

The distance between adjacent fibers of the compressible adjunct assembly 6400 can determine, at least in part, the extent to which such space is filled or bridged by the bonding medium 6410. The greater the distance between adjacent fibers the less likely it is for the melted bonding fibers to bridge the gap between such adjacent fibers. The fluidity of the melted bonding fibers and/or the thickness of the bonding fibers can also determine whether the bonding medium 6410 is capable of filling or bridging a space therebetween. Spaces that remain unfilled define gaps 6408 that can be in different shapes and sizes, as illustrated in FIG. 104. The number and size of the gaps 6408 determine, among other things, the porosity of the compressible adjunct assembly 6400. Accordingly, the porosity of the compressible adjunct assembly 6400 can be increased by increasing the distances between the adjacent fibers. Alternatively, the porosity of the compressible adjunct assembly 6400 can be decreased by decreasing the distances between the adjacent fibers. In at least one instance, a gap 6408 is defined by a plurality of fibers including two of the fibers 6402 and two of the fibers 6403 that intersect to form four bonding nodes 6404 around the gap 6408.

Figure 105:
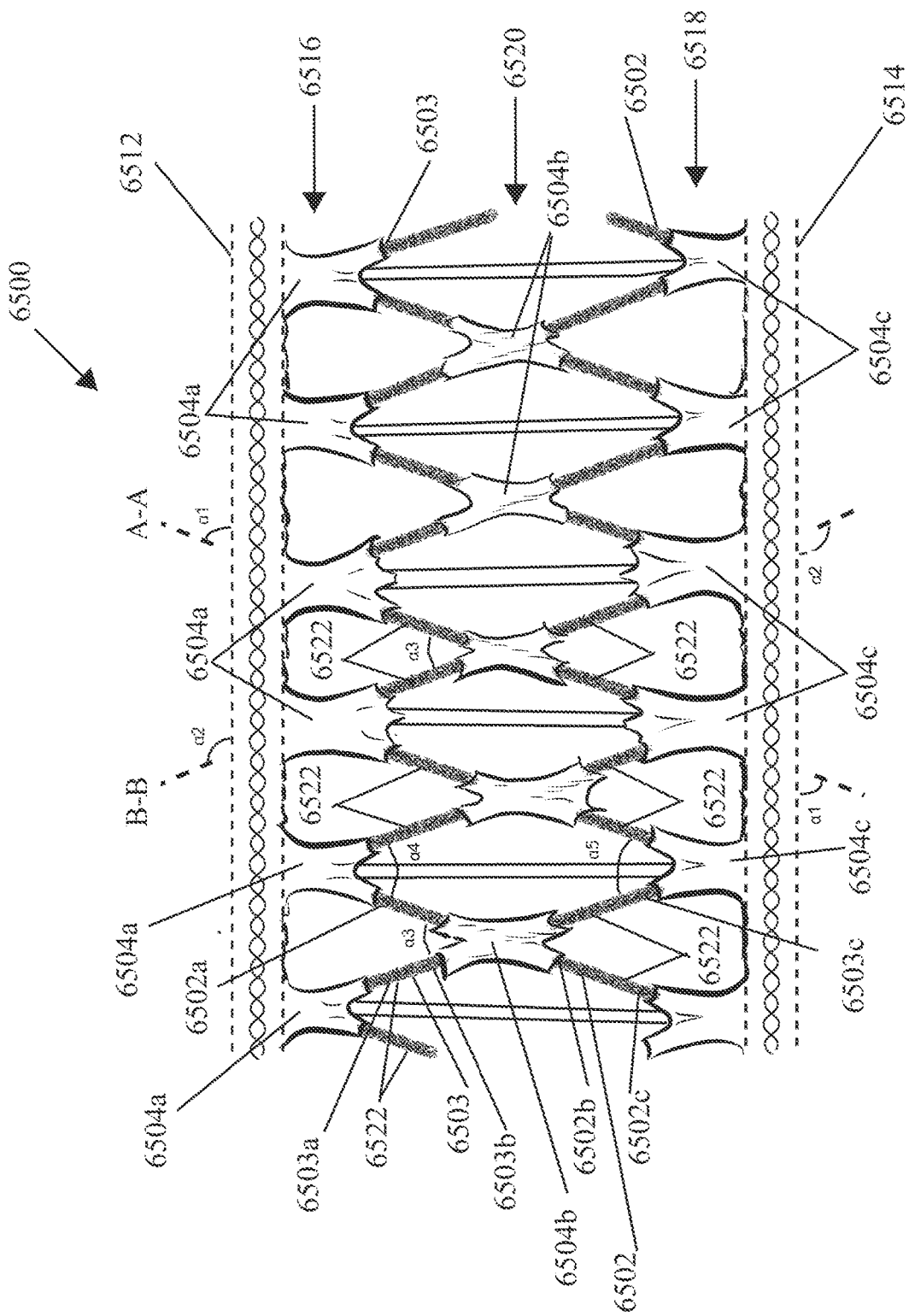
FIG. 105 is a partial cross-sectional view of a compressible adjunct assembly in accordance with at least one embodiment described herein.

Referring now to FIG. 105, a compressible adjunct assembly 6500 is similar in many respects to the compressible adjunct assemblies 6300 and 6400. For example, the compressible adjunct assembly 6400 can be releasably attached to a jaw member of a surgical stapling and severing instrument such as, for example, the anvil 8014 and/or the staple cartridge 10000 of the surgical stapling and severing instrument 8010.

In addition, the compressible adjunct assembly 6500 includes a top portion 6512 and a bottom portion 6514 which is spaced apart from the top portion 6512. A plurality of fibers 6502 and a plurality of fibers 6503 extend between the top portion 6512 and the bottom portion 6514. The fibers 6502 are spaced apart and extend in parallel, or at least substantially in parallel, to one another in a first direction defined by an axis A-A. Likewise, the fibers 6503 are spaced apart and extend in parallel, or at least substantially in parallel, to one another in a second direction defined by an axis B-B. The top portion 6512 and the bottom portion 6514 are parallel, or at least substantially parallel, to one another. The axis A-A intersects the top portion 6512 and the bottom portion 6514 at an angle $\alpha 1$ while the axis B-B intersects the top portion 6512 and the bottom portion 6514 at an angle $\alpha 2$. The angle $\alpha 2$ is greater than the angle $\alpha 1$.

In certain instances, the angle $\alpha 2$ is greater than 90° and the angle $\alpha 1$ is less than 90°, for example. In at least one instance, the angle $\alpha 1$ is selected from a range of about 45° to about 85°, for example. In at least one instance, the angle $\alpha 2$ is selected from a range of about 135° to about 175°, for example. In at least one instance, the angle $\alpha 1$ is about 60°, for example. In at least one instances, the angle $\alpha 2$ is about 150°, for example. Other values for the angles $\alpha 1$ and $\alpha 2$ are contemplated by the present disclosure.

Further to the above, each fiber 6502 includes an intermediate portion 6502*b* extending between two end portions 6502*a* and 6502*c*. Likewise, each fiber 6503 includes an intermediate portion 6503*b* extending between two end portions 6503*a* and 6503*c*. The intermediate portions 6502*b* and 6503*b* intersect forming an angle $\alpha 3$ therebetween, as illustrated in FIG. 105. The angle $\alpha 3$ is less than 90°. In certain instances, the angle α3 is selected from a range of about 15° to about 85°, for example. In at least one instance, the angle α3 is about 35°, for example. Other values for the angle α3 are contemplated by the present disclosure.

Referring again to FIG. 105, an end portion 6502a of a fiber 6502 intersects an end portion 6503a of an adjacent fiber 6503 and defines an angle α4 therebetween. The end portions 6502a and 6503a are anchored to the top portion 6512 at their points of intersection. Likewise, an end portion 6502c intersects an end portion 6503c defining an angle α5 therebetween. The end portions 6502c and 6503c are anchored to the bottom portion 6514 at their points of intersection. In certain instances, the angles α4 and α5 are the same, or at least substantially the same. In at least one instance, the angles α4 and α5 are selected from a range of about 15 to about 85, for example.

Further to the above, the compressible adjunct assembly 6500 includes a bonding medium 6510 that defines nexus points or bonding nodes that reinforce the three-dimensional structure of the compressible adjunct assembly 6500. Bonding nodes 6504a include intersecting the end portions 6502a and 6503a that are surrounded, or at least partially surrounded, by the bonding medium 6510 which affixes the intersecting end portions 6502a and 6503a. Likewise, bonding nodes 6504c include intersecting the end portions 6502c and 6503c that are surrounded, or at least partially surrounded, by the bonding medium 6510 which affixes the intersecting end portions 6502c and 6503c. The compressible adjunct assembly 6500 includes bonding nodes 6504b that include intersecting the intermediate portions 6502b and 6503b that are surrounded, or at least partially surrounded, by the bonding medium 6510 which affixes the intersecting intermediate portions 6502b and 6503b. Like the compressible adjunct assembly 6200, the compressible adjunct assembly 6500 also includes bonding fibers that are melted and resolidified to form the bonding medium 6510 in the same, or at least substantially the same, manner the bonding medium 6310 is formed.

Referring again to FIG. 105, the bonding nodes 6504a are aligned in a top row 6516, the bonding nodes 6504c are aligned in a bottom row 6518, and the bonding nodes 6504b are aligned in an intermediate row 6520 between the top row 6516 and the bottom row 6518. The intermediate row 6520 of the bonding nodes 6504b is out of alignment with the top row 6516 of the bonding nodes 6504a and the bottom row 6518 of the bonding nodes 6504c. Said another way, a bonding node 6504b is aligned with a first gap between two consecutive bonding nodes 6504a, and a second gap between two consecutive bonding nodes 6504c. This arrangement improves the stability of the compressible adjunct assembly 6500. The intermediate row 6520 is equidistant, or at least substantially equidistant, from the rows 6516 and 6518. In certain instances, the intermediate row 6520 is closer to the top row 6516 than the bottom row 6518. Alternatively, in other instances, the intermediate row 6520 can be closer to the bottom row 6518 than the top row 6516. The reader will appreciate that the terms top and bottom as used herein are for convenience purposes only. The compressible adjunct assembly 6500 can be turned up side down such that the bottom row 6516 is on the top and the top row 6518 is on the bottom.

Referring again to FIG. 105, the bonding medium 6510 at the bonding nodes 6504b prevents, or at least resists, translation of the transecting fibers 6502 and 6503 relative to one another. This arrangement can, at least in part, increase the column strength of the compressible adjunct assembly 6500 and/or improve its spring rate. Although the compressible adjunct assembly 6500 is depicted to only have three rows of bonding nodes. It is understood that this number of rows is provided as an example. In certain instances, the compressible adjunct assembly 6500 may include only two rows of bonding nodes. Alternatively, the compressible adjunct assembly 6500 may include four or more rows of bonding nodes.

In certain instances, a first building block of the compressible adjunct assembly 6500 includes five bonding nodes, wherein a central bonding node 6504b is suspended between two first bonding nodes 6504a and two first bonding nodes 6504c. The central bonding node 6504b is tethered to each of the four bonding nodes 6502a and 6502c by a portion of either a fiber 6502 or a fiber 6503. Tethering portions 6522 are not covered by the bonding medium 6510. A second building block of the compressible adjunct assembly 6500 may be positioned on a first side of the first building block. The second building block may also be comprised of five bonding nodes, and may share bonding nodes with the first building block. Moreover, a third building block of the compressible adjunct assembly 6500 may be positioned on a second side of the first building block opposite the first side, for example, such that the first building block is positioned between the second building block and the third building block. The third building block may also be comprised of five bonding nodes, and may share bonding nodes with the first building block.

Referring again to FIG. 105, as described above, the tethering portions 6522 of the fibers 6502 and 6503 are not covered by the bonding medium 6510. Alternatively, one or more of the tethering portions 6522 can be covered, or at least partially covered, by the bonding medium 6510 to increase the stiffness of the building blocks of the compressible adjunct assembly 6500, which increases the overall stiffness of the compressible adjunct assembly 6500. It is envisioned that the stiffness of the compressible adjunct assembly 6500 can be controlled by varying the stiffness of the tethering portions 6522 to selectively produce a more or less compressible adjunct 6522.

Figure 106:
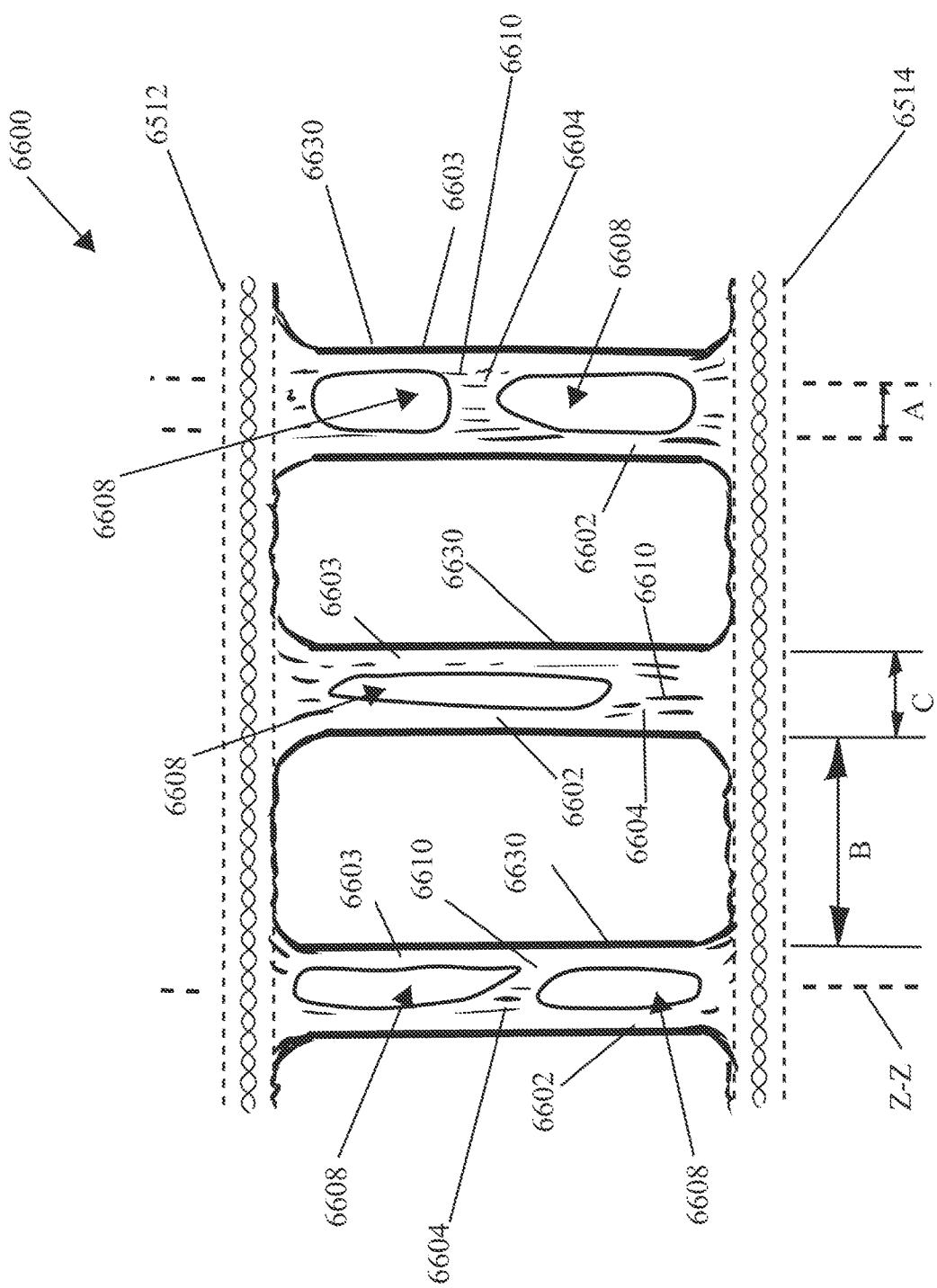
FIG. 106 is a partial cross-sectional view of a compressible adjunct assembly in accordance with at least one embodiment described herein.

Referring now to FIG. 106, a compressible adjunct assembly 6600 is similar in many respects to the compressible adjunct assemblies 6300, 6400, and 6500. For example, the compressible adjunct assembly 6600 can be releasably attached to a jaw member of a surgical stapling and severing instrument such as, for example, the anvil 8014 and/or the staple cartridge 10000 of the surgical stapling and severing instrument 8010. Also, the compressible adjunct assembly 6600 includes the top portion 6512 and the bottom portion 6514.

Further to the above, the compressible adjunct assembly 6600 includes a plurality of building blocks 6630. As illustrated in FIG. 106, a building block 6630 includes a first fiber 6602, a second fiber 6603, and a bonding fiber. The bonding fiber is melted and resolidified to form a bonding medium 6610 in the same, or at least substantially the same, manner that the bonding mediums 6310, 6410, and 6510 are formed. The fibers 6602 and 6603 in a building block 6630 extend in parallel, or at least substantially in parallel, with one another between the top portion 6512 and the bottom portion 6514. An inner transverse distance "A" separates the fibers 6602 and 6603. The bonding fiber extends, or at least partially extends, between the top portion 6512 and the bottom portion 6514 along a transverse axis Z-Z defined in the space between the fibers 6602 and 6603.

Referring again to FIG. 106, the bonding medium 6610 defines nexus points or bonding nodes 6604 that reinforce the three-dimensional structure of the compressible adjunct assembly 6600. The bonding nodes 6604 include adjacent portions of the fibers 6302 and 6603 that are surrounded, or at least partially surrounded, by the bonding medium 6110 which affixes such adjacent portions of the fibers 6302 and 6603. The fibers 6602 and 6603 are completely embedded in the bonding medium 6610. Alternatively, in certain instances, the fibers 6602 and 6603 are only partially embedded in, or covered by, the bonding medium 6610.

The inner transverse distance "A" within a building block 6630 of the compressible adjunct assembly 6600 can determine, at least in part, the extent to which such space is filled or bridged by the bonding medium 6610. The fluidity of the melted bonding fibers and/or the thickness of the bonding fibers can also determine whether the bonding medium 6610 is capable of filling or bridging the inner transverse distance "A". Spaces that remain unfilled define gaps 6608 that can be in different shapes and sizes, as illustrated in FIG. 106. The number and size of the gaps 6608 determine, among other things, the porosity of the compressible adjunct assembly 6600. Accordingly, the porosity of the compressible adjunct assembly 6600 within a building block 6630 can be increased by increasing the inner transverse distance "A". Alternatively, the porosity of the compressible adjunct assembly 6600 within a building block 6630 can be decreased by decreasing the inner transverse distance "A".

Referring again to FIG. 106, adjacent building blocks 6630 are spaced apart with sufficient space therebetween to prevent flow of the melted bonding fibers between the adjacent building blocks 6630. An intermediate distance "B" is defined between adjacent building blocks 6630. The intermediate distance "B" is greater than the inner transverse distance "A". The intermediate distance "B" is also greater than an outer transverse distance "C" defined by the building blocks 6630. In at least one instance, the ratio of the outer transverse distance "C" to the intermediate distance "B" is any ratio selected from a range of about 0.1, for example, to about 0.9, for example. In at least one instance, the ratio of the outer transverse distance "C" to the intermediate distance "B" is any ratio selected from a range of about 0.2, for example, to about 0.8, for example. In at least one instance, the ratio of the outer transverse distance "C" to the intermediate distance "B" is any ratio selected from a range of about 0.3, for example, to about 0.7, for example. In at least one instance, the ratio of the outer transverse distance "C" to the intermediate distance "B" is about 0.4, for example. Other values for the ratio of the outer transverse distance "C" to the intermediate distance "B" are contemplated by the present disclosure.

Figure 107:
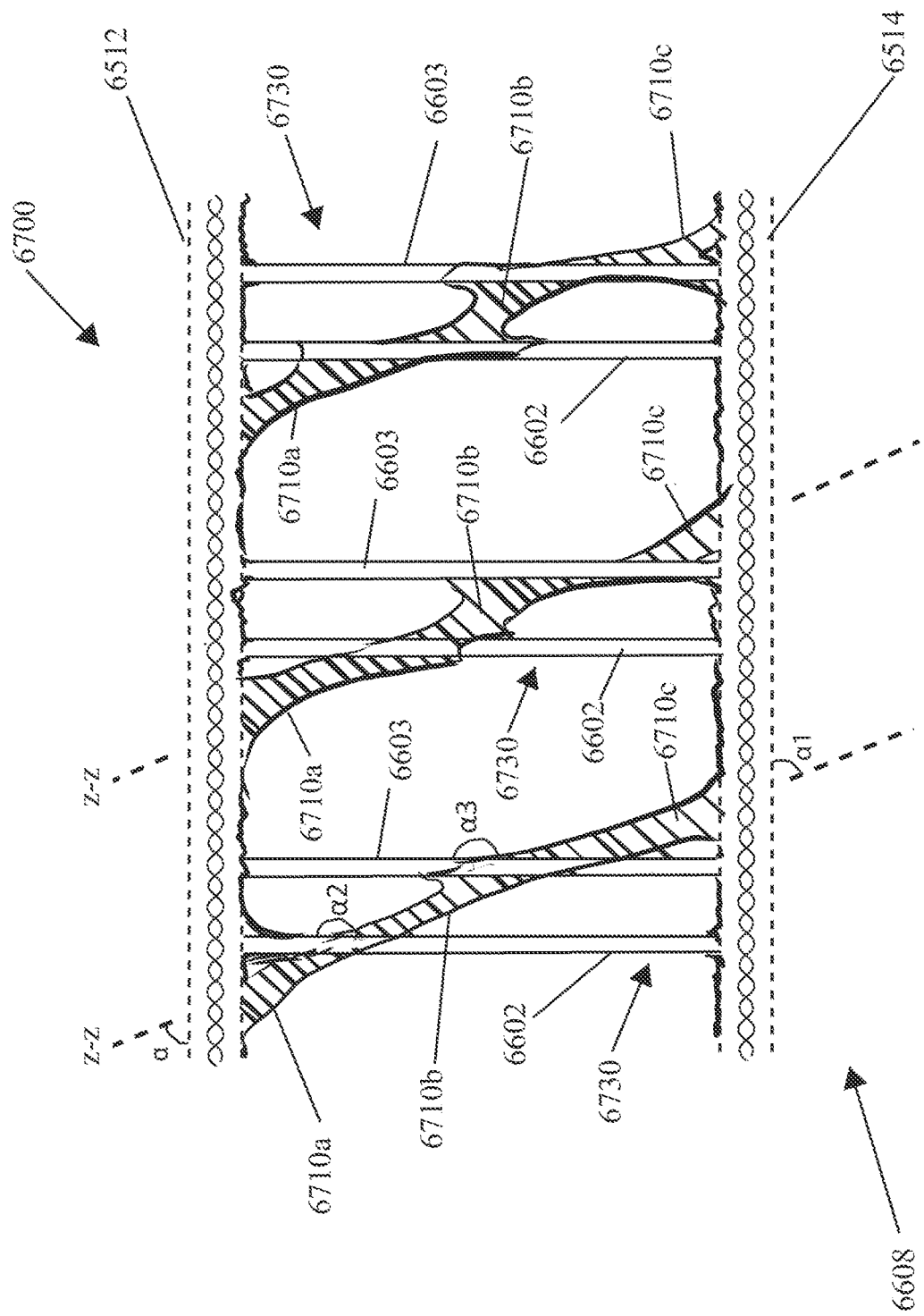
FIG. 107 is a partial cross-sectional view of a compressible adjunct assembly in accordance with at least one embodiment described herein.

Referring now to FIG. 107, a compressible adjunct assembly 6700 is similar in many respects to the compressible adjunct assemblies 6300, 6400, 6500, and 6600. For example, the compressible adjunct assembly 6700 can be releasably attached to a jaw member of a surgical stapling and severing instrument such as, for example, the anvil 8014 and/or the staple cartridge 10000 of the surgical stapling and severing instrument 8010. Also, the compressible adjunct assembly 6700 includes the top portion 6512, the bottom portion 6514, and a plurality of building blocks 6730 that include the first fiber 6602 and the second fiber 6603. In addition, the building blocks 6730 include angled bonding fibers that are melted and resolidified to form a bonding medium 6710 in the same, or at least substantially the same, manner that the bonding mediums 6310, 6410, 6510 and 6610 are formed.

Referring now to FIG. 107, the bonding medium 6710 within a building block 6730 extends, or at least partially extends, along an axis z-z that transects the top portion 6512 and the bottom portion 6514 at an angle $\alpha 1$. The angle $\alpha 1$ is less than 90°. In certain instances, the angle $\alpha 1$ is in a range of about 15° to about 85°. In at least one instance, the angle $\alpha 1$ is about 45°. Other values for the angle $\alpha 1$ are contemplated by the present disclosure.

The bonding medium 6710 within a building block 6730 includes a first bonding portion 6710a extending between the top portion 6512 and a first fiber 6602 on a first side of the fiber 6602. A second bonding portion 6710b extends between a second side of the first fiber 6602 and a first side of a fiber 6603 extending in parallel, or at least substantially in parallel, with the first fiber 6602. In addition, a third bonding portion 6710c extends between a second side of the second fiber 6603 and the bottom portion 6214. The first bonding portion 6710a affixes the first fiber 6602 to the top portion 6512 and the third bonding portion 6710c affixes the second fiber 6603 to the bottom portion 6514. In addition, the second bonding portion 6710b affixes the first fiber 6602 to the second fiber 6603. Such an arrangement stabilizes the building block 6730 by providing additional anchors for the fibers 6602 and 6603 in the form of the bonding portions 6710a and 6710c, respectively, and by affixing the first fiber 6602 to the second fiber 6603 via the second bonding portion 6710b, as illustrated in FIG. 107.

Further to the above, the fiber portion 6710a, 5710b, and 6710c extend along an axis z-z at an intersection angles $\alpha 2$ and $\alpha 3$. In at least one instance, the intersection angles $\alpha 2$ and $\alpha 3$ are the same. In at least one instance, the intersection angles $\alpha 2$ and $\alpha 3$ are different. In at least one instance, one or both of the intersection angles $\alpha 2$ and $\alpha 3$ are in a range of about 105° to about 175°, for example. In at least one instance, one or both of the intersection angles $\alpha 2$ and $\alpha 3$ are in a range of about 125° to about 165°, for example. Other values for the intersection angles $\alpha 2$ and $\alpha 3$ are contemplated by the present disclosure.

Further to the above, an implantable layer, or adjunct, can be manufactured and/or modified utilizing any suitable process to provide the layer with desirable properties. In various instances, an implantable adjunct can be manufactured utilizing fused filament fabrication, for example. In at least one such instance, a polymeric filament, for example, is fed into an extruder, heated, and then forced through a nozzle into a mold and/or directly onto a staple cartridge. The filament is fed into an extruder by a pinch system which can control the direction and/or rate in which the filament is fed into the extruder. The filament is at least partially melted by a heater block. The heater block can be positioned upstream with respect to the nozzle and/or within the nozzle. The mold and/or staple cartridge is positioned on a movable bed which can be moved relative to the nozzle. Such a fused filament fabrication process can be used to control the porosity within the implantable adjunct. In at least one instance, the heated polymeric filament is dispensed in interconnected patterns utilizing triangles, arcs, hexagonal shapes, and/or any suitable polygonal shapes, for example. Moreover, the heated polymeric material can be dispensed in one layer or a plurality of layers stacked on one another. The pattern(s) and the number of layers in which the polymeric material is dispensed can control the porosity of the implantable adjunct. A more porous implantable adjunct can promote tissue in-growth into the implantable adjunct. In addition, such a process can create an implantable adjunct without using a lyophilization process and/or dioxane, for example.

Further to the above, a laser process can be utilized to create openings in an implantable adjunct. In at least one instance, a laser can be utilized to cut holes into an extruded film comprised of PGA and/or PCL, for example. The film can comprise a thickness of approximately 0.003", for example, and the holes can comprise a diameter of approximately 0.001", for example. The holes can be microvoids, for example, and can comprise any suitably-shaped perimeter, such as round, hexagonal, and/or triangular, for example. Any suitable number of holes can be created. For example, hundreds of holes could be utilized in an implantable adjunct. The holes can be uniformly distributed, or distributed in any suitable manner. In various instances, the holes can be distributed in a pattern including rows which are aligned laterally, longitudinally, and/or diagonally, for example. In various instances, several layers of extruded film can be stacked and bonded to one another to form the implantable adjunct. For instance, four or five film layers could be used, for example. Also, for instance, the film layers can be bonded by heating the film layers above the glass transition temperature of at least one of the film layers without utilizing an adhesive. The layers of film can have the same pattern of holes, or different patterns. In certain instances, at least one of the layers has apertures while at least one of the layers does not. In various instances, the laser process could be utilized to remove bulk shapes from the implantable adjunct, or a layer of the implantable adjunct. In at least one such instance, a line could be formed in a layer along the longitudinal cut line and/or toward the outer perimeter of the implantable adjunct, for example, to create a stepped effect, especially when such a layer is stacked with and bonded to another layer not having such bulk shapes removed. In various instances, the laser process can be utilized to create a feathering effect along the outer edges of the implantable adjunct and/or along the inner lines discussed above, for example. For instance, the laser process can be utilized to reduce the thickness of the implantable adjunct along the perimeter, and/or within an opening defined in the implantable adjunct, from approximately 0.006" to approximately 0.002" to 0.003", for example. Moreover, the laser process can be utilized to make any other suitable localized changes to the implantable adjunct. For instance, the density of the holes in the portions of the adjunct that are captured by the staples can be tuned to soften the adjunct in those areas. In at least one instance, the holes can be limited to certain zones. For example, stronger, non-hole zones can be created in the adjunct which are aligned with the staple legs while weaker, hole-zones are aligned with the staple crowns or bases. The reverse of the above-described example is also possible. Although a laser process can be utilized to modify an implantable adjunct comprised of film, for example, the laser process could be utilized to modify an implantable adjunct comprised of foam and/or melt-blown non-woven material, for example. In addition to or in lieu of the laser process described above, water-cutting, stamping, punching and/or piercing, for example, could be utilized. Also, in addition to or in lieu of the laser process described above, an implantable adjunct can undergo a dimpling process which can locally stretch the adjunct. The dimples can have a thickness that is thinner than the non-dimpled areas of the adjunct. The dimples can be used in the same or similar manner as the holes to achieve the same or similar results. In various instances, the dimples and/or holes can be present in any suitable layer of an adjunct. In at least one instance, the dimples and/or holes are buried, or present in an inner layer, of the adjunct, for example. In certain instances, the selective use of low molecular weight polymers within an adjunct comprised of high molecular weight polymers can be utilized to create softer regions within the adjunct. Ultimately, the processes described above can be utilized to create a compliant, highly elastic, and stretchable implantable adjunct having a porosity which is sufficient to promote tissue ingrowth.

EXAMPLES

Example 1

A method of applying an implantable layer to a cartridge body comprising the steps of obtaining a staple cartridge body including staple cavities, heating a polymeric material, and accelerating the heated polymeric material toward the staple cartridge body such that an implantable layer is formed over the staple cavities.

Example 2

The method of Example 1, further comprising the step of inserting staples into the staple cavities before the accelerating step.

Example 3

The method of Examples 1 or 2, further comprising the steps of cooling the heated polymeric material and trimming the polymeric material after the cooling step.

Example 4

The method of Example 3, wherein the cartridge body comprises a periphery, and wherein the implantable layer is trimmed according to the periphery during the trimming step.

Example 5

The method of Examples 1, 2, 3, or 4, wherein the heating step comprises heating the polymeric material above its glass transition temperature.

Example 6

The method of Examples 1, 2, 3, 4, or 5, wherein the heating step comprises heating the polymeric material above its melt temperature.

Example 7

The method of Examples 1, 2, 3, 4, 5, or 6, further comprising the steps of heating a second polymeric material and accelerating the second heated polymeric material toward the staple cartridge body such that a second implantable layer is formed over the staple cavities.

Example 8

The method of Examples 1, 2, 3, 4, 5, 6, or 7, wherein the heated polymeric material comprises a first heated polymeric material, and wherein the accelerating step comprises accelerating a second heated polymeric material with the first heated polymeric material toward the staple cartridge body.

Example 9

The method of Examples 1, 2, 3, 4, 5, 6, 7, or 8, wherein the method is performed without mixing the polymeric material with a solvent.

Example 10

The method of Examples 1, 2, 3, 4, 5, 6, 7, 8, or 9, wherein the method is performed without mixing the polymeric material with dioxane.

Example 11

The method of Examples 1, 2, 3, 4, 5, 6, 7, 8, 9, or 10, wherein the accelerating step comprises accelerating the polymeric material utilizing an electric charge.

Example 12

The method of Examples 1, 2, 3, 4, 5, 6, 7, 8, 9, 10, or 11, wherein the accelerating step comprises accelerating the polymeric material utilizing a voltage differential.

Example 13

The method of Examples 1, 2, 3, 4, 5, 6, 7, 8, 9, 10, 11, or 12, wherein the accelerating step comprises accelerating the polymeric material utilizing a spinning member.

Example 14

The method of Examples 1, 2, 3, 4, 5, 6, 7, 8, 9, 10, 11, 12, or 13, wherein the accelerating step comprises pouring the polymeric material onto the staple cartridge body utilizing gravity.

Example 15

The method of Examples 1, 2, 3, 4, 5, 6, 7, 8, 9, 10, 11, 12, 13, or 14, wherein the accelerating step comprises the steps of applying a translational acceleration to the polymeric material and applying a rotational acceleration to the polymeric material.

Example 16

The method of Examples 1, 2, 3, 4, 5, 6, 7, 8, 9, 10, 11, 12, 13, 14, or 15, wherein the accelerating step comprises creating a random, porous polymeric structure on the staple cartridge body.

Example 17

The method of Examples 1, 2, 3, 4, 5, 6, 7, 8, 9, 10, 11, 12, 13, 14, 15, or 16, wherein the heating step comprises liquefying the polymeric material.

Example 18

The method of Examples 1, 2, 3, 4, 5, 6, 7, 8, 9, 10, 11, 12, 13, 14, 15, or 16, wherein the heating step does not comprise liquefying the polymeric material.

Example 19

A method of applying an implantable layer to a cartridge body comprising the steps of obtaining a staple cartridge body including staple cavities, heating a polymeric material, and applying the heated polymeric material directly onto the staple cartridge body such that an implantable layer is formed over the staple cavities.

Example 20

A method of applying an implantable layer to a cartridge body comprising the steps of obtaining a staple cartridge body including staple cavities, heating a material, and accelerating the heated material toward the staple cartridge body such that an implantable layer is formed over the staple cavities.

Example 21

A staple cartridge assembly comprising a cartridge body comprising a deck, a plurality of staples and an implantable layer positioned over the deck. The implantable layer comprises a first plurality of fibers comprised of a first material having a first thermal transition temperature and a second plurality of fibers comprised of a second material having a second thermal transition temperature, wherein the second thermal transition temperature is lower than the first thermal transition temperature, wherein the second material is intermixed with the first material, and wherein the second fibers are contracted within the layer during a process which exposes the layer to a process temperature which exceeds the second thermal transition temperature.

Example 22

The staple cartridge assembly of Example 21, wherein the second plurality of fibers are arranged in a structural lattice frame, and wherein the structural lattice frame contracts during the process.

Example 23

The staple cartridge assembly of Examples 21 or 22, wherein the second material comprises polydioxanone.

Example 24

The staple cartridge assembly of Examples 21, 22, or 23, wherein the first material comprises polyglycolic acid.

Example 25

The staple cartridge assembly of Examples 21, 22, 23, or 24, wherein the implantable layer is part of an implantable layer assembly which further comprises a laminate film.

Example 26

The staple cartridge assembly of Examples 21, 22, 23, 24, or 25, wherein the process temperature is less than the first thermal transition temperature.

Example 27

A staple cartridge assembly comprising a cartridge body comprising a deck, a plurality of staples, and an implantable layer positioned over the deck. The implantable layer comprises a mesh comprised of a first material having a first thermal transition temperature and fibers comprised of a second material having a second thermal transition temperature, wherein the first thermal transition temperature is lower than the second thermal transition temperature, wherein the fibers are interwoven with the mesh, and wherein the mesh is constricted during a process which exposes the layer to a process temperature which exceeds the first thermal transition temperature.

Example 28

The staple cartridge assembly of Example 27, wherein the first material comprises polydioxanone.

Example 29

The staple cartridge assembly of Examples 27 or 28, wherein the second material comprises polyglycolic acid.

Example 30

The staple cartridge assembly of Examples 27, 28, or 29, wherein the implantable layer is part of an implantable layer assembly which further comprises a laminate film.

Example 31

The staple cartridge assembly of Examples 27, 28, 29, or 30, wherein the process temperature is less than the second thermal transition temperature.

Example 32

A staple cartridge assembly comprising a cartridge body comprising a deck, a plurality of staples, and an implantable layer positioned over the deck. The implantable layer comprises a first plurality of fibers comprised of a first material having a first glass transition temperature and a second plurality of fibers comprised of a second material having a second glass transition temperature, wherein the second glass transition temperature is lower than the first glass transition temperature, wherein the second material is interwoven with the first material, and wherein the second glass transition temperature has been previously exceeded to contract the second fibers.

Example 33

The staple cartridge assembly of Example 32, wherein the first material comprises polydioxanone.

Example 34

The staple cartridge assembly of Examples 32 or 33, wherein the second material comprises polyglycolic acid.

Example 35

The staple cartridge assembly of Examples 32, 33, or 34, wherein the implantable layer is part of an implantable layer assembly which further comprises a laminate film.

Example 36

A method of manufacturing an implantable layer, the method comprising the steps of obtaining first fibers comprised of a first material having a first thermal transition temperature, obtaining second fibers comprised of a second material having a second thermal transition temperature, wherein the second thermal transition temperature is lower than the first thermal transition temperature, intermixing the first fibers with the second fibers, and heating the second fibers to a processing temperature which exceeds the second thermal transition temperature so that the second fibers contract after the intermixing step.

Example 37

The method of Example 36, wherein the intermixing step comprises interweaving the first fibers and the second fibers.

Example 38

The method of Examples 36 or 37, wherein the processing temperature does not exceed the first thermal transition temperature.

Example 39

The method of Examples 36, 37, or 38, wherein the intermixing step comprises interweaving the first fibers into a mesh of the second fibers.

Example 40

A compressible adjunct for use with a surgical instrument, wherein the compressible adjunct comprises a hollow fibrous construct and a core fibrous construct housed within the hollow fibrous construct, wherein the hollow fibrous construct comprises at least one biocompatible material that experienced at least one transition from a more ordered phase to a less ordered phase in response to heating the hollow fibrous construct to a predetermined temperature.

Example 41

The compressible adjunct of Example 40, wherein the at least one transition constricts the hollow fibrous construct around the core fibrous construct.

Example 42

The compressible adjunct of Examples 40 or 41, wherein the at least one transition comprises an increase in entropy.

Example 43

The compressible adjunct of Examples 40, 41, or 42, wherein the at least one biocompatible material is an elastomer.

Example 44

The compressible adjunct of Examples 40, 41, 42, or 43, wherein the core fibrous construct comprises the at least one biocompatible material.

Example 45

The compressible adjunct of Examples 40, 41, 42, 43, or 44, wherein the hollow fibrous construct is transitioned from a first size to a second size smaller than the first size in response to the at least one transition.

Example 46

The compressible adjunct of Examples 40, 41, 42, 43, 44, or 45, further comprising an elongate slot, wherein the elongate slot extends along a length of the hollow fibrous construct, and wherein the elongate slot extends along a length of the core fibrous construct.

Example 47

A compressible adjunct for use with a surgical instrument, the compressible adjunct comprising a hollow fibrous construct comprising a first fibrous tubular member defining a space within and a second fibrous tubular member treated with at least one thermal treatment, wherein the hollow fibrous construct extends at least partially through the space.

Example 48

The compressible adjunct of Example 47, wherein the first fibrous tubular member is shrunk around the second fibrous tubular member in response to the at least one thermal treatment.

Example 49

The compressible adjunct of Examples 47 or 48, wherein the first fibrous tubular member comprises at least one biocompatible material that experienced at least one transition from a more ordered phase to a less ordered phase in response to the at least one thermal treatment.

Example 50

The compressible adjunct of Examples 47, 48, or 49, wherein the hollow fibrous construct comprises at least one biocompatible material that experienced a temporary phase transition in response to the at least one thermal treatment.

Example 51

The compressible adjunct of Examples 49 or 50, wherein the at least one biocompatible material is an elastomer.

Example 52

The compressible adjunct of Examples 49, 50, or 51, wherein the at least one biocompatible material is absorbable.

Example 53

The compressible adjunct of Examples 47, 48, 49, 50, 51, or 52, wherein the hollow fibrous construct comprises a first biocompatible material that experienced a temporary phase change in response to the at least one thermal treatment and a second biocompatible material that remained in a solid phase during the at least one thermal treatment.

Example 54

The compressible adjunct of Example 47, wherein the hollow fibrous construct is transitioned from a first size to a second size smaller than the first size in response to the at least one thermal treatment.

Example 55

A method for preparing a compressible adjunct for use with a surgical instrument, the method comprising providing a first fibrous tubular member defining a space there within, providing a second fibrous tubular member sized to fit into the space, inserting the second fibrous tubular member into the space, and effecting an at least one change in at least one of the first fibrous tubular member and the second fibrous tubular member through at least one thermal treatment.

Example 56

The method of Example 55, wherein the effecting step comprises shrinking the first fibrous tubular member around the second fibrous tubular member.

Example 57

The method of Examples 55 or 56, wherein at least one of the first fibrous tubular member and the second fibrous tubular member comprises at least one biocompatible material, and wherein the effecting step comprises effecting a temporary phase change in the at least one biocompatible material.

Example 58

The method of Examples 55, 56, or 57, wherein at least one of the first fibrous tubular member and the second fibrous tubular member comprises at least one biocompatible material, and wherein the effecting step comprises at least one transition in the at least one biocompatible material from a more ordered phase to a less ordered phase.

Example 59

The method of Examples 55, 56, 57, or 58, wherein the effecting step comprises at least one change in size in the at least one of the first fibrous tubular member around the second fibrous tubular member.

Example 60

A staple cartridge assembly comprising a cartridge body comprising a deck, a plurality of staples, and an implantable layer positioned over the deck, wherein the implantable layer comprises a plurality of interwoven fibers, and wherein each fiber comprises a strand having a kinked configuration.

Example 61

The staple cartridge assembly of Example 60, wherein the kinked configuration of the fibers is produced by exposing the fibers to heat.

Example 62

The staple cartridge assembly of Examples 60 or 61, wherein the kinked fibers are interwoven into a first woven zone and a second woven zone, wherein the first woven zone has a first density and the second woven zone has a second density, and wherein the first density is different than the second density.

Example 63

The staple cartridge assembly of Example 62, wherein the implantable layer comprises a perimeter, wherein the second density is greater than the first density, and wherein the second woven zone is defined along the perimeter.

Example 64

The staple cartridge assembly of Example 62, wherein the cartridge body comprises a longitudinal slot configured to receive a cutting portion, wherein the first density is less than the second density, and wherein the first woven zone is aligned with the longitudinal slot.

Example 65

The staple cartridge assembly of Examples 62 or 63, further comprising an anchor extending over the implantable layer to releasably hold the layer to the cartridge body, wherein the second density is greater than the first density, and wherein the anchor is aligned with the second woven zone.

Example 66

The staple cartridge assembly of Example 65, wherein the cartridge body further comprises a longitudinal slot, wherein the longitudinal slot is configured to receive a cutting member, and wherein the cutting member is configured to transect the anchor as the cutting member moves within the longitudinal slot.

Example 67

The staple cartridge assembly of Examples 65 or 66, further comprising a proximal end, wherein the anchor and the second woven zone are adjacent the proximal end.

Example 68

The staple cartridge assembly of Example 67, further comprising a distal end opposite the proximal end, a distal anchor extending over the implantable layer to releasably hold the layer to the cartridge body, and a third woven zone defined in the layer having a third density which is greater than the first density, wherein the distal anchor is aligned with the third woven zone.

Example 69

The staple cartridge assembly of Examples 62, 63, 64, 65, 66, 67, or 68, wherein the cartridge body comprises a first longitudinal row of staple cavities and a second longitudinal row of staple cavities, wherein the first woven zone is aligned with the first row of staple cavities and the second woven zone is aligned with the second row of staple cavities.

Example 70

The staple cartridge assembly of Examples 60, 61, 62, 63, 64, 65, 66, 67, 68, or 69, wherein the kinked fibers are interwoven into a first woven zone and a second woven zone, wherein the first woven zone has a first modulus of elasticity and the second woven zone has a second modulus of elasticity, and wherein the first modulus of elasticity is different than the second modulus of elasticity.

Example 71

The staple cartridge assembly of Example 70, wherein the implantable layer comprises a perimeter, wherein the second density is greater than the first density, and wherein the second woven zone is defined along the perimeter.

Example 72

The staple cartridge assembly of Examples 70 or 71, wherein the cartridge body comprises a longitudinal slot configured to receive a cutting portion, wherein the first modulus of elasticity is less than the second modulus of elasticity, and wherein the first woven zone is aligned with the longitudinal slot.

Example 73

The staple cartridge assembly of Examples 70 or 71, further comprising an anchor extending over the implantable layer to releasably hold the layer to the cartridge body, wherein the second modulus of elasticity is greater than the first modulus of elasticity, and wherein the anchor is aligned with the second woven zone.

Example 74

The staple cartridge assembly of Example 73, wherein the cartridge body further comprises a longitudinal slot, wherein the longitudinal slot is configured to receive a cutting member, and wherein the cutting member is configured to transect the anchor as the cutting member moves within the longitudinal slot.

Example 75

The staple cartridge assembly of Examples 73 or 74, further comprising a proximal end, wherein the anchor and the second woven zone are adjacent the proximal end.

Example 76

The staple cartridge assembly of Example 75, further comprising a distal end opposite the proximal end, a distal anchor extending over the implantable layer to releasably hold the layer to the cartridge body, and a third woven zone defined in the layer having a third modulus of elasticity which is greater than the first modulus of elasticity, wherein the distal anchor is aligned with the third woven zone.

Example 77

The staple cartridge assembly of Examples 70, 71, 72, 73, 74, 75, or 76, wherein the cartridge body comprises a first longitudinal row of staple cavities and a second longitudinal row of staple cavities, wherein the first woven zone is aligned with the first row of staple cavities and the second woven zone is aligned with the second row of staple cavities.

Example 78

A method of manufacturing an implantable layer, the method comprising the steps of obtaining fibers, weaving the fibers, unweaving the fibers after the weaving step, kinking the fibers after the unweaving step, and reweaving the fibers into an implantable layer after the kinking step.

Example 79

The method of Example 78, wherein the reweaving step comprises knitting the fibers into a fluffy fabric.

Example 80

A compressible adjunct for use with a surgical instrument including a staple cartridge deck, wherein the compressible adjunct comprises a first biocompatible material, a second biocompatible material with a lower melting temperature than the first biocompatible material, and a body comprising a face positionable against a length of the staple cartridge deck. The face comprises a plurality of attachment regions spaced apart from one another, wherein the plurality of attachment regions include the second biocompatible material, and wherein the face is selectively attachable to the staple cartridge deck at the plurality of attachment regions. The face further comprises a plurality of non-attachment regions extending between the plurality of attachment regions, wherein the second biocompatible material is selectively disposed outside the non-attachment regions.

Example 81

The compressible adjunct of Example 80, wherein the plurality of attachment regions define an attachment pattern.

Example 82

The compressible adjunct of Examples 80 or 81, wherein the body comprises a woven fibrous construct.

Example 83

The compressible adjunct of Examples 80, 81, or 82, wherein at least one of the first biocompatible material and the second biocompatible material is absorbable.

Example 84

The compressible adjunct of Examples 80, 81, 82, or 83 wherein the second biocompatible material is poly-p-dioxanone (PDS).

Example 85

A staple cartridge assembly for use with a surgical stapling instrument, wherein the staple cartridge assembly comprises a staple cartridge comprising a plurality of staples and a cartridge deck comprising an outer surface. The staple cartridge further comprises a fibrous construct comprising, one, a body comprising a first plurality of fibers comprised of a first biocompatible material having a first melting temperature and, two, a face positioned against the outer surface of the cartridge deck. The face comprises a plurality of attachment regions spaced apart from one another, wherein each of the plurality of attachment regions comprises a second plurality of fibers comprised of a second biocompatible material having a second melting temperature lower than the first melting temperature and a plurality of non-attachment regions extending between the plurality of attachment regions, wherein the non-attachment regions exclude the second plurality of fibers, and wherein the face is selectively attached to the outer surface at the plurality of attachment regions by temporarily heating the face to a temperature greater than or equal to the second melting temperature but less than the first melting temperature.

Example 86

The staple cartridge assembly of Example 85, wherein the plurality of attachment regions define an attachment pattern.

Example 87

The staple cartridge assembly of Examples 85 or 86, wherein the fibrous construct is a woven fibrous construct.

Example 88

The staple cartridge assembly of Examples 85, 86, or 87, wherein at least one of the first biocompatible material and the second biocompatible material is absorbable.

Example 89

The staple cartridge assembly of Examples 85, 86, 87, or 88, wherein the second biocompatible material is poly-p-dioxanone (PDS).

Example 90

The staple cartridge assembly of Examples 85, 86, 87, 88, or 89, wherein the cartridge deck further comprises at least one attachment member configured to secure the fibrous construct to the outer surface.

Example 91

The staple cartridge assembly of Example 90, wherein the at least one attachment member comprises a mechanical barb.

Example 92

The staple cartridge assembly of Examples 85, 86, 87, 88, 89, 90, or 91, wherein the outer surface comprises a plurality of rough zones.

Example 93

The staple cartridge assembly of Example 92, wherein the rough zones are etched into the outer surface.

Example 94

A staple cartridge assembly for use with a surgical stapling instrument, wherein the staple cartridge assembly comprises a staple cartridge comprising a plurality of staples and a cartridge deck. The cartridge deck comprises an outer surface comprising a plurality of attachment zones spaced apart from one another and a plurality of bonding islands, wherein each of the plurality of bonding islands is disposed within one of the attachment zones, and wherein each of the plurality of bonding islands is comprised of a first biocompatible material. The staple cartridge assembly further comprises a compressible layer positioned against the cartridge deck, wherein the compressible layer is comprised of a second biocompatible material different from the first biocompatible material, and wherein the compressible layer is secured to the cartridge deck by a temporary phase transition in the first biocompatible material.

Example 95

The staple cartridge assembly of Example 94, wherein the temporary phase transition in the first biocompatible material is not accompanied by a phase transition in the second biocompatible material.

Example 96

The staple cartridge assembly of Examples 94 or 95, wherein the cartridge deck further comprises at least one attachment member configured to secure the compressible layer to the cartridge deck.

Example 97

The staple cartridge assembly of Example 96, wherein the at least one attachment member comprises a mechanical barb.

Example 98

The staple cartridge assembly of Examples 94, 95, 96, or 97, wherein the attachment zones are etched into the outer surface.

Example 99

A surgical instrument comprising a jaw member comprising an elongate slot extending along a longitudinal axis, a first outer surface on a first side of the elongate slot, and a second outer surface on a second side of the elongate slot opposite the first side. The surgical instrument further comprises a compressible adjunct assembly comprising an attachment layer comprising a first section on the first side of the elongate slot, wherein the first section is attached to the first outer surface, a second section on the second side of the elongate slot, wherein the second section is attached to the second outer surface, and an intermediary section extending between the first section and the second section, wherein the intermediary section at least partially bridges the elongate slot. The compressible adjunct assembly further comprises a first compressible adjunct on the first side of the elongate slot, and a second compressible adjunct on the second side of the elongate slot, wherein the first compressible adjunct is spaced apart from the second compressible adjunct, wherein the first section is attached to the first compressible adjunct, and wherein the second section is attached to the second compressible adjunct.

Example 100

The surgical instrument of Example 99, wherein the intermediary section comprises a bar extending along a length of the intermediary section, wherein the bar is stepped up from the first section, and wherein the bar is stepped up from the second section.

Example 101

The surgical instrument of Example 100, wherein the bar is aligned longitudinally with the elongate slot.

Example 102

The surgical instrument of Examples 100 or 101, wherein the bar protrudes into a gap defined between the first compressible adjunct and the second compressible adjunct.

Example 103

The surgical instrument of Examples 100, 101, or 102 wherein the bar protrudes into the elongate slot.

Example 104

The surgical instrument of Examples 99, 100, 101, 102, or 103, wherein the intermediary section comprises at least one anchoring feature for securing the compressible adjunct assembly to the jaw member.

Example 105

The surgical instrument of Examples 99, 100, 101, 102, 103, or 104, wherein the intermediary section comprises a plurality of projections spaced apart from one another.

Example 106

The surgical instrument of Example 105, wherein the projections are aligned longitudinally with the elongate slot.

Example 107

The surgical instrument of Examples 105 or 106, wherein the projections protrude into a gap defined between the first compressible adjunct and the second compressible adjunct.

Example 108

The surgical instrument of Examples 105, 106, or 107, wherein the projections protrude into the elongate slot.

Example 109

The surgical instrument of Examples 100, 101, 102, 103, 104, 105, 106, 107, or 108, wherein the attachment layer comprises a film.

Example 110

The surgical instrument of Examples 100, 101, 102, 103, 104, 105, 106, 107, 108, or 109, wherein the attachment layer is thinner than the first compressible adjunct, and wherein the attachment layer is thinner than the second compressible adjunct.

Example 111

The surgical instrument of Examples 100, 101, 102, 103, 104, 105, 106, 107, 108, 109, or 110, wherein the first section completely separates the first compressible adjunct from the first outer surface, and wherein the second section completely separates the second compressible adjunct from the second outer surface.

Example 112

The surgical instrument of Examples 100, 101, 102, 103, 104, 105, 106, 107, 108, 109, 110, or 111, wherein the first compressible adjunct extends laterally beyond the first section in a first direction away from the elongate slot, and wherein the first outer surface extends laterally beyond the first section in the first direction.

Example 113

The surgical instrument of Example 112, wherein the second compressible adjunct extends laterally beyond the second section in a second direction away from the elongate slot, wherein the second outer surface extends laterally beyond the second compressible adjunct in the second direction, and wherein the second direction is opposite the first direction.

Example 114

The surgical instrument of Examples 100, 101, 102, 103, 104, 105, 106, 107, 108, 109, 110, 111, 112, or 113, wherein the first outer surface comprises a first plurality of pockets, wherein the second outer surface comprises a second plurality of pockets, wherein the attachment layer is positioned between the first plurality of pockets and the second plurality of pockets.

Example 115

A surgical instrument comprising a jaw member comprising an elongate slot extending along a longitudinal axis, a first outer surface on a first side of the elongate slot, and a second outer surface on a second side of the elongate slot opposite the first side. The surgical instrument further comprises a compressible adjunct assembly comprising a compressible layer comprising a first compressible portion on the first side of the elongate slot, a second compressible portion on the second side of the elongate slot, and a first plurality of bridging portions separated by a plurality of gaps, wherein the first plurality of bridging portions extend between the first compressible portion and the second compressible portion, wherein the first plurality of bridging portions are arranged along a length of the elongate slot, and wherein each of the first plurality of bridging portions bridges the elongate slot. The compressible adjunct assembly further comprises an attachment layer comprising a first attachment portion on the first side of the elongate slot, wherein the first attachment portion is attached to the first outer surface, and wherein the first attachment portion is attached to the first compressible portion, and a second attachment portion on the second side of the elongate slot, wherein the second attachment portion is attached to the second outer surface, and wherein the second attachment portion is attached to the second compressible portion. The attachment layer further comprises a second plurality of bridging portions separated by the plurality of gaps, wherein the second plurality of bridging portions extend between the first attachment portion and the second attachment portion, wherein the second plurality of bridging portions are arranged along the length of the elongate slot, and wherein each of the second plurality of bridging portions bridges the elongate slot.

Example 116

The surgical instrument of Example 115, wherein the attachment layer comprises a film.

Example 117

The surgical instrument of Examples 115 or 116, wherein the attachment layer is thinner than the compressible layer.

Example 118

A surgical instrument comprising an anvil comprising an elongate slot extending along a longitudinal axis, an internal surface defining an internal gap connected to the elongate slot, a first outer surface on a first side of the elongate slot, and a second outer surface on a second side of the elongate slot opposite the first side. The surgical instrument further comprises a compressible adjunct assembly comprising a compressible layer comprising a first compressible portion on the first side of the elongate slot a second compressible portion on the second side of the elongate slot, and an intermediate compressible portion extending between the first compressible portion and the second compressible portion, wherein the intermediate compressible portion bridges the slot. The compressible adjunct assembly further comprises at least one attachment member comprising a first attachment portion positioned against the internal surface, a second attachment portion attached to the intermediate compressible portion, and a coupling portion connecting the first attachment portion to the second attachment portion.

Example 119

The surgical instrument of Example 118, wherein the coupling portion extends into the elongate slot.

Example 120

The surgical instrument of Examples 118 or 119, wherein the second attachment portion is embedded in the intermediate compressible portion.

Example 121

A staple cartridge assembly for use with a surgical stapling instrument, wherein the staple cartridge assembly is configured to receive a firing actuation such that, upon receiving the firing actuation, a firing assembly is configured to translate through the staple cartridge assembly from a proximal end to a distal end during a firing progression, and wherein the staple cartridge assembly comprises a cartridge body, a plurality of staples removably stored within the cartridge body, and an implantable adjunct. The implantable adjunct comprises a body portion and a plurality of distinct attachment portions configured to retain the implantable adjunct against the cartridge body, wherein the firing assembly is configured to engage each attachment portion during the firing progression, and wherein the attachment portions are progressively released from the cartridge body during the advancement of the firing assembly from the proximal end to the distal end.

Example 122

The staple cartridge assembly of Example 121, wherein each staple is configured to separate each attachment portion from the cartridge body.

Example 123

The staple cartridge assembly of Examples 121 or 122, wherein the firing assembly is configured to lift the implantable adjunct away from the cartridge body to release the implantable adjunct from the cartridge body.

Example 124

The staple cartridge assembly of Examples 121, 122, or 123, further comprising a plurality of drivers, wherein the cartridge body comprises a deck surface, wherein the firing assembly is configured to lift the drivers above the deck surface.

Example 125

The staple cartridge assembly of Examples 121, 122, 123, or 124, wherein the cartridge body comprises a plurality of staple cavities, and wherein the attachment portions extend at least partially into the staple cavities.

Example 126

The staple cartridge assembly of Examples 121, 122, 123, 124, or 125, wherein the implantable adjunct comprises a unitary piece of material.

Example 127

The staple cartridge assembly of Examples 121, 122, 123, 124, 125, or 126, wherein the cartridge body comprises a slot, wherein the attachment portions are positioned adjacent the slot, and wherein the firing assembly comprises a release portion configured to engage the attachment portions to release the implantable adjunct from the cartridge body as the firing assembly advances from the proximal end to the distal end.

Example 128

The staple cartridge assembly of Examples 121, 122, 123, 124, 125, 126, or 127, wherein the implantable adjunct comprises a first portion and second portion wherein the first portion is configured to be detached from the second portion, and wherein the second portion is configured to be retained against the cartridge body by a staple that has not been deployed by the firing assembly.

Example 129

The staple cartridge assembly of Examples 121, 122, 123, 124, 125, 126, 127, or 128, wherein the implantable adjunct further comprises a discontinuity, and wherein the first portion is detachable from the second portion at the discontinuity.

Example 130

The staple cartridge assembly of Example 129, wherein the discontinuity comprises at least one perforation.

Example 131

The staple cartridge assembly of Examples 121, 122, 123, 124, 125, 126, 127, 128, 129, or 130 wherein each staple comprises a pair of staple legs, and wherein each staple leg comprises a barb embedded in the implantable adjunct.

Example 132

The staple cartridge assembly of Example 131, wherein the barbs extend outwardly.

Example 133

The staple cartridge assembly of Examples 121, 122, 123, 124, 125, 126, 127, 128, 129, 130, 131, or 132, wherein the cartridge body comprises a plurality of staple cavities, and wherein each attachment portion extends over a staple cavity.

Example 134

The staple cartridge assembly of Examples 121, 122, 123, 124, 125, 126, 127, 128, 129, 130, 131, 132, or 133, wherein the staples engage the attachment portions and detach the attachment portions from the cartridge body when the staples are ejected from the cartridge body.

Example 135

A staple cartridge assembly comprising a cartridge body comprising a proximal end, a distal end, a deck, a plurality of staple cavities defined in the deck, and a longitudinal slot defined in the deck extending from the proximal end toward the distal end. The staple cartridge assembly further comprises a plurality of staples removably stored within the staple cavities, a firing member configured to eject the staples from the staple cavities during a firing progression of the firing member from the proximal end toward the distal end, and an implantable adjunct. The implantable adjunct comprises a body portion and a plurality of distinct attachment portions configured to releasably retain the implantable adjunct against the cartridge body, wherein the firing member is configured to progressively release the attachment portions from the cartridge body during the firing progression.

Example 136

The staple cartridge assembly of Example 135, wherein the firing member extends over the deck and directly engages the attachment portions.

Example 137

The staple cartridge assembly of Examples 135 or 136, wherein the staple cavities are arranged in longitudinal rows, wherein the longitudinal rows comprise inner longitudinal rows adjacent the longitudinal slot, and wherein the attachment portions are positioned intermediate the longitudinal slot and the inner longitudinal rows.

Example 138

The staple cartridge assembly of Example 137, wherein the firing member slides along the deck between the longitudinal slot and the inner longitudinal rows.

Example 139

A method for assembling a surgical stapling assembly for use with a surgical stapling instrument, the surgical stapling assembly comprising a staple cartridge, a plurality of staples, and a fibrous adjunct positioned at least partially on the staple cartridge, the method comprising pouring fibrous adjunct material onto a mold resembling the staple cartridge, allowing the fibrous adjunct material to cool, removing the fibrous adjunct material from the mold, and placing the fibrous adjunct material onto the staple cartridge, wherein the fibrous adjunct material maintains a continuous, fibrous structure upon being placed onto the staple cartridge.

Example 140

A staple cartridge assembly comprising a cartridge body comprising a deck, staples removably stored in the cartridge body, and an implantable adjunct positioned over the deck. The implantable adjunct comprises a first outer layer comprised of interwoven fibers, a second outer layer comprised of interwoven fibers, and a bonding layer positioned intermediate the first outer layer and the second outer layer, wherein the bonding layer is comprised of a meltable material having a threshold melt temperature, and wherein the adjunct has previously been exposed to a temperature in excess of the threshold melt temperature such that the bonding layer is bonded with the first outer layer and the second outer layer.

Example 141

The staple cartridge assembly of Example 140, wherein the interwoven fibers of the first outer layer are comprised of a first material having a first melt temperature which is greater than the threshold melt temperature, and wherein the interwoven fibers of the first outer layer have not been melted.

Example 142

The staple cartridge assembly of Example 141, wherein the interwoven fibers of the second outer layer are comprised of a second material having a second melt temperature which is different than the first melt temperature and greater than the threshold melt temperature, and wherein the interwoven fibers of the second outer layer have not been melted.

Example 143

The staple cartridge assembly of Examples 140, 141, or 142, wherein the bonding layer comprises a first bonding layer, and wherein the adjunct further comprises a spacer layer comprised of a material having a melt temperature which is greater than the threshold melt temperature and a second bonding layer comprised of the meltable material, wherein the first bonding layer is positioned intermediate the first outer layer and the spacer layer, and wherein the second bonding layer is positioned intermediate the second outer layer and the spacer layer.

Example 144

The staple cartridge assembly of Example 143, wherein the spacer layer comprises a plurality of openings defined therein which are configured to receive melted portions of the first bonding layer and the second bonding layer when the adjunct is exposed to a temperature in excess of the threshold melt temperature.

Example 145

The staple cartridge assembly of Examples 143 or 144, wherein melted portions of the first bonding layer has penetrated the first outside layer, and wherein melted portions of the second bonding layer has penetrated the second outside layer.

Example 146

The staple cartridge assembly of Examples 143, 144, or 145, wherein the plurality of openings are arranged in a first density in a first portion of the spacer layer and a second density in a second portion of the spacer layer, wherein the first density is greater than the second density, and wherein the bond between the first portion and the bonding layers is stronger than the bond between the second portion and the bonding layers.

Example 147

The staple cartridge assembly of Examples 143, 144, 145, or 146, wherein the spacer layer comprises a lofted weave.

Example 148

The staple cartridge assembly of Examples 140, 141, 142, 143, 144, 145, 146, or 147, wherein the bonding layer comprises a PDS film.

Example 149

The staple cartridge assembly of Examples 140, 141, 142, 143, 144, 145, 146, 147, or 148, wherein the bonding layer comprises apertures defined therein.

Example 150

The staple cartridge assembly of Examples 140, 141, 142, 143, 144, 145, 146, 147, 148, or 149, wherein the bonding layer has penetrated the first outside layer and the second outside layer.

Example 151

The staple cartridge assembly of Examples 140, 141, 142, 143, 144, 145, 146, 147, 148, 149, or 150, wherein the first outside layer and the second outside layer include meltable portions which are comprised of the meltable material, and wherein the meltable portions of the first outside layer and the second outside layer are merged with the bonding layer after the adjunct is exposed to a temperature in excess of the threshold melt temperature.

Example 152

A staple cartridge assembly comprising a cartridge body comprising a deck, staples removably stored in the cartridge body, and an implantable layer assembly positioned over the deck. The implantable layer comprises a first layer, a second layer, and a bonding layer positioned intermediate the first layer and the second layer, wherein the bonding layer is comprised of a meltable material having a threshold melt temperature, and wherein the implantable layer assembly has been previously exposed to a temperature at least equaling the threshold melt temperature such that the bonding layer is bonded with at least one of the first layer and the second layer.

Example 153

The staple cartridge assembly of Example 152, wherein the bonding layer is mechanically bonded to the first layer and the second layer.

Example 154

The staple cartridge assembly of Examples 152 or 153, wherein the interwoven fibers of the first layer are comprised of a first material having a first melt temperature which is greater than the threshold melt temperature, and wherein the interwoven fibers of the first layer have not been melted.

Example 155

The staple cartridge assembly of Example 154, wherein the interwoven fibers of the second layer are comprised of a second material having a second melt temperature which is different than the first melt temperature and greater than the threshold melt temperature, and wherein the interwoven fibers of the second layer have not been melted.

Example 156

The staple cartridge assembly of Examples 152, 153, 154, or 155, wherein the bonding layer comprises a first bonding layer, and wherein the implantable layer assembly further comprises a spacer layer comprised of a material having a melt temperature which is greater than the threshold melt temperature and a second bonding layer comprised of the meltable material, wherein the first bonding layer is positioned intermediate the first layer and the spacer layer, and wherein the second bonding layer is positioned intermediate the second layer and the spacer layer.

Example 157

The staple cartridge assembly of Example 156, wherein the spacer layer comprises a plurality of openings defined therein which are configured to receive melted portions of the first bonding layer and the second bonding layer when the adjunct is exposed to a temperature that at least equals the threshold melt temperature.

Example 158

The staple cartridge assembly of Example 157, wherein the plurality of openings are arranged in a first density in a first portion of the spacer layer and a second density in a second portion of the spacer layer, wherein the first density is greater than the second density, and wherein a bond between the first portion and the bonding layers is stronger than a bond between the second portion and the bonding layers.

Example 159

The staple cartridge assembly of Examples 156, 157, or 158, wherein melted portions of the first bonding layer has penetrated the first layer, and wherein melted portions of the second bonding layer has penetrated the second layer.

Example 160

A method of manufacturing a staple cartridge assembly comprising the steps of obtaining a first layer, a second layer, and a bonding layer, positioning the bonding layer intermediate the first layer and the second layer, heating the bonding layer to a temperature which at least partially melts the bonding layer, obtaining a cartridge body, positioning staples in the cartridge body, and attaching the first layer, the second layer, and the bonding layer to the cartridge body.

Example 161

The method of Example 160, wherein the heating step does not melt the first layer and the second layer.

Example 162

A staple cartridge assembly for use with a surgical stapler, wherein the staple cartridge assembly comprises a staple cartridge comprising a cartridge body, a cartridge deck, and a plurality of staples deployable from the cartridge body through the cartridge deck. The staple cartridge assembly further comprises a compressible adjunct positionable against the cartridge deck, wherein the compressible adjunct comprises a plurality of unaltered fibers comprising a first fiber including a first fiber portion and a second fiber including a second fiber portion extending over the first fiber portion. The compressible adjunct further comprises a plurality of altered fibers that are melted and resolidified and a node comprising the first fiber portion, the second fiber portion, and at least a portion of the plurality of altered fibers, wherein the at least a portion of the plurality of altered fibers affixes the first fiber portion and the second fiber portion.

Example 163

The staple cartridge assembly of Example 162, wherein the first fiber and the second fiber are comprised of a first biocompatible material comprising a first melting point.

Example 164

The staple cartridge assembly of Example 163, wherein the plurality of altered fibers comprises a second biocompatible material comprising a second melting point lower than the first melting point.

Example 165

The staple cartridge assembly of Example 164, wherein the first fiber is at least partially covered with the second biocompatible material.

Example 166

The staple cartridge assembly of Examples 162, 163, 164, or 165, wherein the plurality of unaltered fibers further comprises a third fiber including a third fiber portion extending over the first fiber portion.

Example 167

The staple cartridge assembly of Examples 162, 163, 164, 165, or 166, wherein the node releasably attaches the compressible adjunct to the cartridge deck.

Example 168

The staple cartridge assembly of Examples 162, 163, 164, 165, 166, or 167, further comprising a plurality of nodes defining attachment zones.

Example 169

The staple cartridge assembly of Example 168, further comprising unattached zones between the attachment zones.

Example 170

The staple cartridge assembly of Example 169, wherein the attachment zones comprise greater densities than the unattached zones.

Example 171

A staple cartridge assembly for use with a surgical stapler, wherein the staple cartridge assembly comprises a staple cartridge comprising a cartridge body, a cartridge deck, and a plurality of staples deployable from the cartridge body through the cartridge deck. The staple cartridge assembly further comprises a compressible adjunct positionable against the cartridge deck, wherein the compressible adjunct comprises a plurality of unaltered fibers comprising a first fiber including a first fiber portion and a second fiber including a second fiber portion extending over the first fiber portion. The compressible adjunct further comprises a plurality of altered fibers melted and resolidified to define a bonding medium and a node comprising the first fiber portion, the second fiber portion, and at least a portion of the bonding medium at least partially surrounding the first fiber portion and the second fiber portion.

Example 172

The staple cartridge assembly of Example 171, wherein the first fiber and the second fiber are comprised of a first biocompatible material comprising a first melting point.

Example 173

The staple cartridge assembly of Example 172, wherein the plurality of altered fibers comprises a second biocompatible material comprising a second melting point lower than the first melting point.

Example 174

The staple cartridge assembly of Example 173, wherein the first fiber is at least partially covered with the second biocompatible material.

Example 175

The staple cartridge assembly of Examples 171, 172, 173, or 174, wherein the plurality of unaltered fibers further comprises a third fiber including a third fiber portion extending over the first fiber portion.

Example 176

The staple cartridge assembly of Examples 171, 172, 173, 174, or 175, wherein the node releasably attaches the compressible adjunct to the cartridge deck.

Example 177

The staple cartridge assembly of Examples 171, 172, 173, 174, 175, or 176, further comprising a plurality of nodes defining attachment zones.

Example 178

The staple cartridge assembly of Example 177, further comprising non-attachment zones between the attachment zones.

Example 179

The staple cartridge assembly of Example 178, wherein the attachment zones comprise greater densities than the non-attachment zones.

Example 180

A staple cartridge assembly for use with a surgical stapler, wherein the staple cartridge assembly comprises a staple cartridge comprising a cartridge body, a cartridge deck, and a plurality of staples deployable from the cartridge body through the cartridge deck. The staple cartridge assembly further comprises a compressible adjunct positionable against the cartridge deck, wherein the compressible adjunct comprises a plurality of fibers comprising a first fiber including a first fiber portion and a second fiber including a second fiber portion spaced apart from the first fiber portion. The compressible adjunct further comprises a bonding fiber melted and resolidified, wherein the bonding fiber comprises a bonding fiber portion extending between the first fiber portion and the second fiber portion, wherein the bonding fiber portion is attached to the first fiber portion, and wherein the bonding fiber portion is attached to second fiber portion.

Example 181

The staple cartridge assembly of Example 180, wherein the first fiber and the second fiber are comprised of a first biocompatible material comprising a first melting point, and wherein the bonding fiber comprises a second biocompatible material comprising a second melting point lower than the first melting point.

Various embodiments are disclosed including adjuncts attached to and/or positioned on a staple cartridge. It should be understood that such teachings are applicable to embodiments in which an adjunct is attached to and/or positioned on an anvil of a surgical instrument. In fact, embodiments are envisioned in which a first adjunct is attached to and/or positioned on a cartridge and a second adjunct is attached to and/or positioned on an anvil.

The compressible adjuncts of the present disclosure can be positioned against a cartridge deck of a staple cartridge such as, for example, the cartridge deck 16 of the staple cartridge 12. In at least one instance, a compressible adjunct can be positioned against a cartridge deck of a staple cartridge prior to loading the staple cartridge onto a surgical instrument such as, for example, the surgical stapling and severing instrument 8010 (FIG. 1). Alternatively, a compressible adjunct can be positioned against a cartridge deck of a staple cartridge after the staple cartridge has been loaded into the surgical stapling and severing instrument. A loading unit can be employed to deposit a compressible adjunct onto the cartridge deck of the staple cartridge. The loading unit may include various attachment features and/or placement features for manipulating and positioning the compressible adjunct against the cartridge deck. Once the compressible adjunct is correctly positioned against the cartridge deck, the loading unit can release the compressible adjunct.

Further to the above, a compressible adjunct can be positioned against a cartridge deck without attachment to the staple cartridge. Alternatively, a compressible adjunct can be attached to the staple cartridge prior to or after the staple cartridge is loaded into the surgical stapling and severing instrument. For example, the compressible adjunct can be partially melted onto the cartridge deck then resolidified by cooling which causes the compressible adjunct to bond to the cartridge deck. Various attachment features can also be employed to attach a compressible adjunct to a staple cartridge such as, for example, sutures, straps, barbs, and/or other mechanical attachment mechanisms.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A compressible adjunct for use with a surgical instrument including a staple cartridge deck, wherein said compressible adjunct comprises:
    a first biocompatible material;
    a second biocompatible material with a lower melting temperature than said first biocompatible material, wherein said first biocompatible material and said second biocompatible material are positioned on a first surface of said staple cartridge deck; and
    a body comprising a face positionable against a length of the staple cartridge deck, wherein said face comprises:
        a plurality of attachment regions spaced apart from one another, wherein said plurality of attachment regions include said second biocompatible material, wherein each of said plurality of attachment regions extends across a width of said body, and wherein said face is selectively attachable to the staple cartridge deck at said plurality of attachment regions; and
        a plurality of non-attachment regions extending between said plurality of attachment regions, wherein said second biocompatible material is selectively disposed outside said non-attachment regions, and wherein said compressible adjunct is selectively attached to the staple cartridge deck by temporarily heating said face to a temperature greater than or equal to said melting temperature of said second biocompatible material but less than said melting temperature of said first biocompatible material.

2. The compressible adjunct of claim 1, wherein said plurality of attachment regions define an attachment pattern.

3. The compressible adjunct of claim 1, wherein said body comprises a woven fibrous construct.

4. The compressible adjunct of claim 1, wherein at least one of said first biocompatible material and said second biocompatible material is absorbable.

5. The compressible adjunct of claim 1, wherein said second biocompatible material is poly-p-dioxanone (PDS).

6. A staple cartridge assembly for use with a surgical stapling instrument, wherein said staple cartridge assembly comprises:
    a staple cartridge, comprising:
        a plurality of staples; and
        a cartridge deck comprising an outer surface; and
    a fibrous construct, comprising:
        a first side;
        a second side;
        a body comprising a first plurality of fibers comprised of a first biocompatible material having a first melting temperature; and
        a face positioned against said outer surface of said cartridge deck, wherein said face comprises:
            a plurality of attachment regions spaced apart from one another, wherein each of said plurality of attachment regions comprises a second plurality of fibers comprised of a second biocompatible material having a second melting temperature lower than said first melting temperature, wherein each of said plurality of attachment regions extends between said first side and said second side; and
            a plurality of non-attachment regions extending between said plurality of attachment regions, wherein said non-attachment regions exclude said second plurality of fibers, and wherein said face is selectively attached to said outer surface at said plurality of attachment regions by temporarily heating said face to a temperature greater than or equal to said second melting temperature but less than said first melting temperature.

7. The staple cartridge assembly of claim 6, wherein said plurality of attachment regions define an attachment pattern.

8. The staple cartridge assembly of claim 6, wherein said fibrous construct is a woven fibrous construct.

9. The staple cartridge assembly of claim 6, wherein at least one of said first biocompatible material and said second biocompatible material is absorbable.

10. The staple cartridge assembly of claim 6, wherein said second biocompatible material is poly-p-dioxanone (PDS).

11. The staple cartridge assembly of claim 6, wherein said cartridge deck further comprises at least one attachment member configured to secure said fibrous construct to said outer surface.

12. The staple cartridge assembly of claim 11, wherein said at least one attachment member comprises a mechanical barb.

13. The staple cartridge assembly of claim 6, wherein said outer surface comprises a plurality of rough zones, wherein said rough zones comprise a greater roughness than a remainder of said outer surface.

14. The staple cartridge assembly of claim 13, wherein said rough zones are etched into said outer surface.

15. A staple cartridge assembly for use with a surgical stapling instrument, wherein said staple cartridge assembly comprises:
    a staple cartridge, comprising:
        a base;
        a first sidewall extending from said base;
        a second sidewall extending from said base;
        a longitudinal slot;
        a plurality of staples; and
        a cartridge deck, comprising:
            an outer surface comprising a plurality of attachment zones spaced apart from one another; and
            a plurality of bonding islands, wherein each of said plurality of bonding islands is disposed within one of said attachment zones, wherein each of said plurality of bonding islands is comprised of a first biocompatible material, wherein said first biocompatible material comprises a first melting temperature, and wherein each of said plurality of bonding islands extends across said outer surface between said longitudinal slot and one of said first sidewall and said second sidewall; and a compressible layer positioned against said cartridge deck, wherein said compressible layer is comprised of a second biocompatible material different from said first biocompatible material, wherein said second biocompatible material comprises a second melting temperature higher than said first melting temperature, wherein said compressible layer is selectively attached to said outer surface at said plurality of attachment zones by temporarily heating said plurality of bonding islands to a temperature greater than or equal to said first melting temperature but less than said second melting temperature, and wherein said compressible layer is secured to said cartridge deck by a temporary phase transition in said first biocompatible material.

16. The staple cartridge assembly of claim 15, wherein said temporary phase transition in said first biocompatible material is not accompanied by a phase transition in said second biocompatible material.

17. The staple cartridge assembly of claim 15, wherein said cartridge deck further comprises at least one attachment member configured to secure said compressible layer to said cartridge deck.

18. The staple cartridge assembly of claim 17, wherein said at least one attachment member comprises a mechanical barb.

19. The staple cartridge assembly of claim 15, wherein said attachment zones are etched into said outer surface.

* * * * *